(12) United States Patent
Kwong et al.

(10) Patent No.: US 9,871,212 B2
(45) Date of Patent: Jan. 16, 2018

(54) ORGANIC ELECTROLUMINESCENT MATERIALS AND DEVICES

(71) Applicant: Universal Display Corporation, Ewing, NJ (US)

(72) Inventors: Raymond Kwong, Fo Tan (KR); Kit Yee Tsang, Shatin (KR)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 173 days.

(21) Appl. No.: 14/933,510

(22) Filed: Nov. 5, 2015

(65) Prior Publication Data

US 2016/0233423 A1    Aug. 11, 2016

Related U.S. Application Data

(60) Provisional application No. 62/079,665, filed on Nov. 14, 2014.

(51) Int. Cl.
  *C09K 11/06*    (2006.01)
  *H01L 51/00*    (2006.01)
  (Continued)

(52) U.S. Cl.
  CPC .............. *H01L 51/008* (2013.01); *C07F 5/02* (2013.01); *C09K 11/025* (2013.01); *C09K 11/06* (2013.01);
  (Continued)

(58) Field of Classification Search
  CPC ........ C07F 5/02; C07F 5/027; H01L 51/5012; C09K 11/06
  (Continued)

(56) References Cited

U.S. PATENT DOCUMENTS 4,769,292 A    9/1988  Tang et al.
5,061,569 A    10/1991 VanSlyke et al.
(Continued)

FOREIGN PATENT DOCUMENTS

EP    0650955    5/1995
EP    1725079    11/2006
(Continued)

OTHER PUBLICATIONS

Adachi, Chihaya et al., "Organic Electroluminescent Device Having a Hole Conductor as an Emitting Layer," Appl. Phys. Lett. 55(15): 1489-1491 (1989).

(Continued)

*Primary Examiner* — Amanda C Walke
(74) *Attorney, Agent, or Firm* — Duane Morris, LLC

(57) ABSTRACT

Compounds having a structure according to Formula I, $G^1$-$L^1$-$G^2$, or Formula V, (Continued)

are described. In Formula I, $G^1$ and $G^2$ independently have a structure of Formula II,

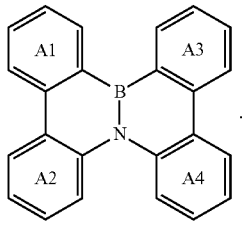

In the structures of Formulae I, II, and V, $L^1$ connects one of rings A1-A4 of $G^1$ to one of rings A1-A4 of $G^2$; $L^1$ is selected from a direct bond, BR, NR, PR, O, S, Se, C═O, S═O, $SO_2$, SiRR', GeRR', alkyl, cycloalkyl, aryl, heteroaryl, and combinations thereof; each ring A1, A2, A3, and A4, as well as R, R'R", and $R^1$ to $R^{19}$ can be hydrogen or a variety of substituents, including a fused ring between adjacent substituents; and at least two adjacent $R^1$ to $R^{16}$ on the same ring are

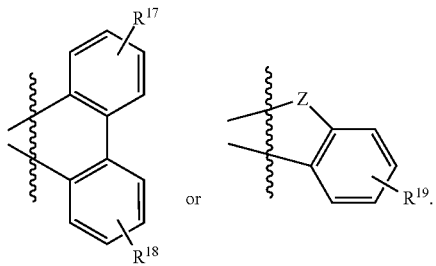

Formulations and devices, such as an OLEDs, that include the compound of Formula I or V are also described.

20 Claims, 3 Drawing Sheets

(51) Int. Cl.
  *C09K 11/02* (2006.01)
  *C07F 5/02* (2006.01)
  *H01L 51/50* (2006.01)
(52) U.S. Cl.
  CPC .. H01L 51/0085 (2013.01); *C09K 2211/1007* (2013.01); *C09K 2211/1029* (2013.01); *C09K 2211/185* (2013.01); *H01L 51/5012* (2013.01); *H01L 51/5072* (2013.01); *H01L 51/5096* (2013.01)
(58) Field of Classification Search
  USPC ......... 548/405, 110; 546/13; 549/213; 568/1
  See application file for complete search history.

(56) References Cited

U.S. PATENT DOCUMENTS

| | | | |
|---|---|---|---|
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 9,166,176 B2* | 10/2015 | Hatakeyama | C07F 9/65846 |
| 9,231,218 B2* | 1/2016 | Lin | |
| 9,318,710 B2* | 4/2016 | Kwong | H01L 51/0071 |
| 9,557,105 B2* | 1/2017 | Bjorklund | C10L 5/442 |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0151042 A1 | 8/2003 | Marks et al. | |
| 2003/0152802 A1 | 8/2003 | Tsuboyama et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101670 A1 | 4/2009 | Pakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2011/0021818 A1* | 1/2011 | Liu | C01B 3/22 564/10 |
| 2011/0278556 A1* | 11/2011 | Kottas | C07F 5/027 257/40 |
| 2014/0005399 A1 | 1/2014 | Hatakeyama et al. | |

(56) References Cited

U.S. PATENT DOCUMENTS

| | | | |
|---|---|---|---|
| 2015/0097162 A1* | 4/2015 | Ono | H01L 51/0071 257/40 |
| 2015/0236274 A1* | 8/2015 | Hatakeyama | H01L 51/0072 257/40 |
| 2016/0351811 A1* | 12/2016 | Lam | C07F 5/027 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 2001039234 | 5/2001 |
| WO | 2002002714 | 1/2002 |
| WO | 200215645 | 2/2002 |
| WO | 2003040257 | 5/2003 |
| WO | 2003060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056745 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009016009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ler-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).

Huang, Wei-Sheng et al., "Highly Phosphorescent Bis-Cyclornetalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF2," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2): 156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18 (21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

(56) References Cited

OTHER PUBLICATIONS

Noda, Tetsuya and Shirota, Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands of Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 67:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69 (15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

Hashimoto, S., et al., "Triplet-Energy Control of Polycyclic Aromatic Hydrocarbons by BN Replacement: Development of Ambipolar Host Materials for Phosphorescent Organic Light-Emitting Diodes," Chem. Mater., 2014, vol. 26, pp. 6265-6271.

* cited by examiner

ORGANIC ELECTROLUMINESCENT MATERIALS AND DEVICES

CROSS-REFERENCE TO RELATED APPLICATIONS

This application claims priority to U.S. Provisional Patent Application Ser. No. 62/079,665 filed Nov. 14, 2014, the entire content of which is incorporated herein by reference.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and Universal Display Corporation, The agreement was in effect on and before the date the claimed invention was made, and the claimed invention was made as a result of activities undertaken within the scope of the agreement.

FIELD OF THE INVENTION

The present invention relates to compounds for use as hosts and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

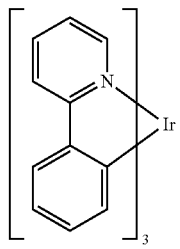

In this, and later figures herein, we depict the dative bond from nitrogen to metal (here, Ir) as a straight line, As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive materia. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO ) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an embodiment, a compound is provided that has the structure of Formula I, $G^1$-$L^1$-$G^2$ is described in Formula I, $G^1$ and $G^2$ independently have a structure of Formula II,

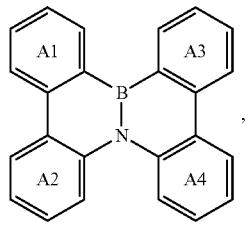

where:

$G^1$ and $G^2$ can be same or different;

$L^1$ connects one of rings A1, A2, A3, and A4 of $G^1$ to one of rings A1, A2, A3, and A4 of $G^2$;

$L^1$ is selected from the group consisting of a direct bond, BR, NR, PR, O, S, Se, C=O, S=O, $SO_2$, SiRR', GeRR', alkyl, cycloalkyl, aryl, heteroaryl, and combinations thereof;

each ring A1, A2, A3, and A4 in Formula II can be further substituted by one or more substituents selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

R, R' are each independently selected from the group consisting of hydrogen, deuterium, halide, alkyl, cycloalkyl, heteroalkyl, arylalkyl, alkoxy, aryloxy, amino, sibyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and any adjacent substitutions are optionally joined or fused into a ring.

In another embodiment, a compound having the structure of Formula V,

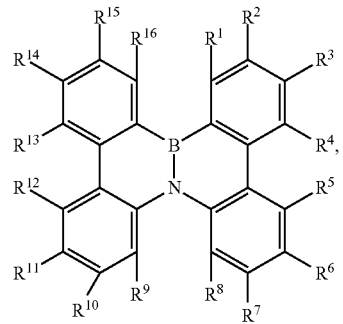

is described. In Formula V, at least two adjacent $R^1$ to $R^{16}$ on the same ring are:

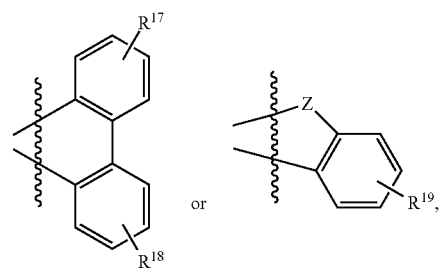

where:

$R^{17}$ to $R^{19}$ each independently represent mono, di, tri, or tetra substitution, or no substitution;

Z is selected from the group consisting of NR", O, S and Se;

R", $R^1$ to $R^{19}$ are each independently selected from the group consisting of hydrogen, deuterium, halide, alkyl, cycloalkyl, heteroalkyl, arylalkyl, alkoxy, aryloxy, amino, silyl, alkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and any adjacent substitutions of $R^{17}$ to $R^{19}$ are optionally joined or fused into a ring.

According to another embodiment, a device comprising one or more organic light emitting devices is also provided. At least one of the one or more organic light emitting devices can include an anode, a cathode, and an organic layer, disposed between the anode and the cathode, wherein the organic layer can include a compound of Formula I or Formula V. The device can be a consumer product, an electronic component module, an organic light-emitting device, and/or a lighting panel.

According to yet another embodiment, a formulation containing a compound of Formula I or Formula V is provided.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial LEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated, Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
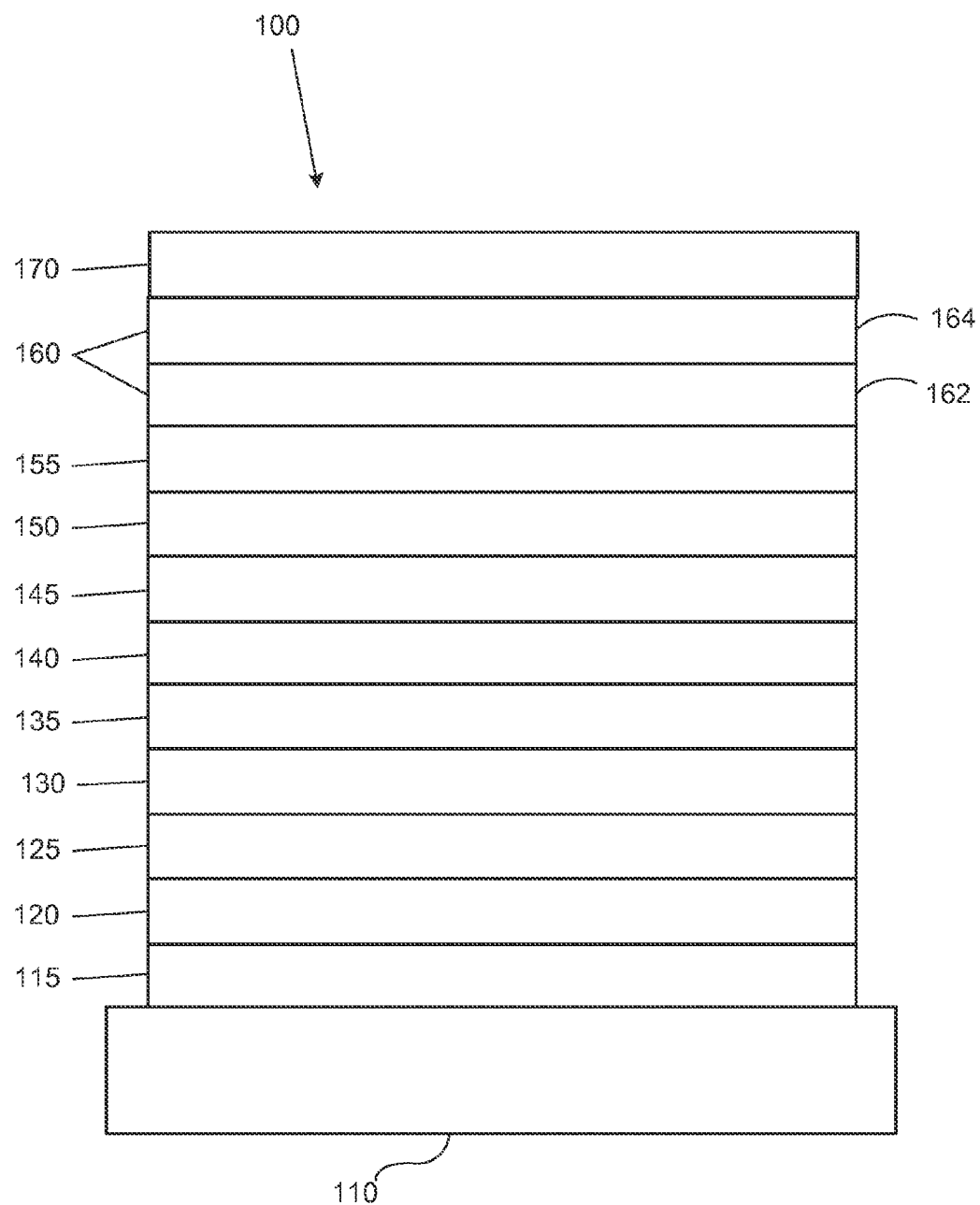
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
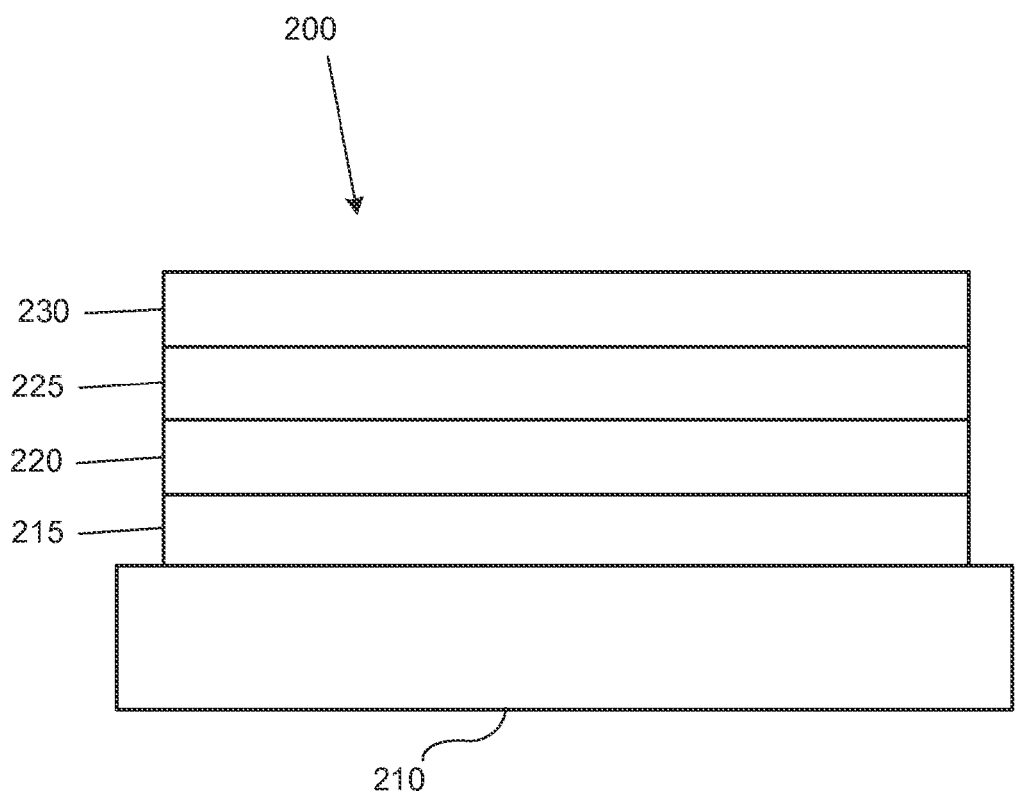
FIG. 2 shows an inverted organic light emitting device that does not have a separate electron transport layer.
Figure 5:
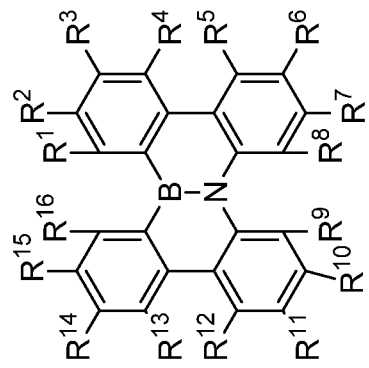
FIG. 5 shows Formula V as disclosed herein.
Figure 4:
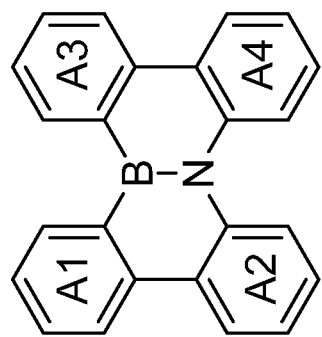
FIG. 4 shows Formula II as disclosed herein.
Figure 3:
FIG. 3 shows Formula I as disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (OLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al, which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing, Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymetric material may be in the range of 95:5 to 5:95. The polymeric material and the non-polymetric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, microdisplays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 or 7 ring atoms which includes at least one hetero atom, and includes cyclic amines such as morpholino, piperidino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g., phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

According to one embodiment, a compound having a structure of Formula I, $G^1$-$L^1$-$G^2$ is described. In Formula I, $G^1$ and $G^2$ independently have a structure of Formula II,

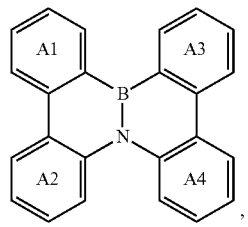

where:
$G^1$ and $G^2$ can be same or different;
$L^1$ connects one of rings A1, A2, A3, and A4 of $G^1$ one of rings A1, A2, A3, and A4 of $G^2$;

$L^1$ is selected from the group consisting of a direct bond, BR, NR, PR, O, S, Se, C=O, S=O, SO$_2$, SiRR', GeRR', alkyl, cycloalkyl, aryl, heteroaryl, and combinations thereof;

each ring A1, A2, A3, and A4 in Formula II can be further substituted by one or more substituents selected from the group consisting of hydrogen, deuterium, halide, alkyl, cycloalkyl, heteroalkyl, arylalkyl, alkoxy, aryloxy, amino, silyl, alkenyl, cycloalkenyl heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

R, R' are each independently selected from the group consisting of hydrogen, deuterium, halide, alkyl, cycloalkyl, heteroalkyl, arylalkyl, alkoxy, aryloxy, amino, silyl, alkenyl, cycloalkenyl heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and any adjacent substitutions are optionally joined or fused into a ring.

In some embodiments, $L^1$ is a direct bond. In some $L^1$ is selected from the group consisting of SiRR', GeRR', alkyl, cycloalkyl, and combinations thereof.

In some embodiments, the compound comprises a structure selected from the group consisting of:

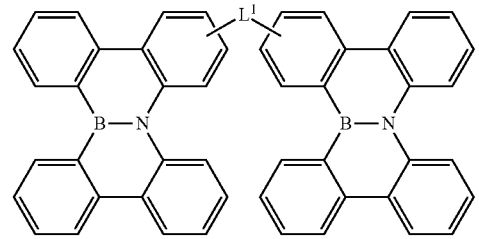

Structure 1

Structure 2

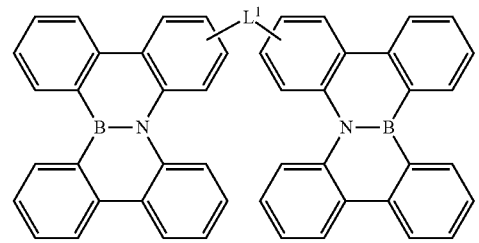

, and

Structure 3

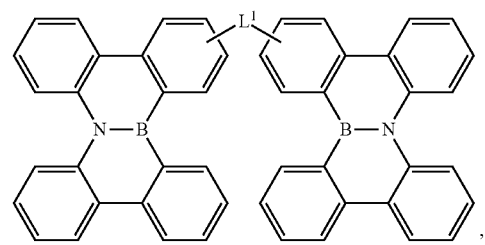

, which may be further substituted by one or more substituents independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrite, isonitrile, sulfanyl, sulfonyl, phosphino, and combinations thereof, and wherein any adjacent substitutions are optionally joined or fused into a ring. In some embodiments, Structures 1-3 are not further substituted.

In some embodiments, the compound has a structure selected from Formula III, $G^1$-$L^1$-$G^2$-$L^2$-$G^3$, and Formula IV,

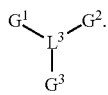

In the structures of Formula III and Formula IV:
$G^3$ has a structure of Formula II,
$G^3$ can be same as or different from $G^1$ and $G^2$,
in Formula III: $L^2$ is selected from the group consisting of a direct bond, BR, NR, PR, O, S, Se, C=O, S=O, $SO_2$, SiRR', GeRR', alkyl, cycloalkyl, aryl, heteroaryl, and combinations thereof, and $L^2$ connects one of the rings of A1, A2, A3, and A4 of $G^2$ to one of the rings of A1, A2, A3, and A4 of $G^3$; and
in Formula IV: $L^3$ is selected from the group consisting of B, N, P, SiR, GeR, alkyl, cycloalkyl, aryl, heteroaryl, and combinations thereof, and $L^3$ connects one of the rings of A1, A2, A3, and A4 of $G^1$, one of the rings of A1, A2, A3, and A4 of $G^2$ and one of the rings of A1, A2, A3, and A4 of $G^3$.

In some embodiments, the compound comprises at least four chemical groups of Formula II,

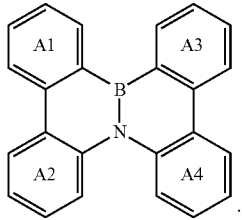

In some embodiments, at least two adjacent substituents on the same ring in rings of A1, A2, A3, or A4 are

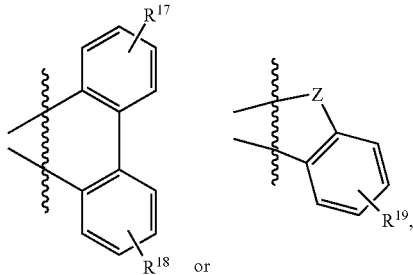

where:
$R^{17}$ to $R^{19}$ each independently represent mono, di, tri, or tetra substitution, or no substitution;
Z is selected from the group consisting of NR, O, S and Se;
R, $R^{17}$ to $R^{19}$ are each independently selected from the group A; and
any adjacent substitutions of $R^{17}$ to $R^{19}$ are optionally joined or fused into a ring.

In some embodiments, the compound comprises at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene.

In some embodiments, the compound comprises a structure selected from the group consisting of:

Structure A1

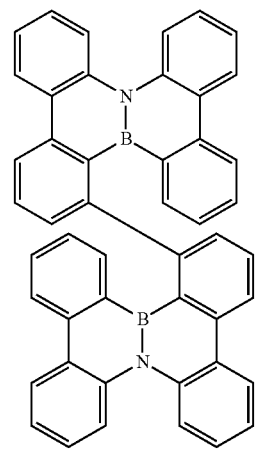

Structure A2

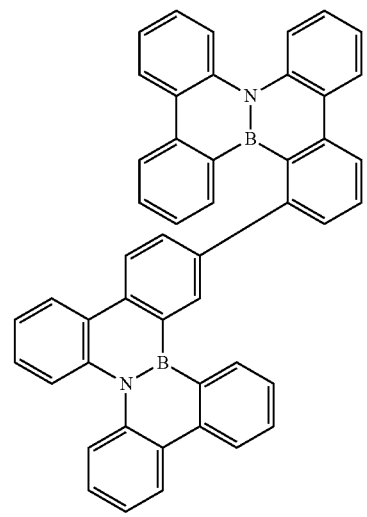

Structure A3

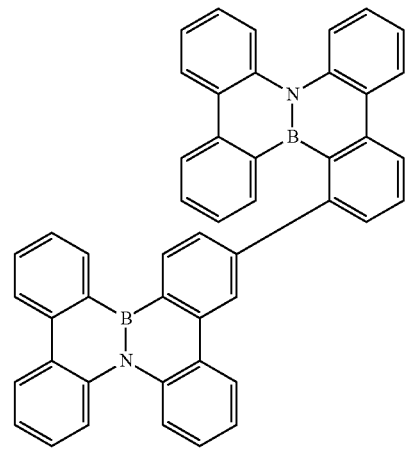

Structure A4
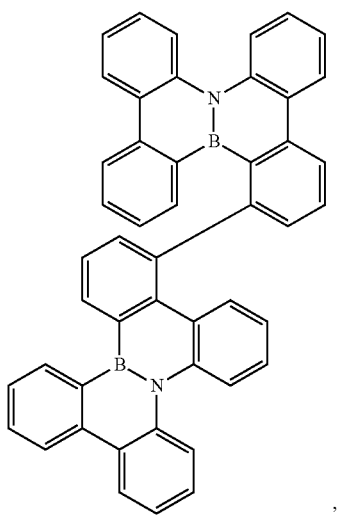
Structure A5
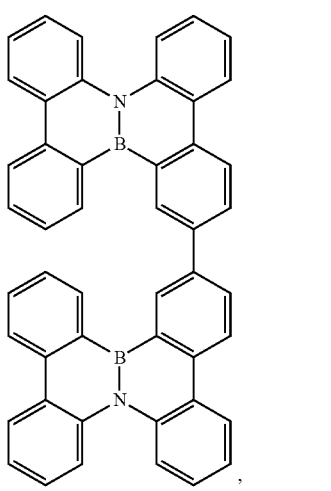
Structure A6
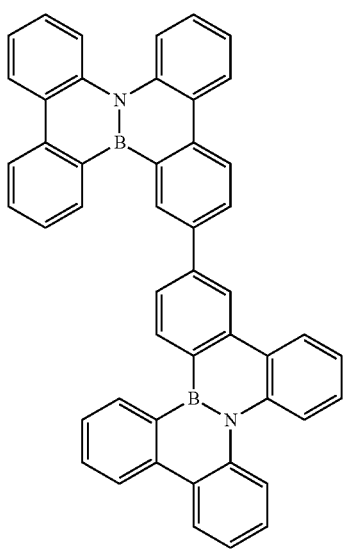
Structure A7
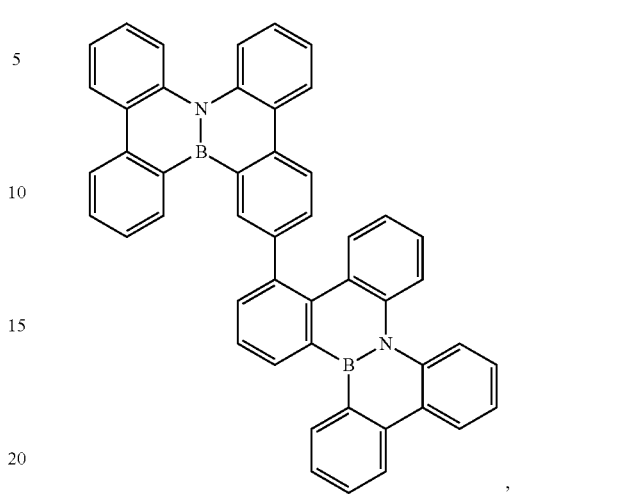
Structure A8
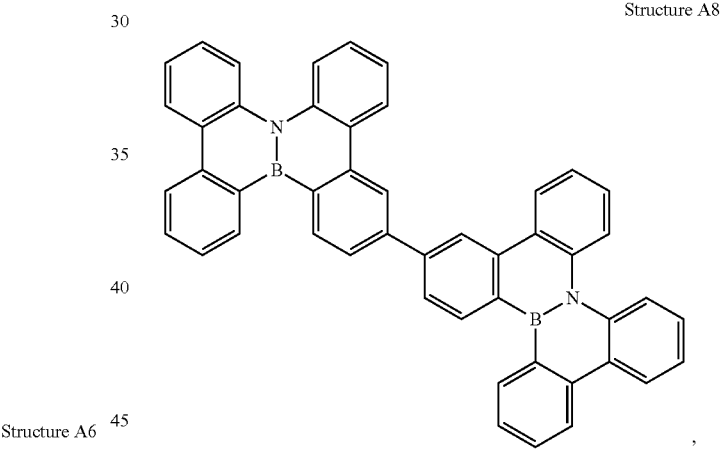
Structure A9
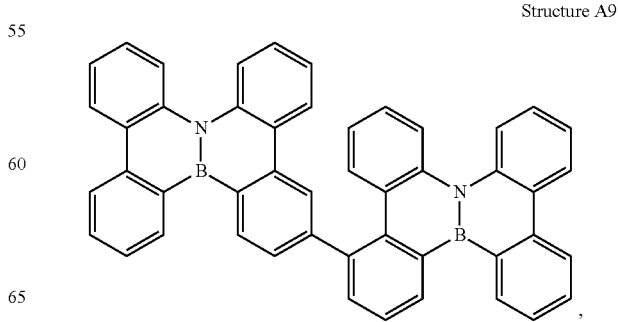

Structure A10
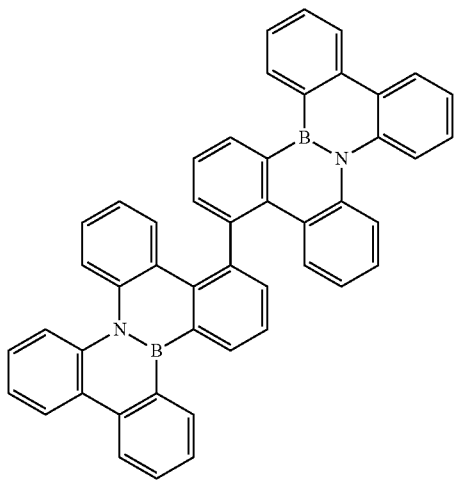
Structure A11
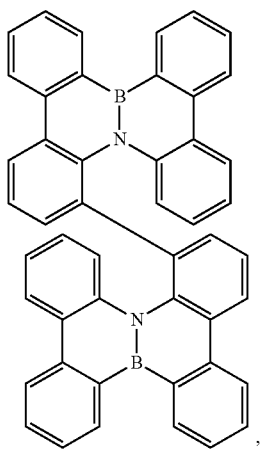
Structure A12
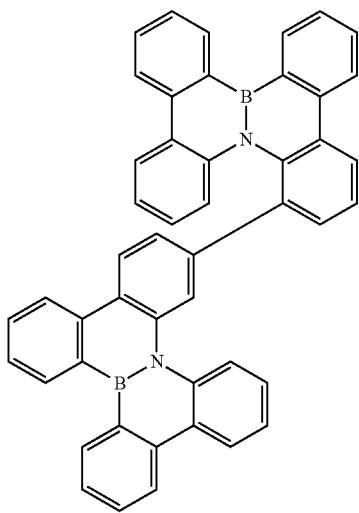
Structure A13
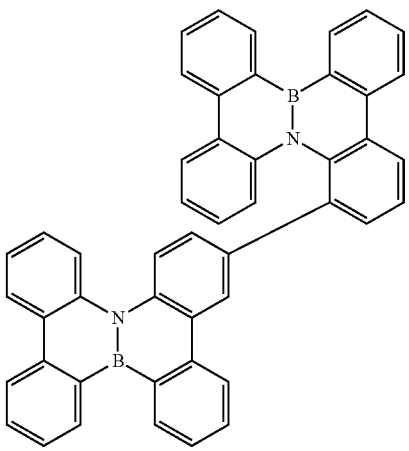
Structure A14
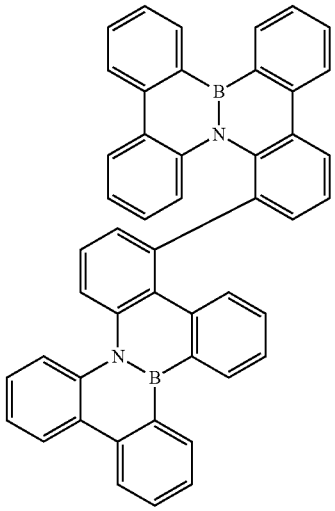
Structure A15
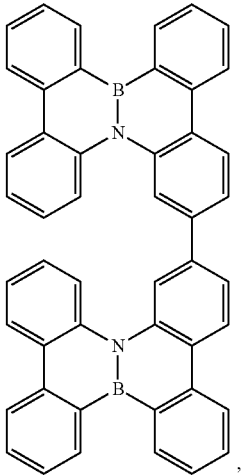

Structure A16
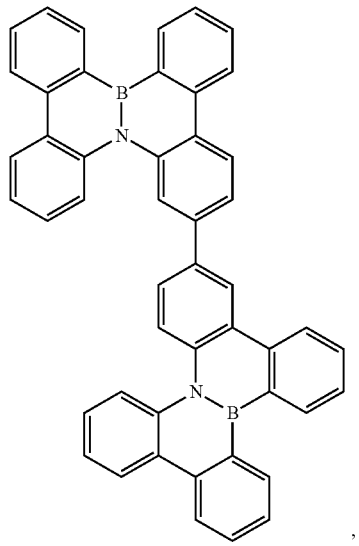
Structure A17
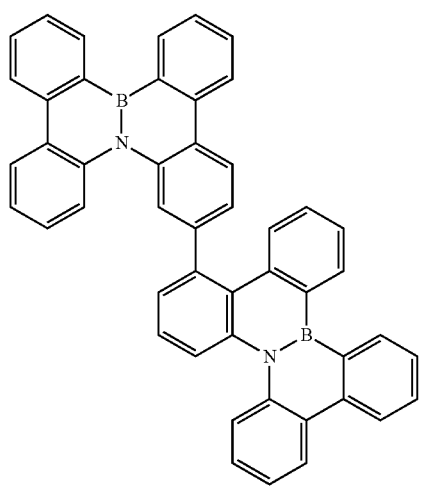
Structure A18
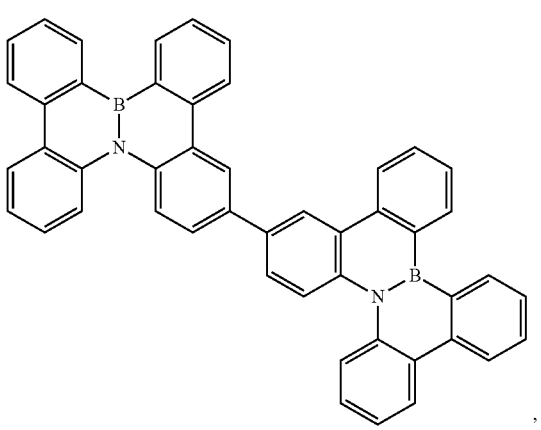
Structure A19
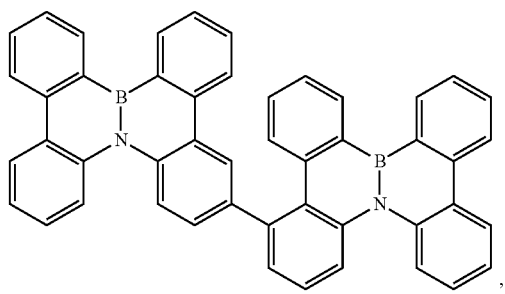
Structure A20
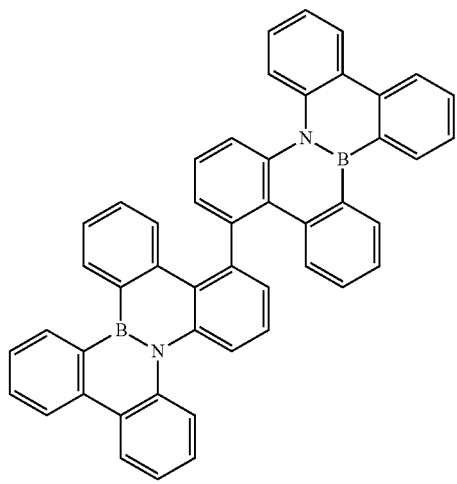
Structure A21
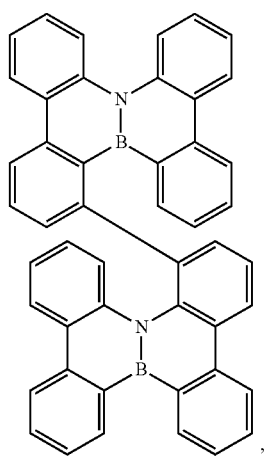

Structure A22
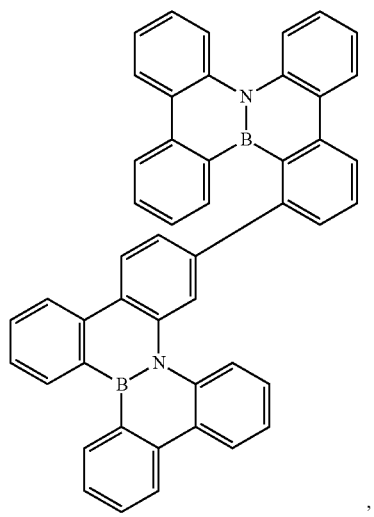
Structure A23
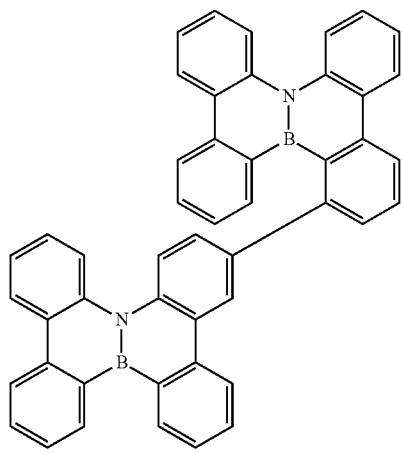
Structure A24
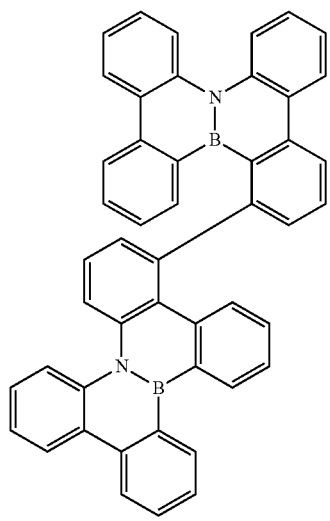
Structure A25
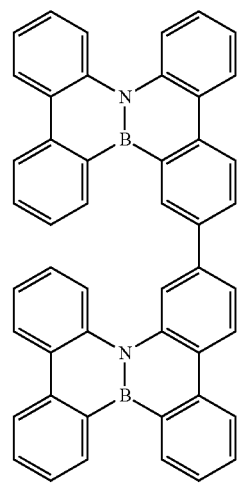
Structure A26
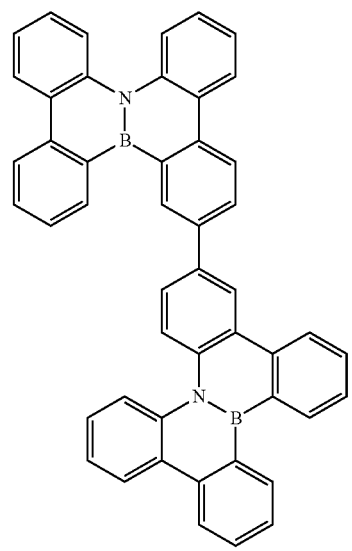
Structure A27
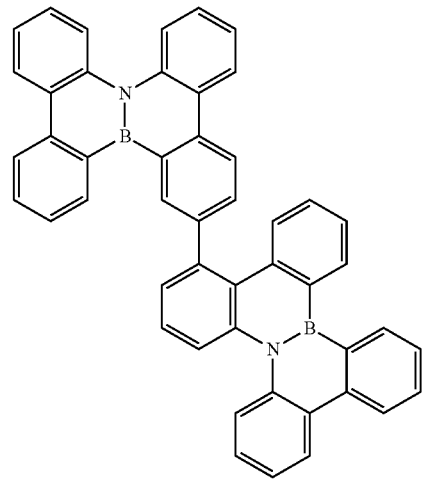

-continued

Structure A28

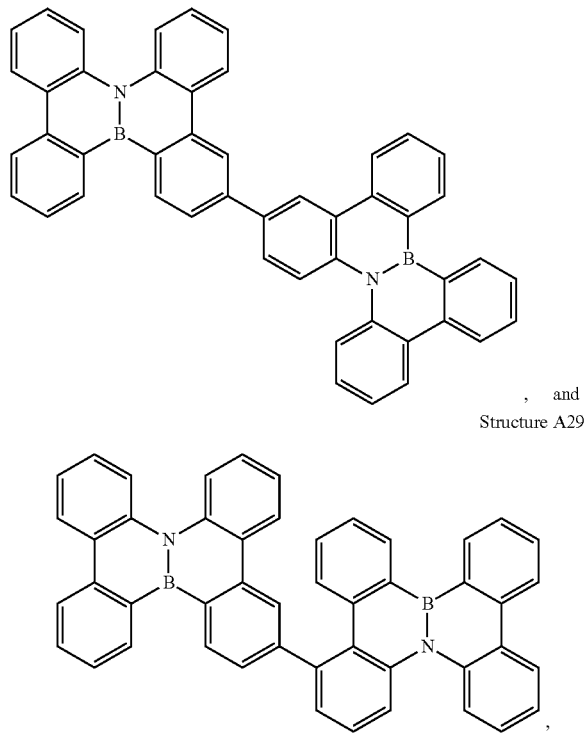

, and

Structure A29 which may be further substituted by one or more substituents independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and where any adjacent substitutions are optionally joined or fused into a ring.

In some embodiments, Structures A1-A29 are not further substituted. For example,

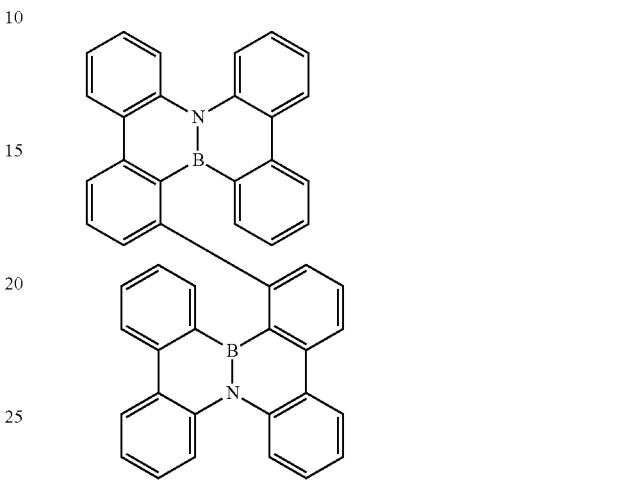

is denoted as Compound A1 which represents there is no further substitution. Thus, unsubstituted variants of Structures A1 through A29 are referred to Compounds A1 through A29, respectively.

In some embodiments, the compound comprises a structure selected from the group consisting of:

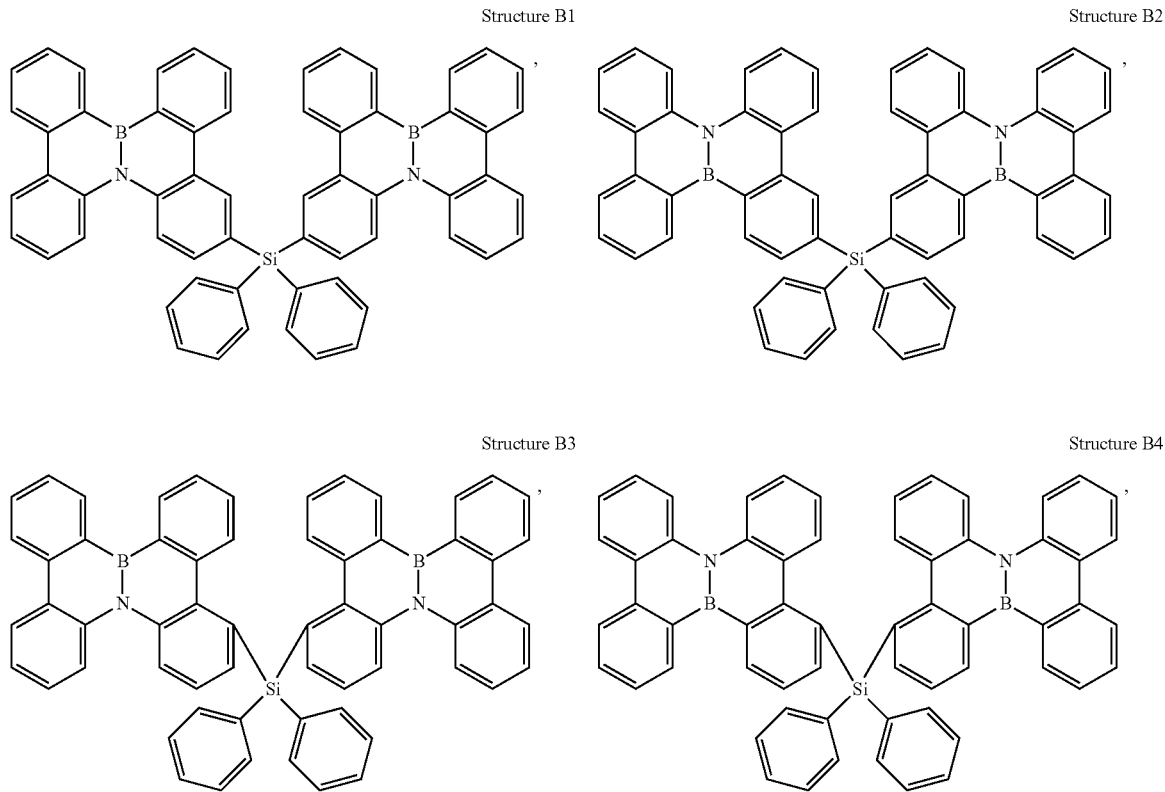

Structure B1, Structure B2, Structure B3, Structure B4

-continued
Structure B5
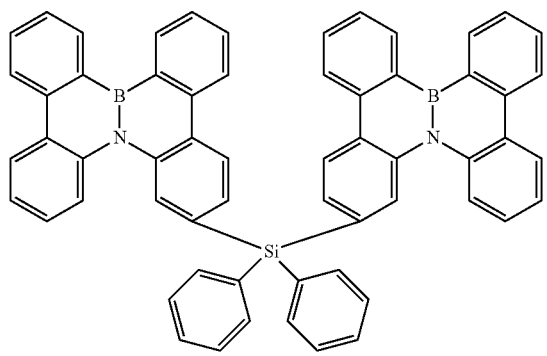
Structure B6
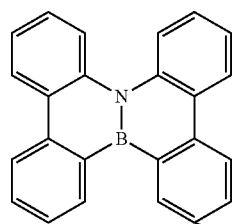
Structure B7
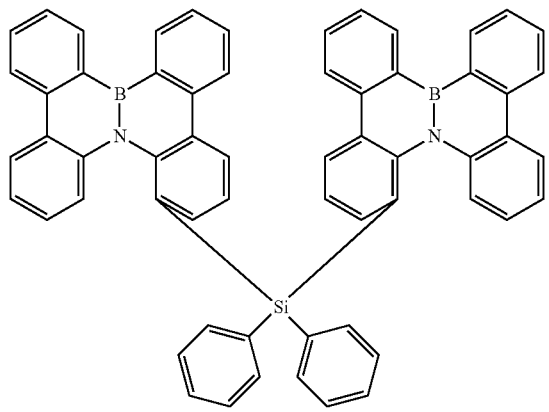
Structure B8
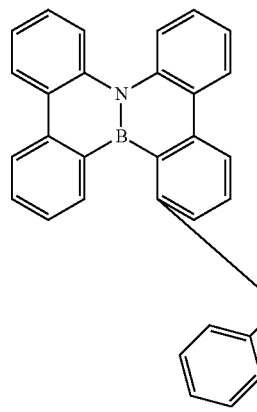
Structure B9
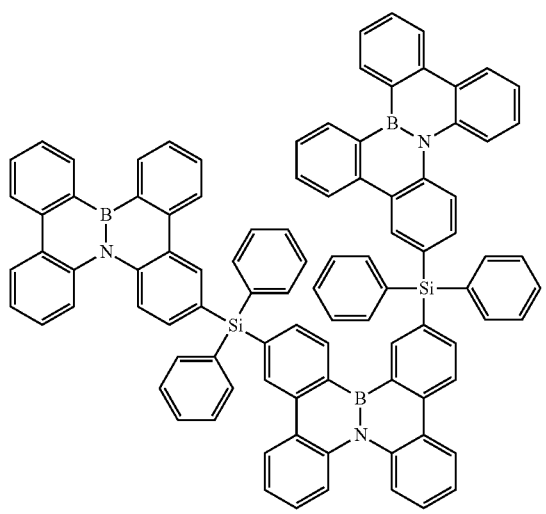
Structure B10
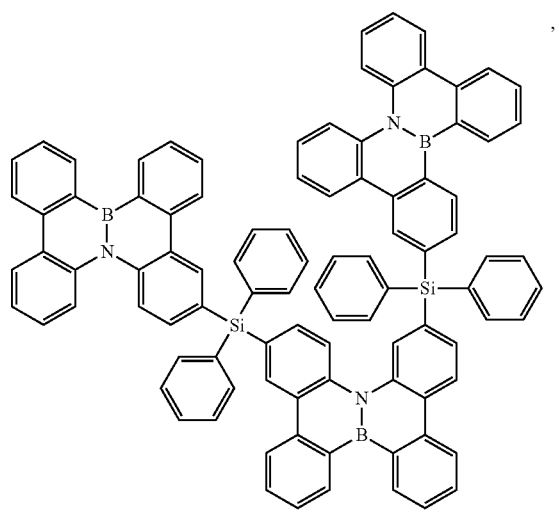

-continued
Structure B11
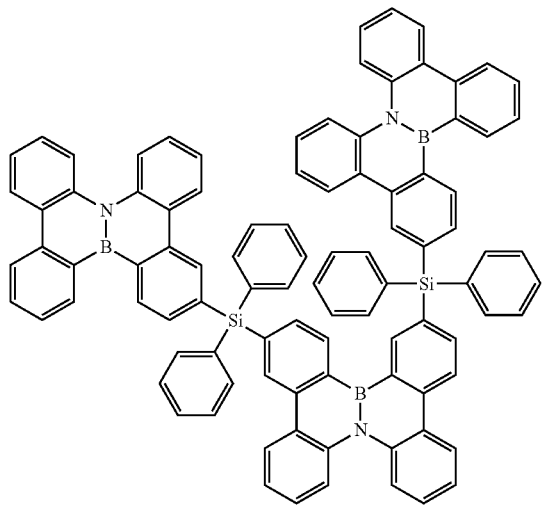
Structure B12
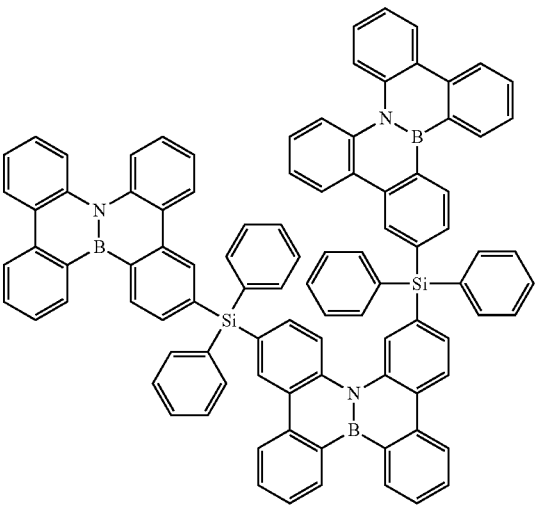
Structure B13
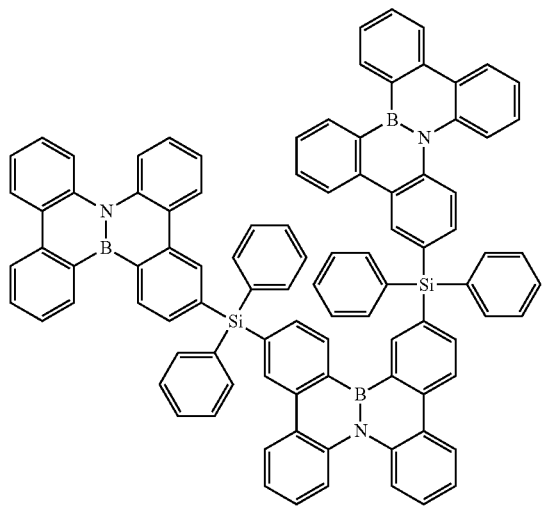
Structure B14
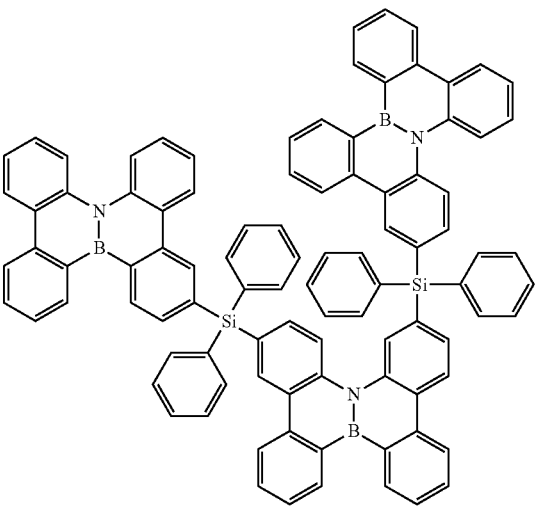
Structure B15
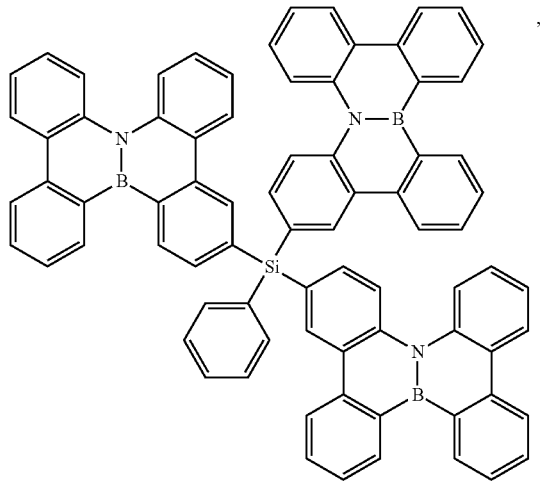
Structure B16
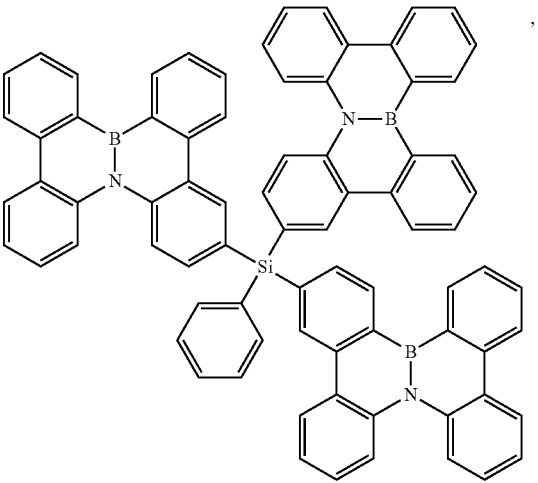

-continued
Structure B17
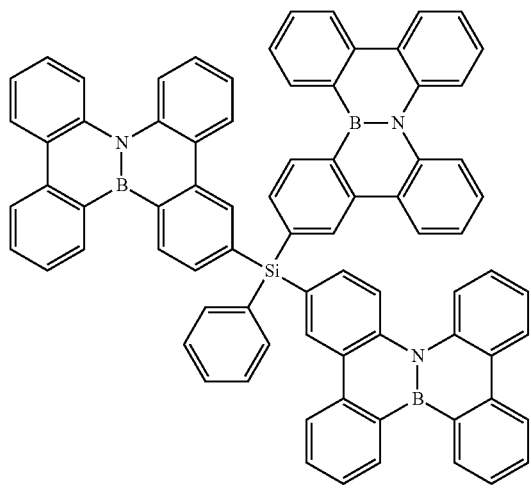
Structure B18
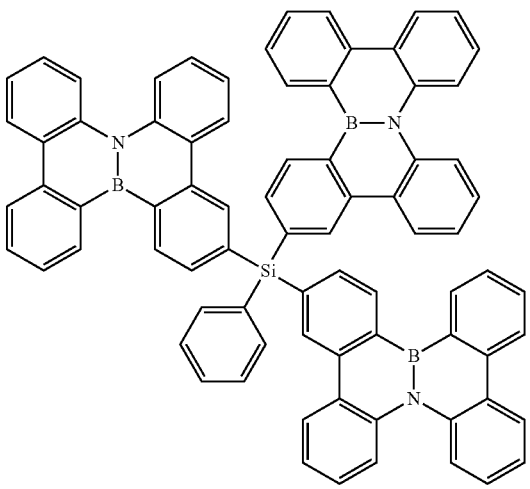
Structure B19
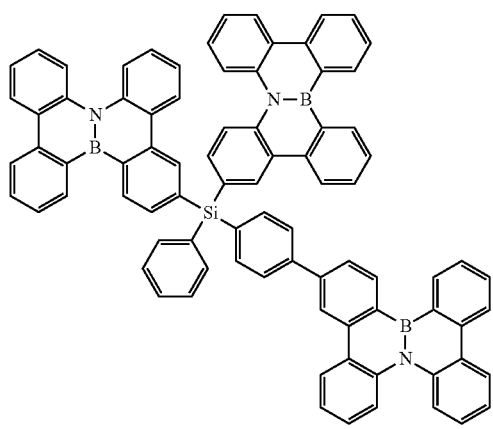
Structure B20
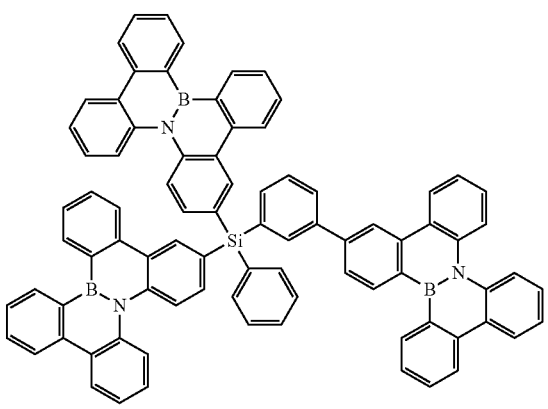
Structure B21
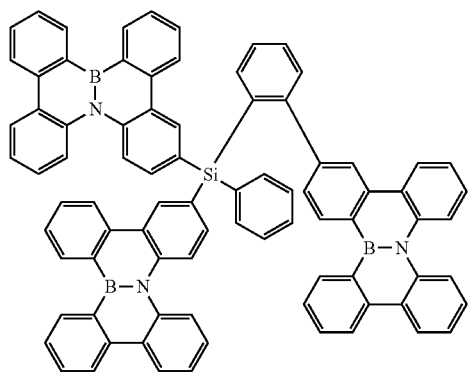
Structure B22
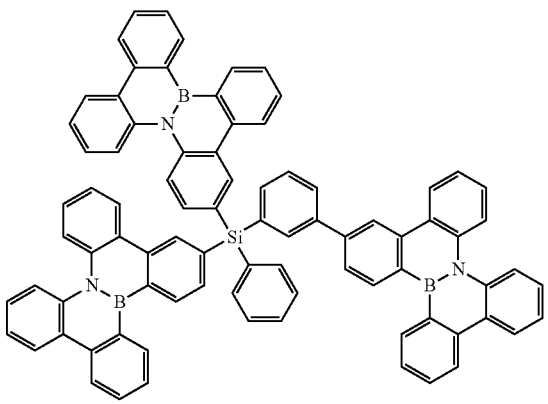

-continued
Structure B23
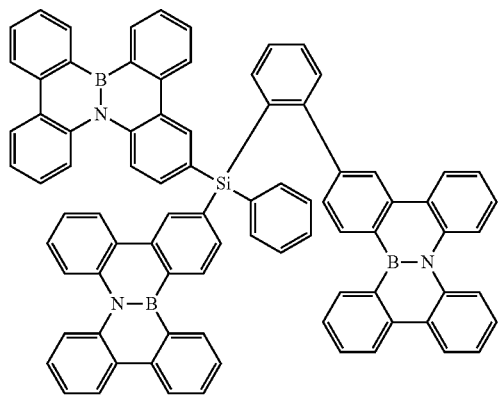
,
Structure B24
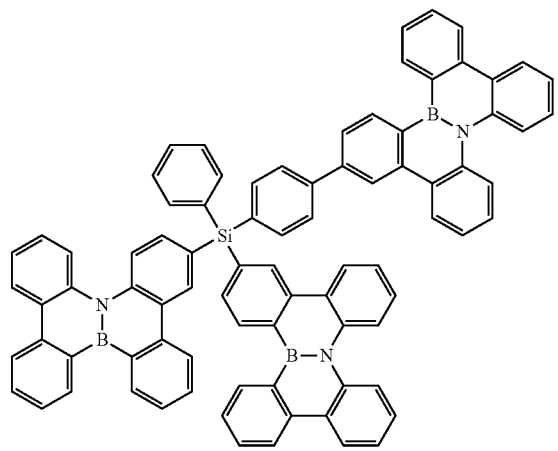
,
Structure B25
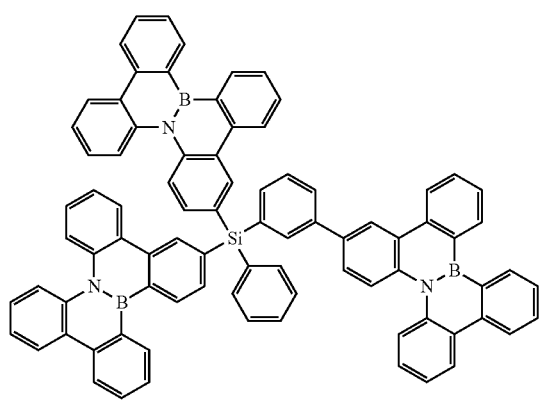
,
Structure B26
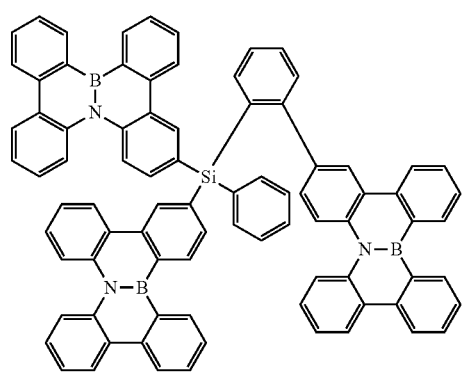
,
Structure B27
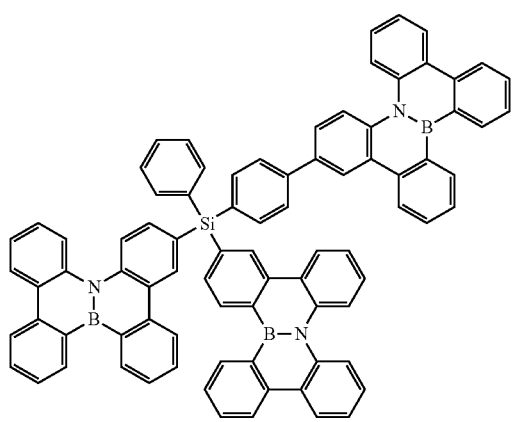
,
Structure B28
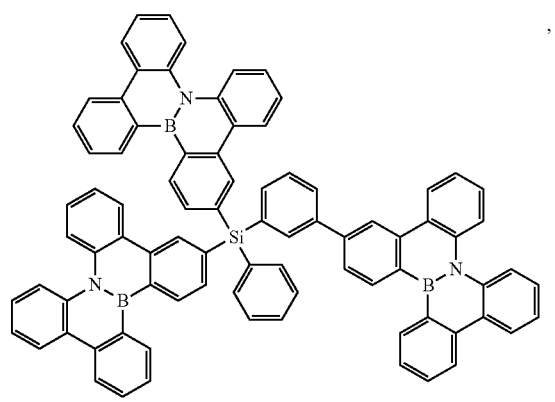
, -continued
Structure B29
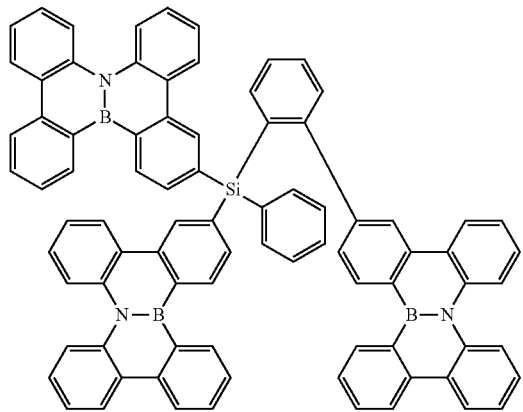
Structure B30
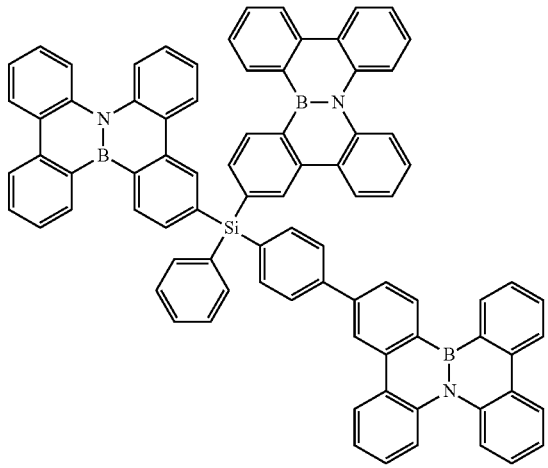
Structure B31
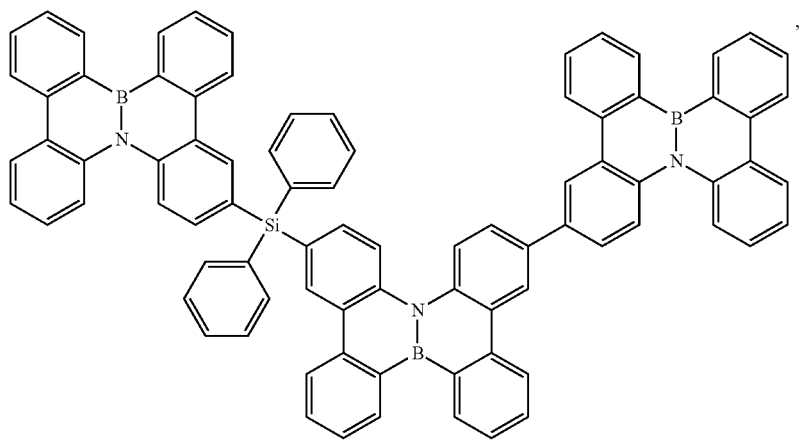
Structure B32
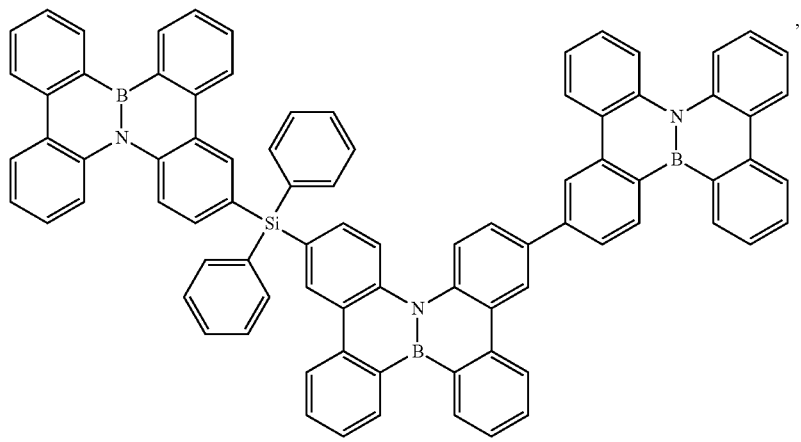

-continued
Structure B33
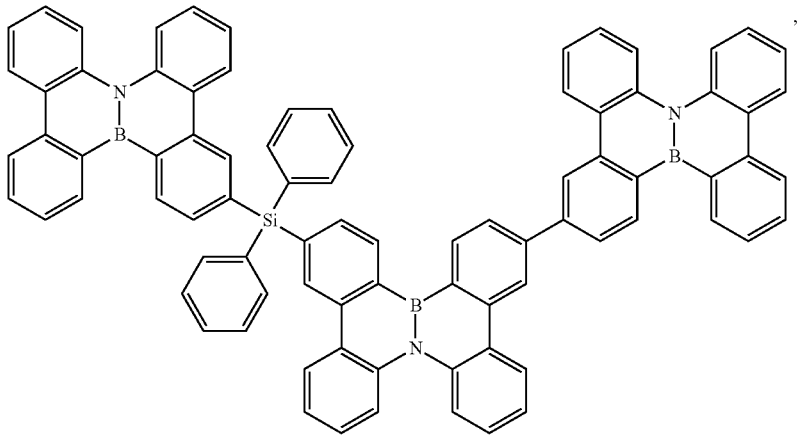
Structure B34
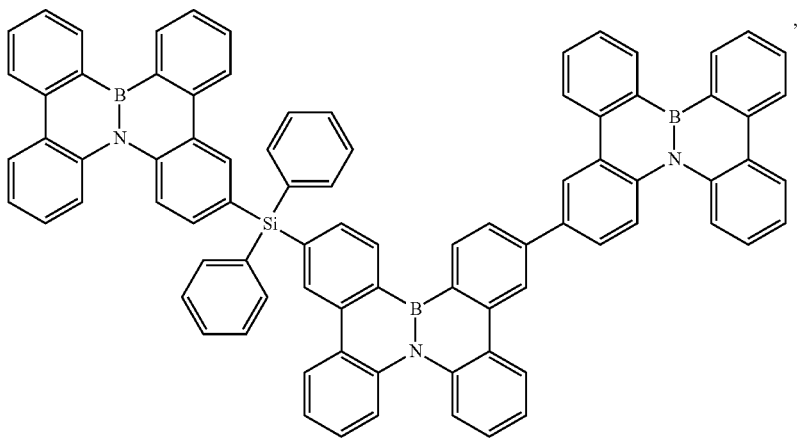
Structure B35
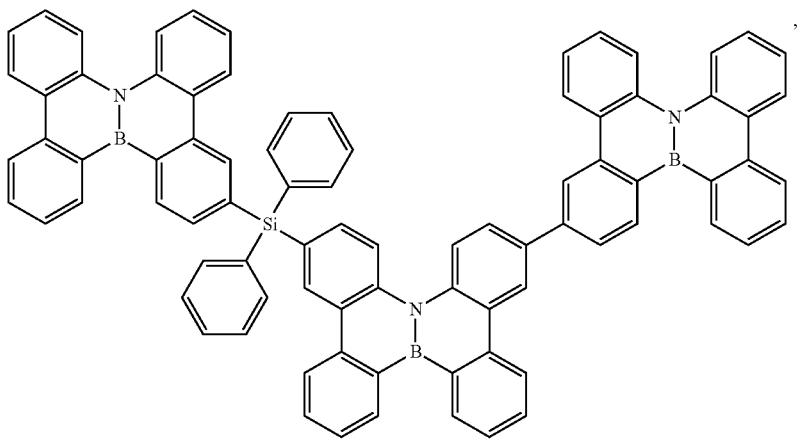

-continued
Structure B36
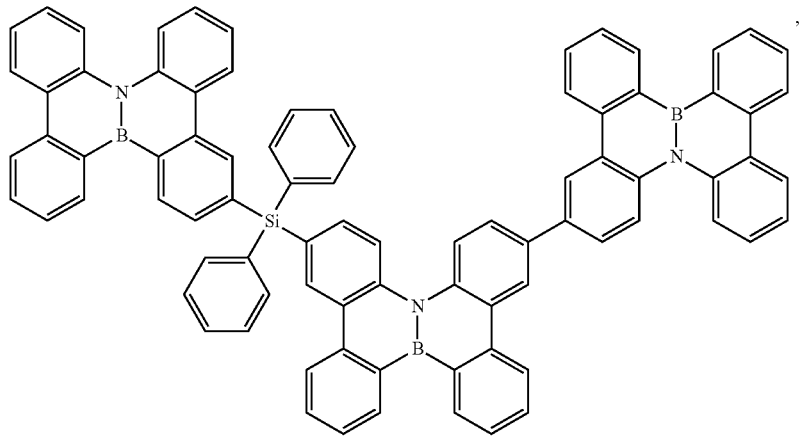
Structure B37
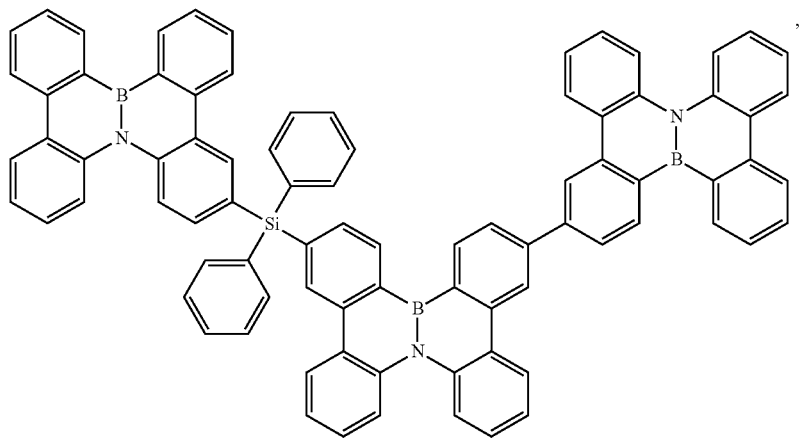
Structure B38
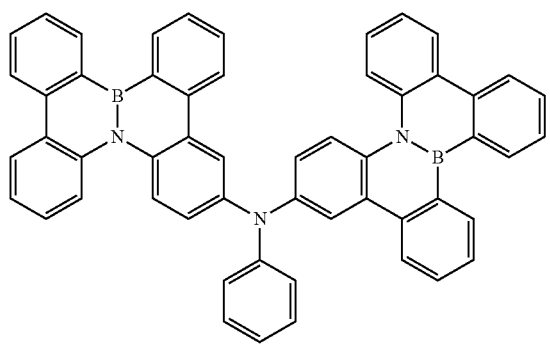
Structure B39
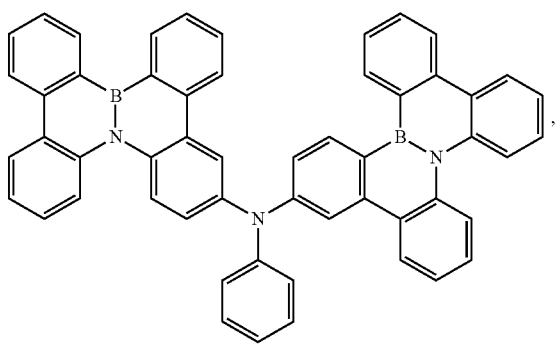

Structure B40
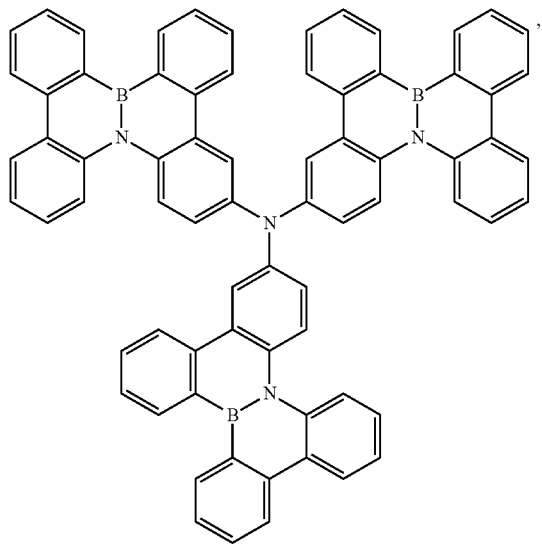
Structure B41
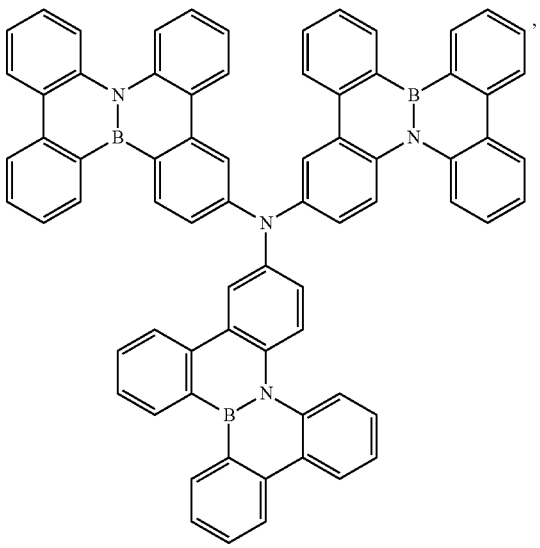
Structure B42
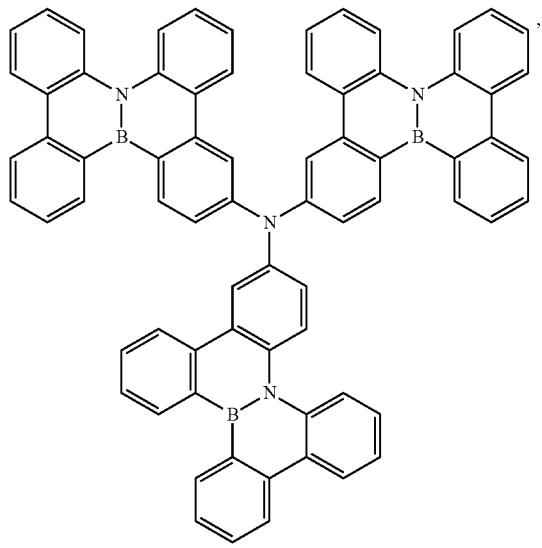
Structure B43
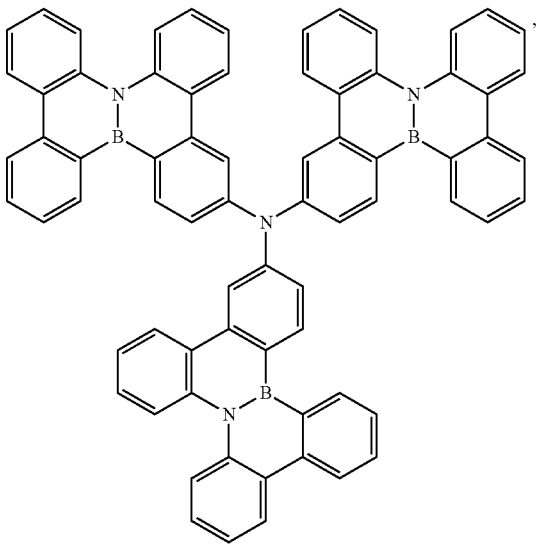

-continued
Structure B44
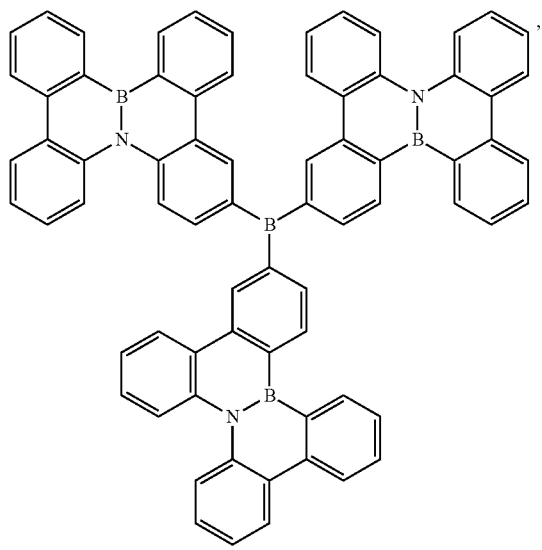
Structure B45
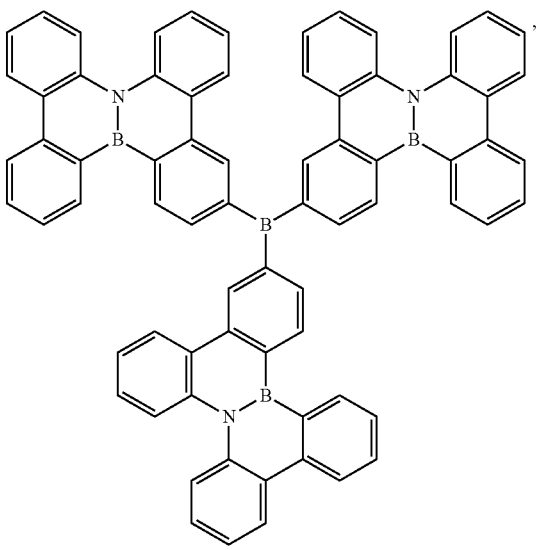
Structure B46
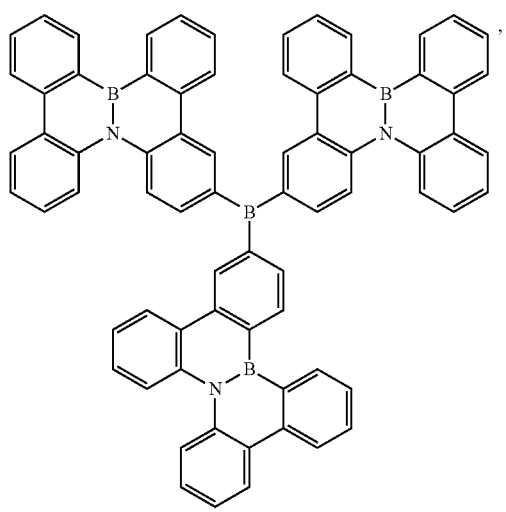
Structure B47
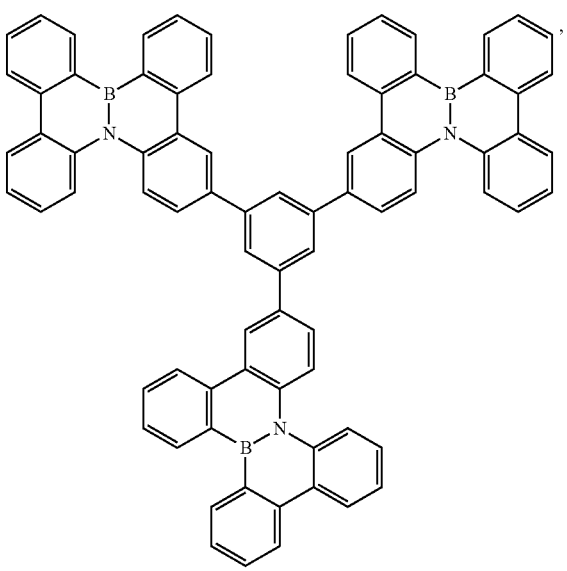

-continued
Structure B48
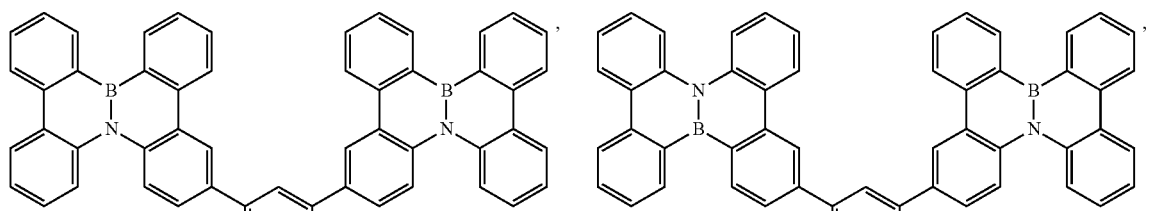
Structure B49
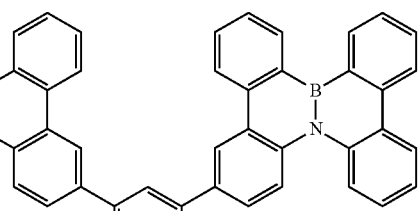
Structure B50
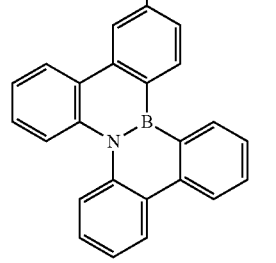
Structure B51
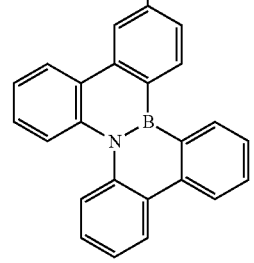
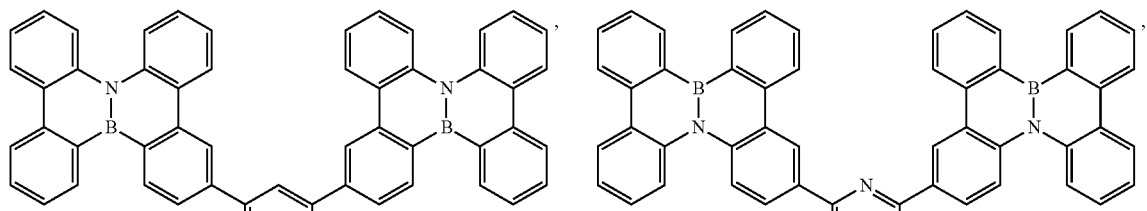
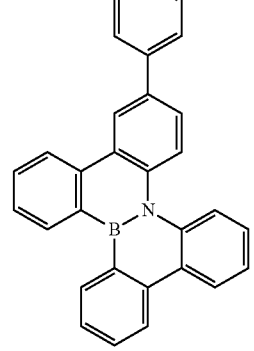
Structure B52
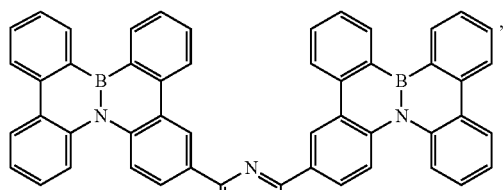
Structure B53, and
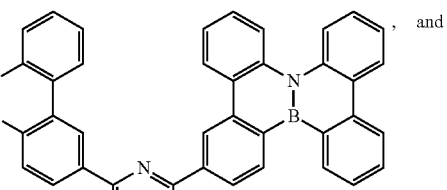
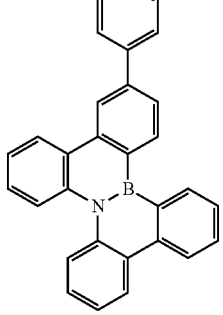
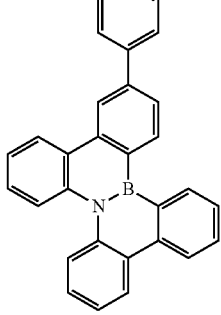

-continued

Structure B54

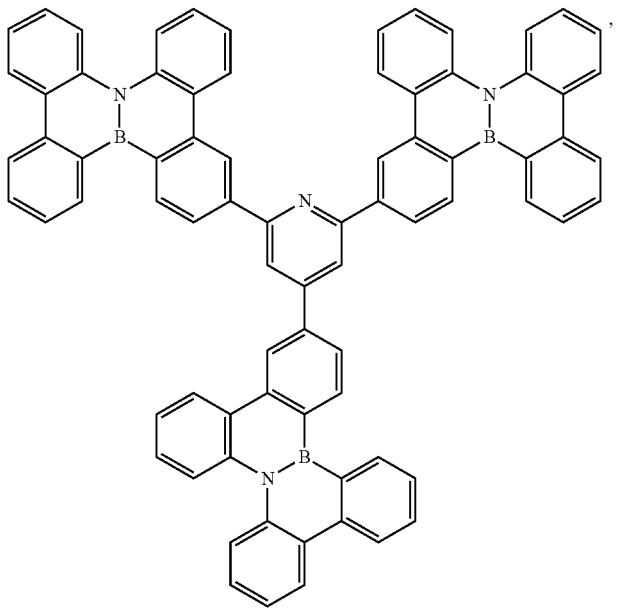

which may be further substituted by one or more substituents independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and where any adjacent substitutions are optionally joined or fused into a ring. In some embodiments, Structures B1 through B54 are not further substituted and are referenced as Compounds B1 through B54, respectively.

In another embodiment, a compound having the structure of Formula V,

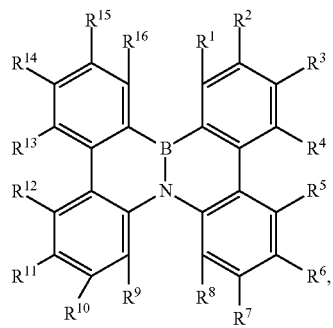

is described. In Formula V, at least two adjacent $R^1$ to $R^{16}$ on the same ring are:

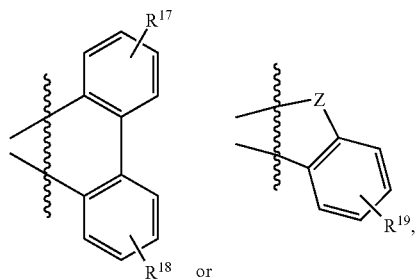

where:

$R^{17}$ to $R^{19}$ each independently represent mono, di, tri, or tetra substitution, or no substitution;

Z is selected from the group consisting of NR", O, S and Se;

R", $R^1$ to $R^{19}$ are each independently selected from the group consisting of hydrogen, deuterium, halide, alkyl, cycloalkyl, heteroalkyl, arylalkyl, alkoxy, aryloxy, amino, silyl, alkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and any adjacent substitutions of $R^{17}$ to $R^{19}$ are optionally joined or fused into a ring.

In some embodiments, the compound of Formula V is selected from the group consisting of:

Structure F1

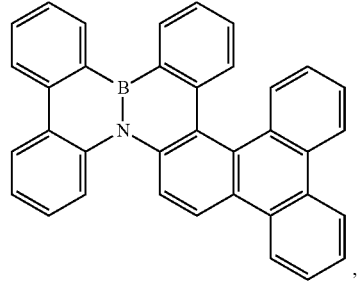

Structure F2

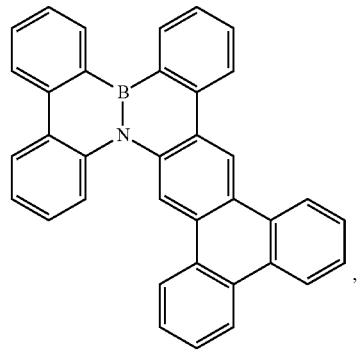

-continued
Structure F3
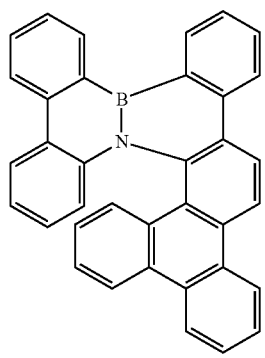
Structure F4
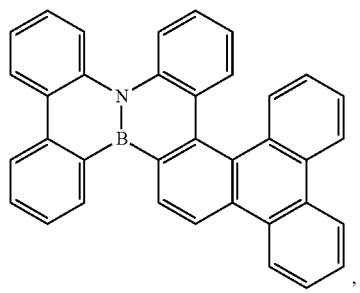
Structure F5
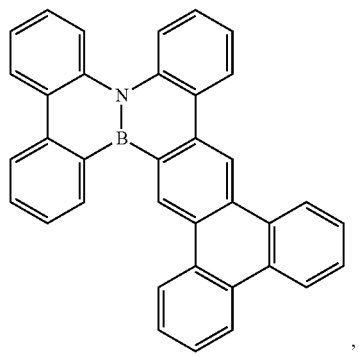
Structure F6
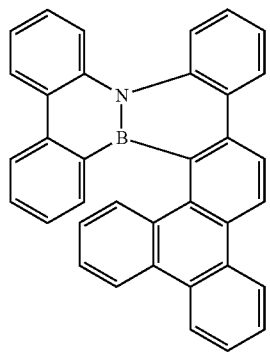
Structure F7
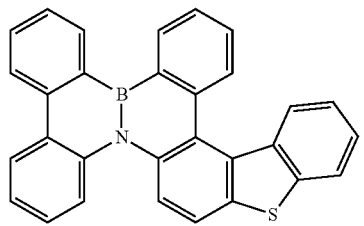
Structure F8
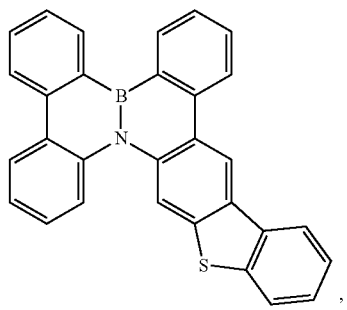
Structure F9
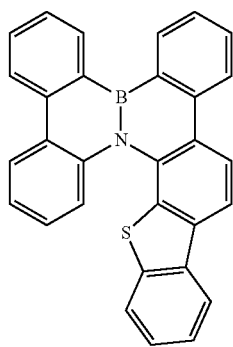
Structure F10
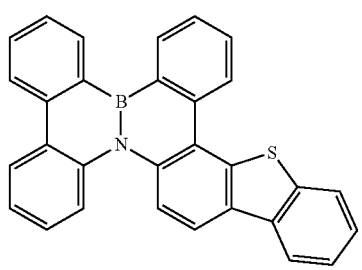
Structure F11
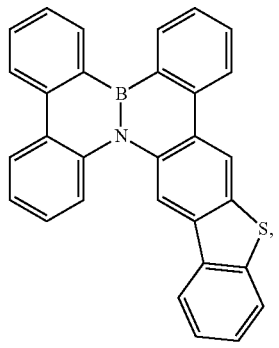
Structure F12
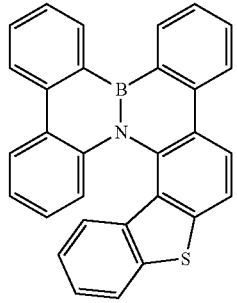

Structure F13
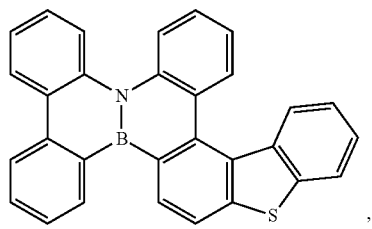
Structure F14
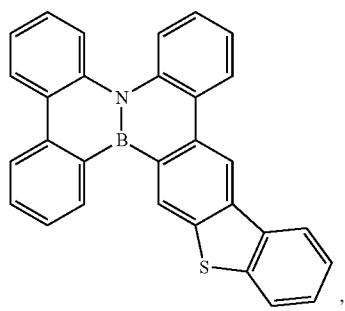
Structure F15
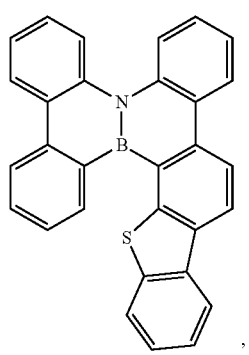
Structure F16
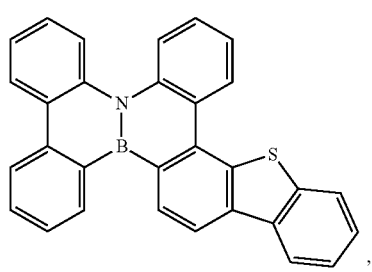
Structure F17
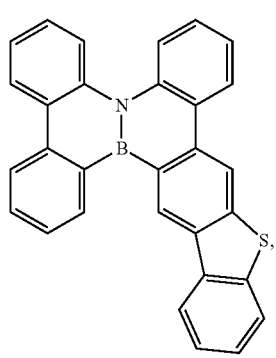
Structure F18
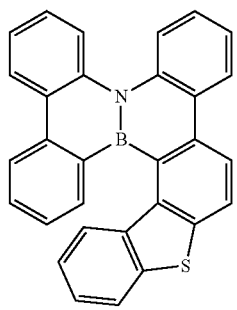
Structure F19
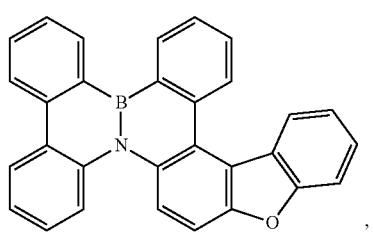
Structure F20
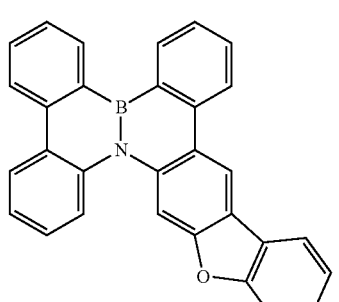
Structure F21
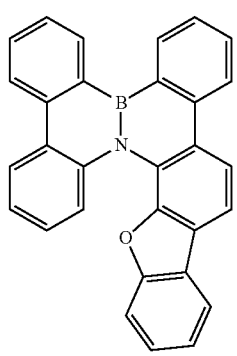
Structure F22
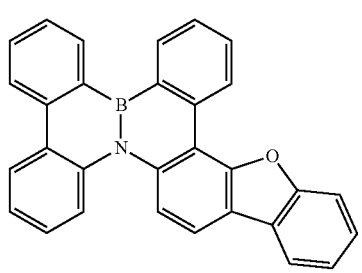

Structure F23
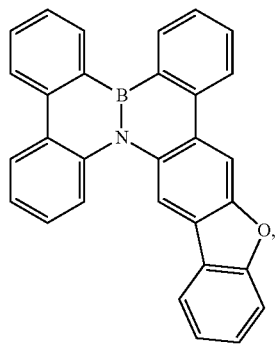
Structure F24
Structure F25
Structure F26
Structure F27
Structure F28
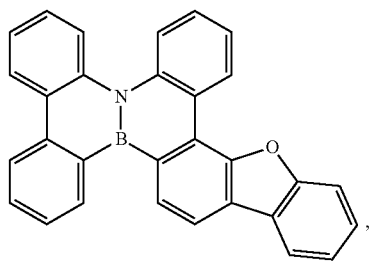
Structure F29
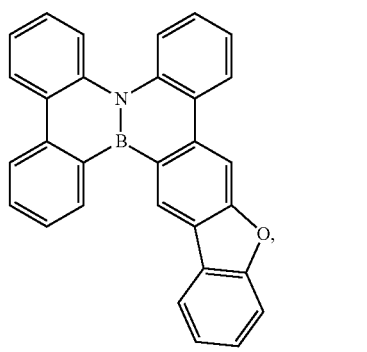
Structure F30
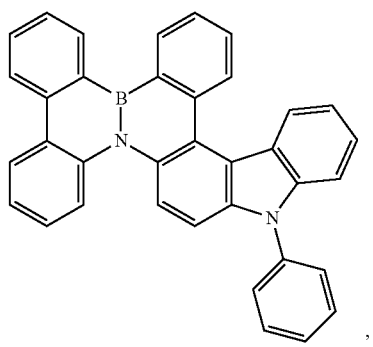
Structure F31
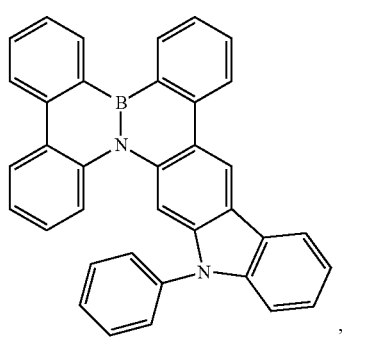
Structure F32
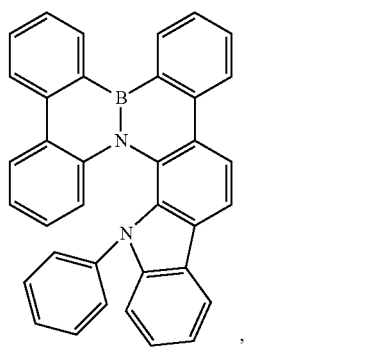

Structure F33
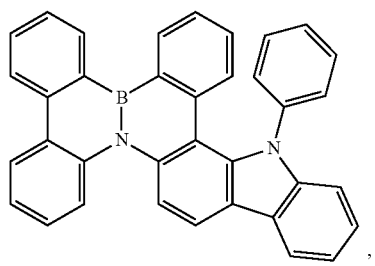
Structure F34
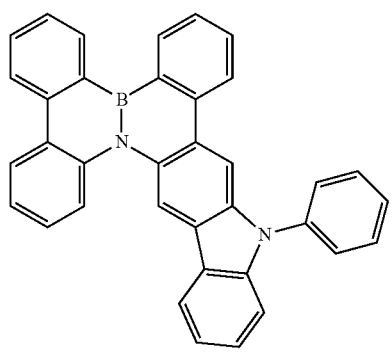
Structure F35
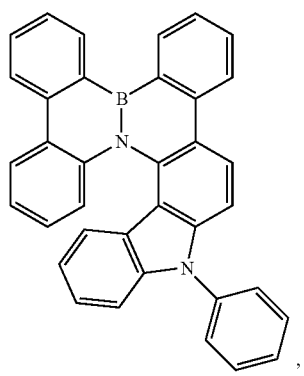
Structure F36
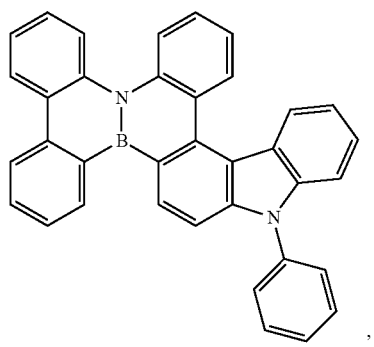
Structure F37
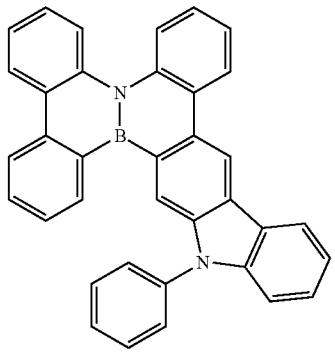
Structure F38
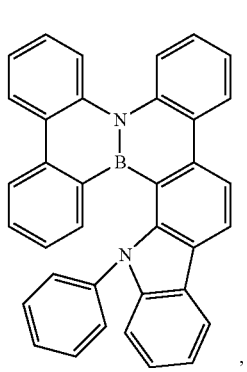
Structure F39
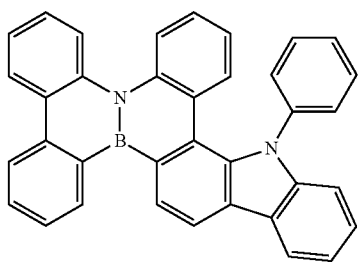
Structure F40
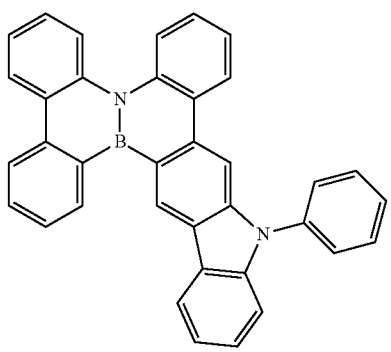

Structure F41
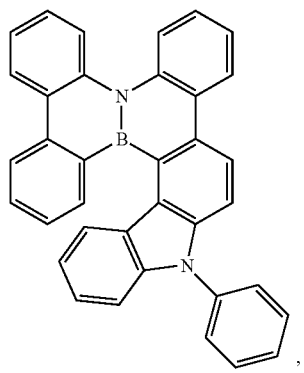
Structure F42
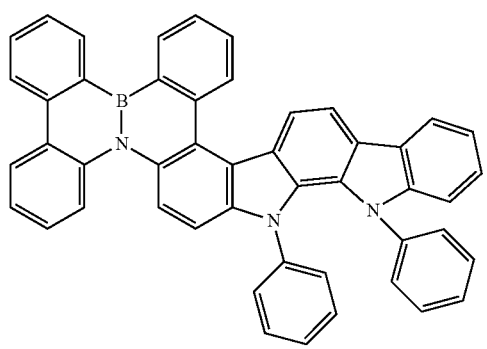
Structure F43
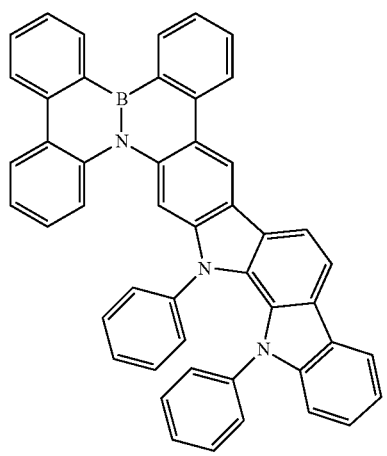
Structure F44
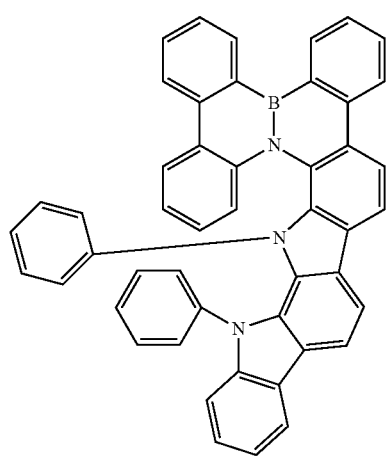
Structure F45
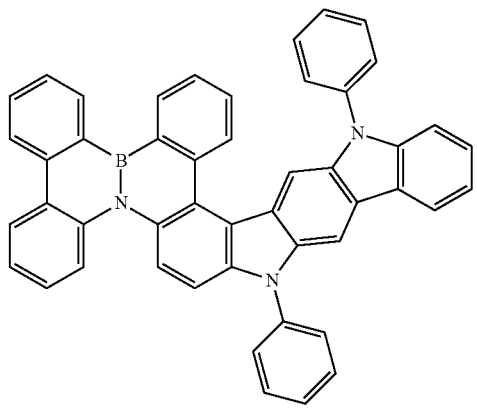
Structure F46
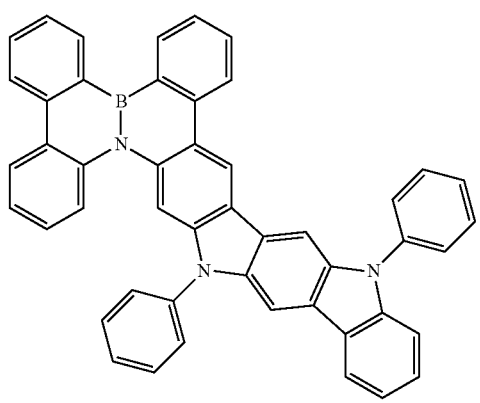
Structure F47
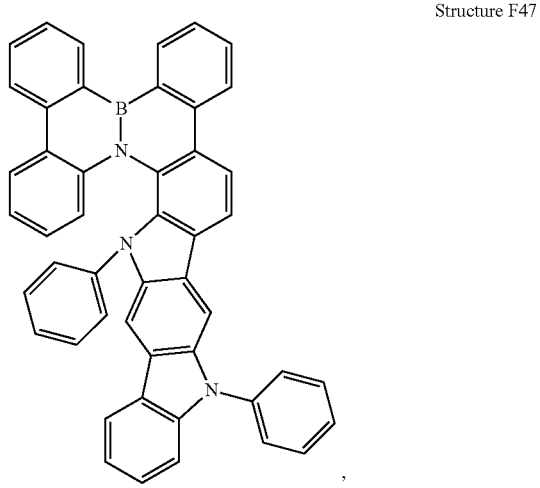

Structure F48
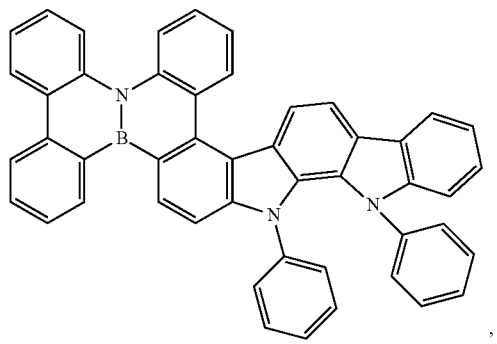
Structure F49
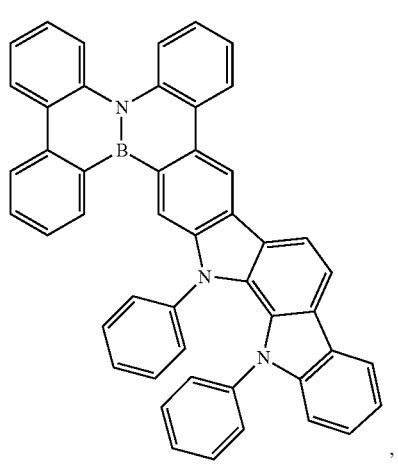
Structure F50
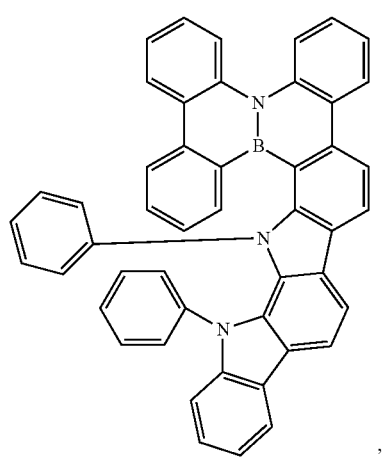
Structure F51
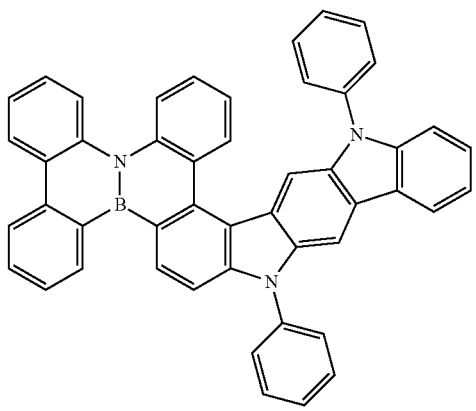
Structure F52
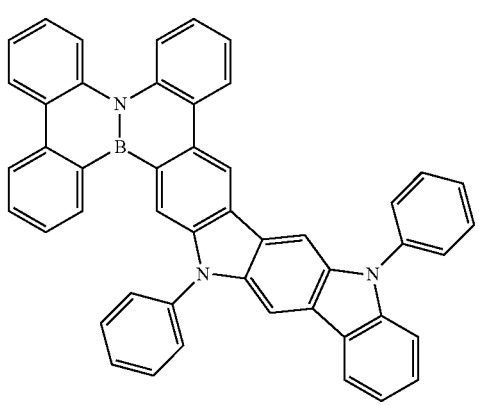
Structure F53
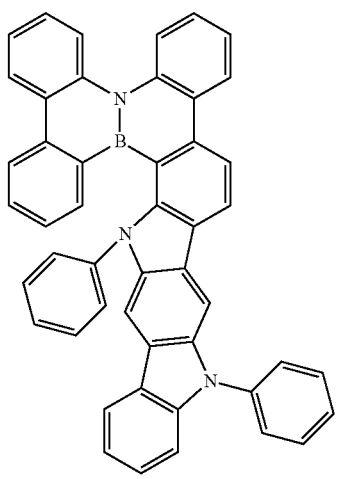

Structure F54
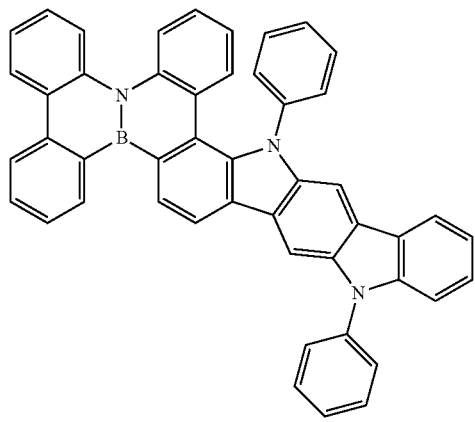
Structure F57
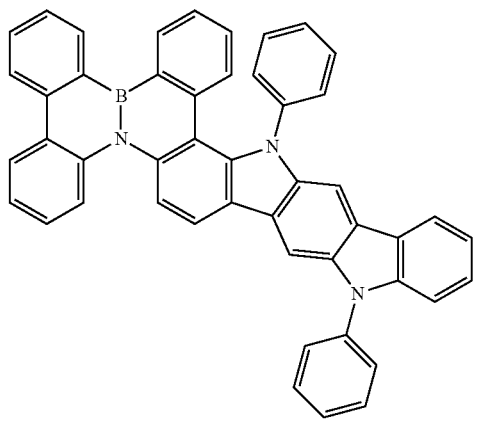
Structure F55
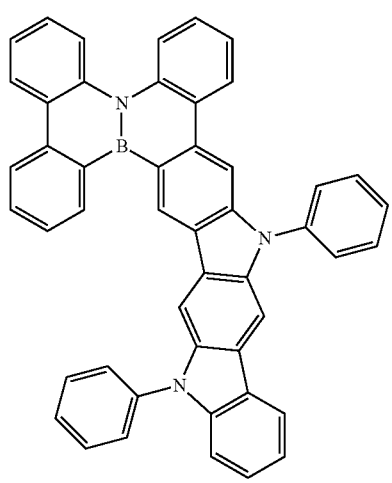
Structure F58
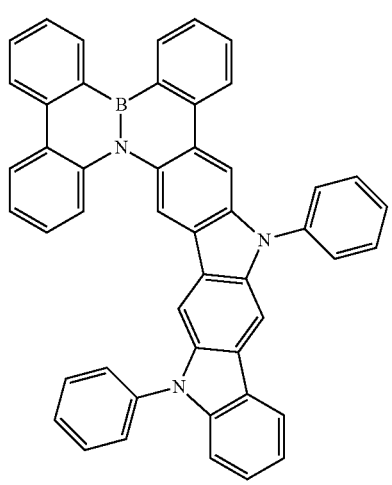
Structure F56
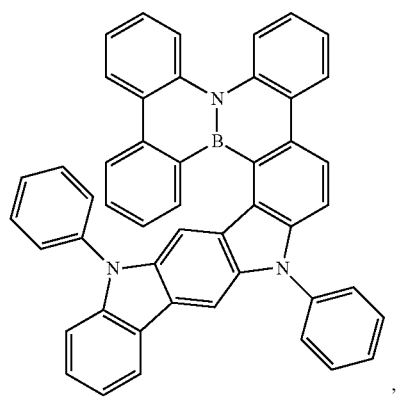
Structure F59
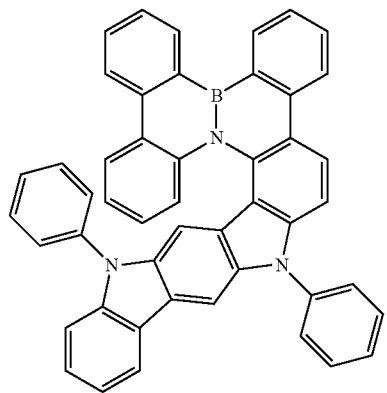

Structure F60
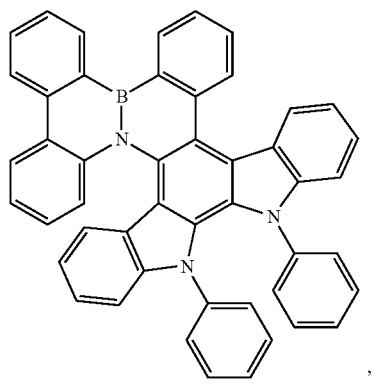
Structure F61
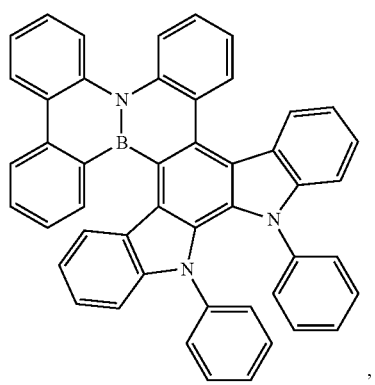
Structure F62
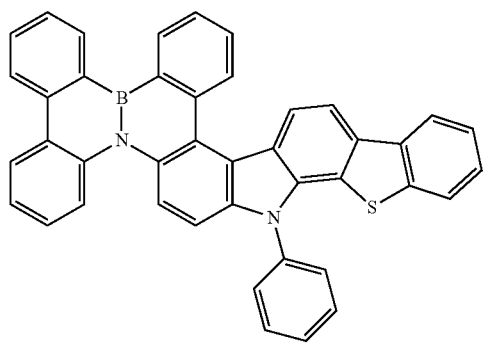
Structure F63
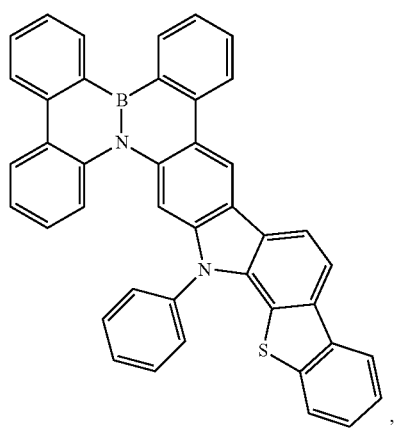
Structure F64
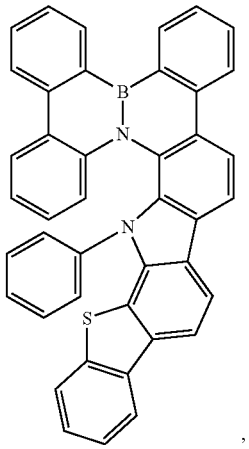
Structure F65
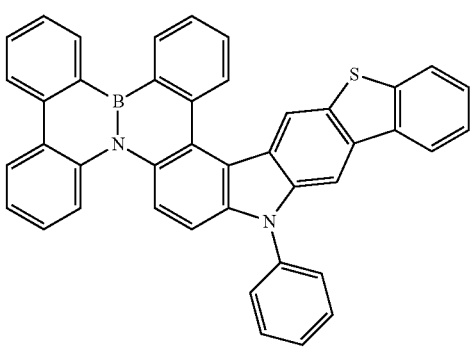
Structure F66
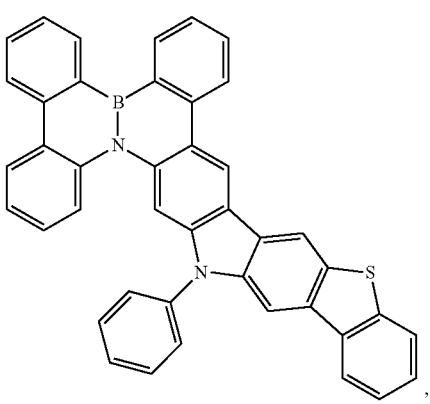

-continued
Structure F67
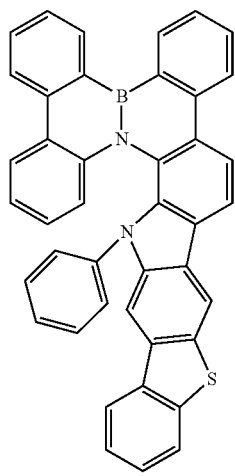
Structure F70
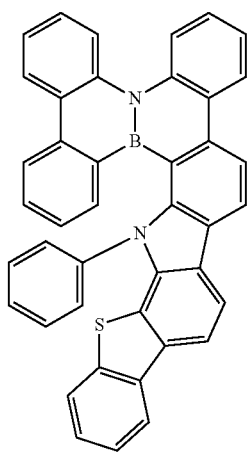
Structure F68
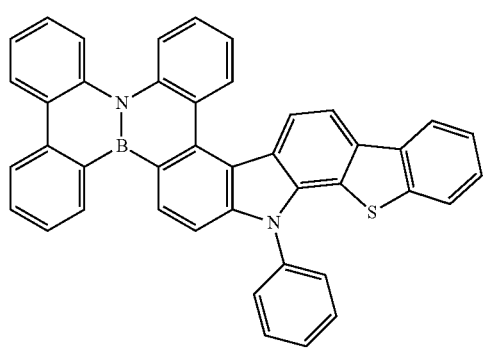
Structure F71
Structure F69
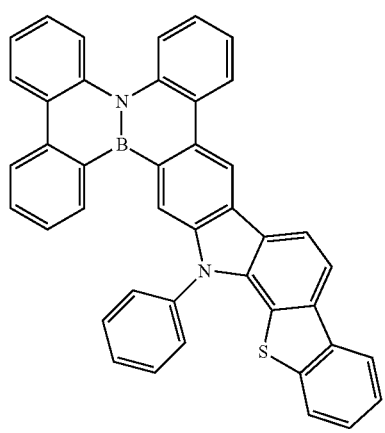
Structure F72
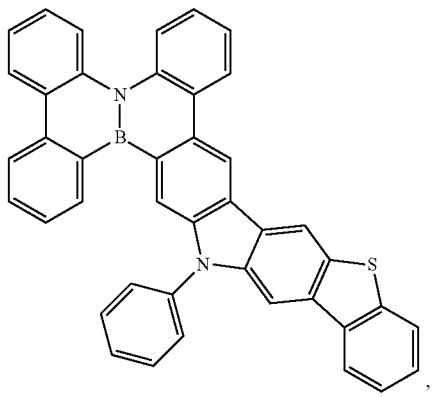

Structure F73
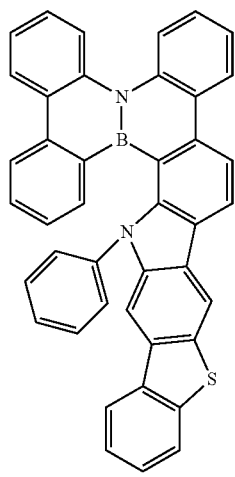
Structure F76
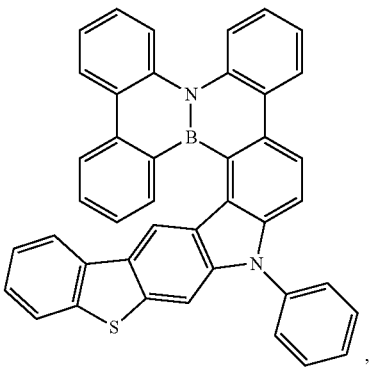
Structure F77
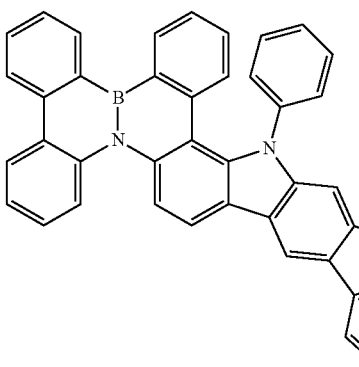
Structure F74
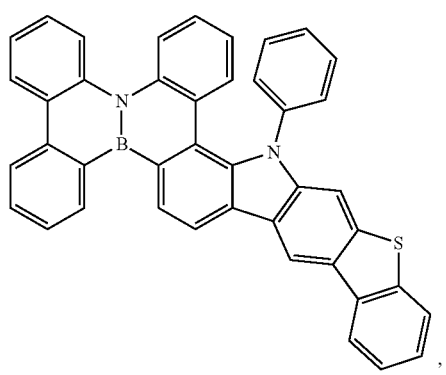
Structure F78
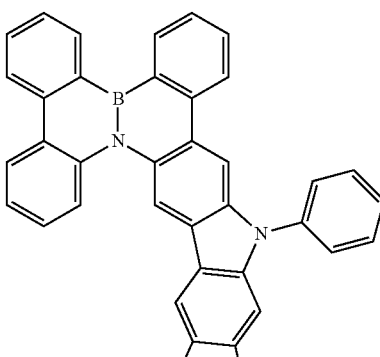
Structure F75
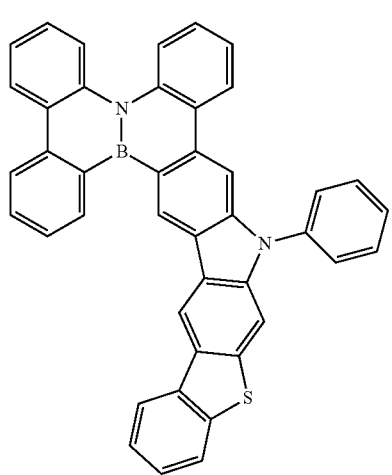
Structure F79
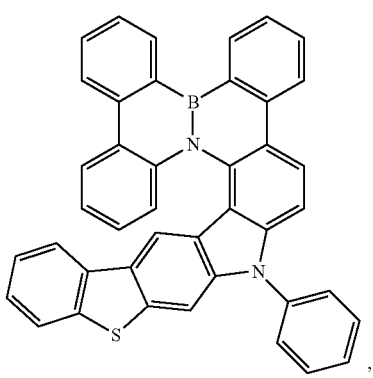

Structure F80
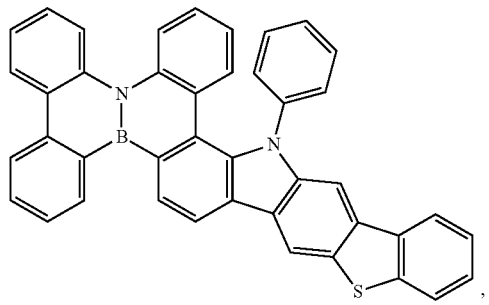
Structure F81
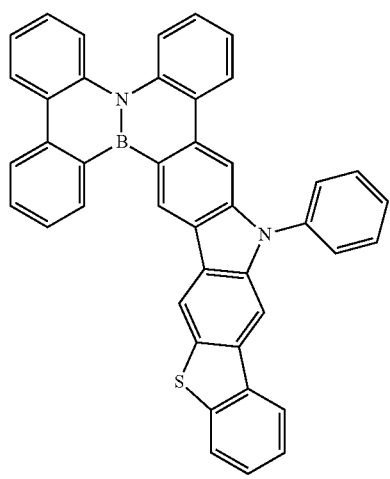
Structure F82
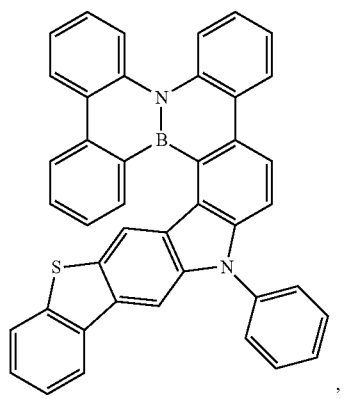
Structure F83
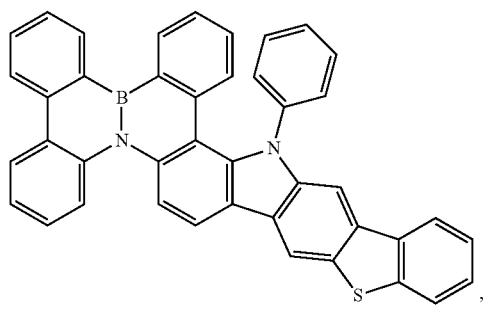
Structure F84
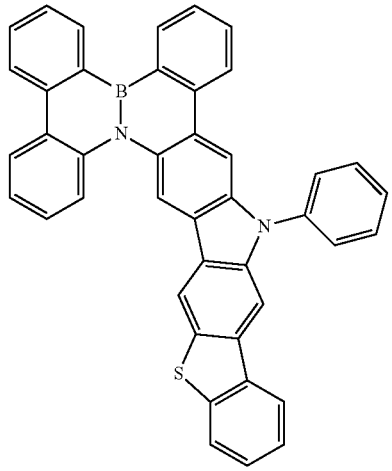
Structure F85
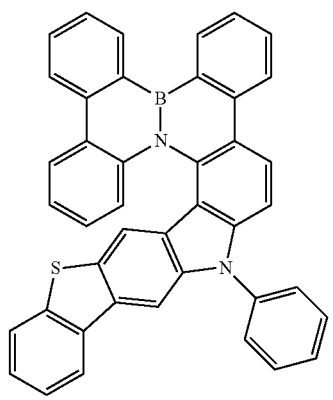
Structure F86
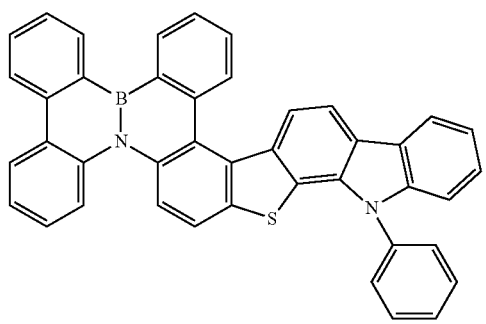
Structure F87
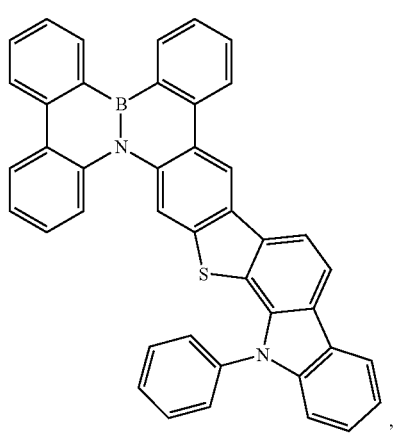

Structure F88
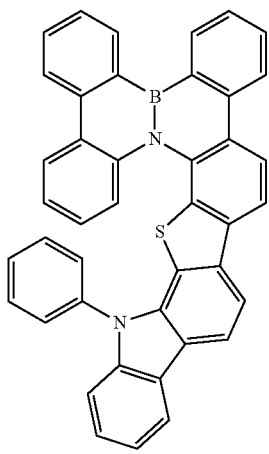
Structure F89
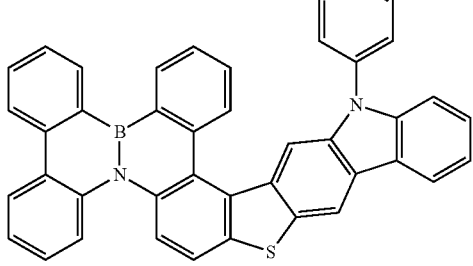
Structure F90
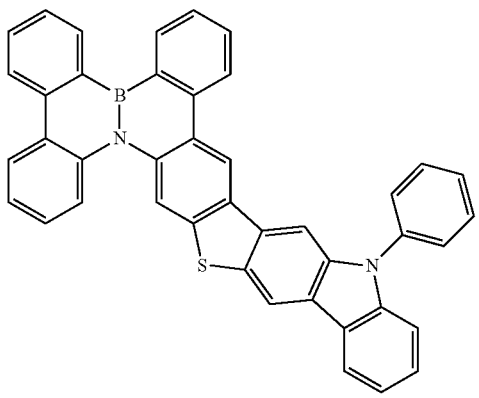
Structure F91
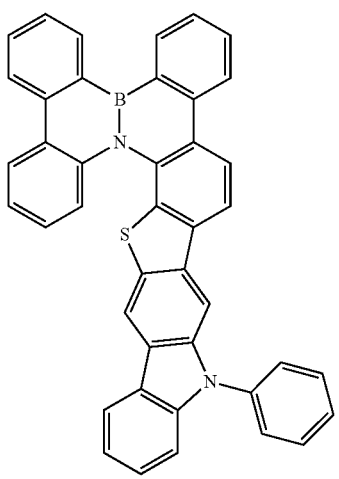
Structure F92
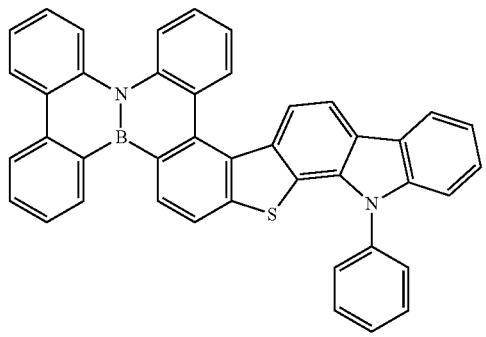
Structure F93
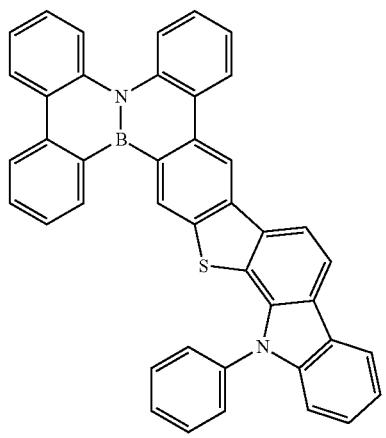
Structure F94
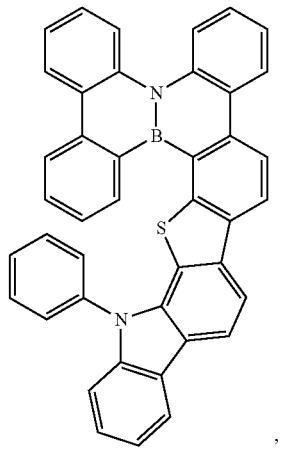
Structure F95
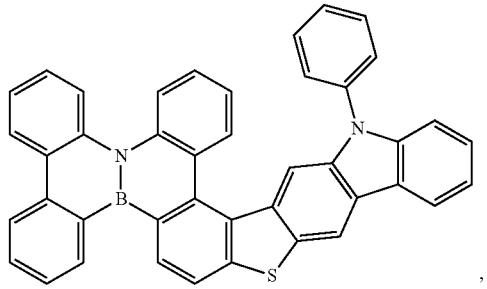

-continued
Structure F96
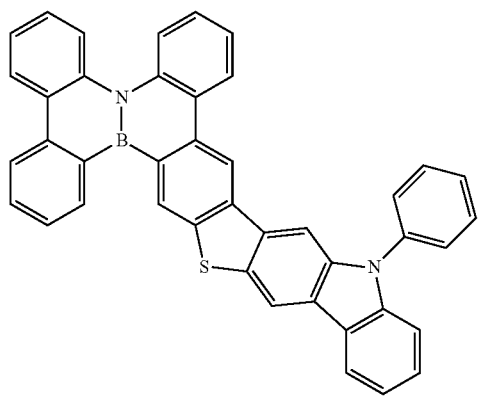
Structure F97
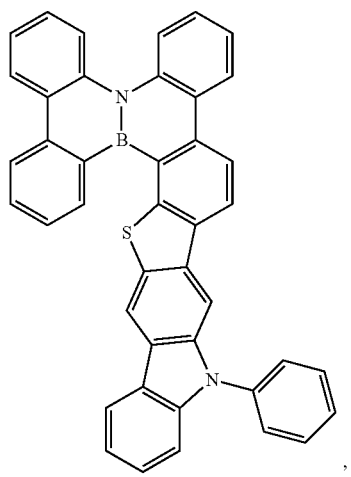
Structure F98
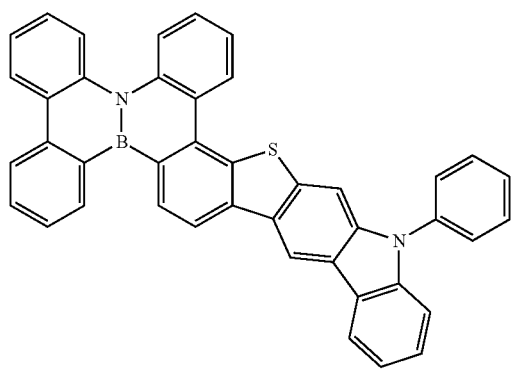
-continued
Structure F99
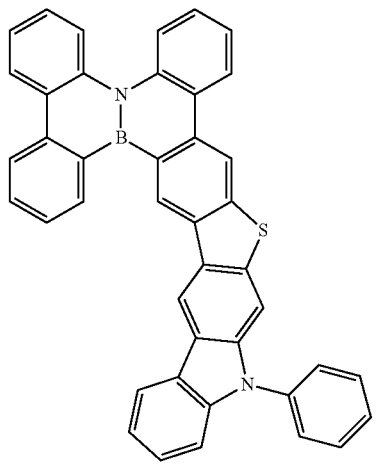
Structure F100
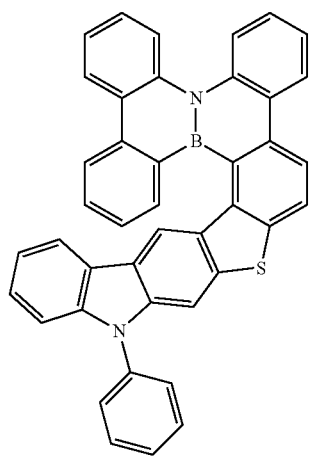
Structure F101
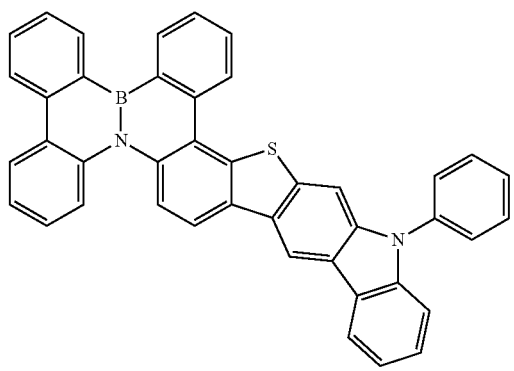

-continued
Structure F102
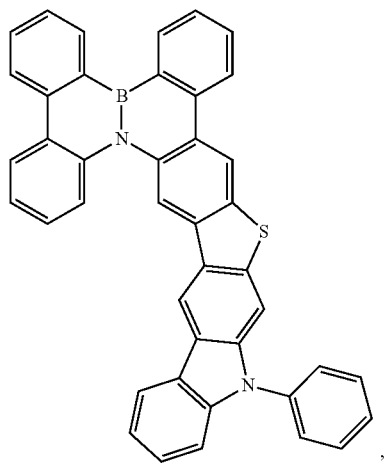
Structure F105
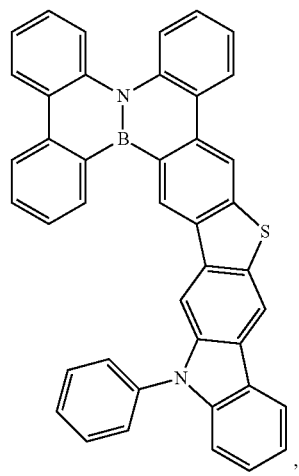
Structure F103
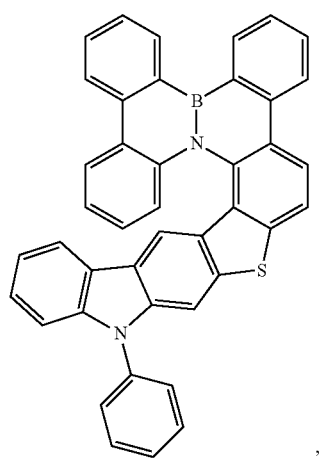
Structure F106
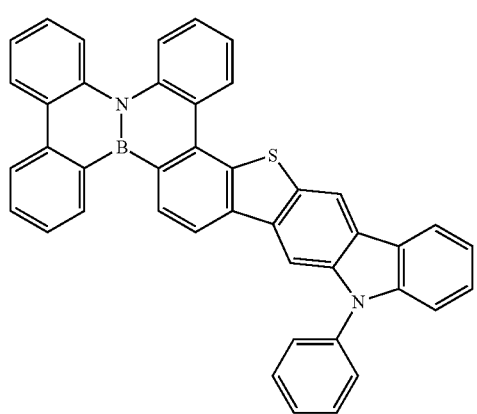
Structure F104
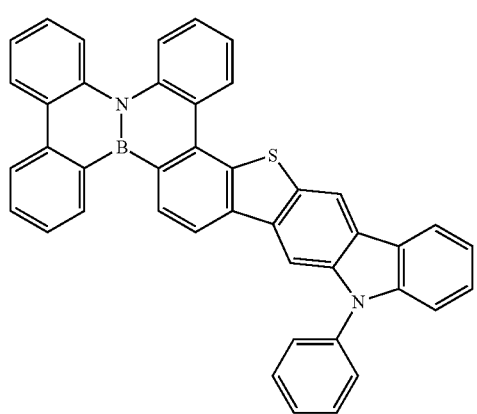
Structure F107
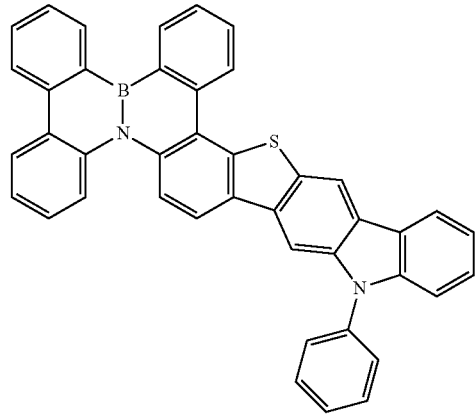

-continued
Structure F108
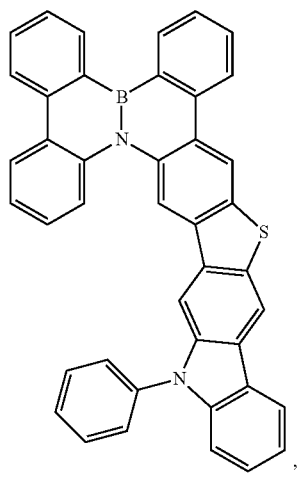
Structure F109
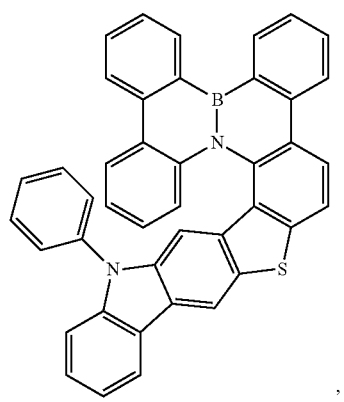
Structure F110
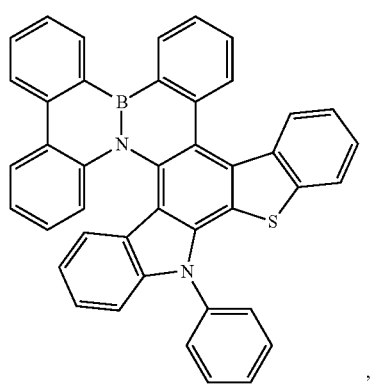
Structure F111
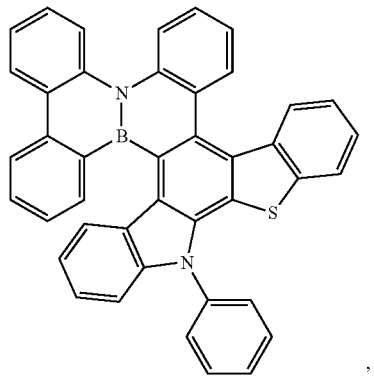
-continued
Structure F112
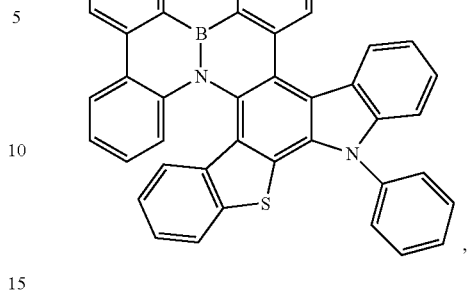
Structure F113
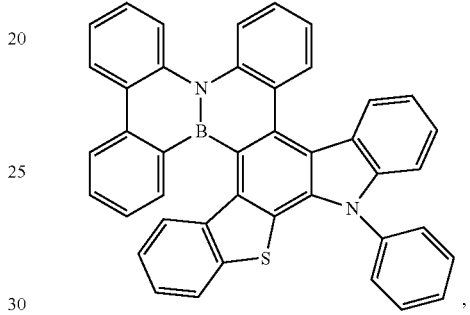
Structure F114
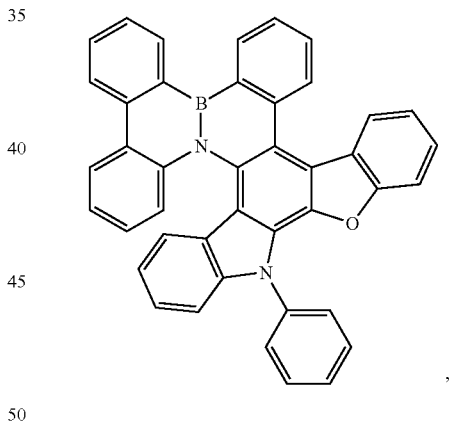
Structure F115
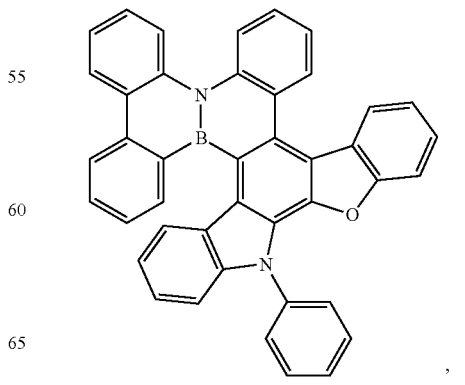

Structure F116
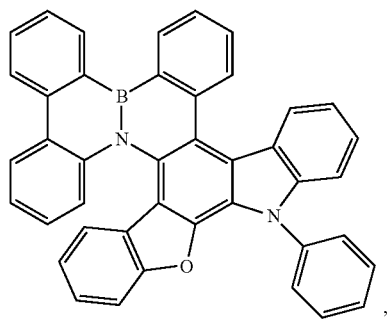
Structure F117
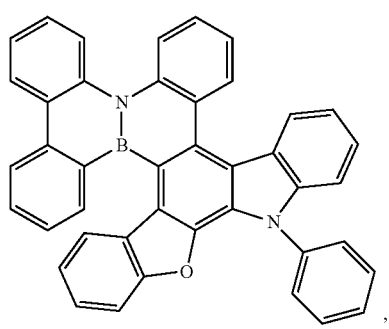
Structure F118
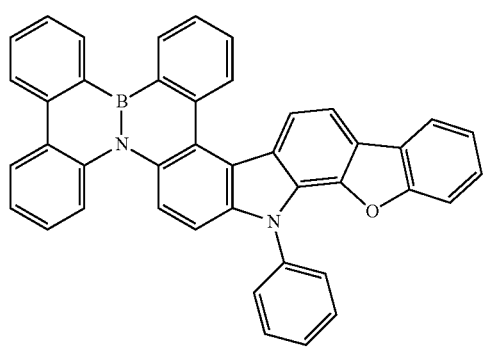
Structure F119
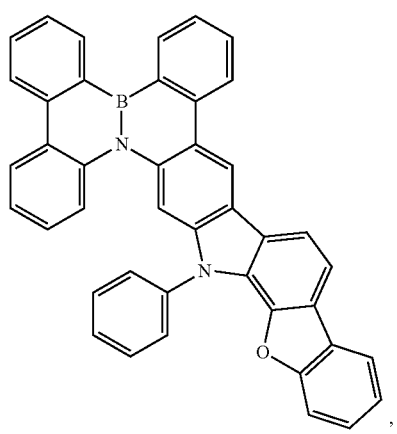
Structure F120
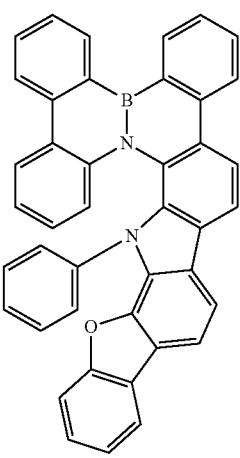
Structure F121
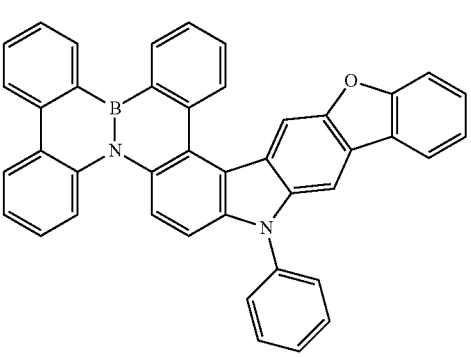
Structure F122
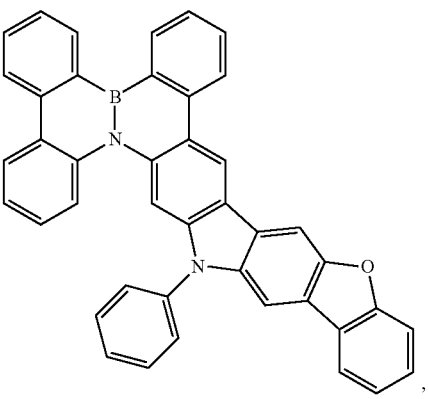

Structure F123
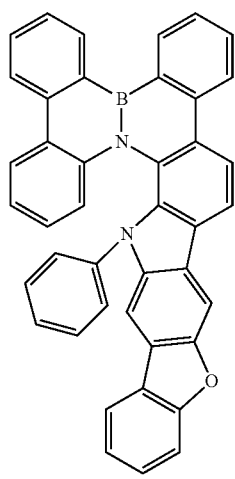
Structure F126
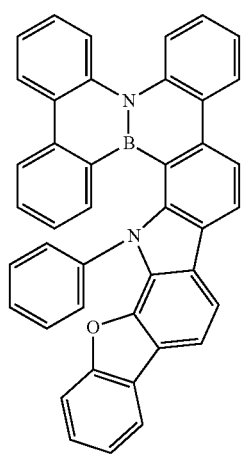
Structure F124
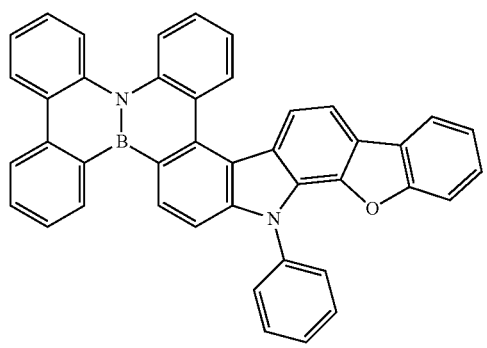
Structure F127
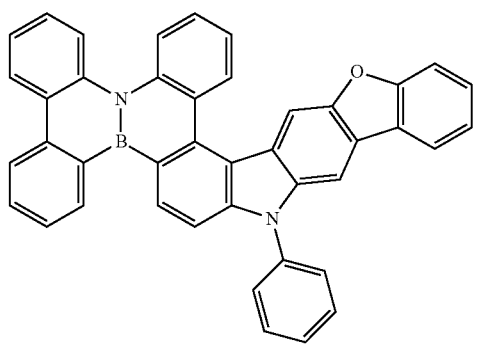
Structure F125
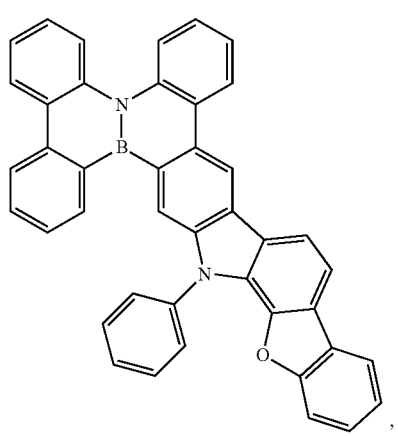
Structure F128
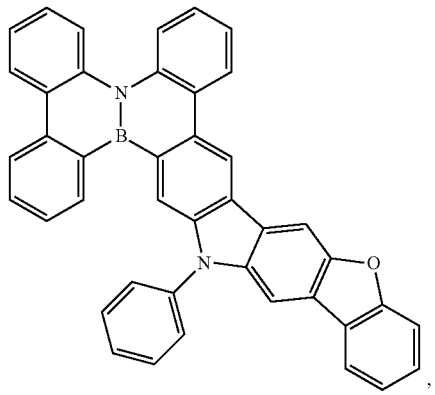

Structure F129
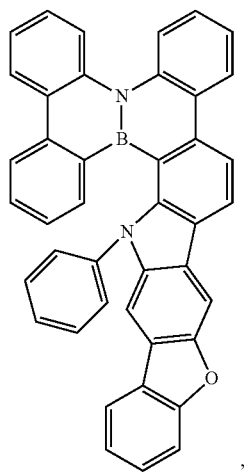
Structure F132
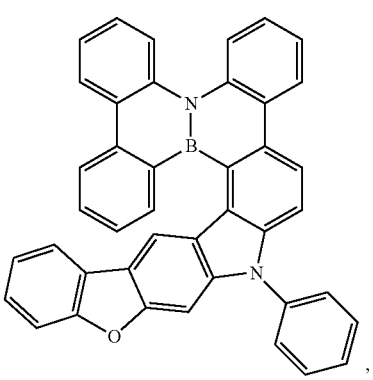
Structure F133
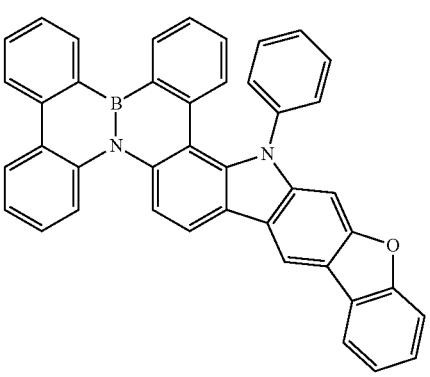
Structure F130
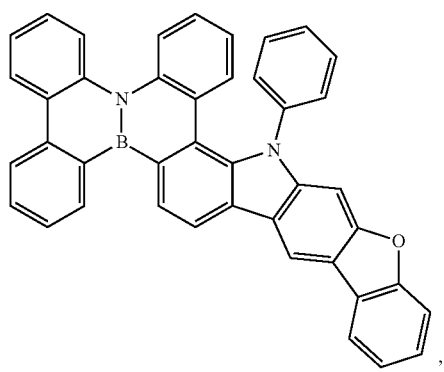
Structure F134
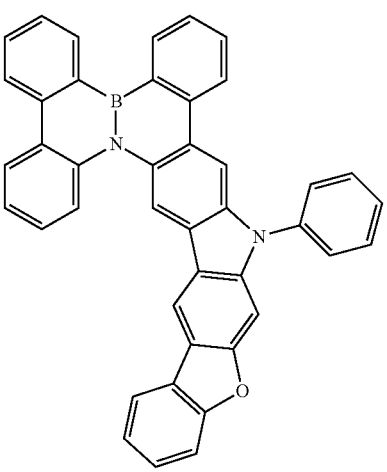
Structure F131
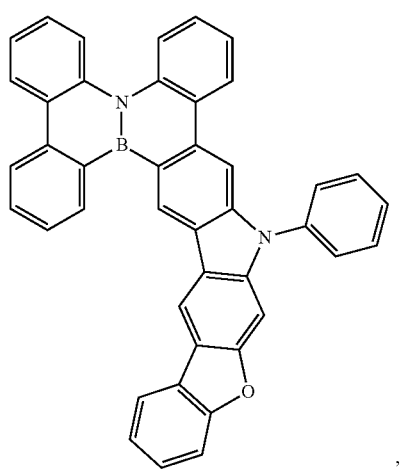
Structure F135
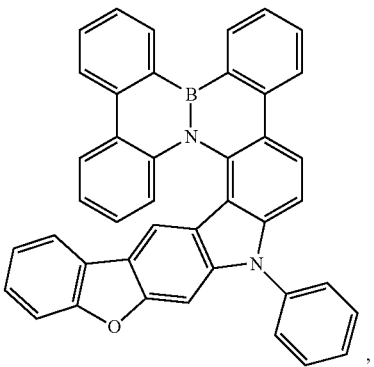

Structure F136
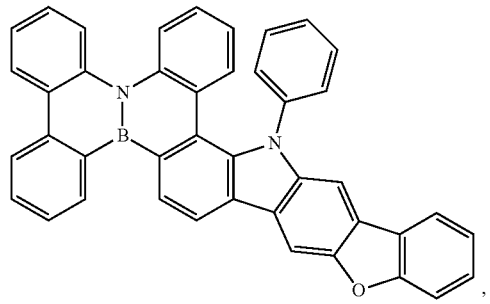
Structure F137
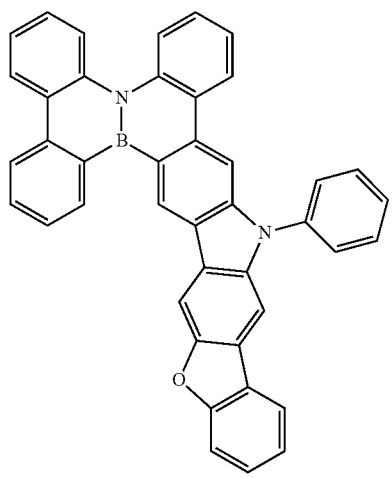
Structure F138
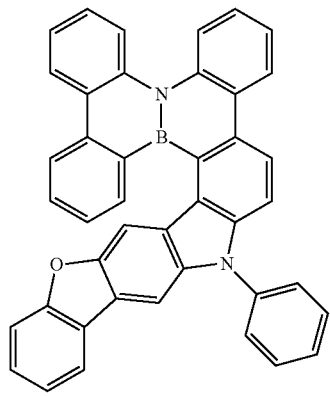
Structure F139
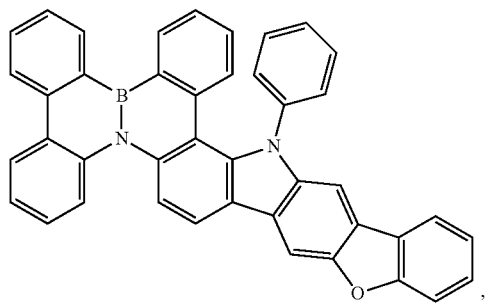
Structure F140
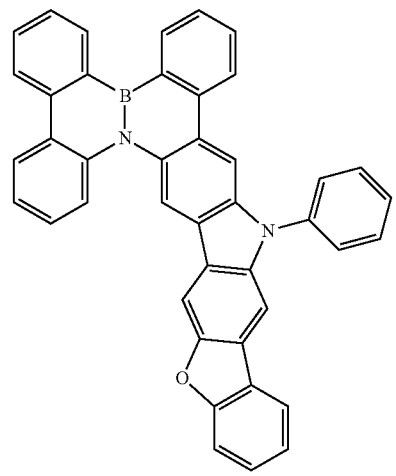
Structure F141
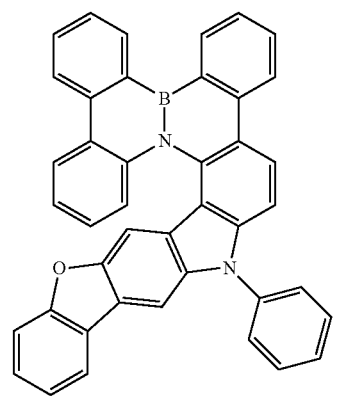
Structure F142
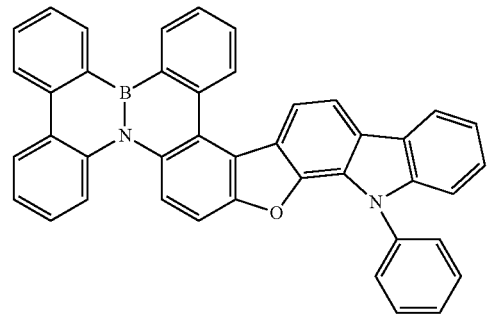
Structure F143
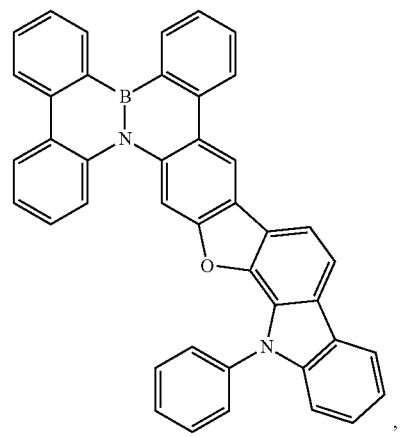

Structure F144
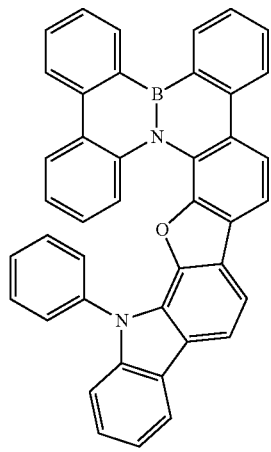
Structure F148
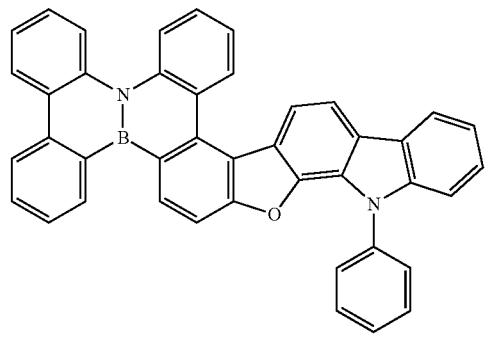
Structure F145
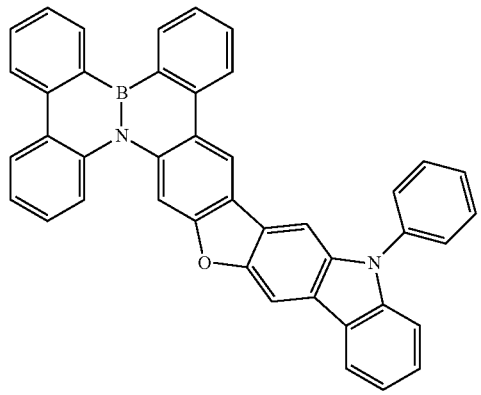
Structure F149
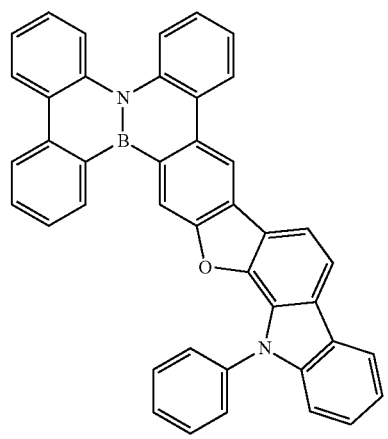
Structure F146
Structure F150
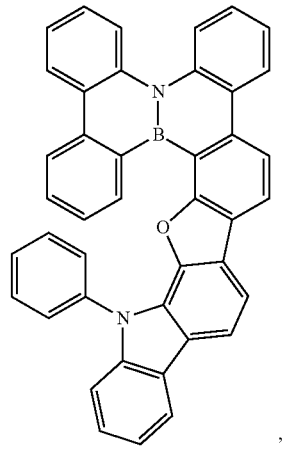
Structure F147
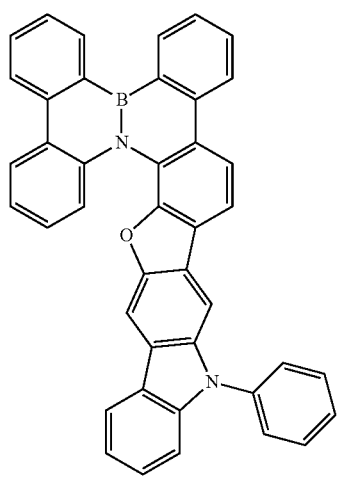
Structure F151
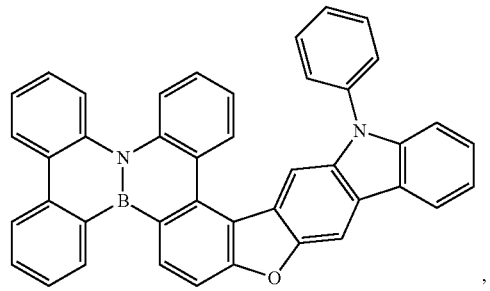

Structure F152
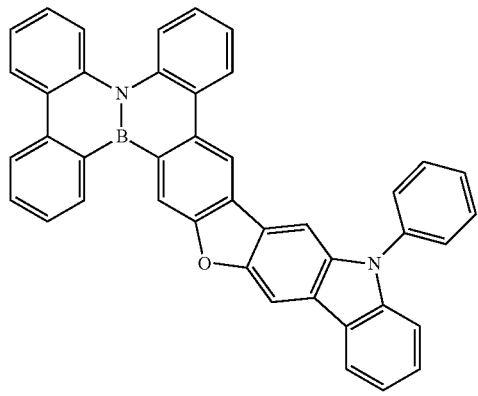
Structure F153
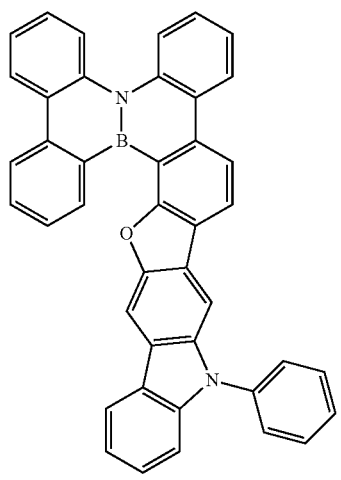
Structure F154
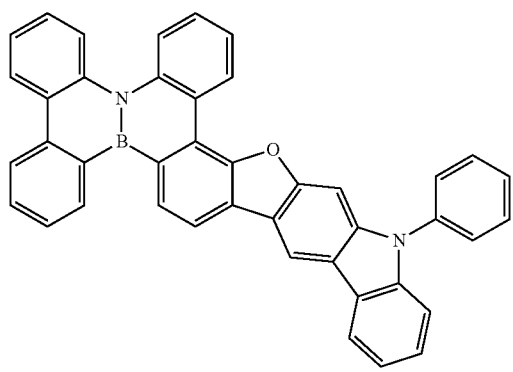
Structure F155
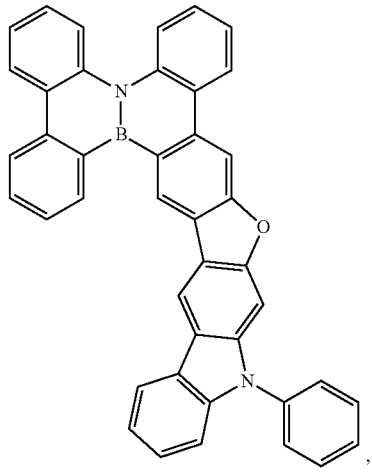
Structure F156
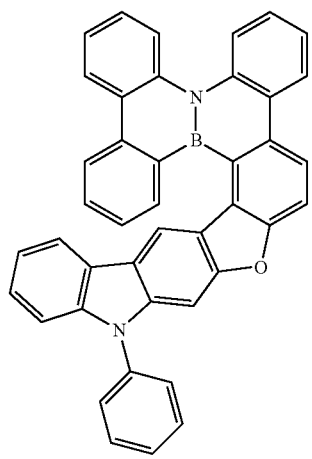
Structure F157
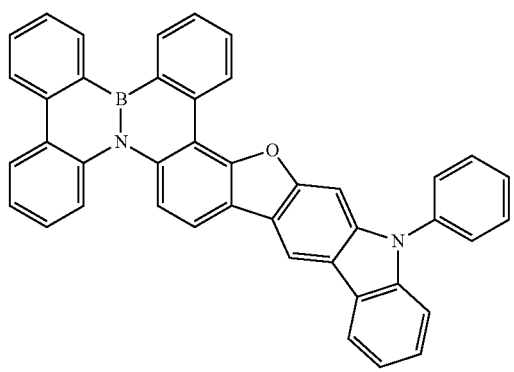

Structure F158
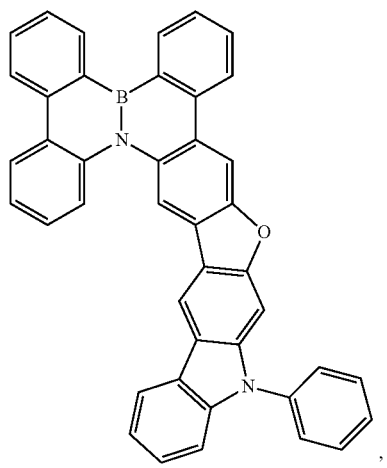
Structure F161
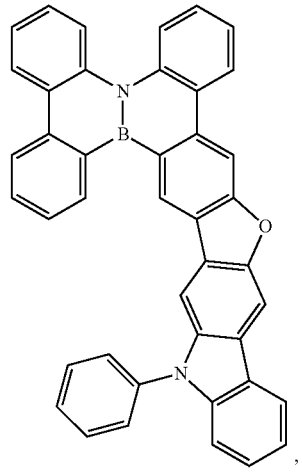
Structure F159
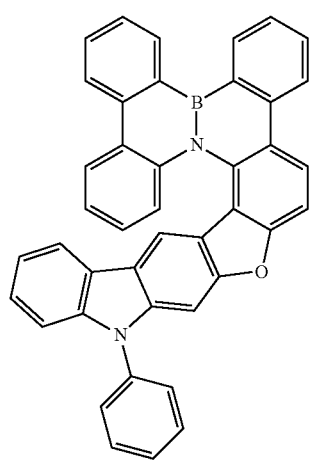
Structure F162
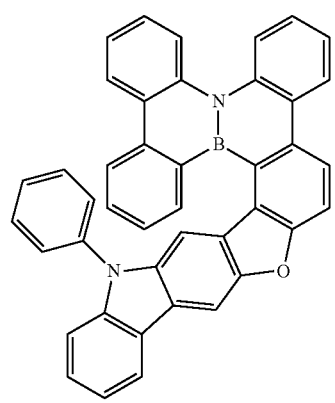
Structure F160
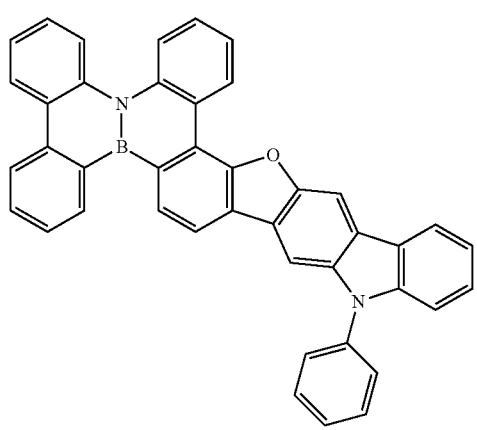
Structure F163
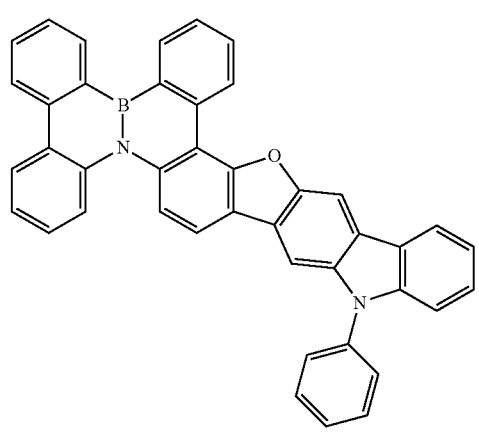

-continued
Structure F164
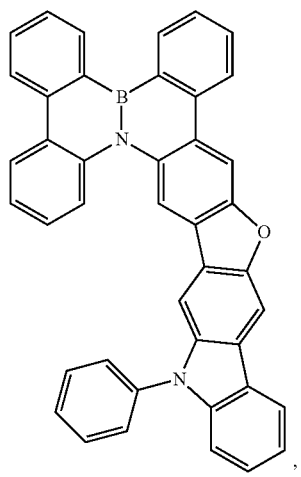
Structure F165
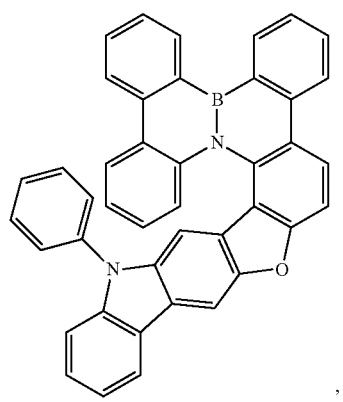
Structure F166
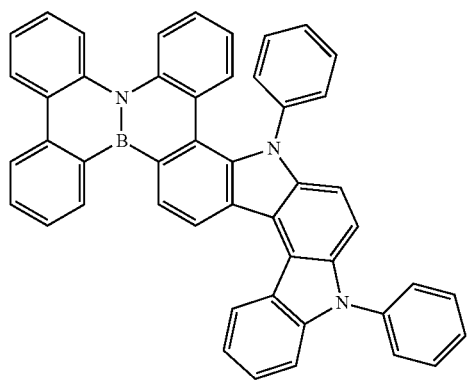
-continued
Structure F167
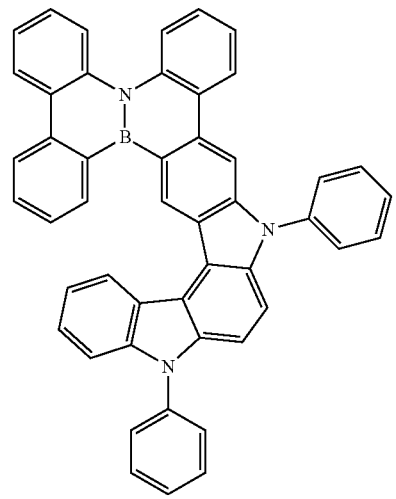
Structure F168
Structure F169
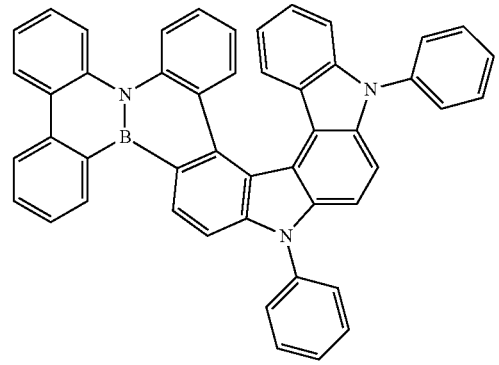

Structure F170
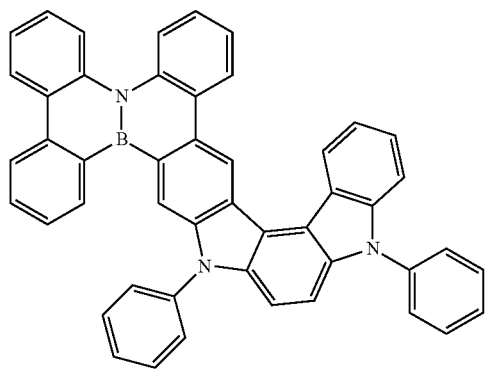
Structure F171
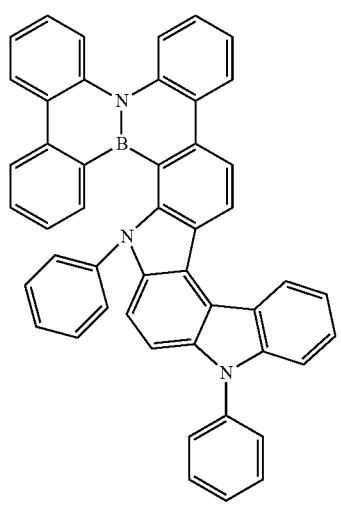
Structure F172
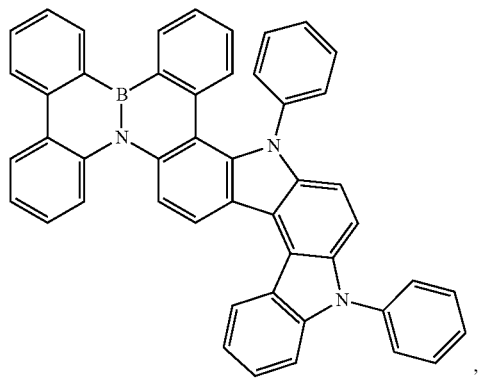
Structure F173
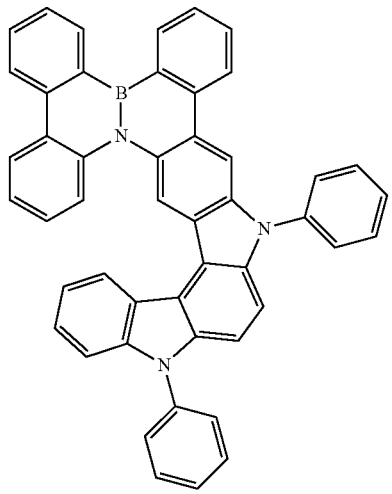
Structure F174
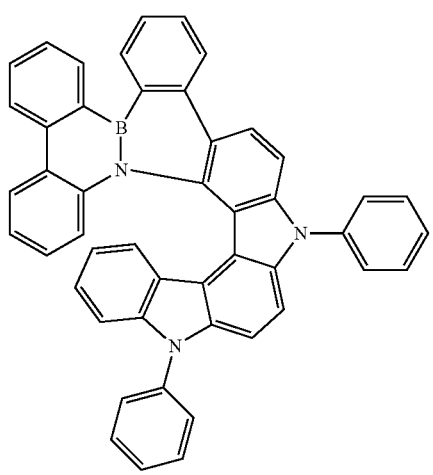
Structure F175
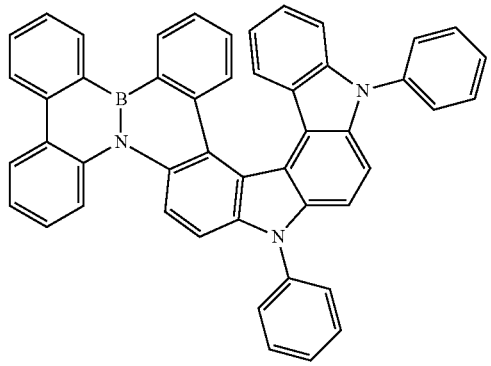

Structure F176

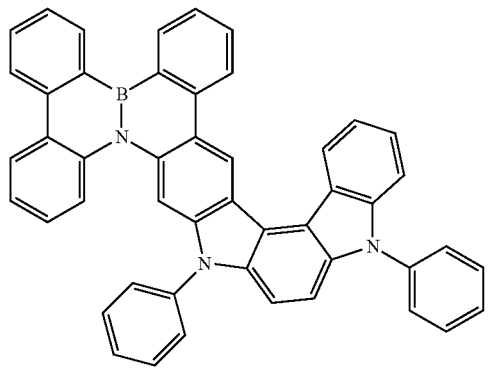

Structure F177

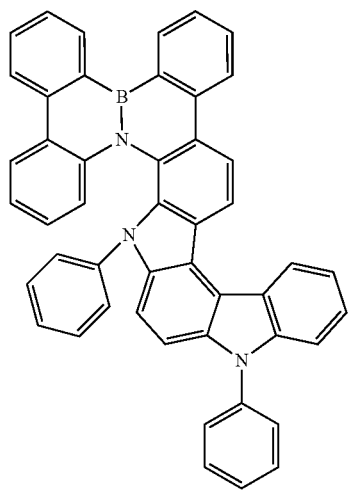

Structure F178

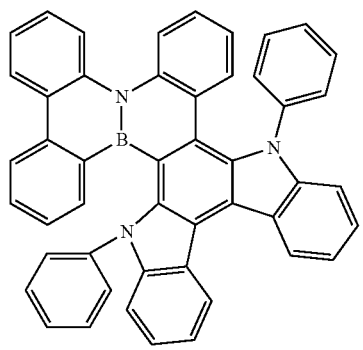

, and

Structure F179

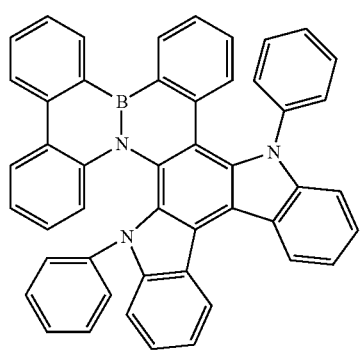

which may be further substituted by one or more substituents independently selected from the group consisting of hydrogen, deuterium, halide, alkyl, cycloalkyl, heteroalkyl, arylalkyl, alkoxy, aryloxy, amino, sibyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and where any adjacent substitutions are optionally joined or fused into a ring. In some embodiments, Structures F1 through F179 are not further substituted and are referenced as Compounds F1 through F179, respectively.

In one embodiment, the following compounds are provided.

Structure S1

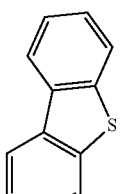
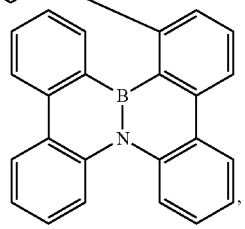

Structure S2

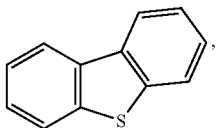
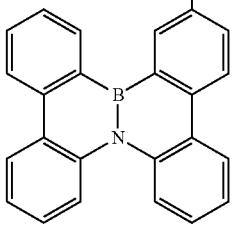

Structure S3

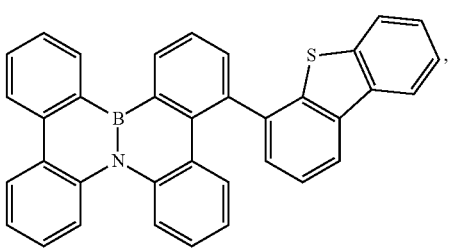

Structure S4
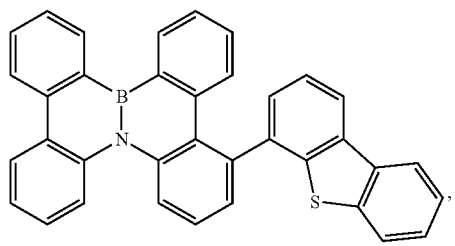
Structure S5
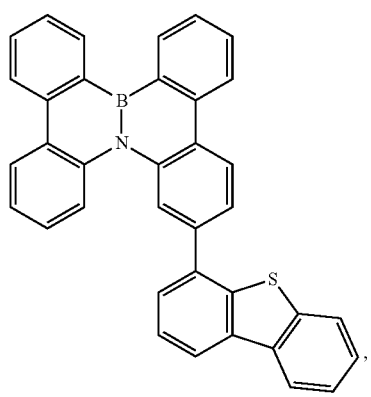
Structure S6
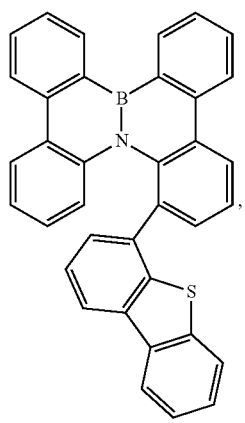
Structure S7
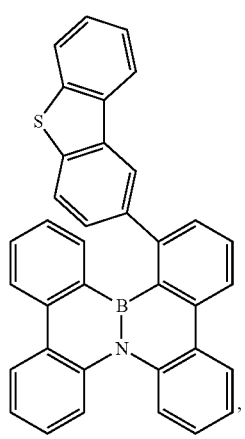
Structure S8
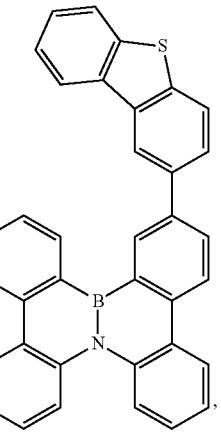
Structure S9
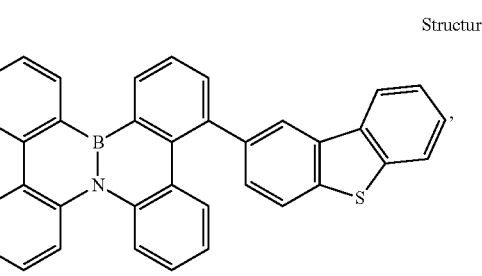
Structure S10
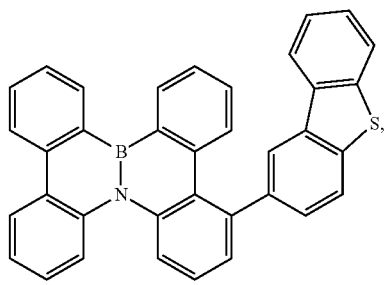
Structure S11
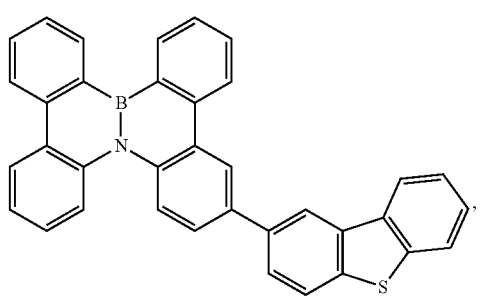

Structure S12
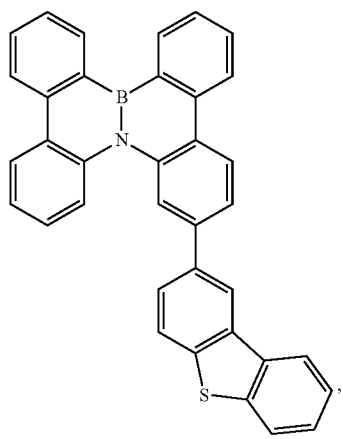
Structure S15
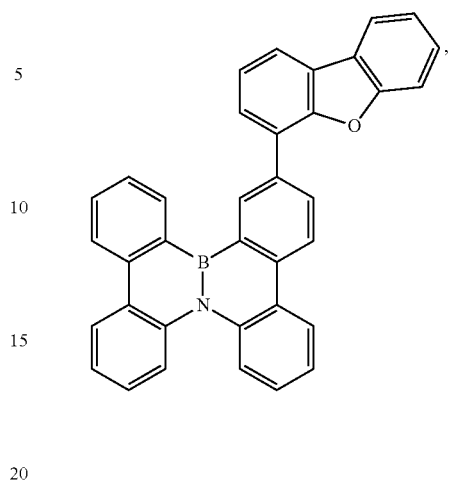
Structure S16
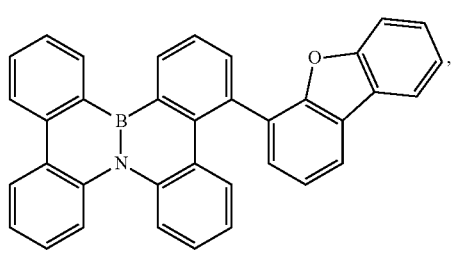
Structure S13
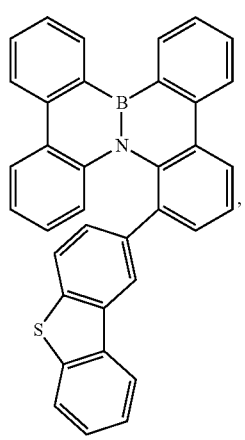
Structure S17
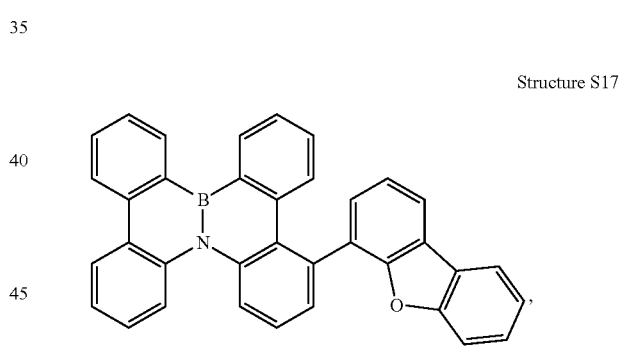
Structure S14
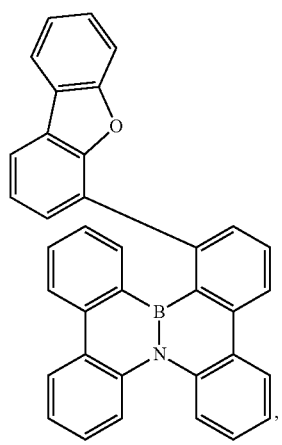
Structure S18
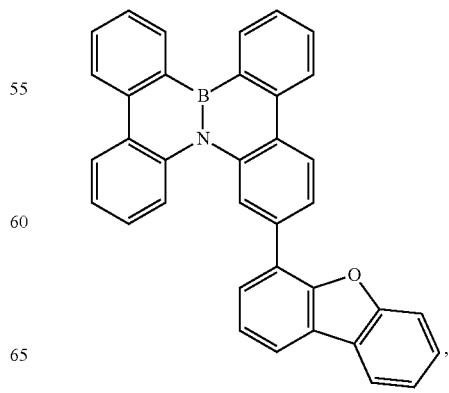

Structure S19
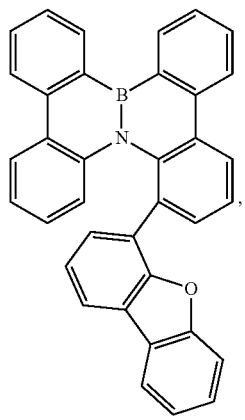
Structure S20
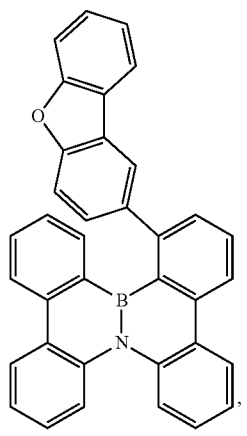
Structure S21
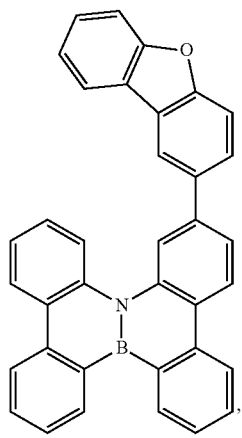
Structure S22
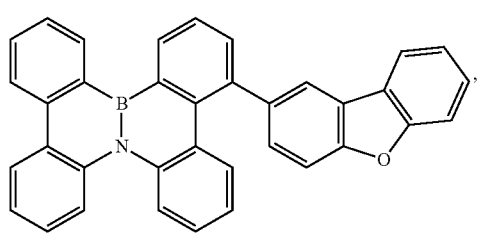
Structure S23
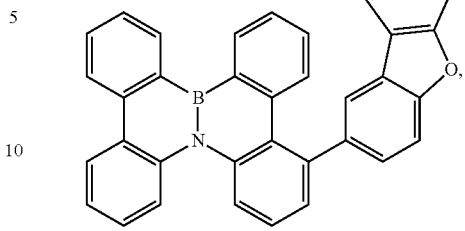
Structure S24
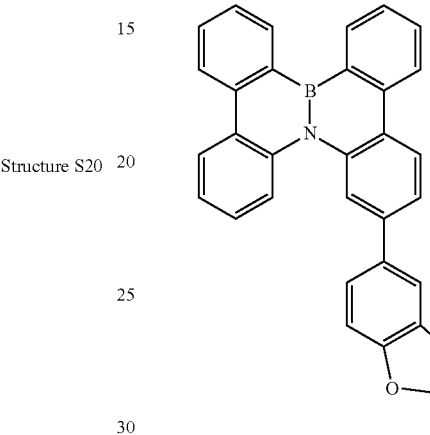
Structure S25
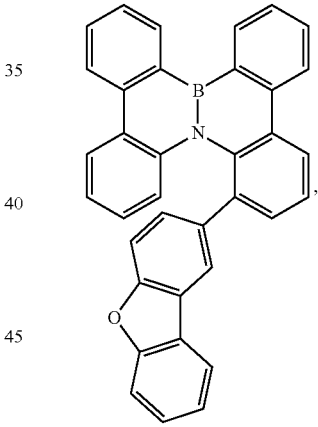
Structure S26
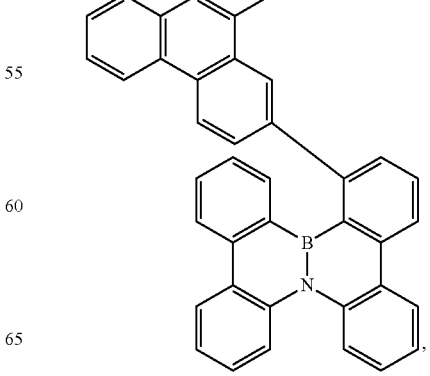

-continued
Structure S27
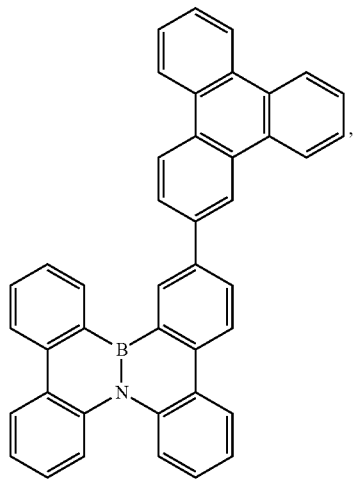
Structure S28
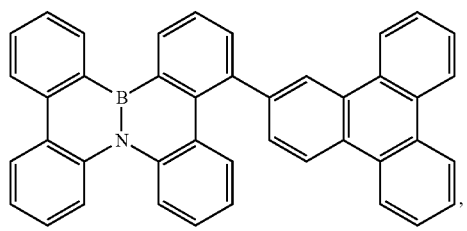
Structure S29
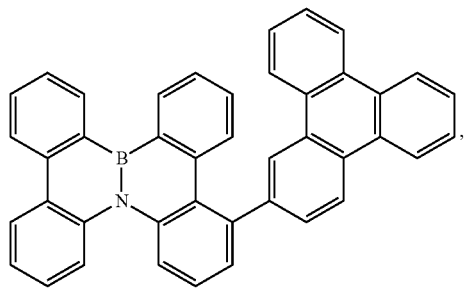
Structure S30
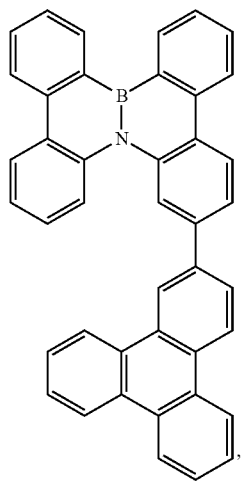
-continued
Structure S31
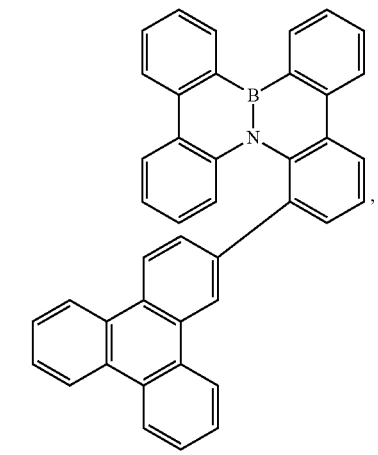
Structure 32
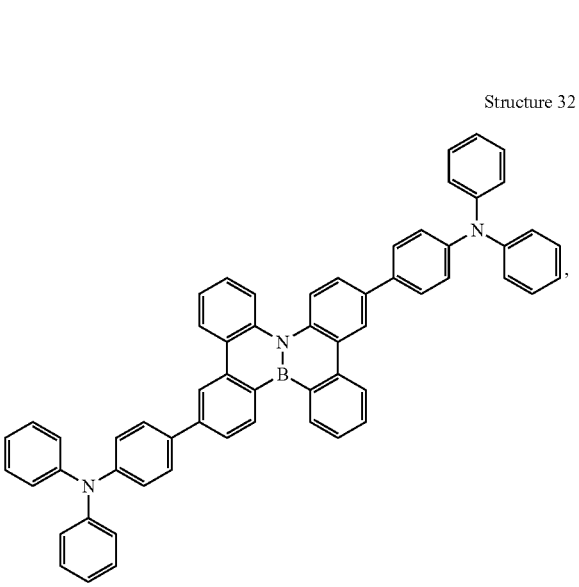
Structure 33
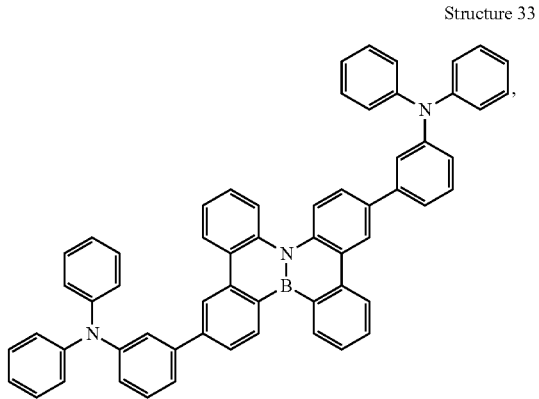

Structure 34
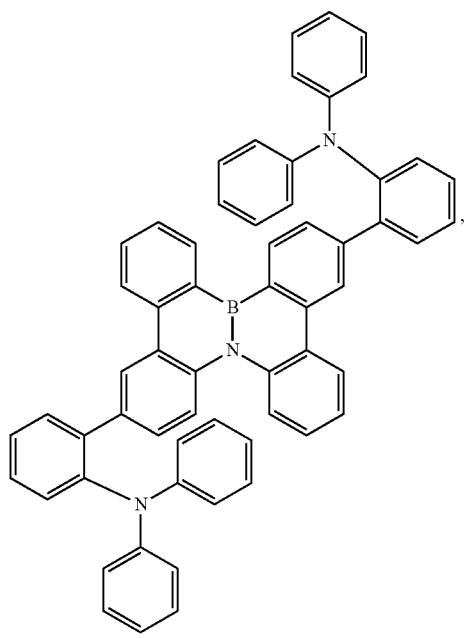
Structure 37
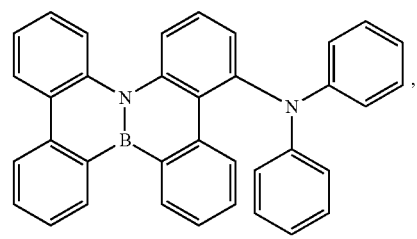
Structure 38
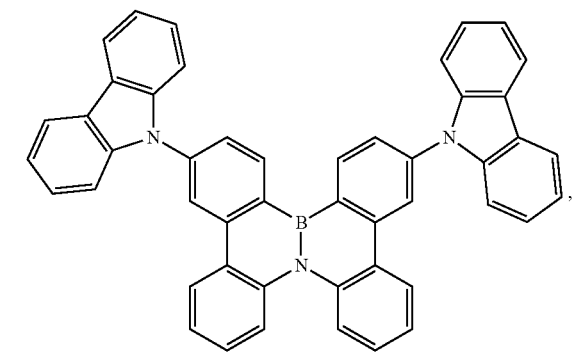
Structure 39
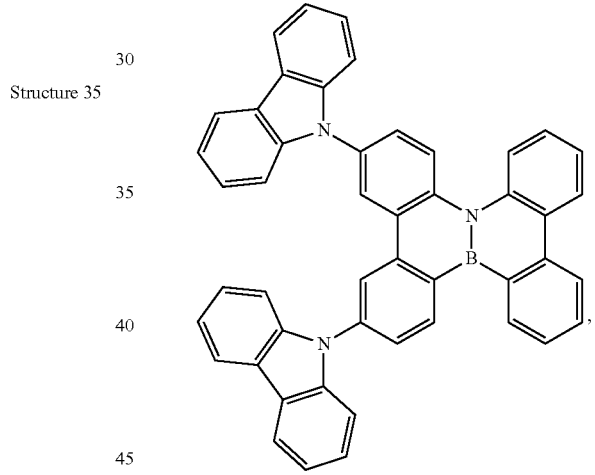
Structure 35
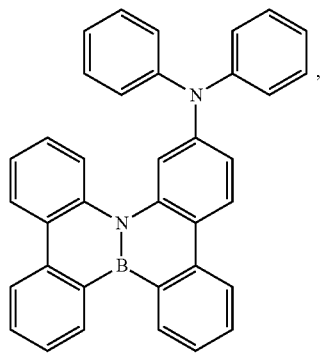
Structure S40
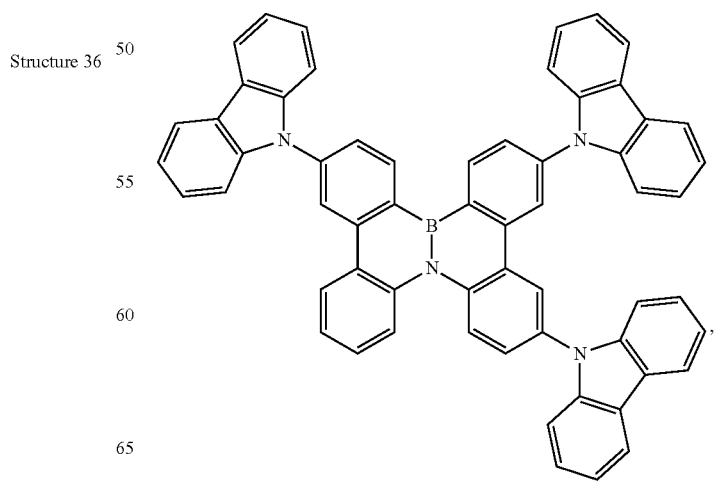
Structure 36
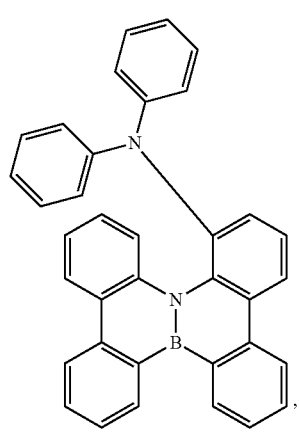

Structure S41
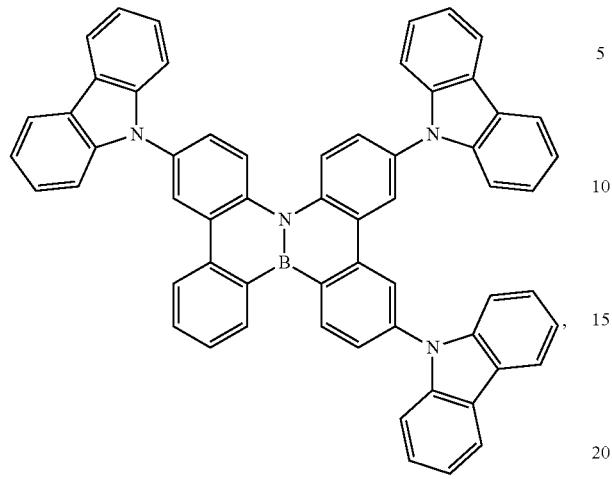
Structure S42
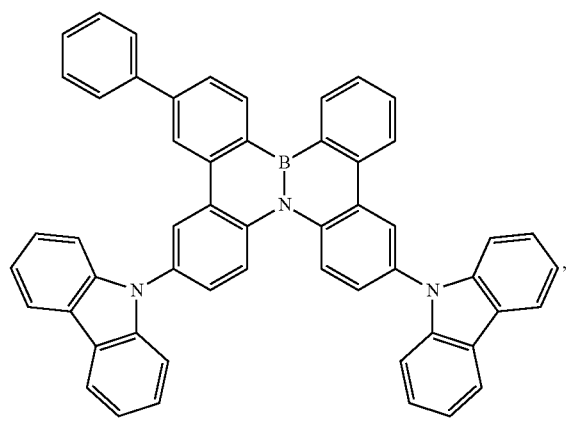
Structure S43
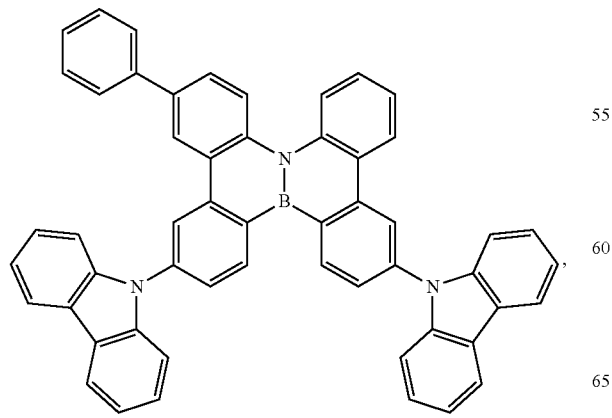
Structure S44
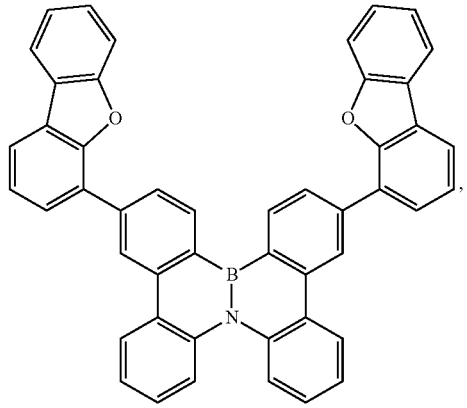
Structure S45
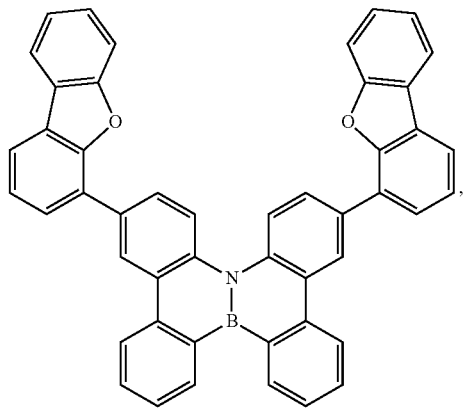
Structure S46
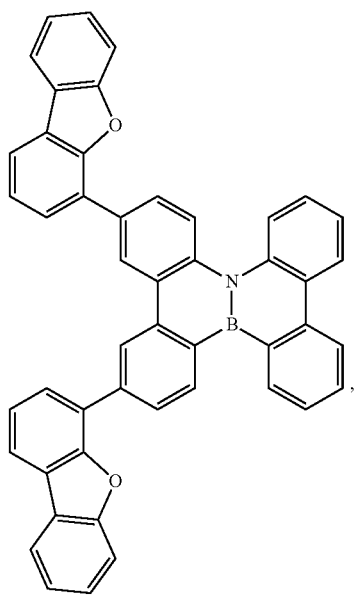

Structure S47
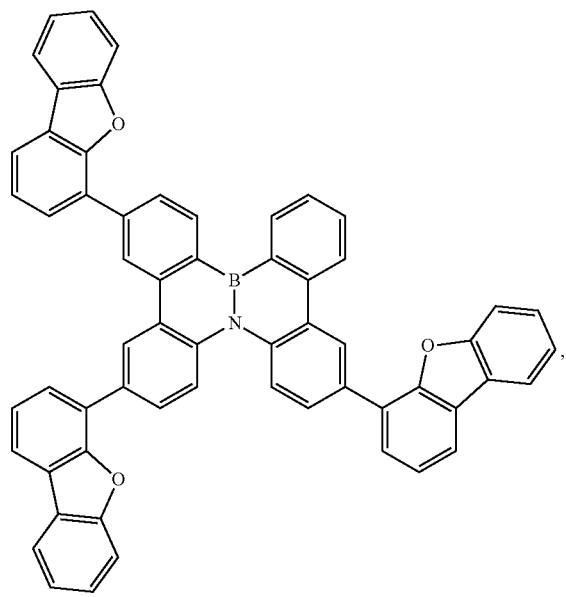
Structure S48
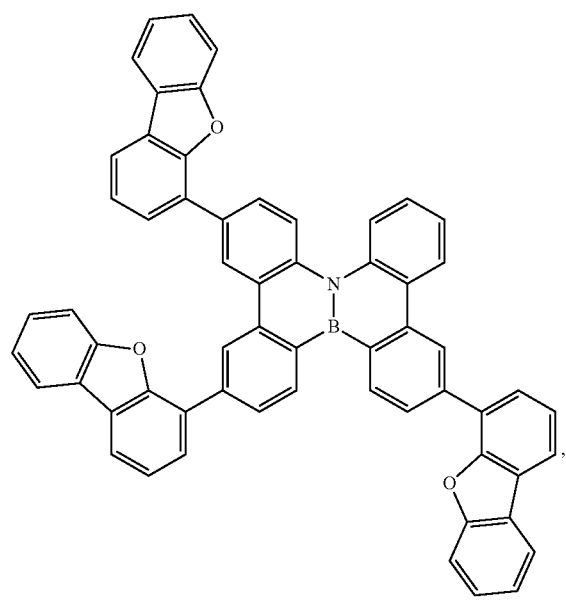
Structure S49
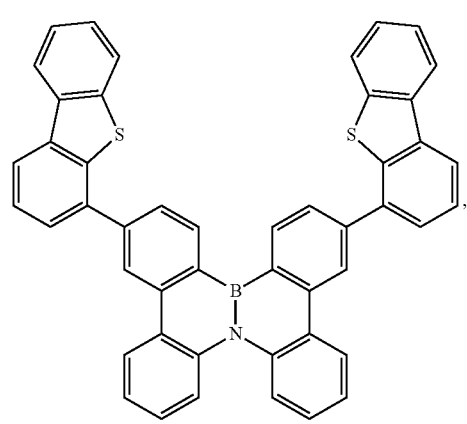
Structure S50
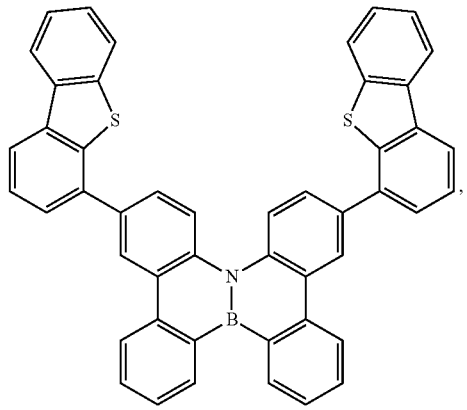
Structure S51
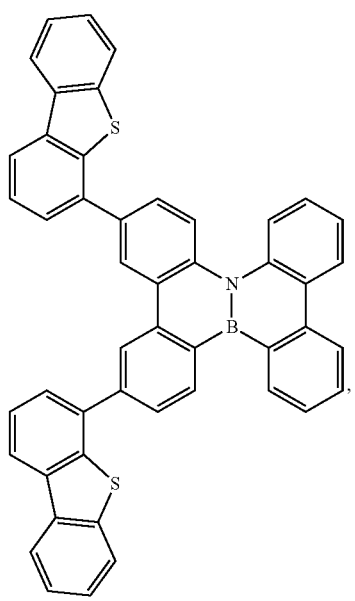
Structure S52
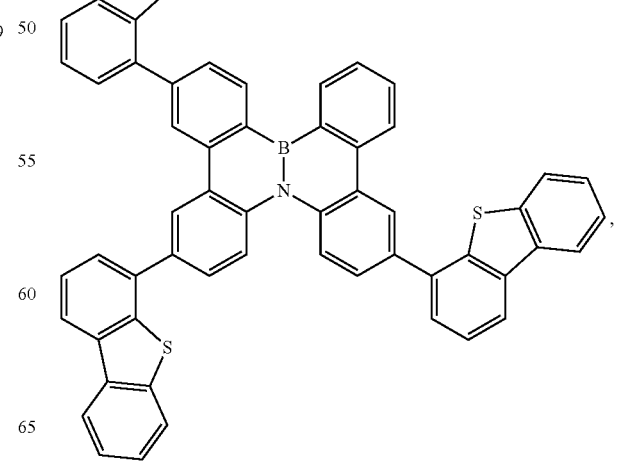

Structure S53
Structure S54
Structure S55
Structure S56
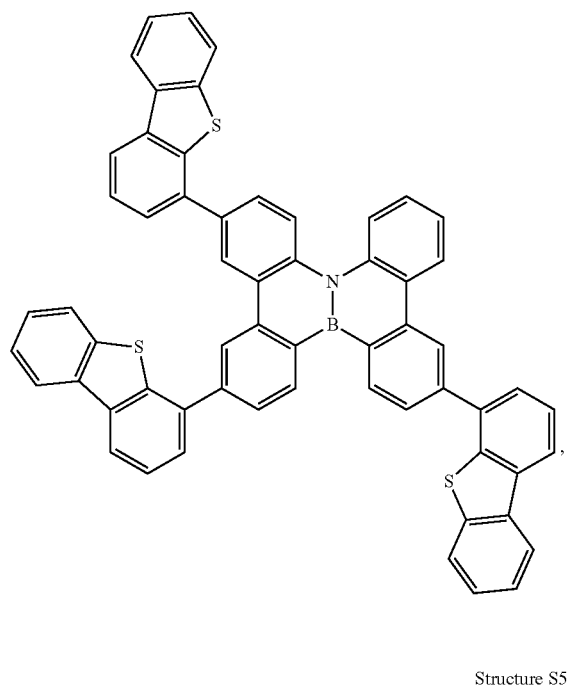
Structure S57
Structure S58
Structure S59
Structure S60
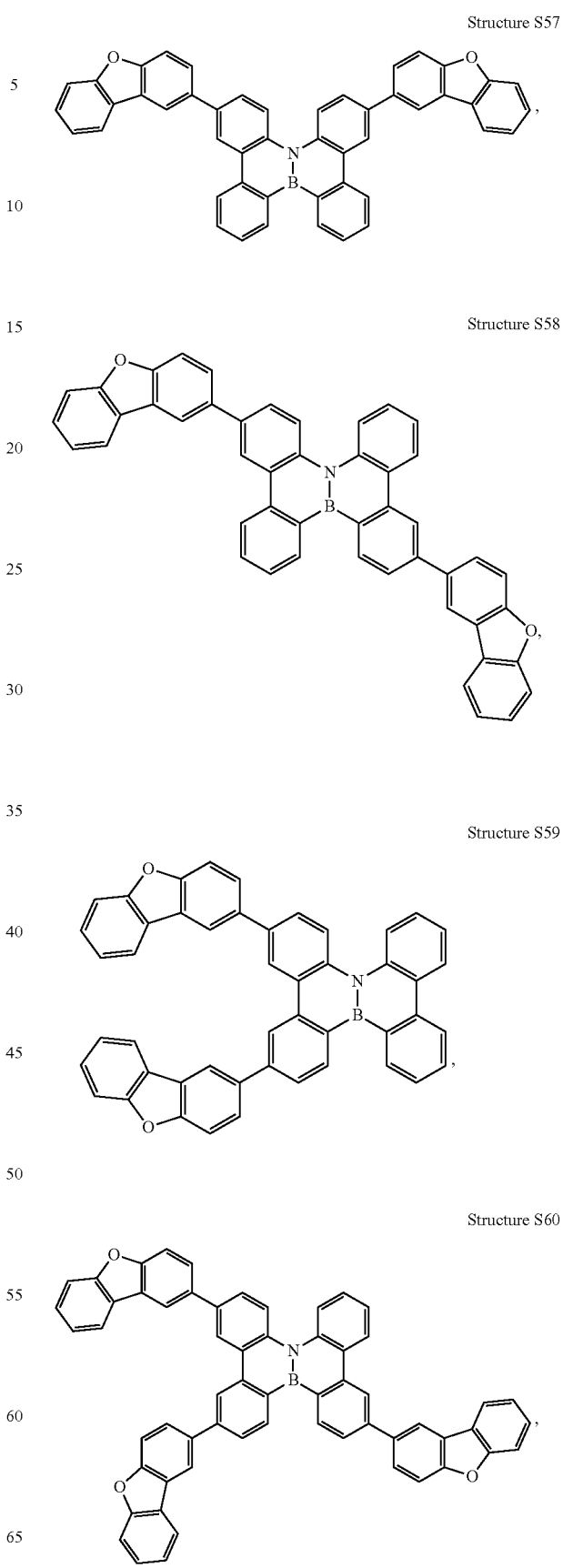

Structure S61
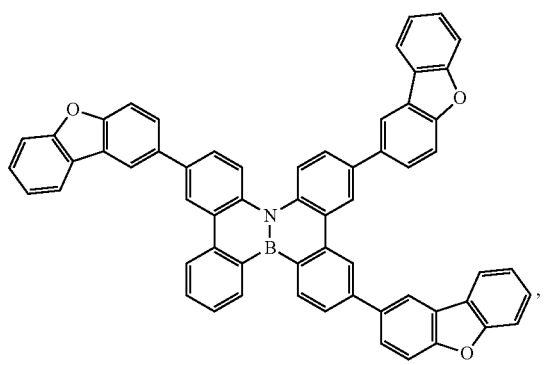
Stucture S62
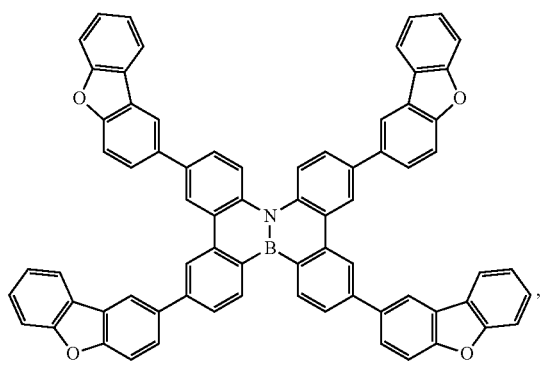
Structure S63
Structure S64
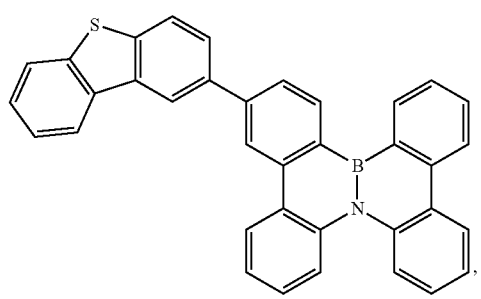
Structure S65
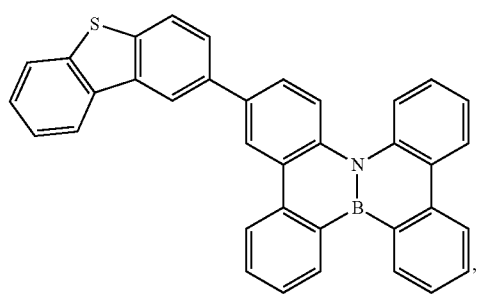
Structure S66
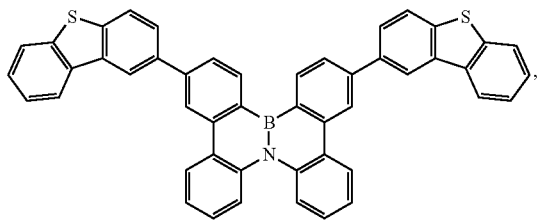
Structure S67
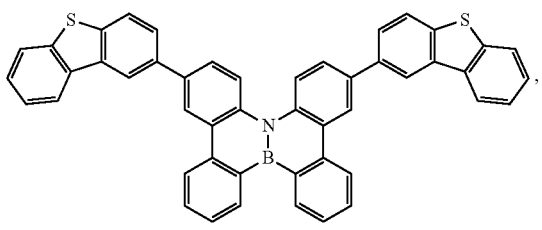
Structure S68
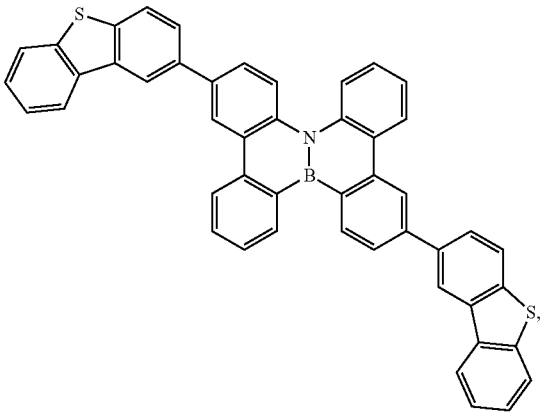

Structure S69
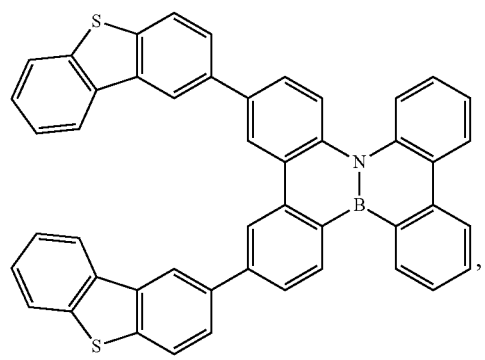
Structure S73
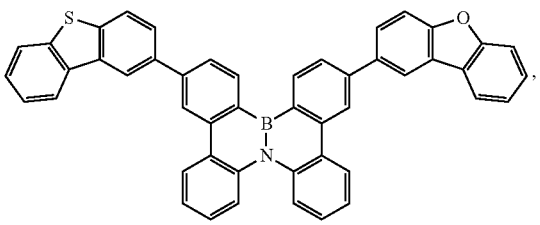
Structure S70
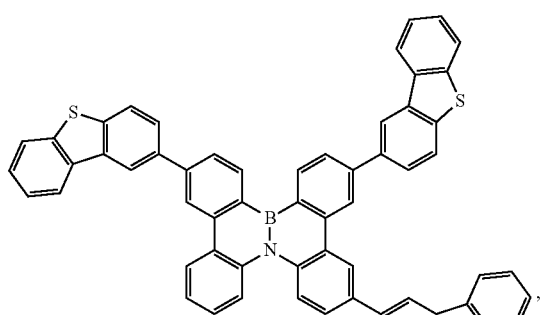
Structure S74
Structure S71
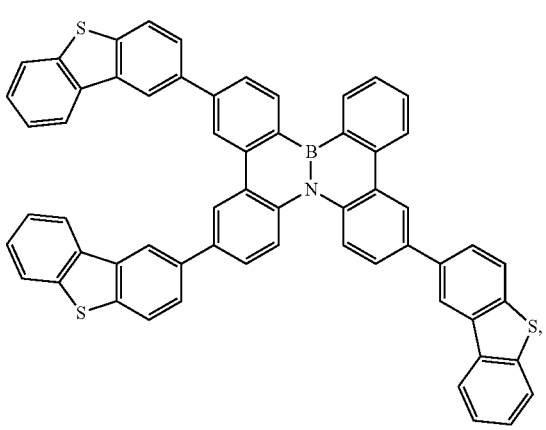
Stucture S75
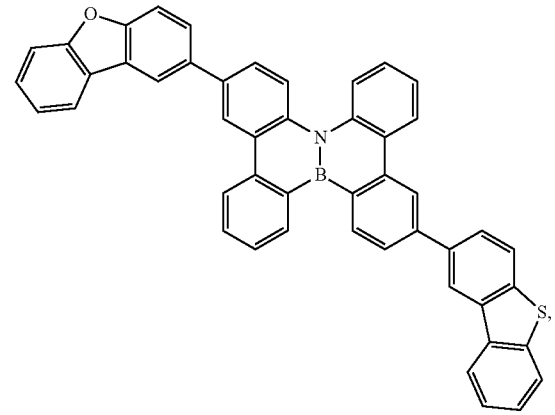
Struture 72
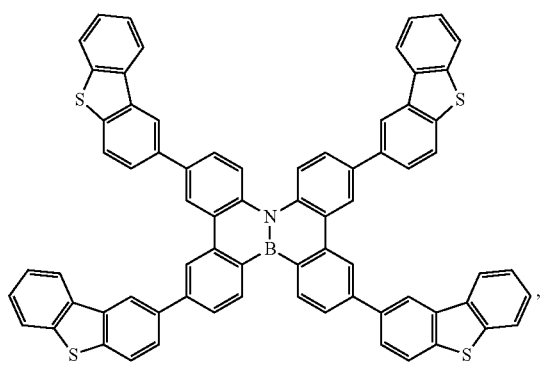
Structure S76
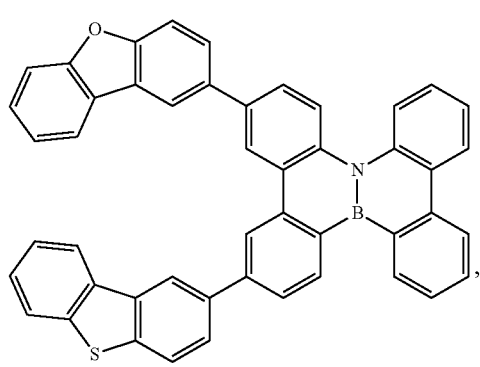

Structure S77
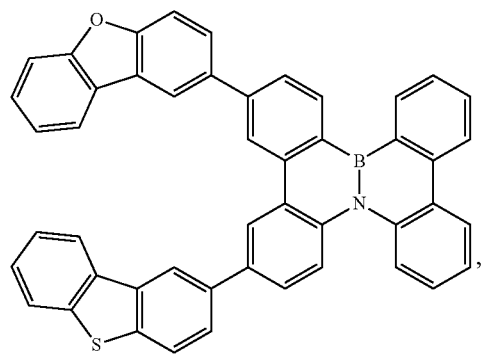
Structure S78
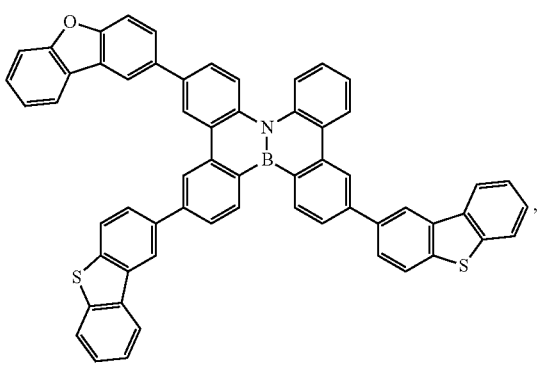
Structure S79
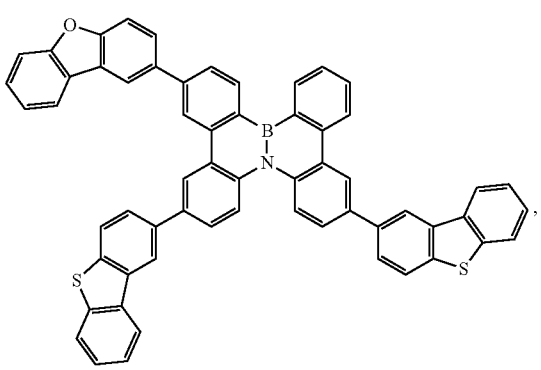
Structure S80
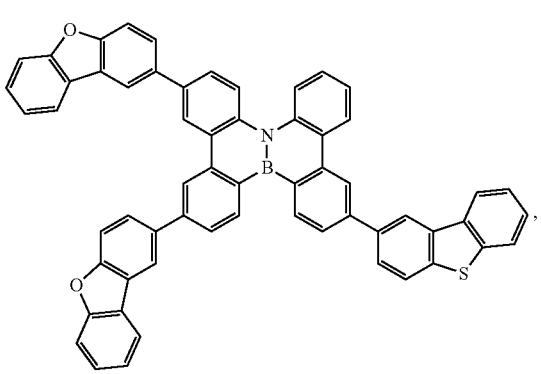
Structure S81
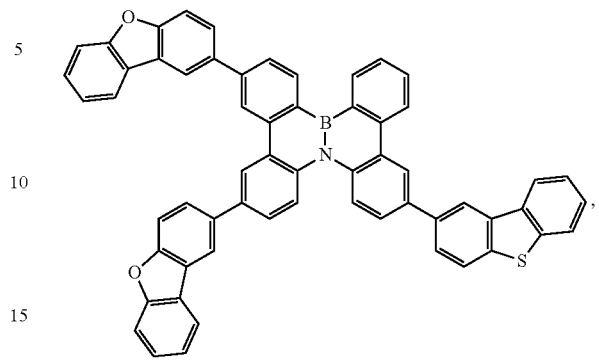
Structure S82
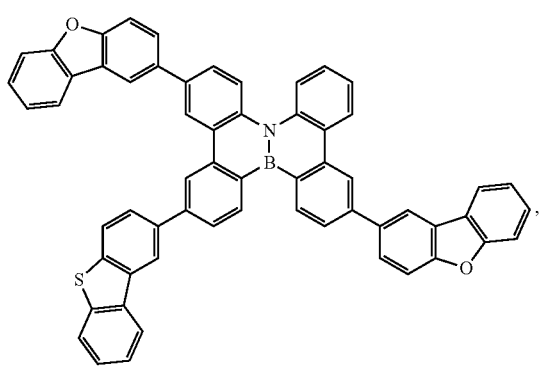
Structure S83
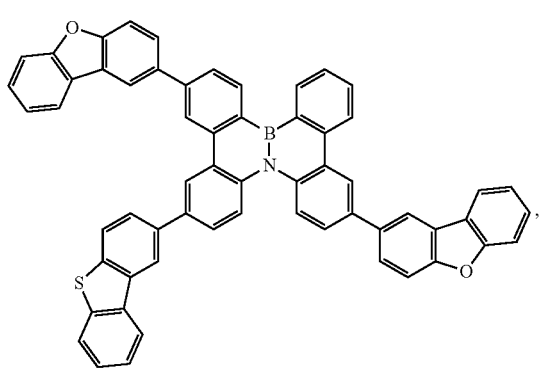
Structure S84
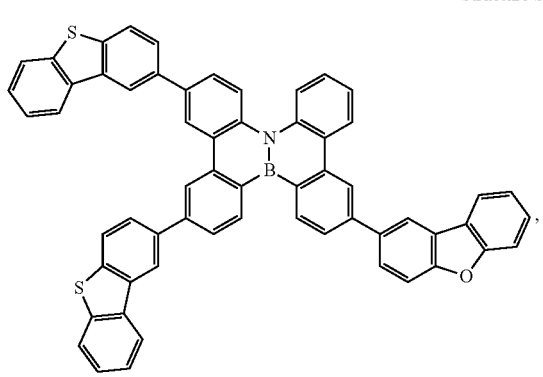

Structure S85
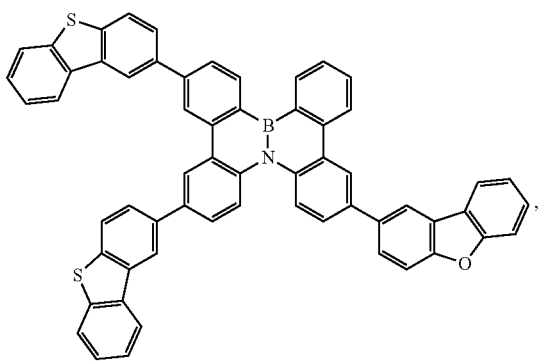
Structure S86
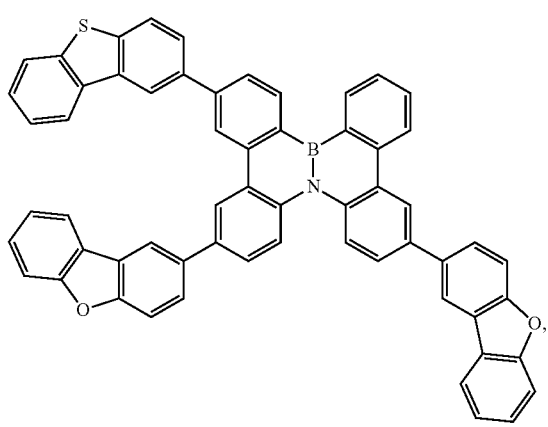
Structure S87
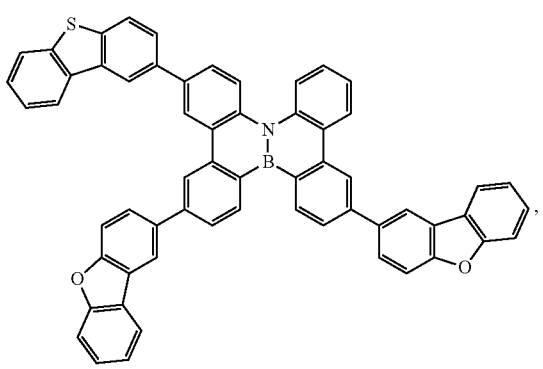
Structure S88
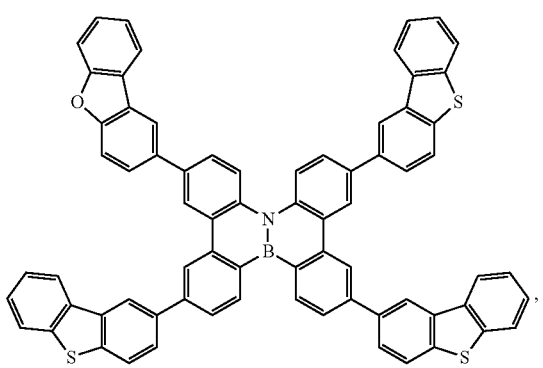
Structure S89
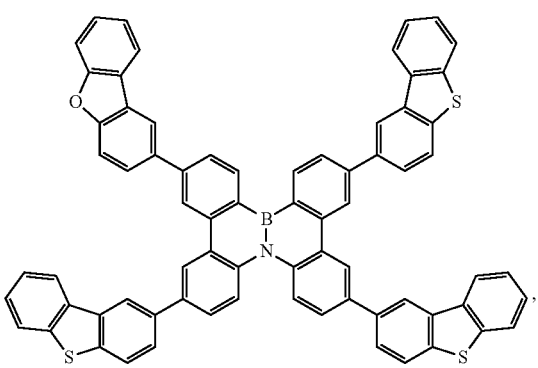
Structure S90
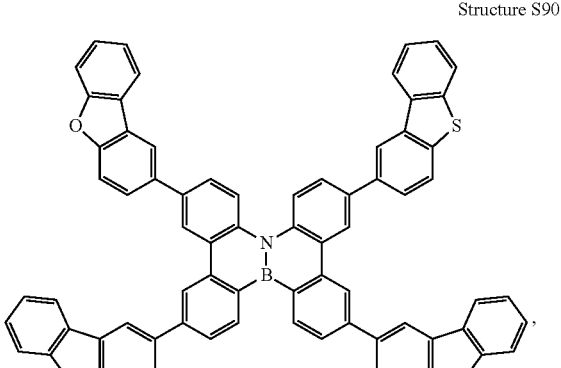
Structure S91
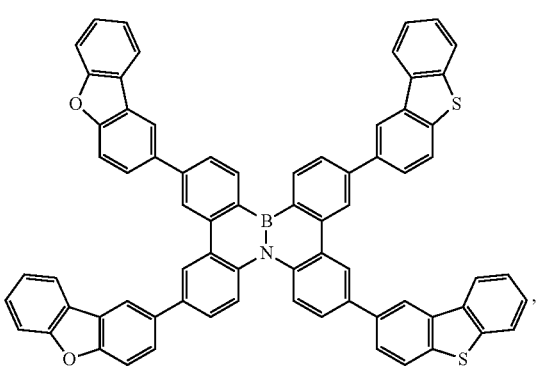
Structure S92
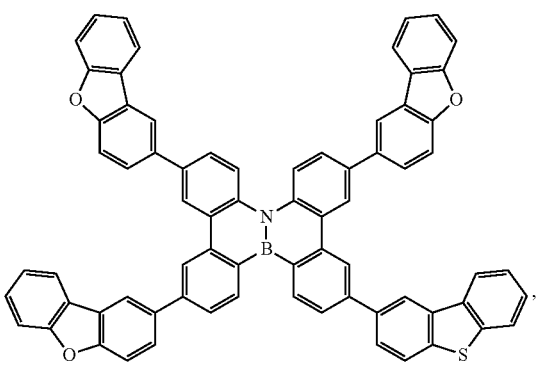

-continued

Structure S93
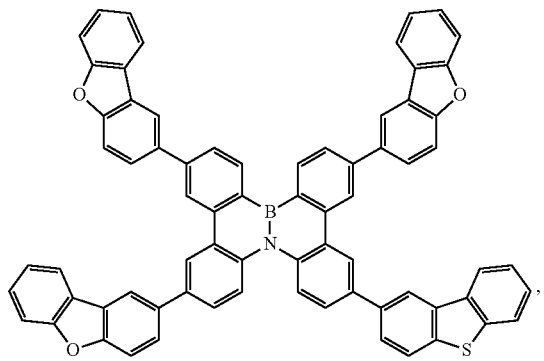

Structure S94
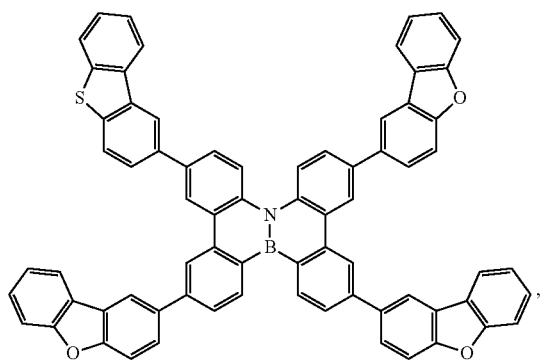

Structure S95
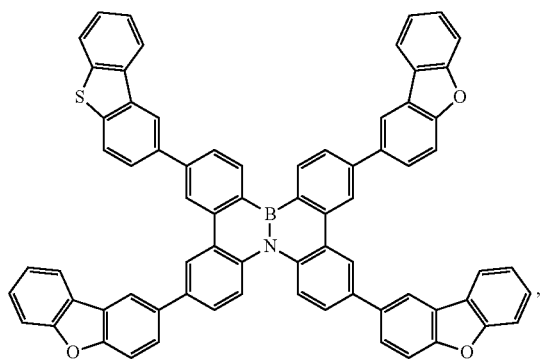

Structure S96
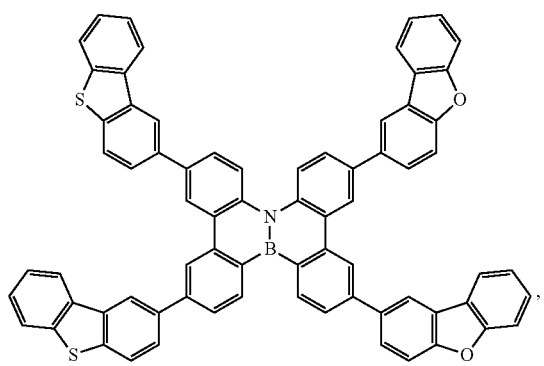

-continued

Structure S97
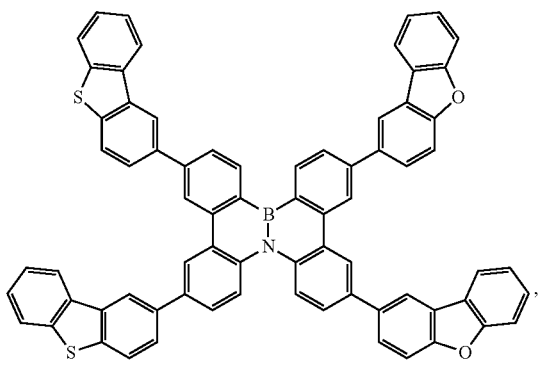

Structure S98
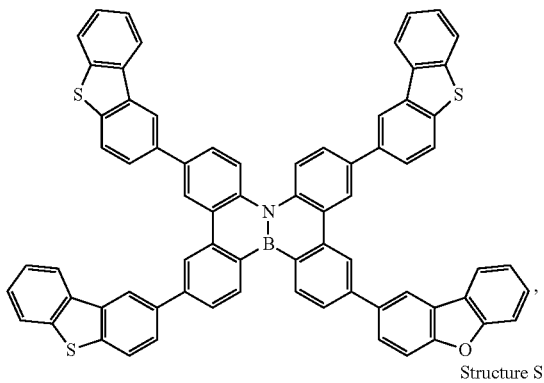

Structure S99
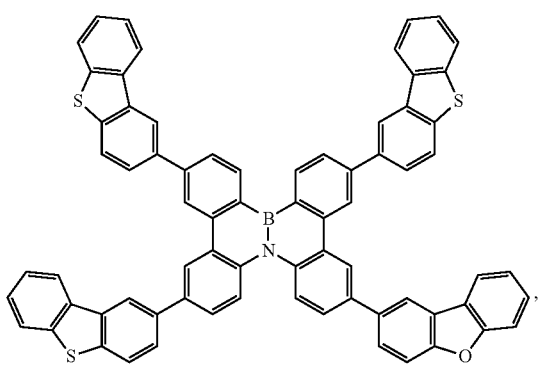

which may be further substituted by one or more substituents independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and where any adjacent substitutions are optionally joined or fused into a ring. In some embodiments, Structures S1 through S99 are not further substituted and are referenced as Compounds S1 through S99, respectively.

According to another aspect of the present disclosure, a device that includes one or more organic light emitting device is also provided. At least one of the one or more organic light emitting devices can include an anode, a cathode, and an organic layer disposed between the anode and the cathode. The organic layer can include one or more emissive dopants. Each of the emissive dopants can be phosphorescent dopant and/or fluorescent dopant. The organic layer can include a compound according to Formula I and its variations as described herein, or Formula V and its variants as described herein. The compound of Formula I or Formula V can be a host. The device can be one or more of a consumer product, an electronic component module, an organic light emitting device, and a lighting panel.

In some embodiments, the emissive dopant is a transition metal complex having at least one ligand or part of the ligand if the ligand is more than bidentate, selected from the group consisting of:

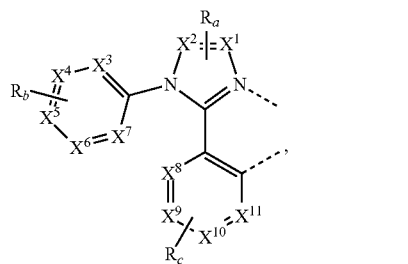

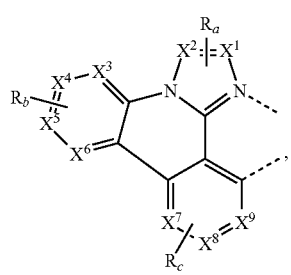

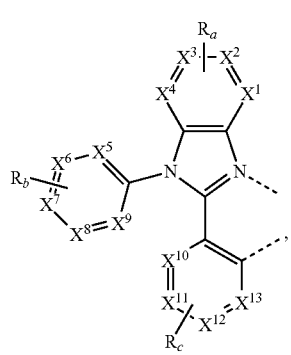

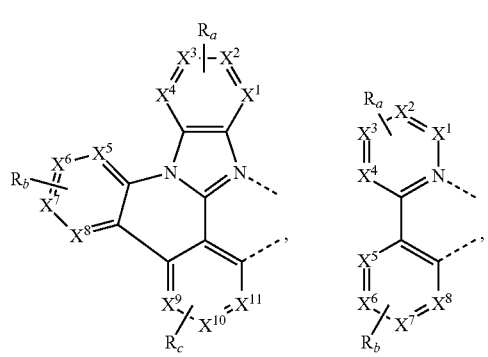

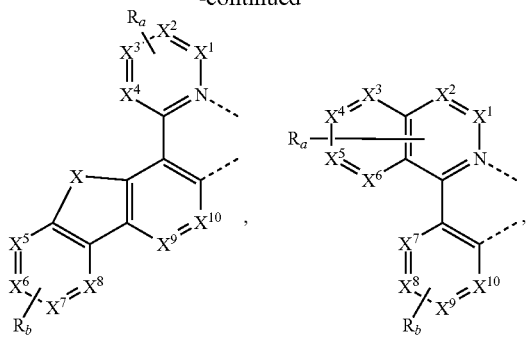

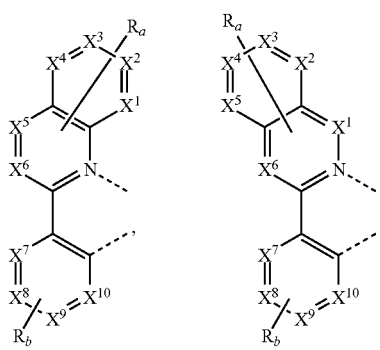

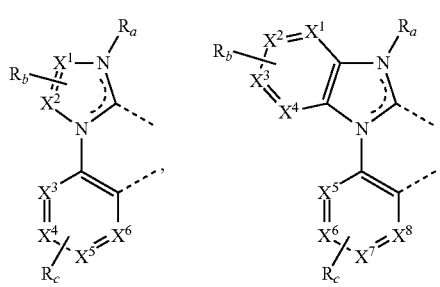

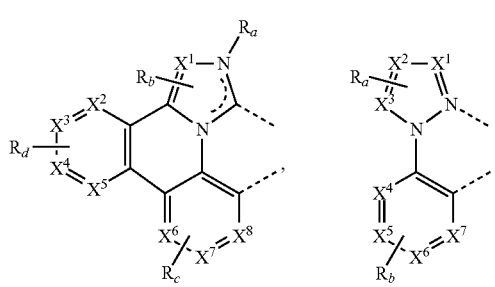

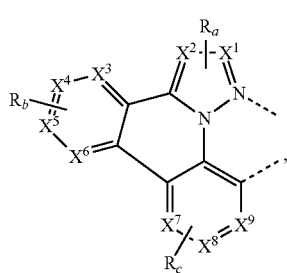

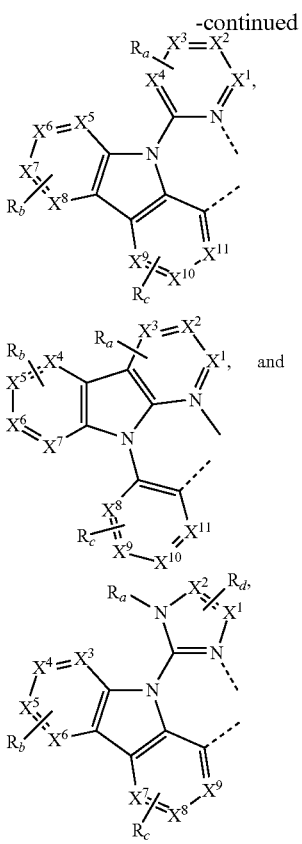

where
each $X^1$ to $X^{13}$ are independently selected from the group consisting of carbon and nitrogen;

X is selected from the group consisting of BR', NR', PR', O, S, Se, C=O, S=O, SO$_2$, CR'R", SiR'R", and GeR'R";

R' and R" are optionally fused or joined to form a ring;

each $R_a$, $R_b$, $R_c$, and $R_d$ may represent from mono substitution to the possible maximum number of substitution, or no substitution;

R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and any two adjacent substituents of $R_a$, $R_b$, $R_c$, and $R_d$ are optionally fused or joined to form a ring or form a multi-dentate ligand.

In some embodiments, the organic layer is a blocking layer and the compound of Formula I or Formula V is a blocking material in the organic layer. In some embodiments, the organic layer is an electron transporting layer and the compound of Formula I or Formula V is an electron transporting material in the organic layer.

In yet another aspect of the present disclosure, a formulation that comprises a compound according to Formula I and its variants as described herein or Formula V and its variants described herein is provided. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as MoO$_x$; a p-type semiconducting organic compound, such as 1,4,5,8,9,12-Hexaazatriphenylenehexacarbonitrile; a metal complex, and a cross-linkable compound.

Examples of aromatic amine derivatives used in HIL or HIT include, but are not limited to the following general structures:

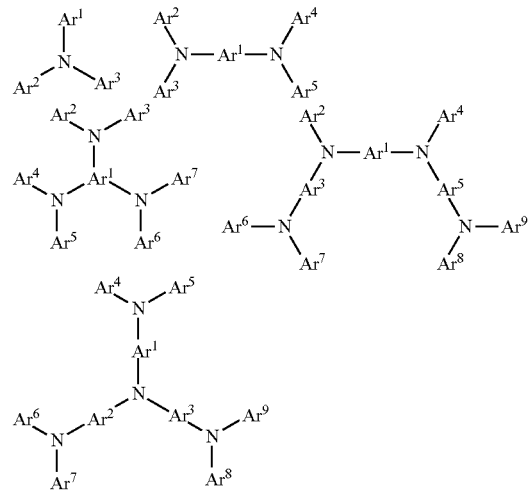

Each of Ar$^1$ to Ar$^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, midazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, cycloalkyl, heteroalkyl, arylalkyl, alkoxy, aryloxy, amino, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof.

In one aspect, $Ar^1$ to $Ar^9$ is independently selected from the group consisting of:

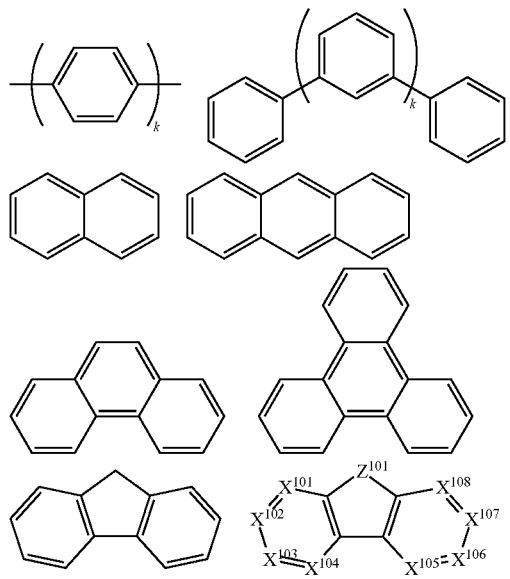

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

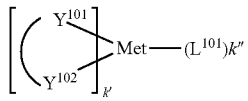

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. Fc/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that e r nit various colors, any host material may be used with any dopant so long as the triplet criteria is satisfied.

Examples of metal complexes used as host are preferred to have the following general formula:

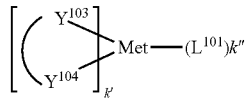

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

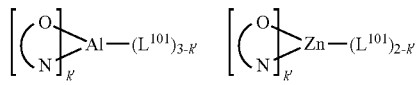

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, aryloxy, amino, silyl, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof.

In one aspect, host compound contains at least one of the following groups in the molecule:

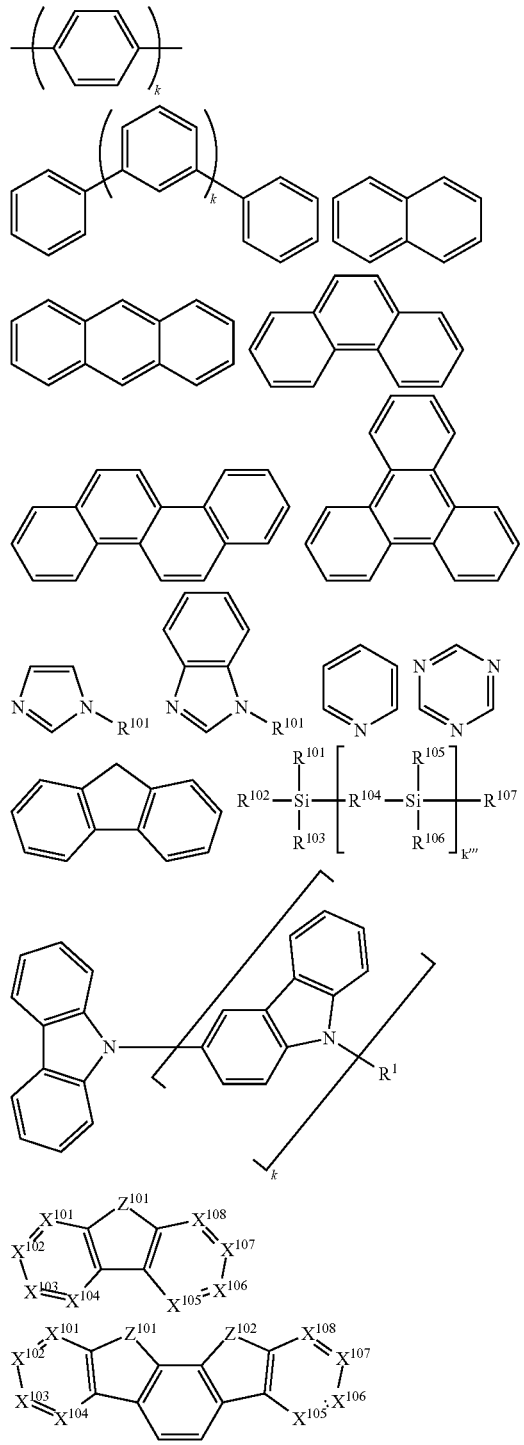

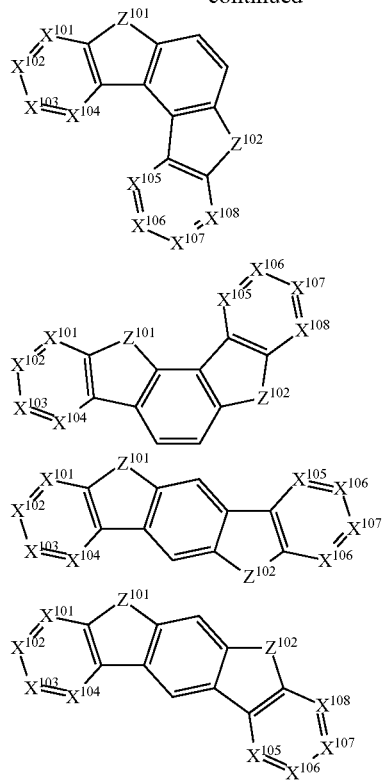

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may he used to confine emission to a desired region of an OLED.

In one aspect, compound used in HBL contains the same molecule or the same functional groups used as host described above.

In another aspect, compound used in HBL contains at least one of the following groups in the molecule:

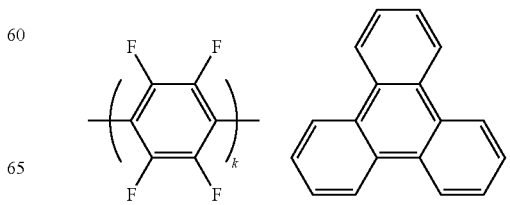

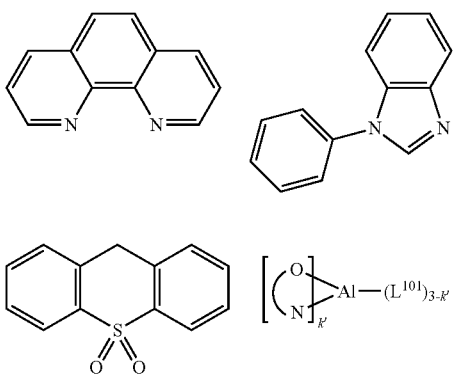

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

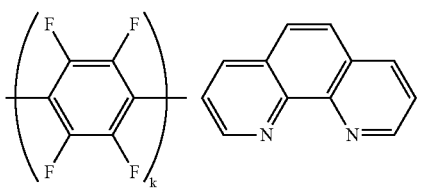

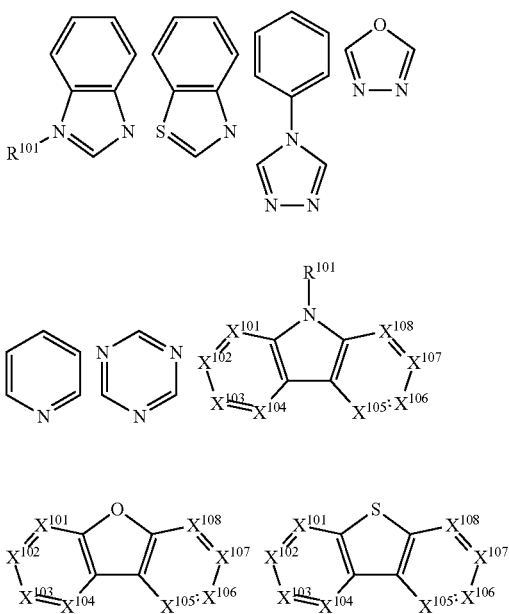

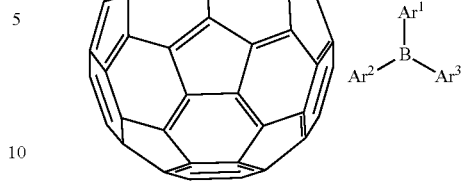

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

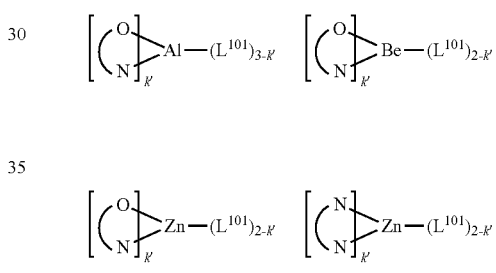

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exciton/hole blocking layer materials, electron transporting and electron injecting materials may be used in OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A
| MATERIAL | EXAMPLES OF MATERIAL | PUBLICATIONS |
|---|---|---|
| Hole injection materials | | |
| Phthalocyanine and porphryin compounds | 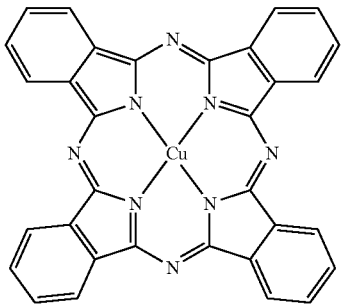 | Appl. Phys. Lett. 69, 2160 (1996) |
| Starburst triarylamines | 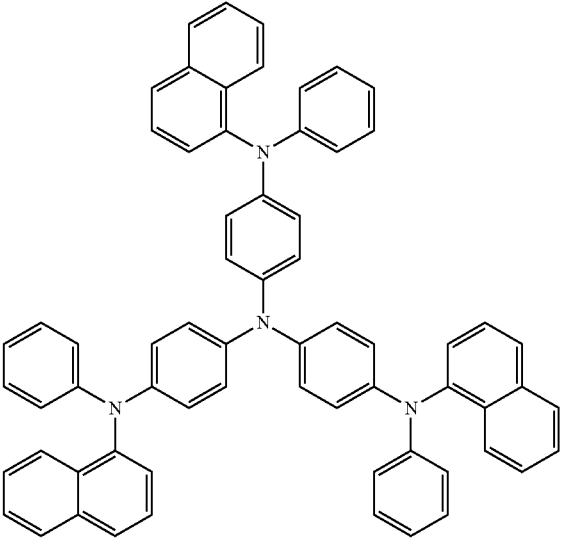 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-(CH_xF_y)_n-$ | Appl. Phys. Lett. 78, 673 (2001) |
| Conducting polymers (e.g., PEDOT:PSS, polyaniline, polythiophene) | 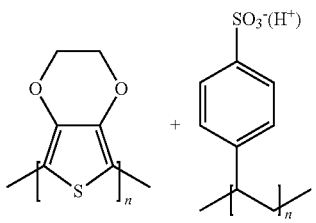 | Synth. Met. 87, 171 (1997) WO2007002683 |
| Phosphonic acid and silane SAMs | 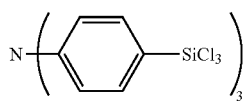 | US20030162053 |

TABLE A-continued
| MATERIAL | EXAMPLES OF MATERIAL | PUBLICATIONS |
|---|---|---|
| Triarylamine or polythiophene polymers with conductivity dopants | 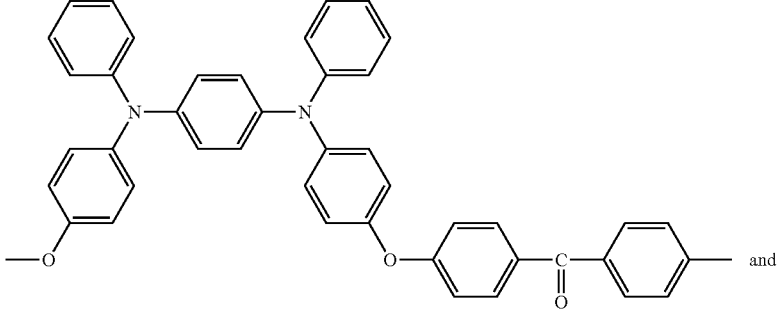 and 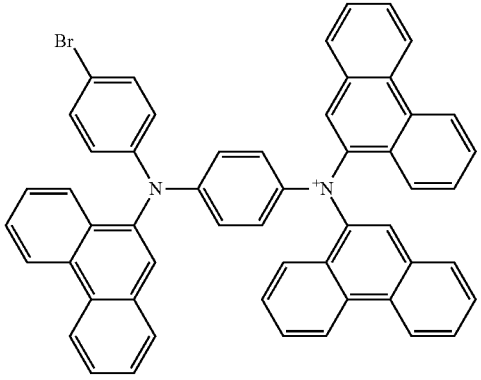 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 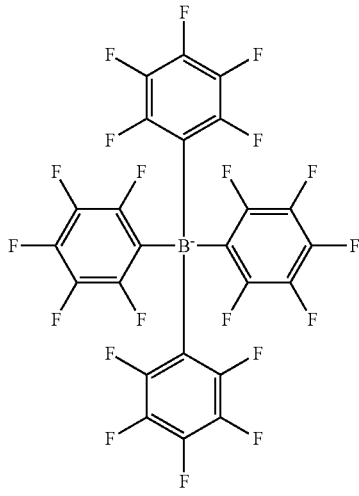 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Organic compounds with conductive inorganic compounds, such as molybdenum and tungsten oxides | 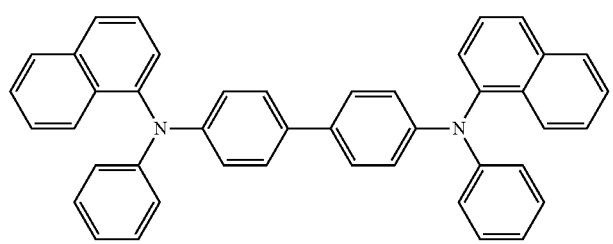 + MoO$_x$ | US20050123751 SID Symposium Digest, 37, 923 (2006) WO2009018009 |

TABLE A-continued
| MATERIAL | EXAMPLES OF MATERIAL | PUBLICATIONS |
|---|---|---|
| n-type semiconducting organic complexes | 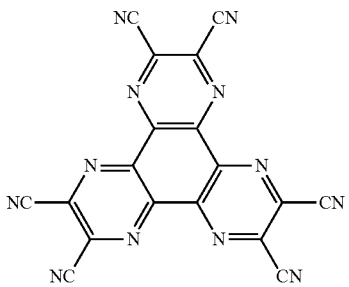 [SMILES: N#Cc1nc2c3nc(C#N)c(C#N)nc3c3nc(C#N)c(C#N)nc3c2nc1C#N] | US20020158242 |
| Metal organometallic complexes | 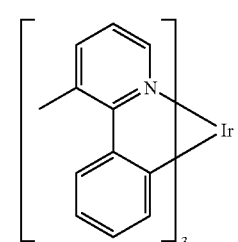 | US20060240279 |
| Cross-linkable compounds | 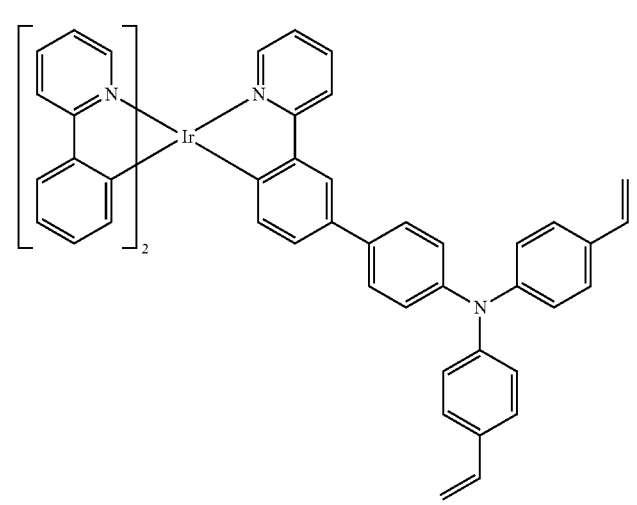 | US20080220265 |
| Polythiophene based polymers and copolymers | 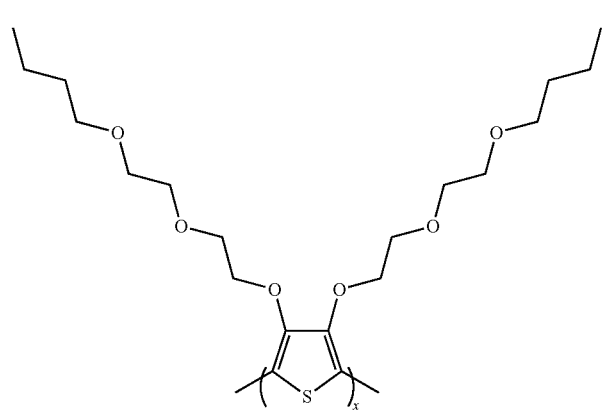 | WO 2011075644<br>EP2350216 |

TABLE A-continued
| MATERIAL | EXAMPLES OF MATERIAL | PUBLICATIONS |
|---|---|---|
| Hole transporting materials | | |
| Triarylamines (e.g., TPD, α-NPD) | 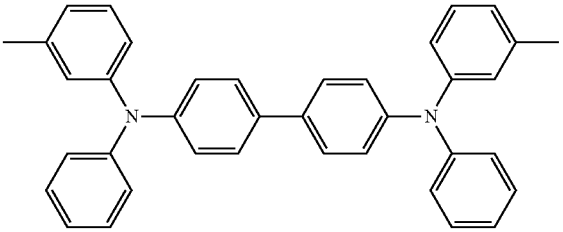 | Appl. Phys. Lett. 51, 913 (1987) |
| | 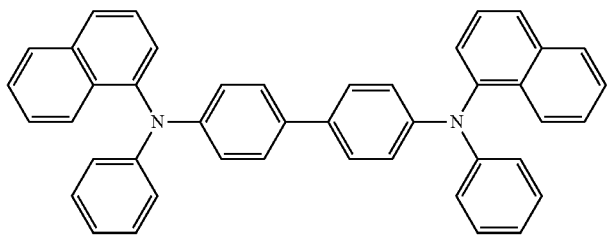 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 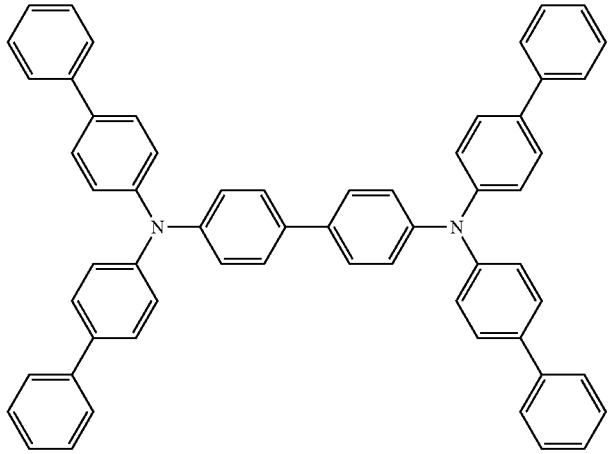 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 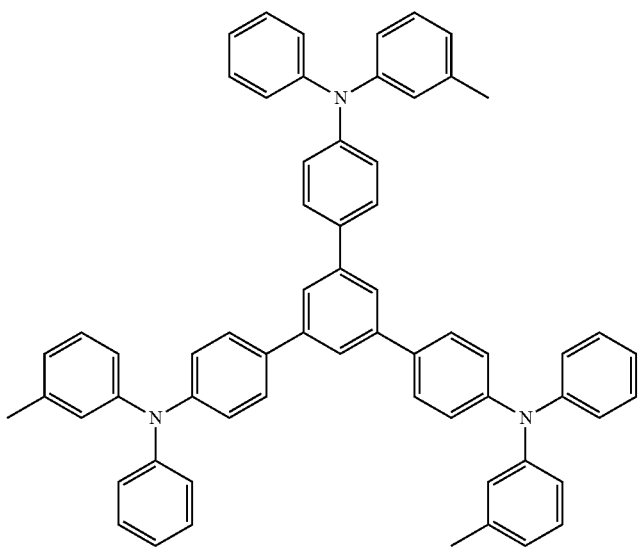 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE A-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triarylamine on spirofluorene core | | Synth. Met. 91, 209 (1997) |
| Arylamine carbazole compounds | | Adv. Mater. 6, 677 (1994), US20080124572 |

TABLE A-continued
| MATERIAL | EXAMPLES OF MATERIAL | PUBLICATIONS |
|---|---|---|
| Triarylamine with (di)benzothiophene/ (di)benzofuran | 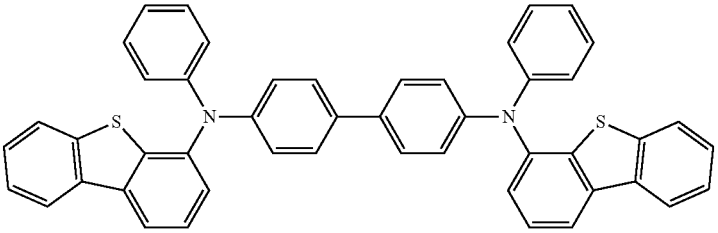 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 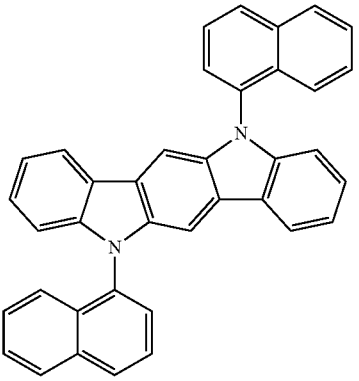 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 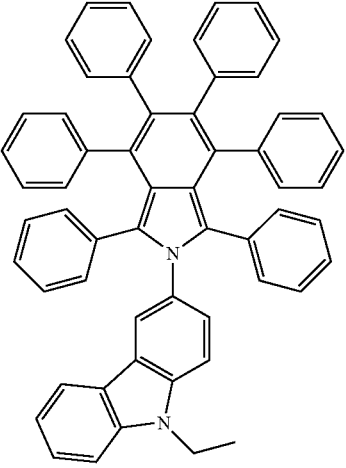 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 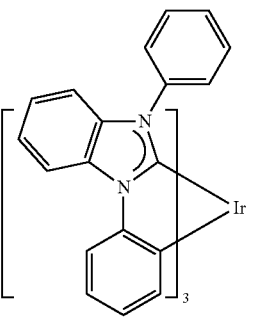 | US20080018221 |

TABLE A-continued

| MATERIAL | EXAMPLES OF MATERIAL | PUBLICATIONS |
| --- | --- | --- |
| Phosphorescent OLED host materials | | |
| Red hosts | | |
| Arylcarbazoles | [structure] | Appl. Phys. Lett. 78, 1622 (2001) |
| Metal 8-hydroxyquinolates (e.g., Alq$_3$, BAlq) | [structure] | Nature 395, 151 (1998) |
| | [structure] | US20060202194 |
| | [structure] | WO2005014551 |
| | [structure] | WO2006072002 |
| Metal phenoxybenzothiazole compounds | [structure] | Appl. Phys. Lett. 90, 123509 (2007) |
| Conjugated oligomers and polymers (e.g., polyfluorene) | [structure] | Org. Electron. 1, 15 (2000) |

TABLE A-continued
| MATERIAL | EXAMPLES OF MATERIAL | PUBLICATIONS |
|---|---|---|
| Aromatic fused rings | 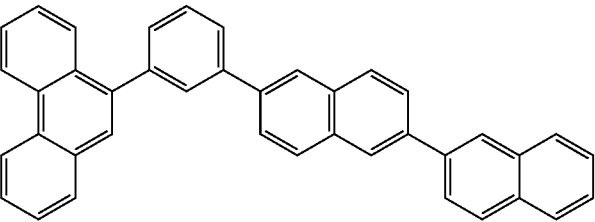 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 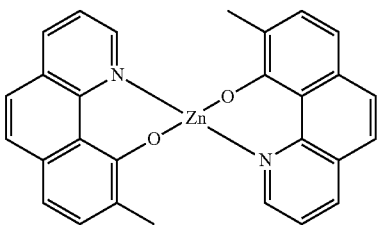 | WO2010056066 |
| Chrysene based compounds | 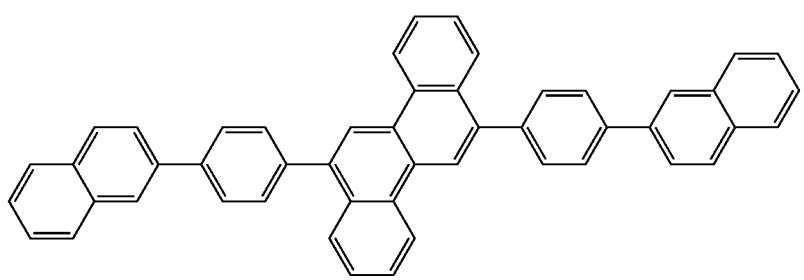 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |
Green hosts
| | | |
|---|---|---|
| Arylcarbazoles | 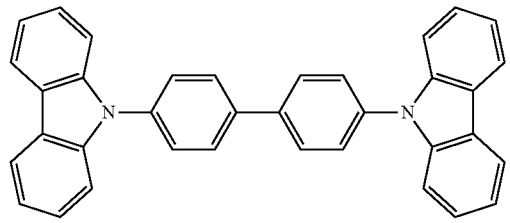 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 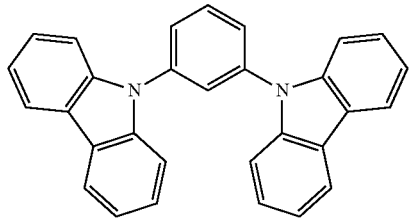 [SMILES: c1cc(-n2c3ccccc3c3ccccc32)cc(-n2c3ccccc3c3ccccc32)c1] | US20030175553 |
| | 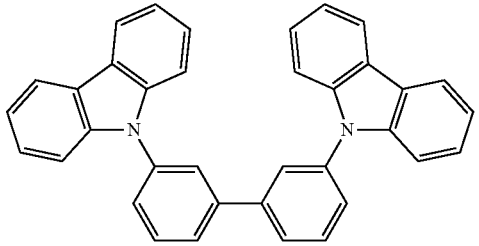 [SMILES: c1cc(-c2cccc(-n3c4ccccc4c4ccccc43)c2)cc(-n2c3ccccc3c3ccccc32)c1] | WO2001039234 |

TABLE A-continued
| MATERIAL | EXAMPLES OF MATERIAL | PUBLICATIONS |
|---|---|---|
| Aryltriphenylene compounds | 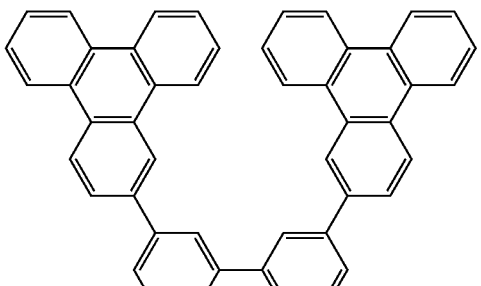 | US20060280965 |
| | 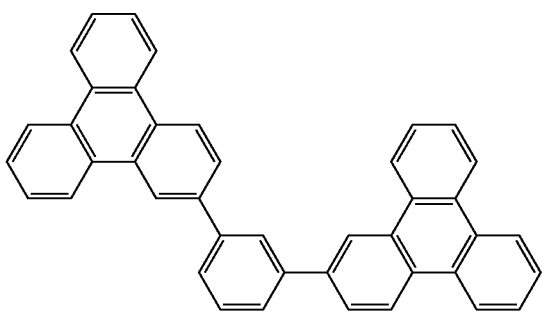 [SMILES: c1cc(-c2ccc3c4ccccc4c4ccccc4c3c2)cc(-c2ccc3c4ccccc4c4ccccc4c3c2)c1] | US20060280965 |
| | 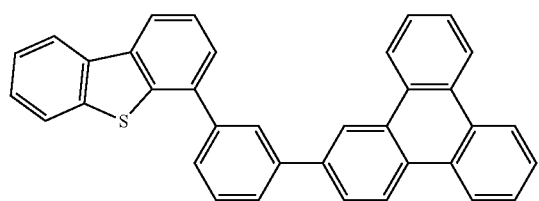 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 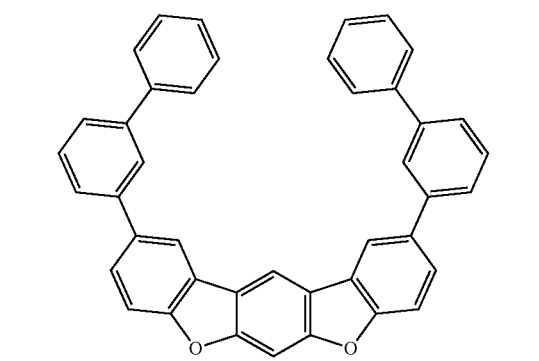 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 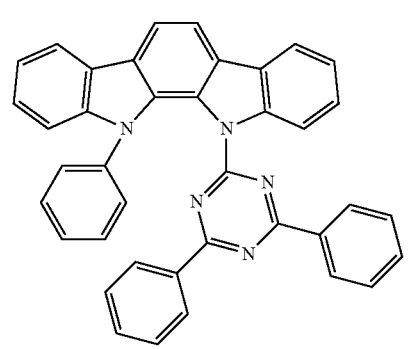 [SMILES: c1ccc(-c2nc(-c3ccccc3)nc(-n3c4ccccc4c4ccc5c6ccccc6n(-c6ccccc6)c5c43)n2)cc1] | WO2008056746 |

| MATERIAL | EXAMPLES OF MATERIAL | PUBLICATIONS |
|---|---|---|
| | 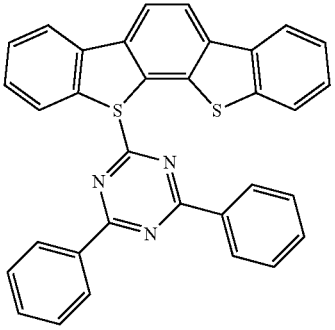 | WO2010107244 |
| Aza-carbazole/ DBT/DBF | 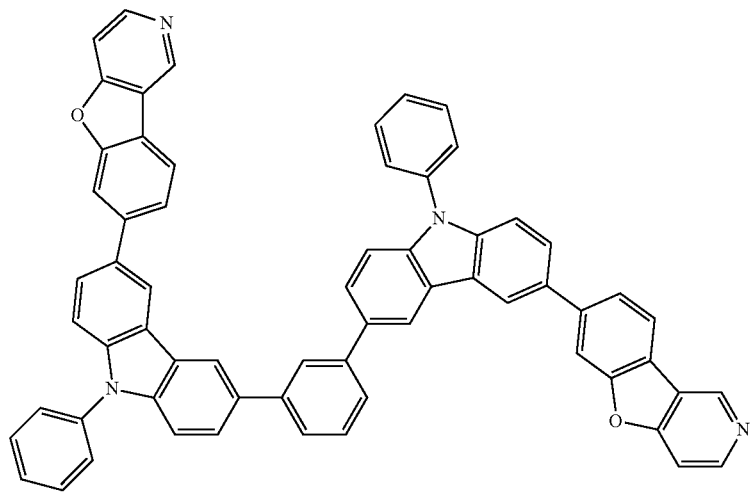 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 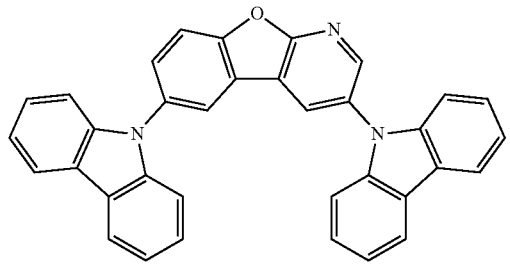 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 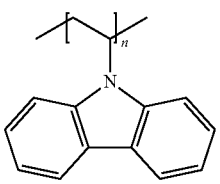 | Appl. Phys. Lett. 77, 2280 (2000) |
| Spirofluorene compounds | 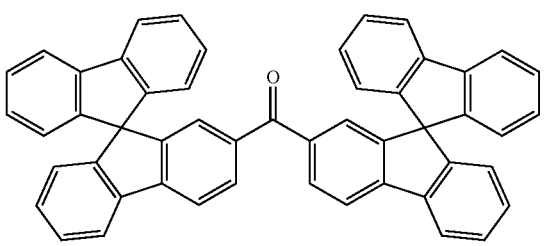 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE A-continued

| MATERIAL | EXAMPLES OF MATERIAL | PUBLICATIONS |
|---|---|---|
| Metal phenoxybenzooxazole compounds | | WO2005089025 |
| | | WO2006132173 |
| | | JP200511610 |
| Spirofluorene-carbazole compounds | | JP2007254297 |
| | | JP2007254297 |

TABLE A-continued

| MATERIAL | EXAMPLES OF MATERIAL | PUBLICATIONS |
| --- | --- | --- |
| Indolocarbazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE A-continued

| MATERIAL | EXAMPLES OF MATERIAL | PUBLICATIONS |
| --- | --- | --- |
| Metal phenoxypyridine compounds | | WO2005030900 |
| Metal coordination complexes (e.g., Zn, Al with N^N ligands) | | US20040137268, US20040137267 |

Blue hosts

| | | |
| --- | --- | --- |
| Arylcarbazoles | | Appl. Phys. Lett. 82, 2422 (2003) |
| | | US20070190359 |
| Dibenzothiophene/ Dibenzofuran-carbazole compounds | | WO2006114966, US20090167162 |
| | | US20090167162 |

TABLE A-continued
| MATERIAL | EXAMPLES OF MATERIAL | PUBLICATIONS |
|---|---|---|
| | 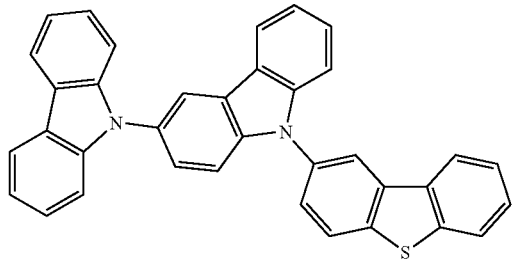 [SMILES: c1ccc2c(c1)sc1ccc(-n3c4ccccc4c4cc(-n5c6ccccc6c6ccccc65)ccc43)cc12] | WO2009086028 |
| | 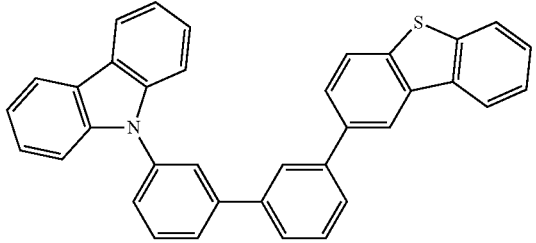 [SMILES: c1cc(-c2cccc(-n3c4ccccc4c4ccccc43)c2)cc(-c2ccc3sc4ccccc4c3c2)c1] | US20090030202, US20090017330 |
| | 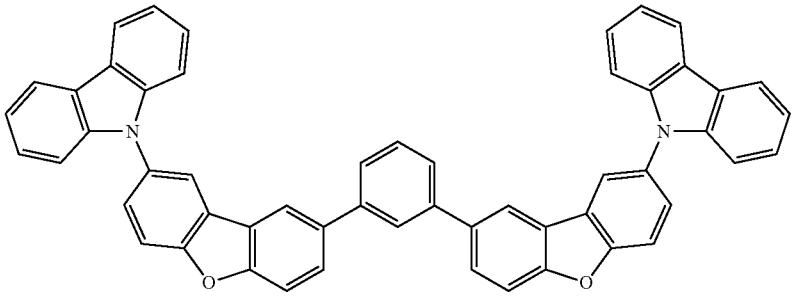 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 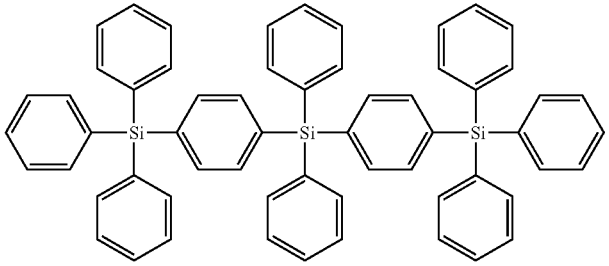 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 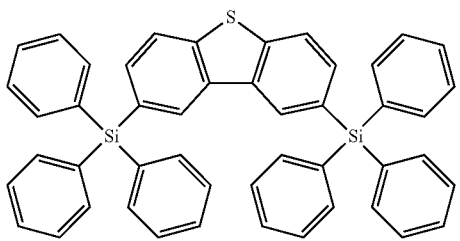 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE A-continued
| MATERIAL | EXAMPLES OF MATERIAL | PUBLICATIONS |
|---|---|---|
| Silicon/Germanium aryl compounds | 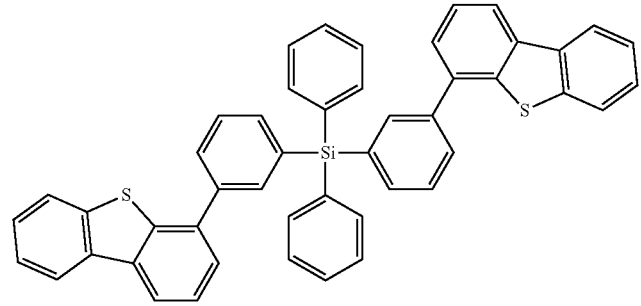 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 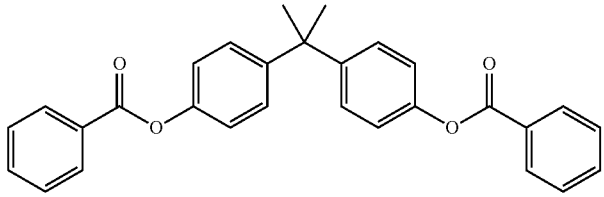 [SMILES: CC(C)(c1ccc(OC(=O)c2ccccc2)cc1)c1ccc(OC(=O)c2ccccc2)cc1] | WO2006100298 |
| Carbazole linked by non-conjugated groups | 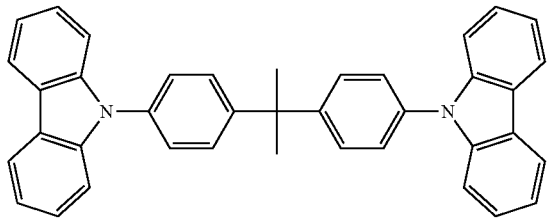 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 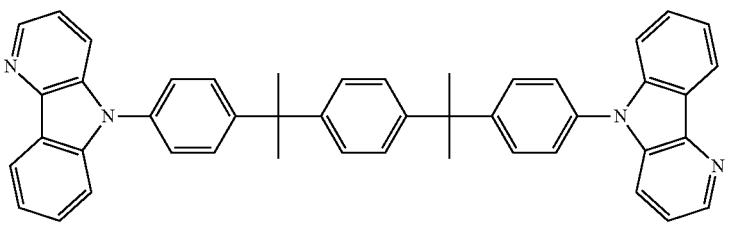 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| High triplet metal organometallic complex | 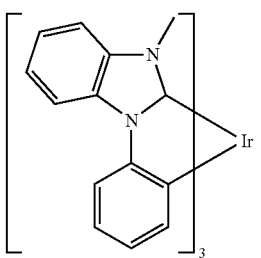 | U.S. Pat. No. 7,154,114 |

TABLE A-continued

| MATERIAL | EXAMPLES OF MATERIAL | PUBLICATIONS |
| --- | --- | --- |
| | Phosphorescent dopants | |
| | Red dopants | |
| Heavy metal porphyrins (e.g., PtOEP) | | Nature 395, 151 (1998) |
| Iridium (III) organometallic complexes | | Appl. Phys. Lett. 78, 1622 (2001) |
| | | US20030072964 |
| | | US20030072964 |
| | | US20060202194 |

TABLE A-continued
| MATERIAL | EXAMPLES OF MATERIAL | PUBLICATIONS |
|---|---|---|
| | 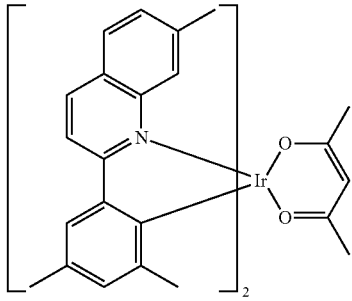 | US20060202194 |
| | 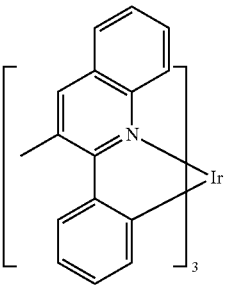 | US20070087321 |
| | 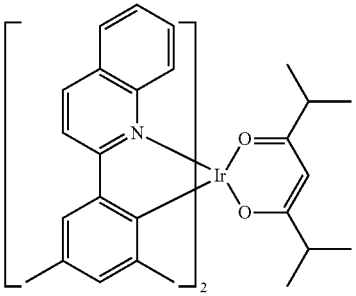 | US20080261076<br>US20100090591 |
| | 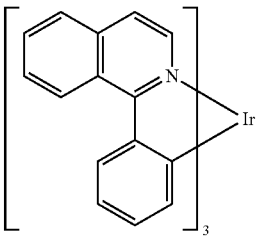 | US20070087321 |
| | 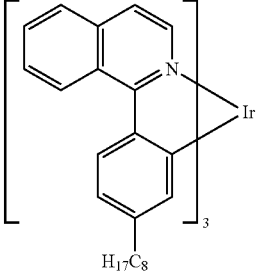 | Adv. Mater. 19, 739 (2007) |

| MATERIAL | EXAMPLES OF MATERIAL | PUBLICATIONS |
|---|---|---|
| | 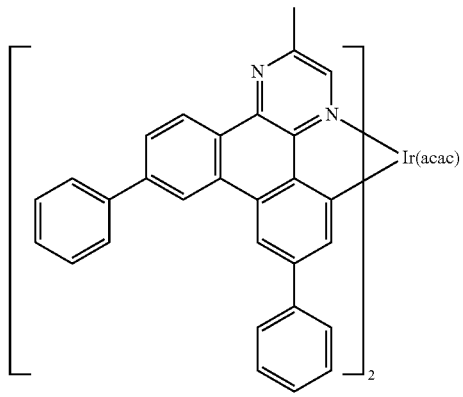 | WO2009100991 |
| | 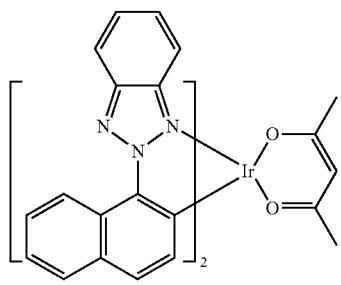 | WO2008101842 |
| | 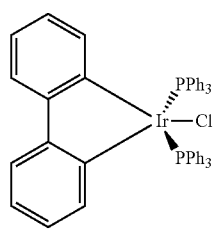 | U.S. Pat. No. 7,232,618 |
| Platinum (II) organometallic complexes | 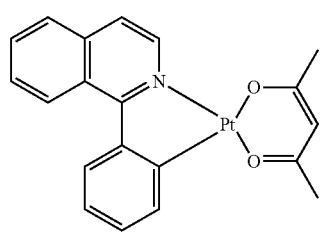 | WO2003040257 |
| | 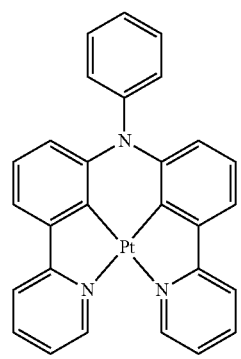 | US20070103060 |

TABLE A-continued

| MATERIAL | EXAMPLES OF MATERIAL | PUBLICATIONS |
|---|---|---|
| Osminum (III) complexes | | Chem. Mater. 17, 3532 (2005) |
| Ruthenium (II) complexes | | Adv. Mater. 17, 1059 (2005) |
| Rhenium (I), (II), and (III) complexes | | US20050244673 |

Green dopants

| | | |
|---|---|---|
| Iridium (III) organometallic complexes | and its derivatives | Inorg. Chem. 40, 1704 (2001) |
| | | US20020034656 |

TABLE A-continued
| MATERIAL | EXAMPLES OF MATERIAL | PUBLICATIONS |
|---|---|---|
| | 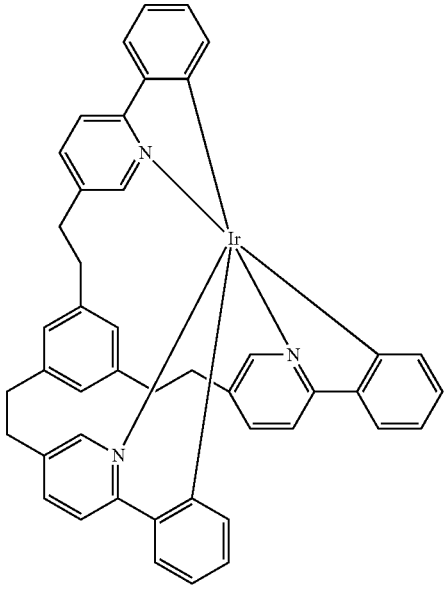 | U.S. Pat. No. 7,332,232 |
| | 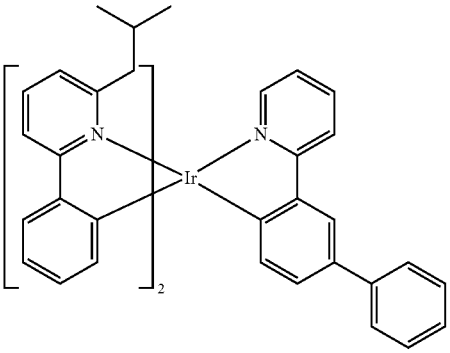 | US20090108737 |
| | 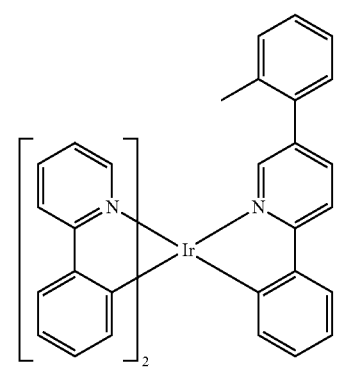 | WO2010028151 |

TABLE A-continued

| MATERIAL | EXAMPLES OF MATERIAL | PUBLICATIONS |
|---|---|---|
| | | EP1841834B |
| | | US20060127696 |
| | | US20090039776 |
| | | U.S. Pat. No. 6,921,915 |
| | | US20100244004 |

TABLE A-continued

| MATERIAL | EXAMPLES OF MATERIAL | PUBLICATIONS |
|---|---|---|
| | | U.S. Pat. No. 6,687,266 |
| | | Chem. Mater. 16, 2480 (2004) |
| | | US20070190359 |
| | | US 20060008670 JP2007123392 |
| | | WO2010086089, WO2011044988 |
| | | Adv. Mater. 16, 2003 (2004) |

TABLE A-continued
| MATERIAL | EXAMPLES OF MATERIAL | PUBLICATIONS |
|---|---|---|
| | 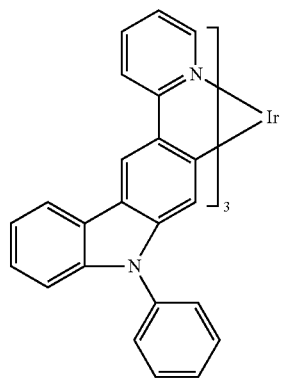 | Angew. Chem. Int. Ed. 2006, 45, 7800 |
| | 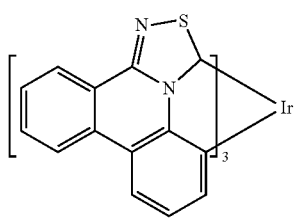 | WO2009050290 |
| | 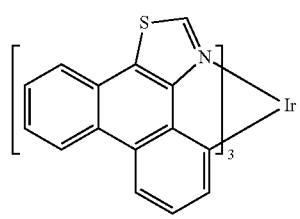 | US20090165846 |
| | 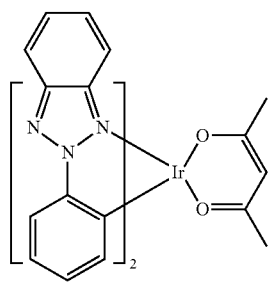 | US20080015355 |
| | 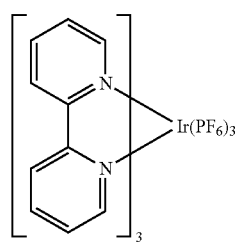 | US20010015432 |
| | 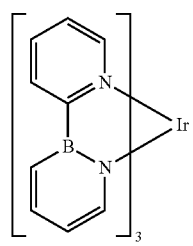 | US20100295032 |

TABLE A-continued
| MATERIAL | EXAMPLES OF MATERIAL | PUBLICATIONS |
|---|---|---|
| Monomer for polymeric metal organometallic compounds | 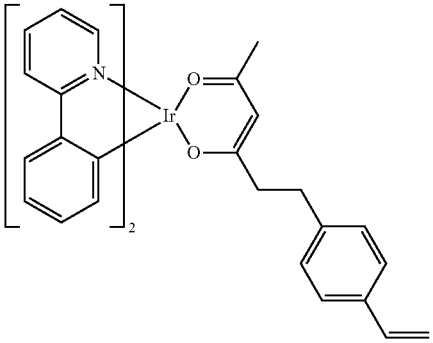 | U.S. Pat. No. 7,250,226, U.S. Pat. No. 7,396,598 |
| Pt (II) organometallic complexes, including polydentated ligands | 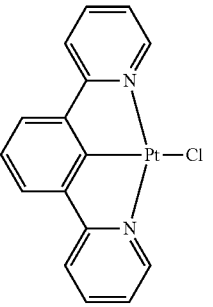 | Appl. Phys. Lett. 86, 153505 (2005) |
| | 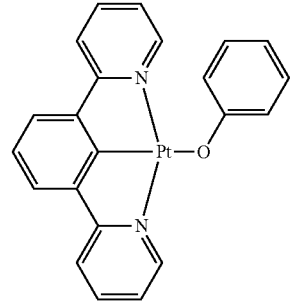 | Appl. Phys. Lett. 86, 153505 (2005) |
| | 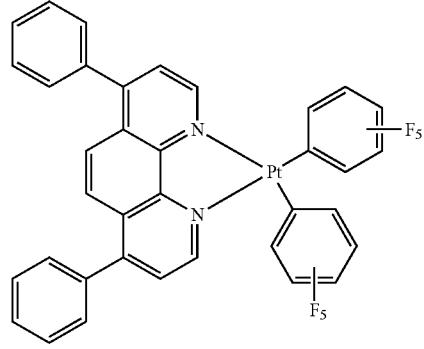 | Chem. Lett. 34, 592 (2005) |
| | 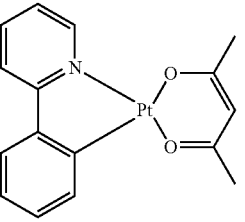 | WO2002015645 |

TABLE A-continued
| MATERIAL | EXAMPLES OF MATERIAL | PUBLICATIONS |
|---|---|---|
| | 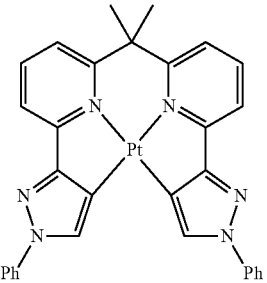 | US20060263635 |
| | 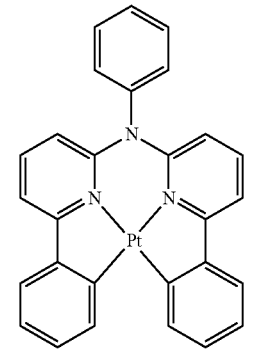 | US20060182992<br>US20070103060 |
| Cu complexes | 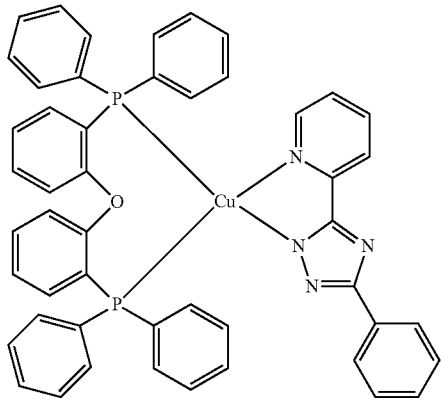 | WO2009000673 |
| | 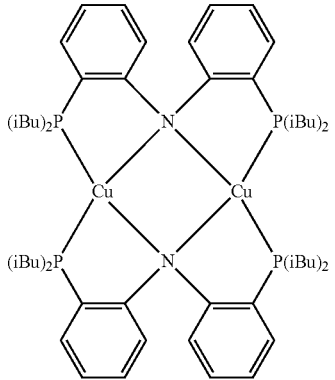 | US20070111026 |

TABLE A-continued

| MATERIAL | EXAMPLES OF MATERIAL | PUBLICATIONS |
| --- | --- | --- |
| Gold complexes | | Chem. Commun. 2906 (2005) |
| Rhenium (III) complexes | | Inorg. Chem. 42, 1248 (2003) |
| Osmium (II) complexes | | U.S. Pat. No. 7,279,704 |
| Deuterated organometallic complexes | | US20030138657 |

TABLE A-continued

| MATERIAL | EXAMPLES OF MATERIAL | PUBLICATIONS |
|---|---|---|
| Organometallic complexes with two or more metal centers | [structure] | US20030152802 |
| | [structure] | U.S. Pat. No. 7,090,928 |
| Blue dopants | | |
| Iridium (III) organometallic complexes | [structure] | WO2002002714 |
| | [structure] | WO2006009024 |
| | [structure] | US20060251923<br>US20110057559<br>US20110204333 |

TABLE A-continued

| MATERIAL | EXAMPLES OF MATERIAL | PUBLICATIONS |
|---|---|---|
| | | U.S. Pat. No. 7,393,599, WO2006056418, US20050260441, WO2005019373 |
| | | U.S. Pat. No. 7,534,505 |
| | | WO2011051404 |
| | | U.S. Pat. No. 7,445,855 |
| | | US20070190359, US20080297033 US20100148663 |

TABLE A-continued
| MATERIAL | EXAMPLES OF MATERIAL | PUBLICATIONS |
|---|---|---|
| | 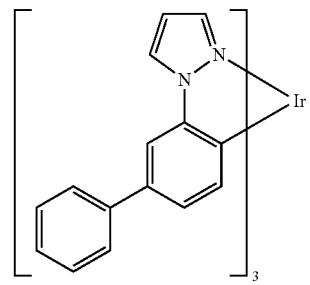 | U.S. Pat. No. 7,338,722 |
| | 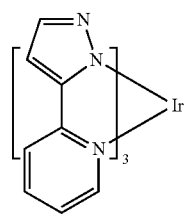 | US20020134984 |
| | 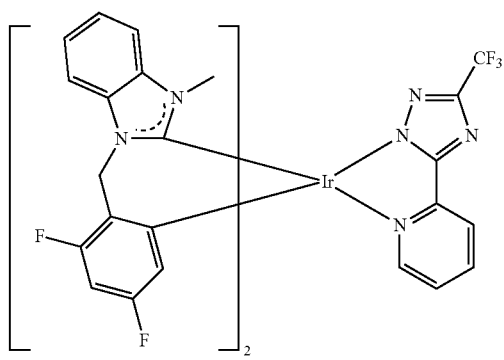 | Angew. Chem. Int. Ed. 47, 4542 (2008) |
| | 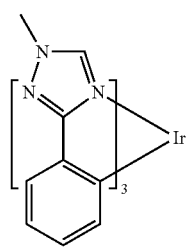 | Chem. Mater. 18, 5119 (2006) |
| | 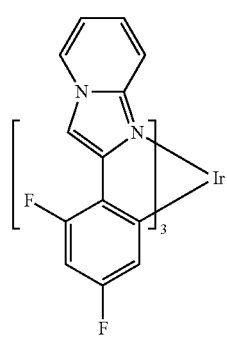 | Inorg. Chem. 46, 4308 (2007) |

TABLE A-continued

| MATERIAL | EXAMPLES OF MATERIAL | PUBLICATIONS |
|---|---|---|
| | | WO2005123873 |
| | | WO2005123873 |
| | | WO2007004380 |
| | | WO2006082742 |
| Osmium (II) complexes | | U.S. Pat. No. 7,279,704 |

| MATERIAL | EXAMPLES OF MATERIAL | PUBLICATIONS |
|---|---|---|
| | 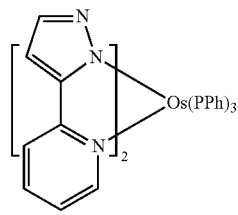 | Organometallics 23, 3745 (2004) |
| Gold complexes | 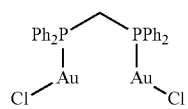 | Appl. Phys. Lett. 74, 1361 (1999) |
| Platinum (II) complexes | 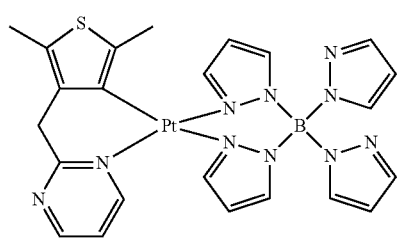 | WO2006098120, WO2006103874 |
| Pt tetradentate complexes with at least one metal-carbene bond | 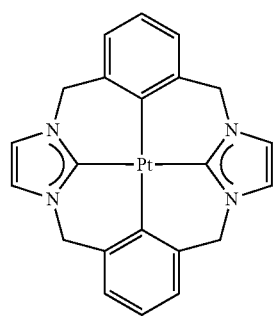 | U.S. Pat. No. 7,655,323 |
| Exciton/hole blocking layer materials | | |
| Bathocuproine compounds (e.g., BCP, BPhen) | 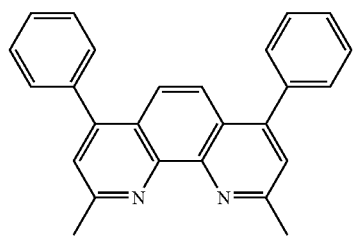 [SMILES: Cc1cc(-c2ccccc2)c2ccc3c(-c4ccccc4)cc(C)nc3c2n1] | Appl. Phys. Lett. 75, 4 (1999) |
| | 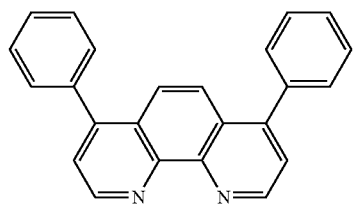 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 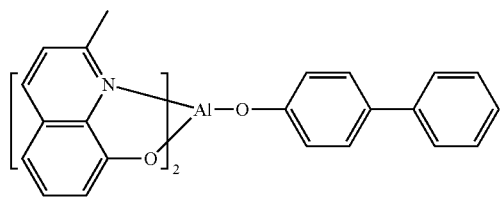 | Appl. Phys. Lett. 81, 162 (2002) |

TABLE A-continued

| MATERIAL | EXAMPLES OF MATERIAL | PUBLICATIONS |
| --- | --- | --- |
| 5-member ring electron deficient heterocycles such as triazole, oxadiazole, imidazole, benzoimidazole | | Appl. Phys. Lett. 81, 162 (2002) |
| Triphenylene compounds | | US20050025993 |
| Fluorinated aromatic compounds | | Appl. Phys. Lett. 79, 156 (2001) |

TABLE A-continued

| MATERIAL | EXAMPLES OF MATERIAL | PUBLICATIONS |
|---|---|---|
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |
| Electron transporting materials | | |
| Anthracene-benzoimidazole compounds | | WO2003060956 |
| | | US20090179554 |

TABLE A-continued

| MATERIAL | EXAMPLES OF MATERIAL | PUBLICATIONS |
| --- | --- | --- |
| Aza triphenylene derivatives | | US20090115316 |
| Anthracene-benzothiazole compounds | | Appl. Phys. Lett. 89, 063504 (2006) |
| Metal 8-hydroxyquinolates (e.g., Alq$_3$, Zrq$_4$) | | Appl. Phys. Lett. 51, 913 (1987) U.S. Pat. No. 7,230,107 |
| Metal hydroxybenzoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

TABLE A-continued

| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |
| Silole compounds | | Org. Electron. 4, 113 (2003) |
| Arylborane compounds | | J. Am. Chem. Soc. 120, 9714 (1998) |

TABLE A-continued
| MATERIAL | EXAMPLES OF MATERIAL | PUBLICATIONS |
|---|---|---|
| Fluorinated aromatic compounds | 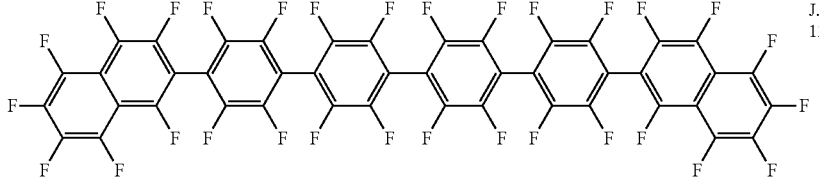 | J. Am. Chem. Soc. 122, 1832 (2000) |
| Fullerene (e.g., $C_{60}$) | 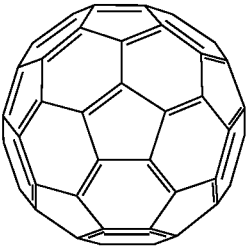 | US20090101870 |
| Triazine complexes | 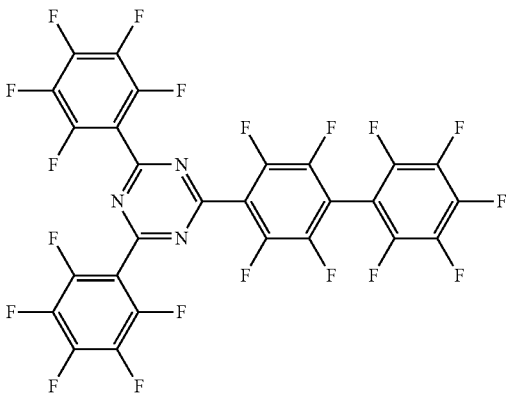 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 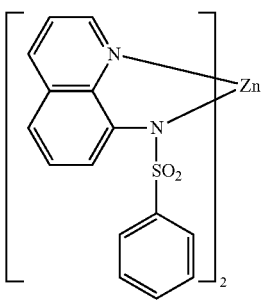 | U.S. Pat. No. 6,528,187 |

EXPERIMENTAL

Synthetic Examples

Synthesis of Compound F14

Synthesis of N-(2-(dibenzo[b,d]thiophen-2-yl)phenyl)-[1,1'-biphenyl]-2-amine

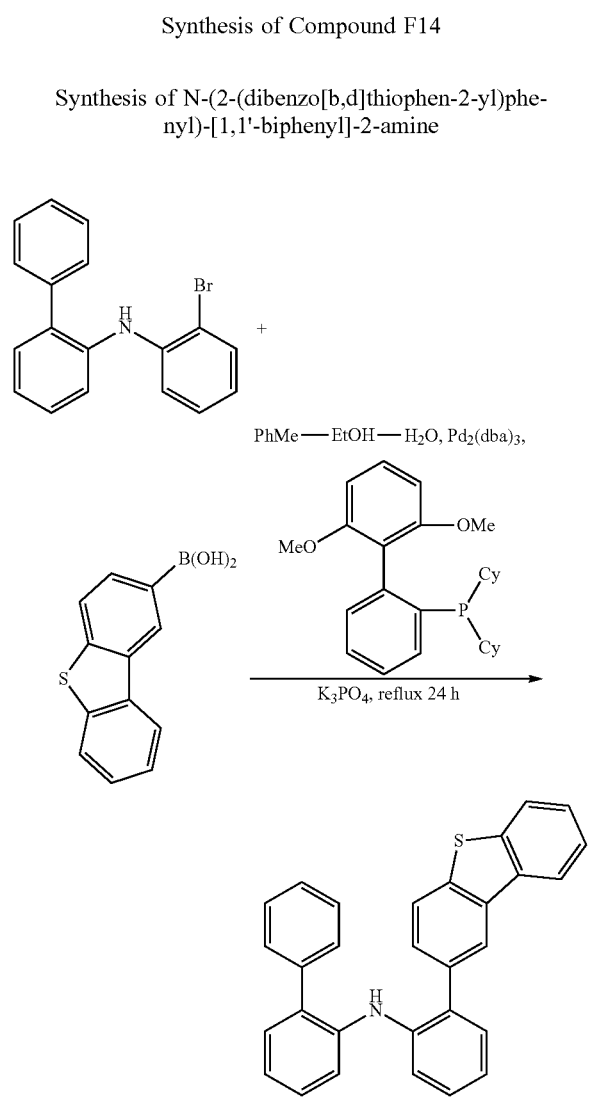

N-(2-bromophenyl)-[1,1'-biphenyl]-2-amine was prepared in accordance with *Journal of Organic Chemistry*, 2009, 74, 4490-4498. Toluene-ethanol-water (50 mL, 9:0.5:0.5) was bubbled with nitrogen for 15 min, followed by addition of 2-dicyclohexylphosphino-2',6'-dimethoxybiphenyl (0.65 g, 1.58 mmol) and Pd$_2$(dba)$_3$ (147 mg, 0.16 mmol). The mixture was bubbled with nitrogen for 15 min, then N-(2-bromophenyl)-[1,1'-biphenyl]-2-amine (4.02 g, 12.41 mmol), dibenzothiophene-2-boronic acid (5.13 g, 16.55 mmol), and K$_3$PO$_4$ (7.90 g, 37.26 mmol) were added. The mixture was bubbled with nitrogen for 15 min and refluxed for 24 h. After cooling, the reaction mixture was filtered through a Celite® (silica gel) pad and washed with toluene. The solvent was removed in vacuo and the residue was purified by flash column chromatography with dichloromethane-hexane (1:9) to give N-(2-(dibenzo[b,d]thiophen-2-yl)phenyl)-[1,1'-biphenyl]-2-amine (2.11 g, 40% yield) as a white solid.

Synthesis of Compound F14

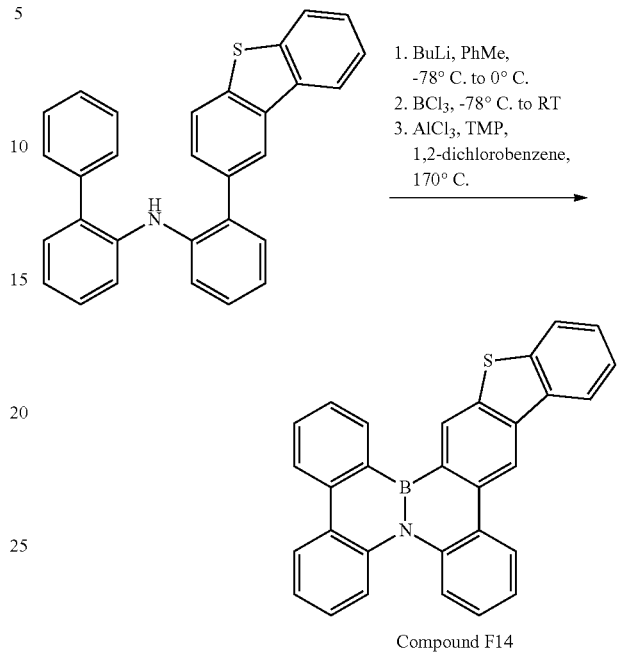

Compound F14

A solution of butyllithium in hexane (3.60 mL, 1.60 M, 5.76 mmol) was added slowly to a solution of the amine compound (2.11 g, 4.94 mmol) in toluene (25 mL) at −78° C. under nitrogen. After the reaction mixture was stirred at 0° C. for 1 h, it was cannulated to a solution of boron trichloride in heptane (12.5 mL, 1.0 M, 12.5 mmol) at −78° C. After being stirred at room temperature (~22° C.), the solvent was removed in vacuo. A mixture of aluminum trichloride (2.64 g, 19.80 mmol) and 2,2,6,6-tetra methylpiperidine (1.67 mL, 9.9 mmol) in 1,2-dichlorobenzene (300 mL) was added to the reaction mixture at room temperature (~22° C.). After stirring at 170° C. for 8 h, the reaction mixture was cooled and quenched with 2M Na$_2$CO$_3$ solution. The reaction mixture was filtered with a pad of Celite®. After the solvent was removed in vacuo, the crude product was purified by flash column chromatography with 10-15% dichloromethane in hexane+2% triethylamine to give Compound F14 (1.20 g, 56% yield) as a white-yellow powder.

Synthesis of Compound S50

Synthesis of 4b-aza-12b-boradibenzo[g,p]chrysene

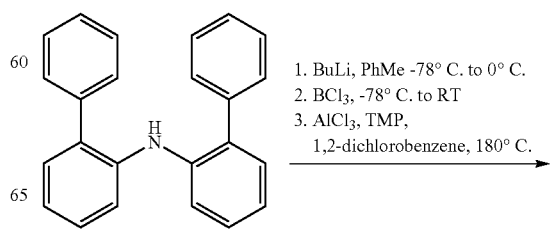

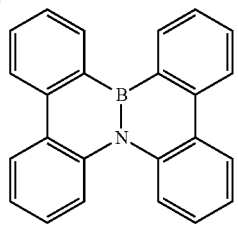

A solution of butyllithium in hexane (29 mL, 1.60 M, 46.4 mmol) was added slowly to a solution of N-[1,1'-biphenyl]-2-yl-[1,1'-biphenyl]-2-amine (12.88 g, 40.1 mmol) in toluene (200 mL) at −78° C. under nitrogen. The reaction mixture was stirred at 0° C. for 1 h and cannulated to a solution of boron trichloride heptane (100 mL, 1.0 M, 100 mmol) at −78° C. The reaction mixture was warmed to room temperature (~22° C.) and the solvent was removed in vacuo. A solution of aluminum trichloride (21.40 g, 160.5 mmol) and 2,2,6-6-tetramethylpiperidine (13.5 mL, 80.0 mmol) in 1,2-dichlorobenzene (200 mL) was added to the reaction mixture, which was then heated to 180° C. for 6 h. The reaction mixture was quenched with 2M $Na_2CO_3$ solution and was filtered with a pad of Celite® and washed with dichloromethane. After the solvent was removed in vacuo, the crude mixture was purified by flash column chromatography with 5-10% dichloromethane in hexane+2% triethylamine to obtain 4b-aza-12b-boradibenzo[g,p]chrysene (6.00 g, 45% yield) as a white powder.

Synthesis of 2,7-dibromo-4b-aza-12b-boradibenzo[g,p]chrysene

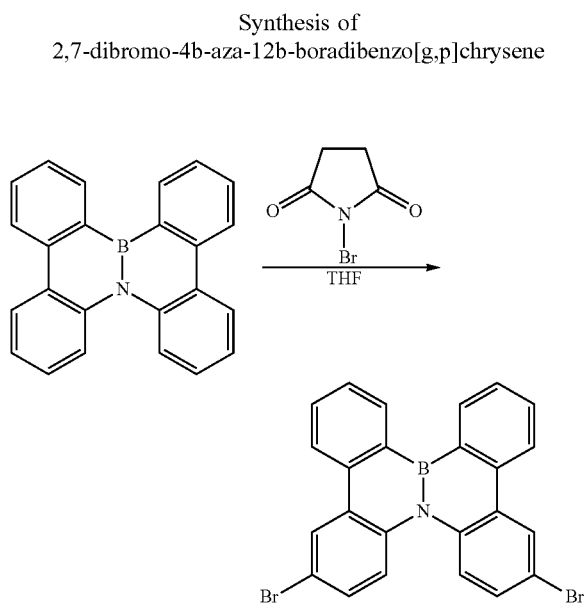

N-Bromosuccinitnide (1.55 g, 8.71 mmol) was added to a solution of 4b-aza-12b-boradibenzo[g,p]chrysene (1.35 g, 4.21 mmol) in THF (15 mL). After the mixture was stirred at room temperature for 50 min, the solvent was removed in vacuo. The residue was triturated with recrystallized in heptane (16 mL) to yield 2,7-dibromo-4b-aza -12b-boradibenzo[g,p]chrysene (1.89 g, 92% yield) as a white powder.

Synthesis of Compound S50

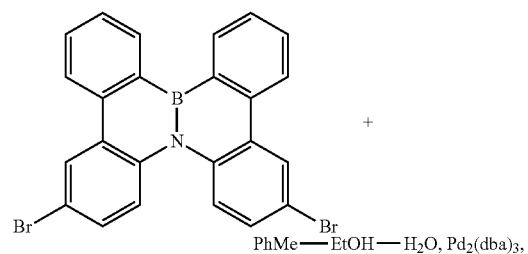

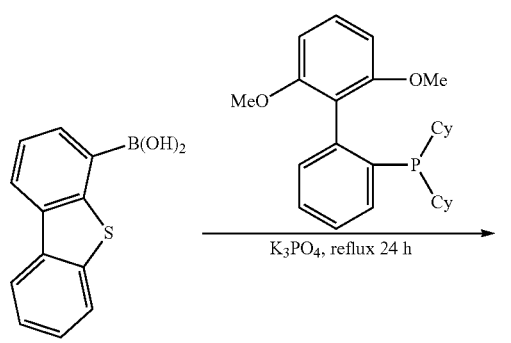

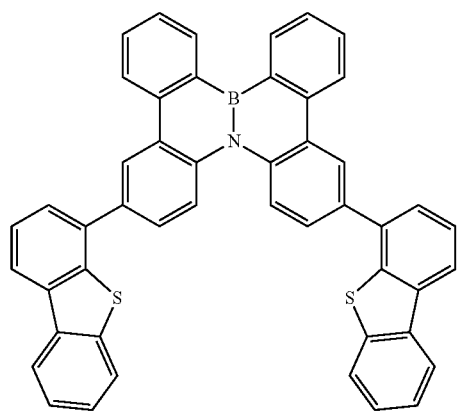

Compound S50

Toluene-ethanol-water (50 mL, 9:0.5:0.5) was bubbled with nitrogen for 15 min, followed by addition of 2-dicyclohexylphosphino-2',6'-dimethoxybiphenyl (0.52 g, 1.27 mmol) and $Pd_2(dba)_3$ (0.38 g, 0.41 mmol). The mixture was bubbled with nitrogen for 15 min, then 2,7-dibromo-4b-aza-12b-boradibenzo[g,p]chrysene (2.56 g, 5.26 mmol), dibenzothiophene-4-boronic acid (3.68 g, 16.14 mmol), and $K_3PO_4$ (6.72 g, 31.70 mmol) were added. The mixture was bubbled with nitrogen for 15 min and refluxed for 24 h. After cooling to room temperature (~22° C.), the reaction mixture was filtered through a Celite® pad and washed with toluene. The solvent was removed in vacuo and the residue was recrystallised with toluene (40 mL) to give Compound S50 (1.60 g, 44% yield) as a white solid.

Device Examples:

All device examples were fabricated by high vacuum (<$10^{-7}$ Torr) thermal evaporation. The anode electrode was ~800 Å of indium tin oxide (ITO). The cathode consisted of 5 Å of LiF followed by 1,000 Å of Al. All devices were encapsulated with a glass lid sealed with an epoxy resin in a nitrogen glove box (<1 ppm of $H_2O$ and $O_2$) and a moisture getter was incorporated inside the package. Compounds A through E have the following meanings:

Compound A

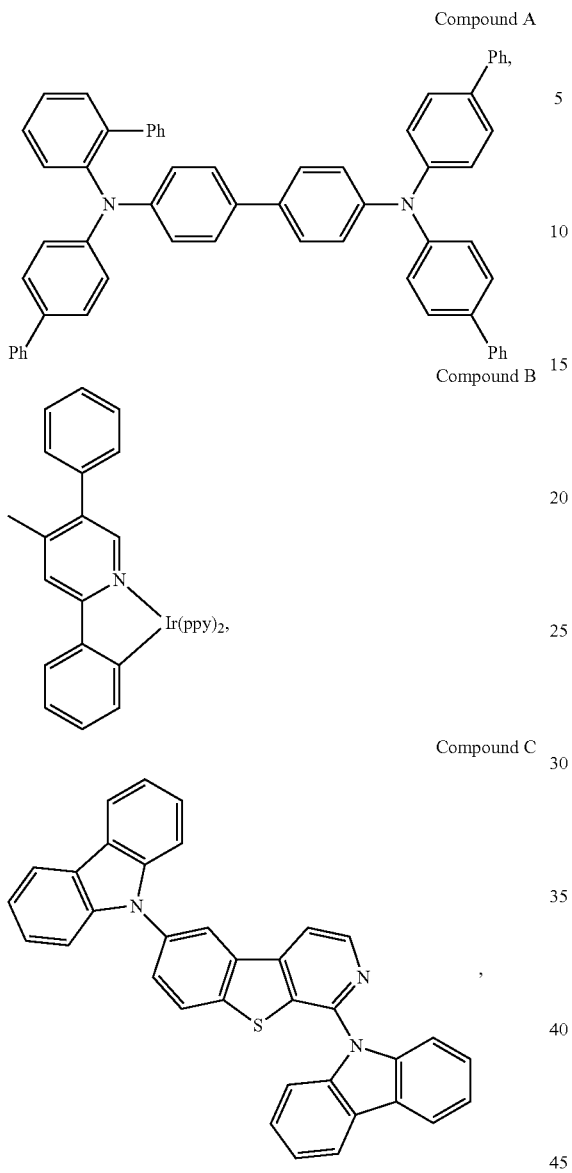

Compound B

Compound C

The organic stack of Device Example 1 consists of 100 Å of LG101 (purchased from LG Chem, Korea) as the hole injection layer (HIL), 450 Å of Compound A as the hole transporting layer (HTL), 400 Å of Compound F14 doped with 20% of Compound B as the emissive layer (EML), 50 Å of Compound C as the ETL2 and 350 Å of Alq$_3$ as the ETL1. At 1000 cd/m$^2$, the CIE is 0.341, 0.618. The external quantum efficiency was 16.1%.

The organic stack of the Device Example 2 consists of 100 Å of LG101 as the hole injection layer (HIL), 450 Å of Compound A as the hole transporting layer (HTL), 400 Å of Compound S50 doped with 10% of Compound B as the emissive layer (EML), 50 Å of Compound C as the ETL2 and 350 Å of Alq$_3$ as the ETL1. At 1000 cd/m$^2$, the CIE is 0343, 0.617. The external quantum efficiency was 15.3%.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A compound having a structure of Formula I:

$$G^1\text{-}L^1\text{-}G^2 \quad \text{Formula I;}$$

wherein $G^1$ and $G^2$ independently have a structure of Formula II:

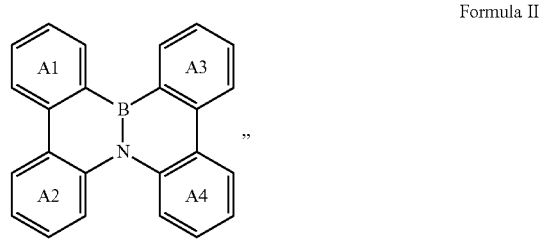

Formula II wherein $G^1$ and $G^2$ can be same or different;
wherein $L^1$ connects one of rings A1, A2, A3, and A4 of $G^1$ to one of rings A1, A2, A3, and A4 of $G^2$;
wherein $L^1$ is selected from the group consisting of a direct bond, BR, NR, PR, O, S, Se, C=O, S=O, SO$_2$, SiRR', GeRR', alkyl, cycloalkyl, aryl, heteroaryl, and combinations thereof;
wherein each ring A1, A2, A3, and A4 in Formula II can be further substituted by one or more substituents selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein R, R' are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein any adjacent substitutions are optionally joined or fused into a ring.

2. The compound of claim 1, wherein $L^1$ is a direct bond.

3. The compound of claim 1, wherein $L^1$ is selected from the group consisting of SiRR', GeRR', alkyl, cycloalkyl, and combinations thereof.

4. The compound of claim 1, wherein the compound comprises a structure selected from the group consisting of:

Structure 1

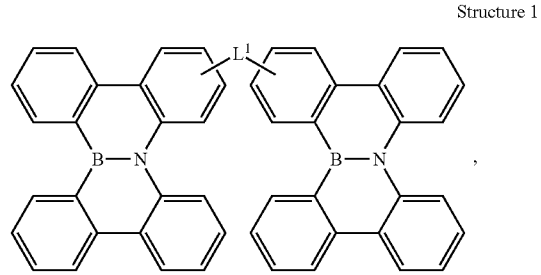

-continued

Structure 2

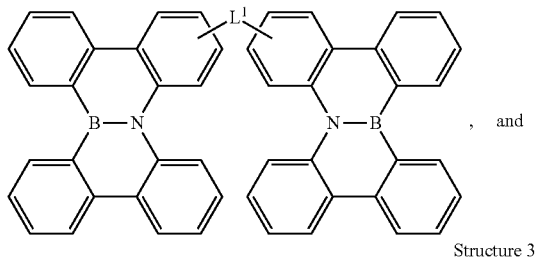

and

Structure 3

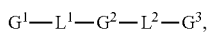

, which may be further substituted by one or more substituents independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein $L^1$ is selected from the group consisting of a direct bond, BR, NR, PR, O, S, Se, C=O, S=O, SO$_2$, SiRR', GeRR', alkyl, cycloalkyl, aryl, heteroaryl, and combinations thereof; and wherein any adjacent substitutions are optionally joined or fused into a ring.

5. The compound of claim 1, wherein the compound has a structure selected from Formula III and Formula IV:

$$G^1-L^1-G^2-L^2-G^3, \quad \text{Formula III}$$

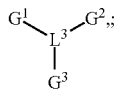 Formula IV wherein $G^3$ has a structure of Formula II,
wherein $G^3$ can be same as or different from $G^1$ and $G^2$;
wherein, in Formula III:
  $L^2$ is selected from the group consisting of a direct bond, BR, NR, PR, O, S, Se, C=O, S=O, SO$_2$, SiRR', GeRR', alkyl, cycloalkyl, aryl, heteroaryl, and combinations thereof, and
  $L^2$ connects one of the rings of A1, A2, A3, and A4 of $G^2$ to one of the rings of A1, A2, A3, and A4 of $G^3$;
wherein, in Formula IV:
  $L^3$ is selected from the group consisting of B, N, P, SiR, GeR, alkyl, cycloalkyl, aryl, heteroaryl, and combinations thereof, and
  $L^3$ connects one of the rings of A1, A2, A3, and A4 of $G^1$, one of the rings of A1, A2, A3, and A4 of $G^2$ and one of the rings of A1, A2, A3, and A4 of $G^3$;and
wherein $G^1$, $L^1$, $G^2$, R and R' have the same definitions as in claim 1.

6. The compound of claim 1, wherein the compound further comprises $G^3$ and $G^4$, both of which have a structure of Formula II,
  wherein $G^3$ is substituted on a ring selected from the group consisting of ring A1, A2, A3, and A4 of $G^1$, and ring A1, A2, A3, and A4 of $G^2$, and
  wherein $G^4$ is substituted on a ring selected from the group consisting of ring A1, A2, A3, and A4 of $G^1$, and ring A1, A2, A3, and A4 of $G^2$.

7. The compound of claim 1, wherein the compound comprises a chemical group selected from

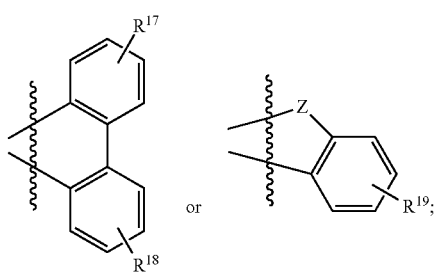

wherein the chemical group is bonded to two adjacent substituents of one of rings A1, A2, A3, and A4 of $G^1$ or $G^2$;
wherein $R^{17}$ to $R^{19}$ each independently represent mono, di, tri, or tetra substitution, or no substitution;
wherein Z is selected from the group consisting of NR, O, S and Se;
wherein R, $R^{17}$ to $R^{19}$ are each independently selected from the group A; and
wherein any adjacent substitutions of $R^{17}$ to $R^{19}$ are optionally joined or fused into a ring.

8. The compound of claim 1, wherein at least one of the one or more substituents is a chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene.

9. The compound of claim 1, wherein the compound comprises a structure selected from the group consisting of:

Structure A1

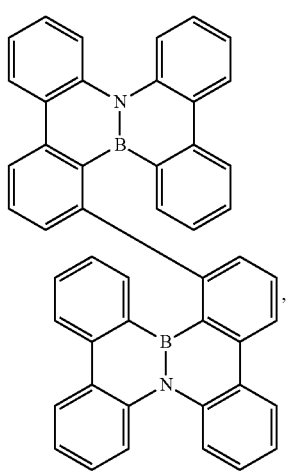

,

Structure A2
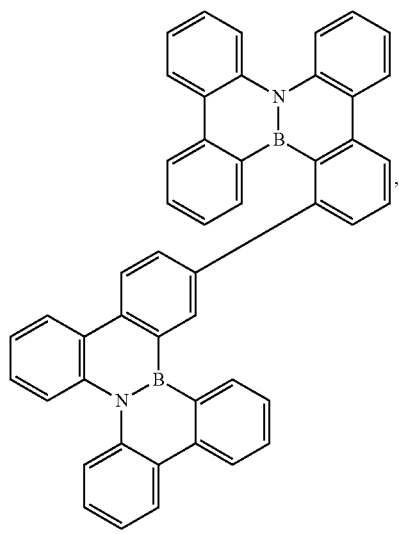
Structure A3
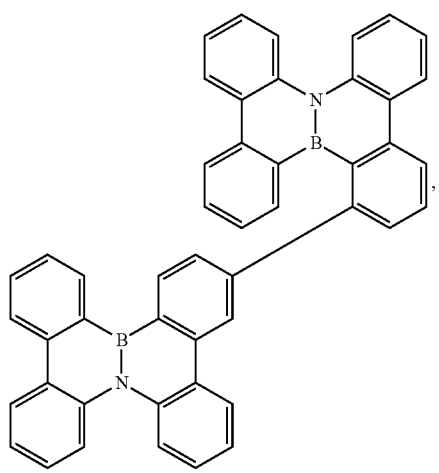
Structure A4
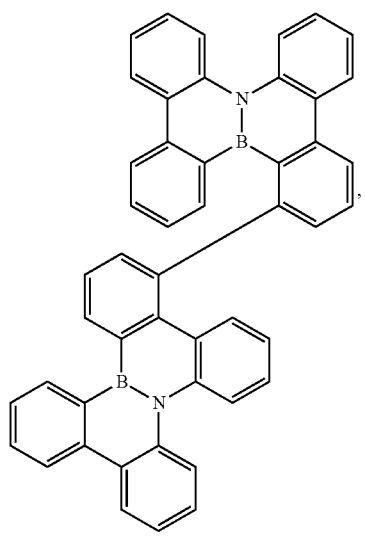
Structure A5
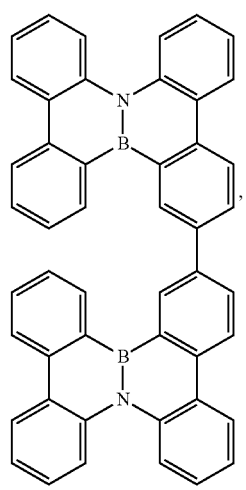
Structure A6
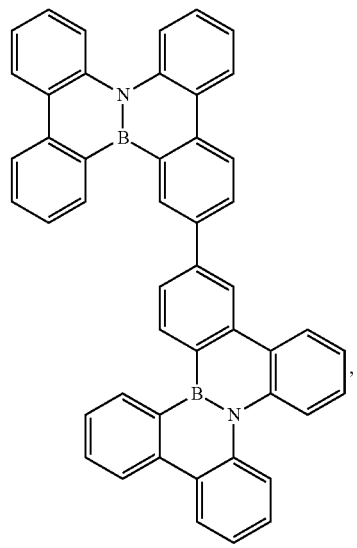
Structure A7
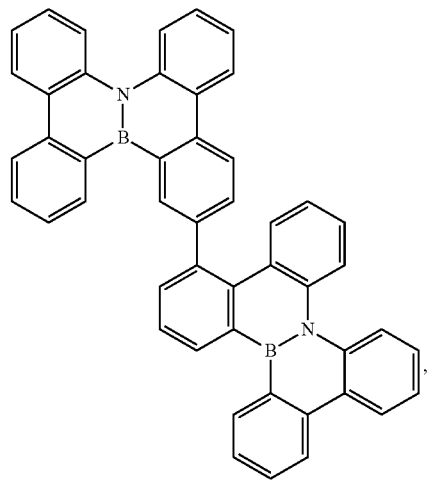

Structure A8
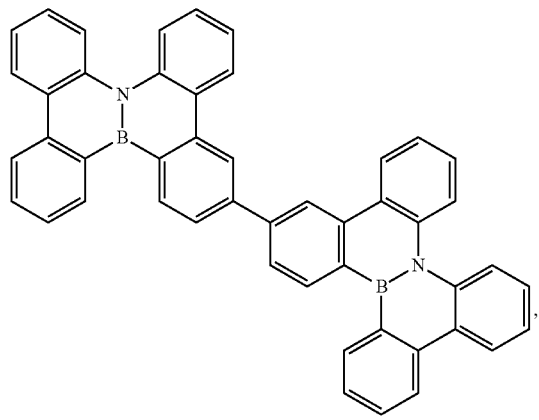
Structure A9
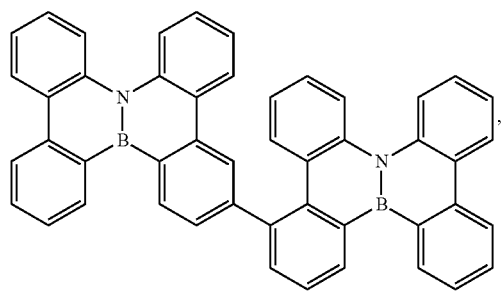
Structure A10
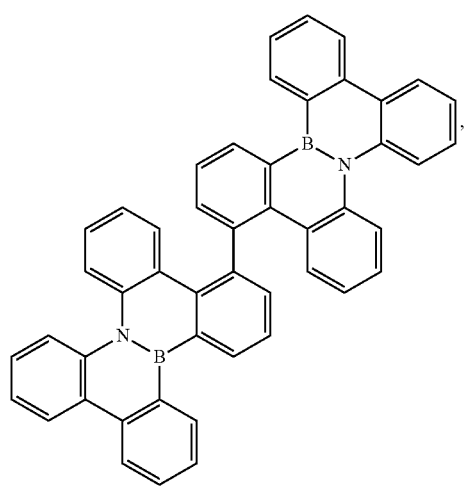
Structure A11
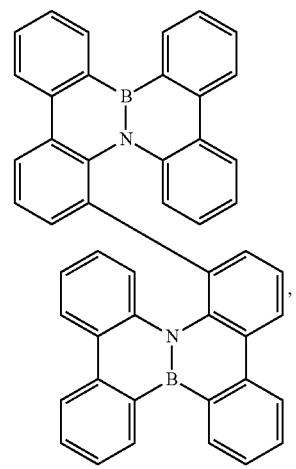
Structure A12
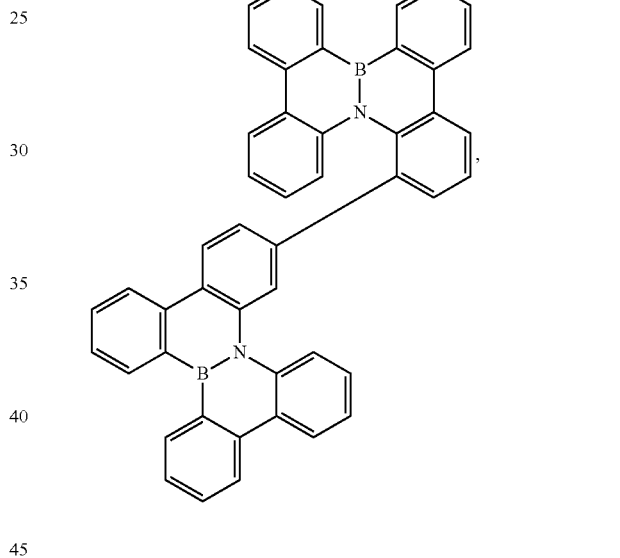
Structure A13
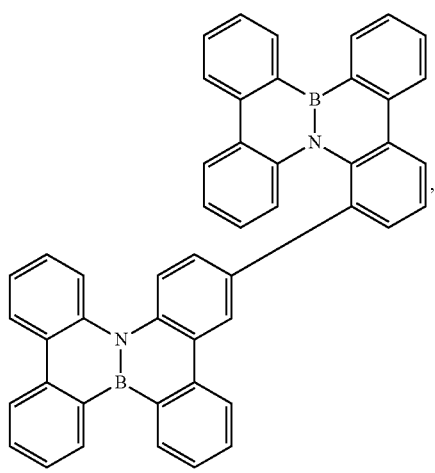

Structure A14
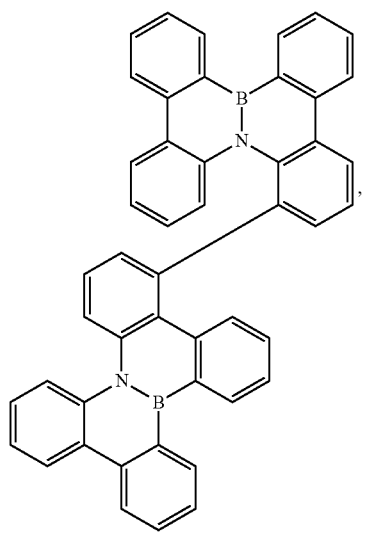
Structure A15
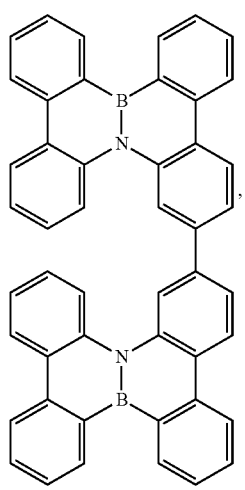
Structure A16
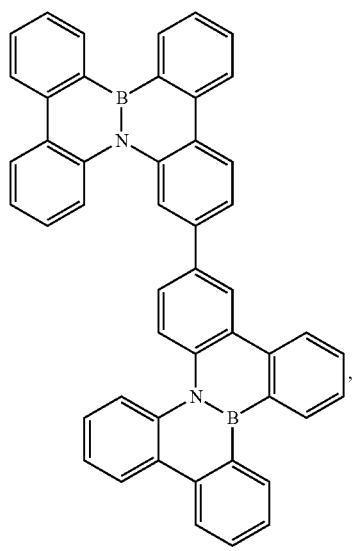
Structure A17
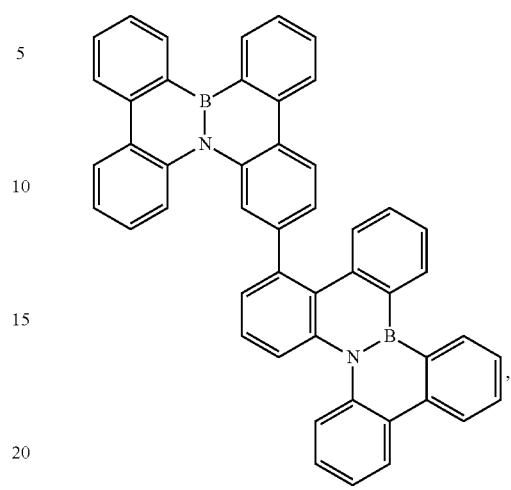
Structure A18
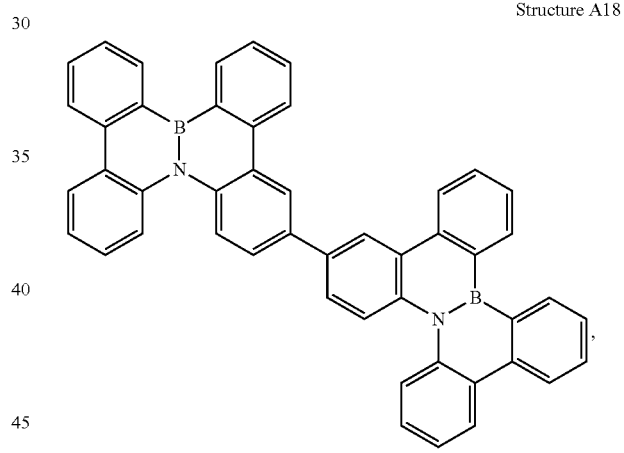
Structure A19
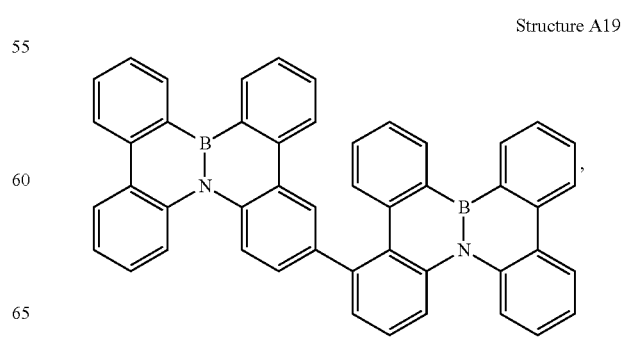

Structure A20
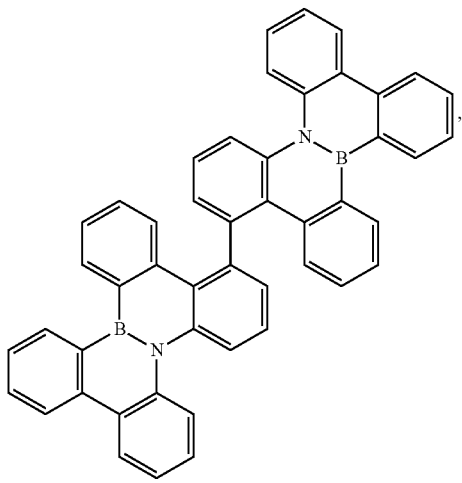
Structure A21
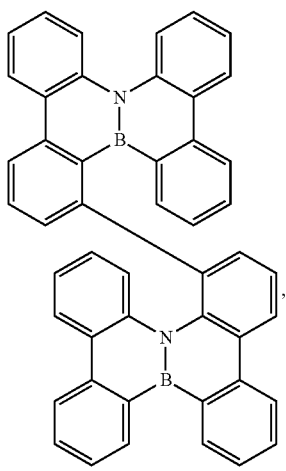
Structure A22
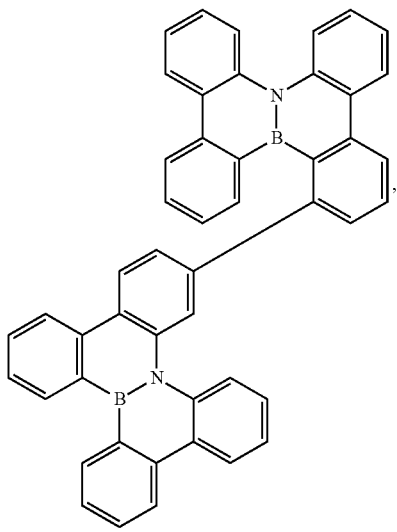
Structure A23
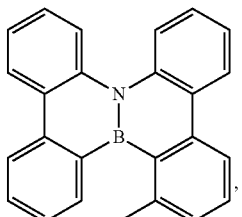
Structure A24
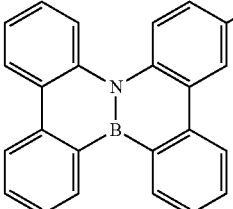
Structure A25
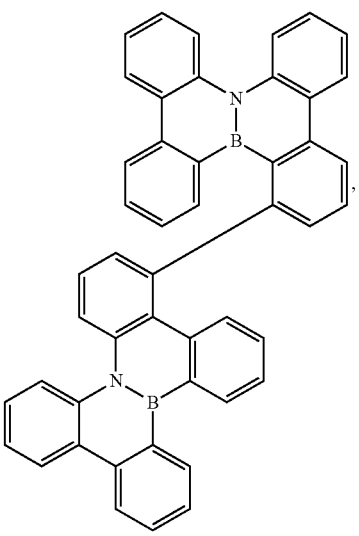

Structure A26

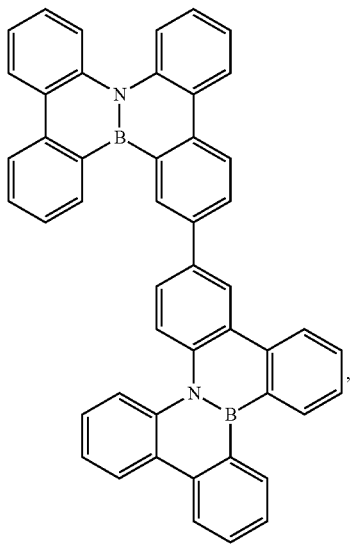

Structure A28

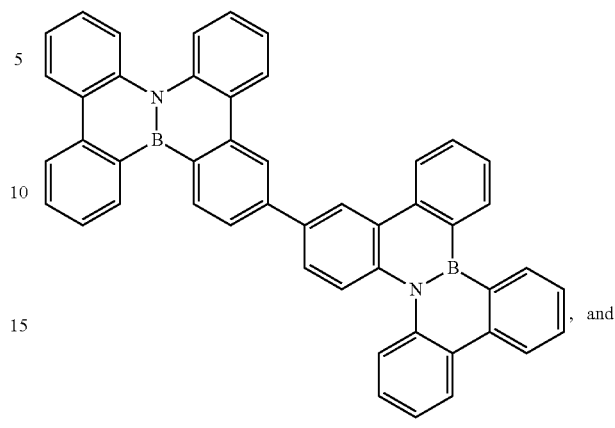
, and

Structure A29

Structure A27

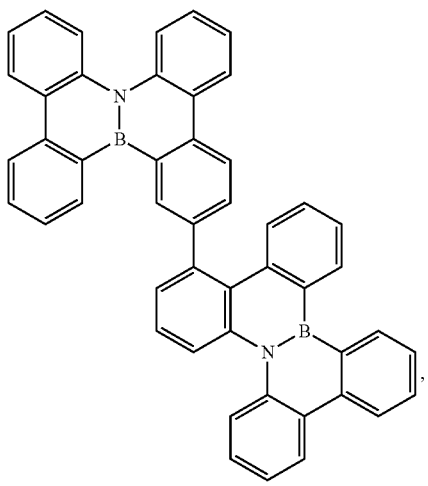

which may be further substituted by one or more substituents independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein any adjacent substitutions are optionally joined or fused into a ring.

10. The compound of claim 1, wherein the compound comprises a structure selected from the group consisting of:

Structure B1

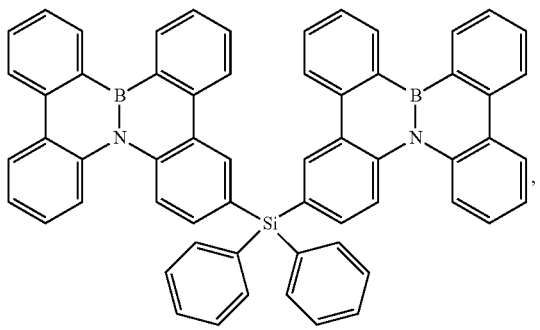
,

Structure B2

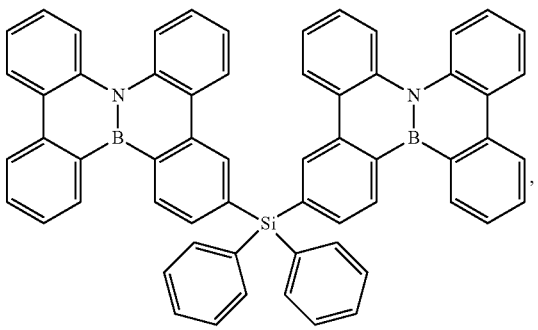
,

-continued
Structure B3
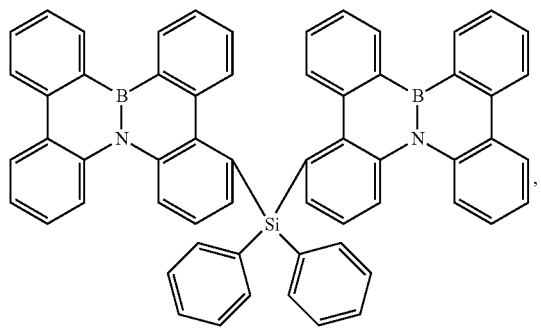
Structure B4
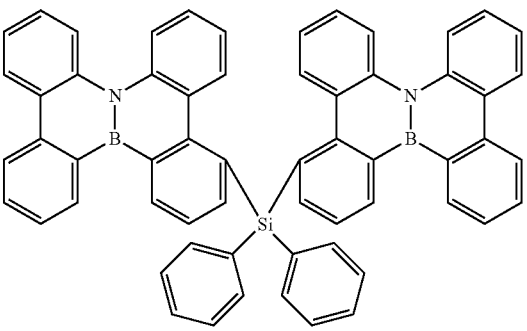
Structure B3
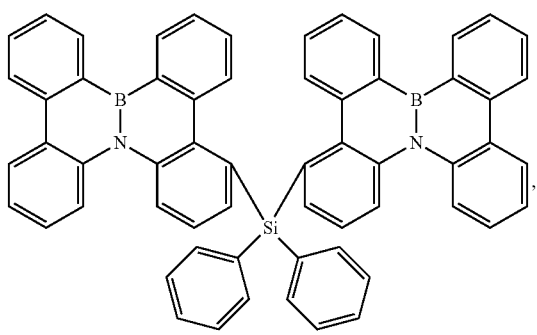
Structure B5
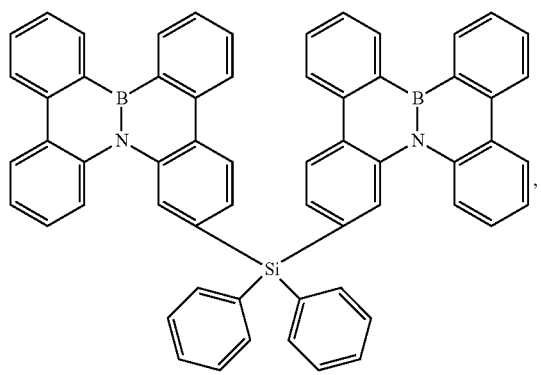
Structure B6
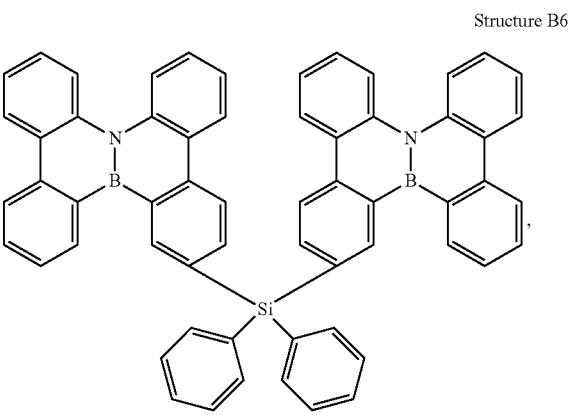
Structure B7
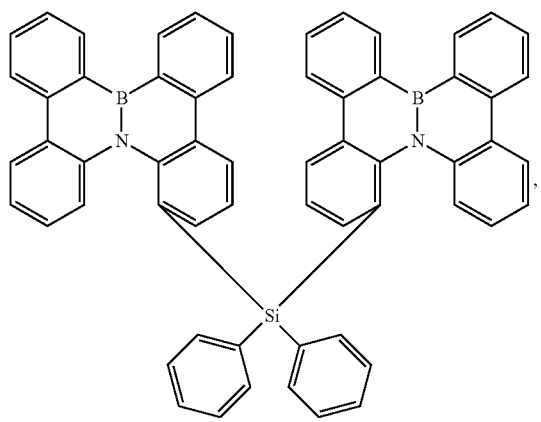
Structure B8
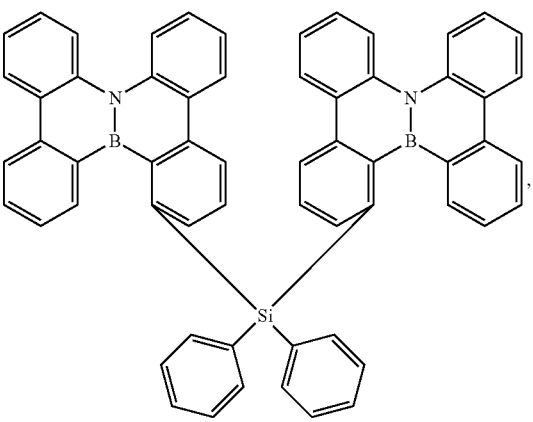

-continued
Structure B9
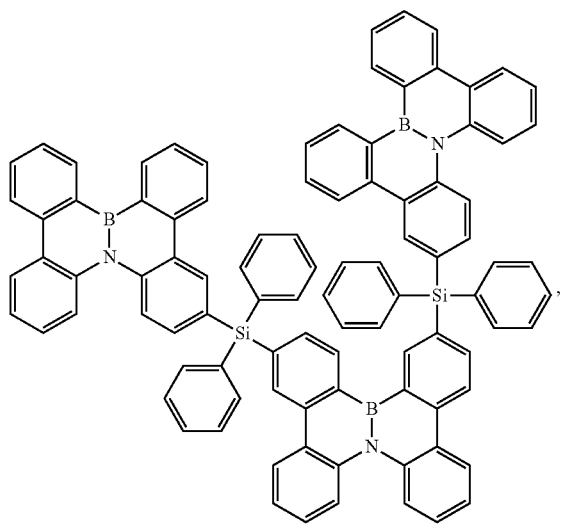
Structure B10
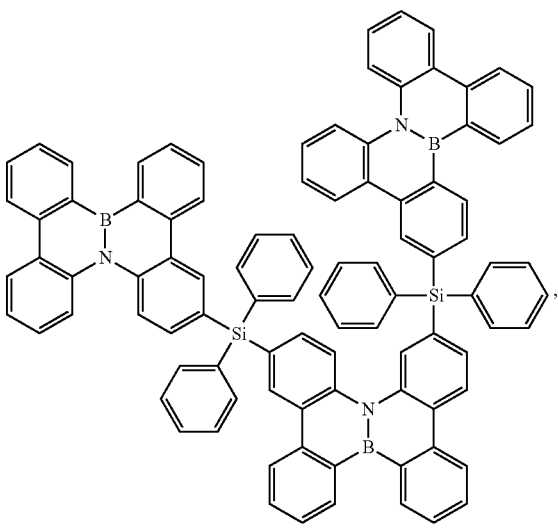
Structure B11
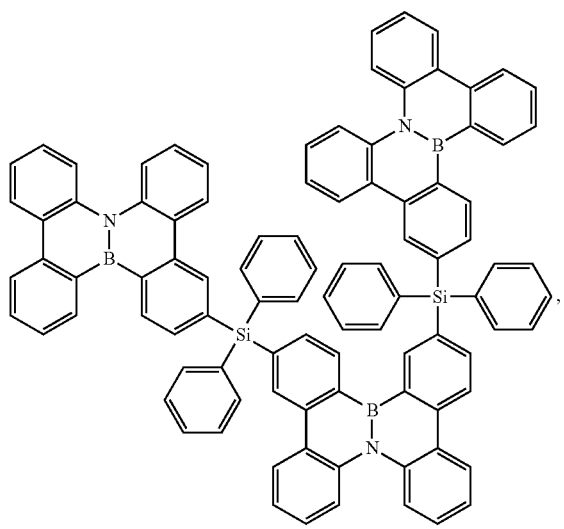
Structure B12
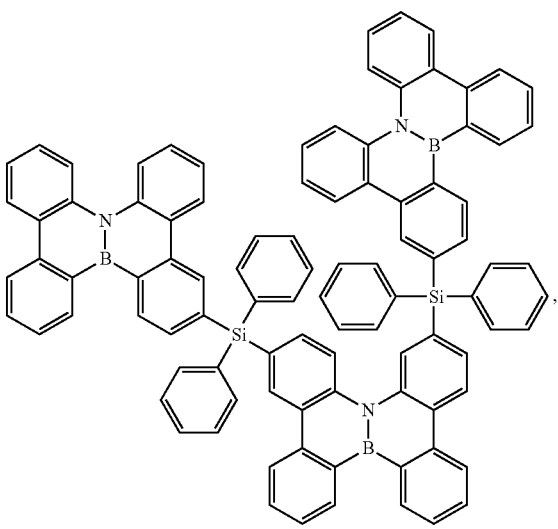
Structure B13
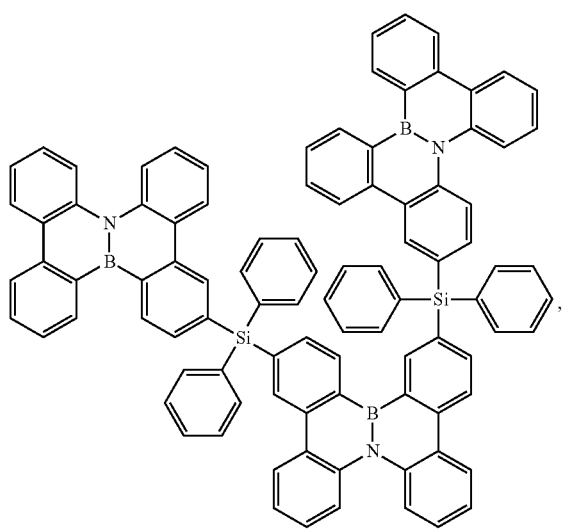
Structure B14
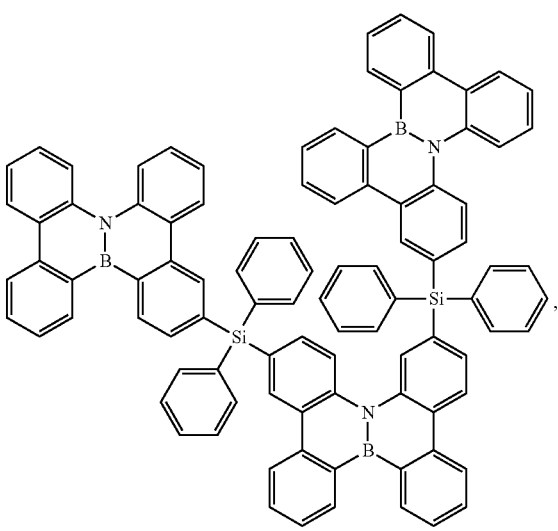

-continued
Structure B15
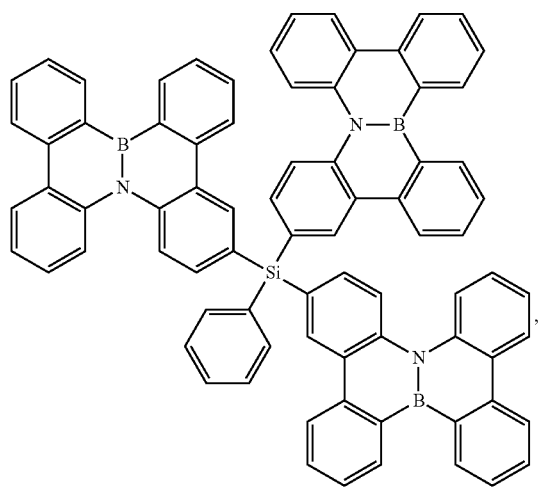
Structure B16
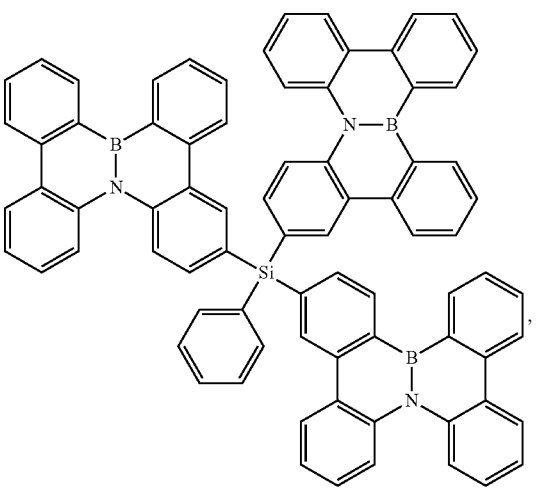
Structure B17
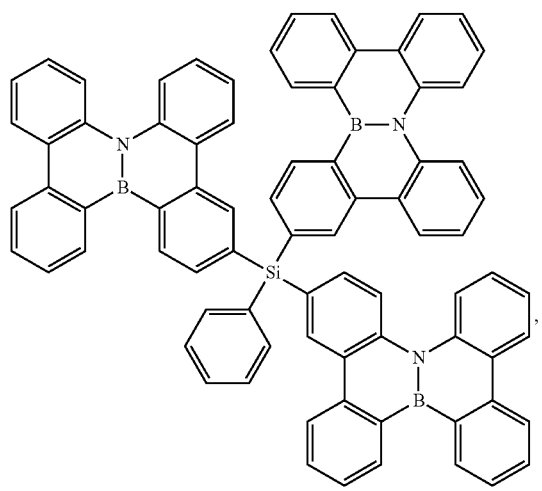
Structure B18
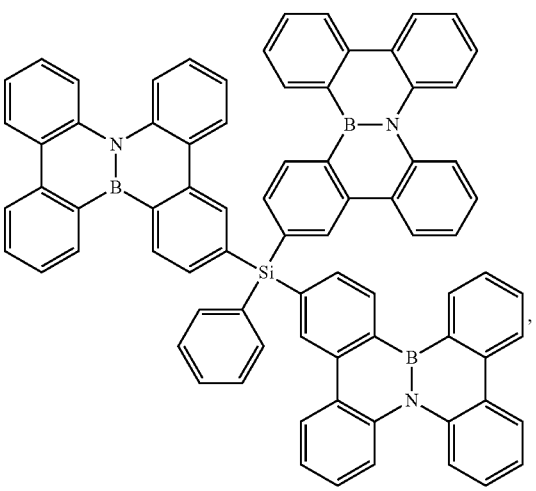

-continued
Structure B19
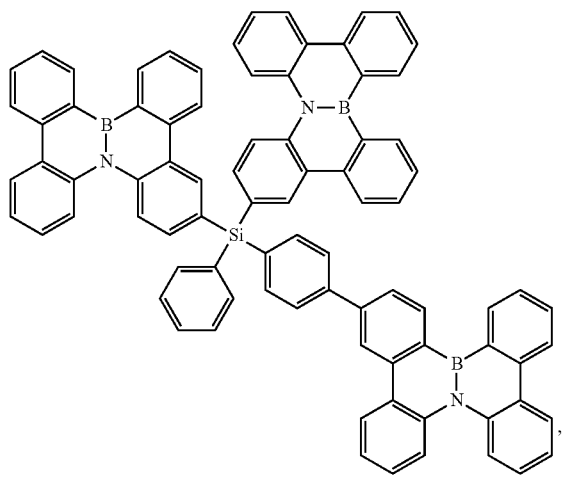
Structure B20
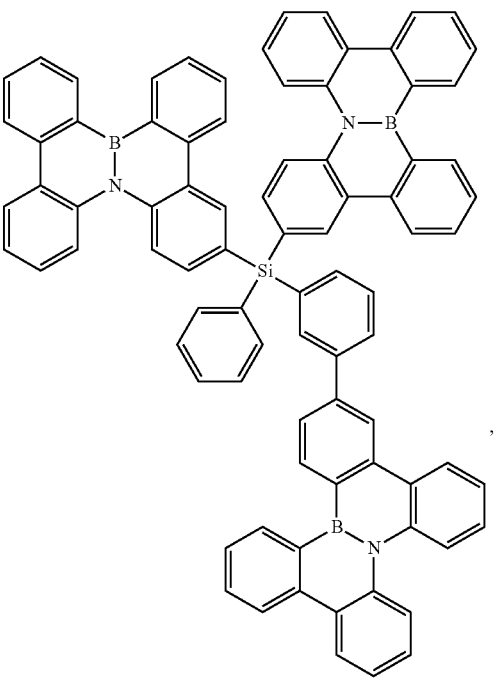
Structure B21
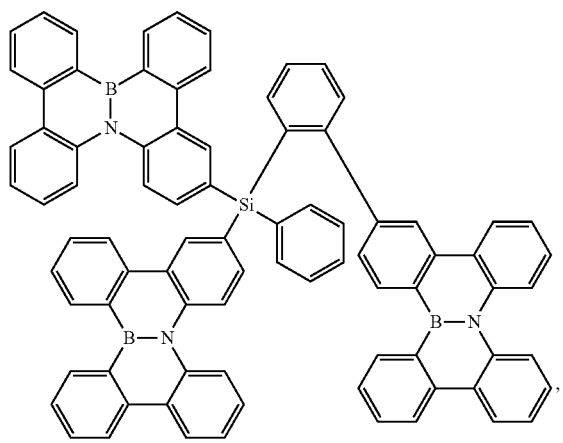
Structure B22
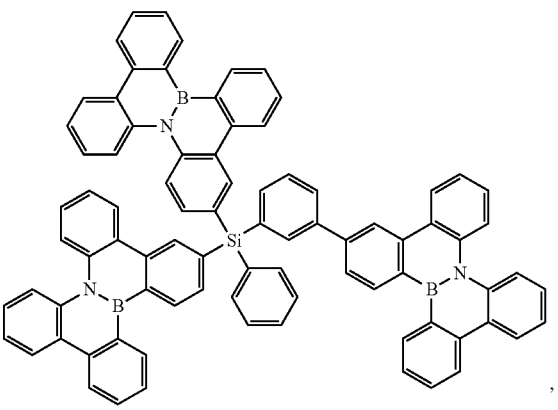
Structure B23
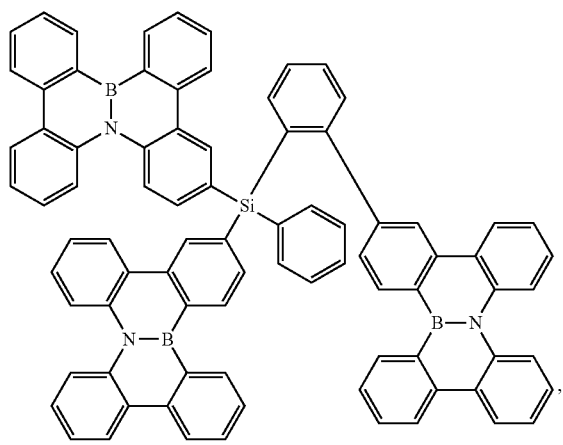
Structure B24
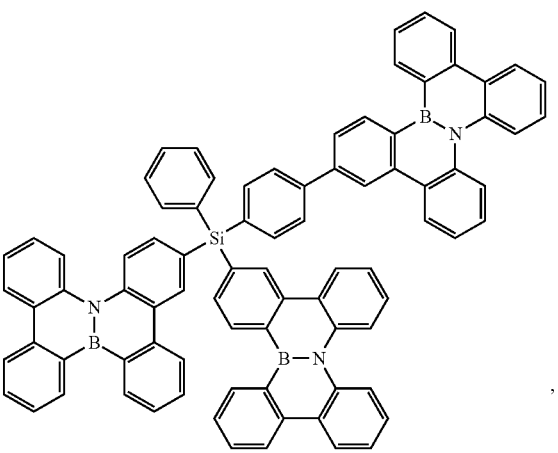

-continued
Structure B25
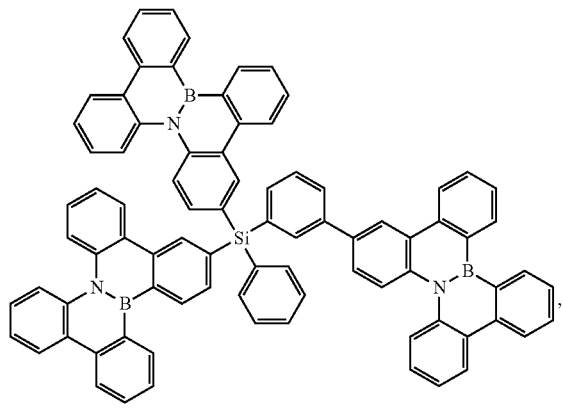
Structure B26
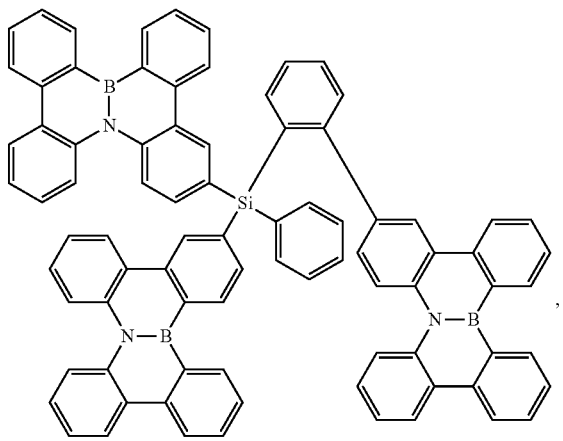
Structure B27
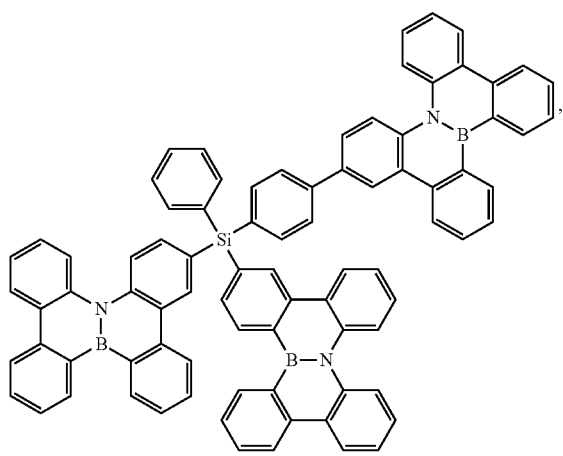
Structure B28
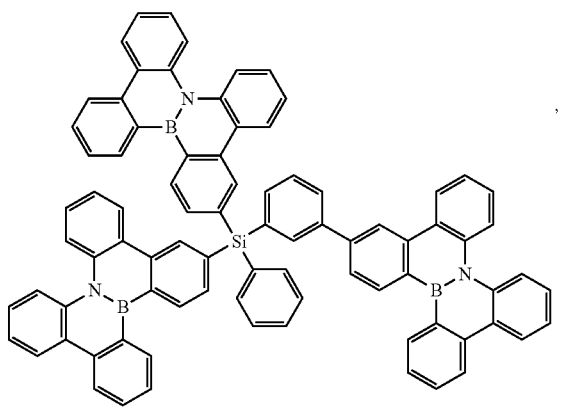
Structure B29
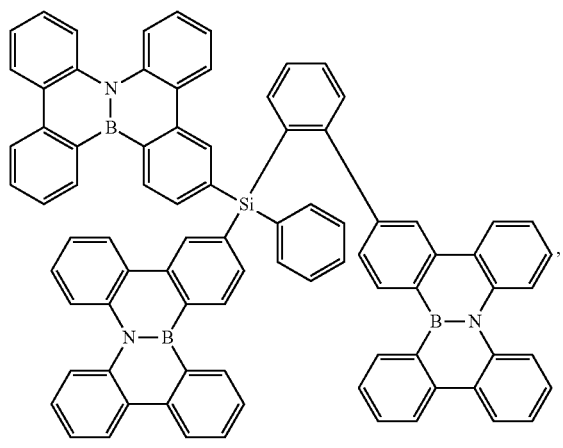
Structure B30
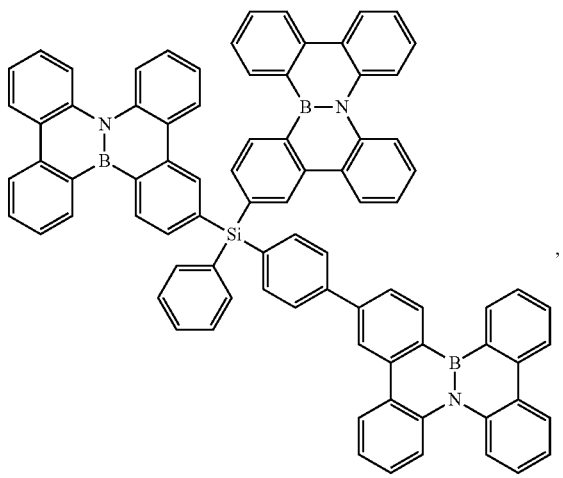

-continued
Structure B31
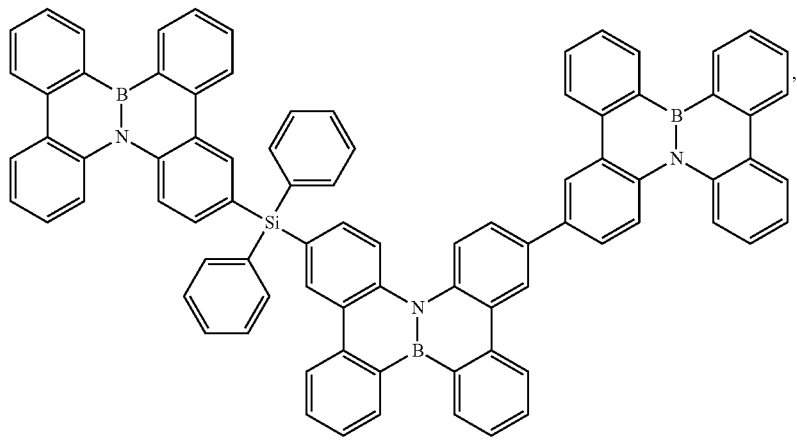
Structure B32
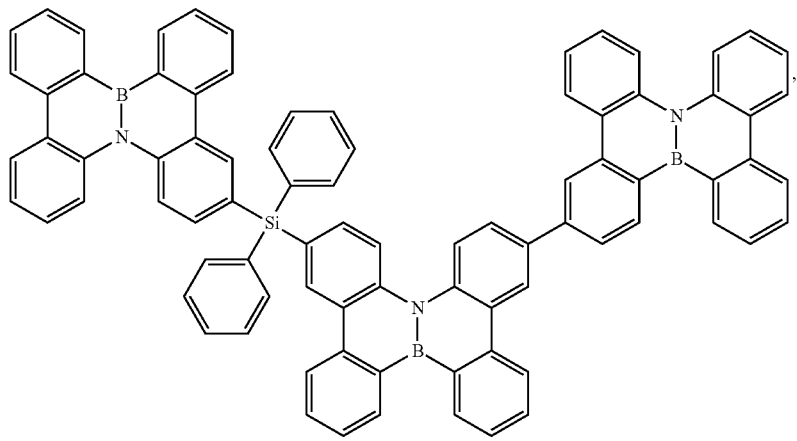
Structure B33
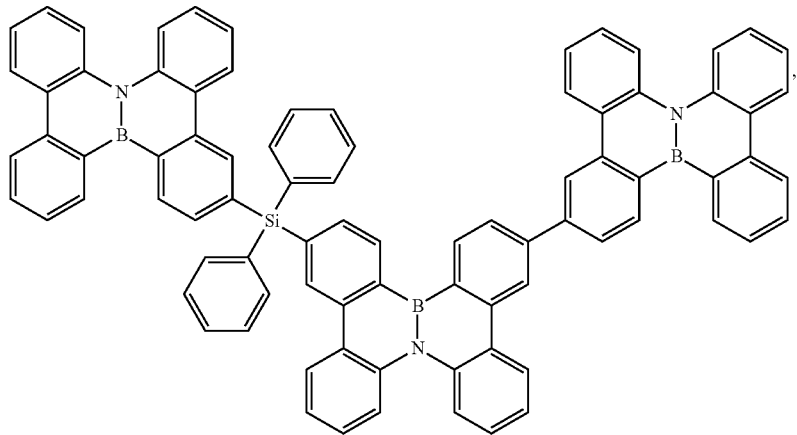

-continued
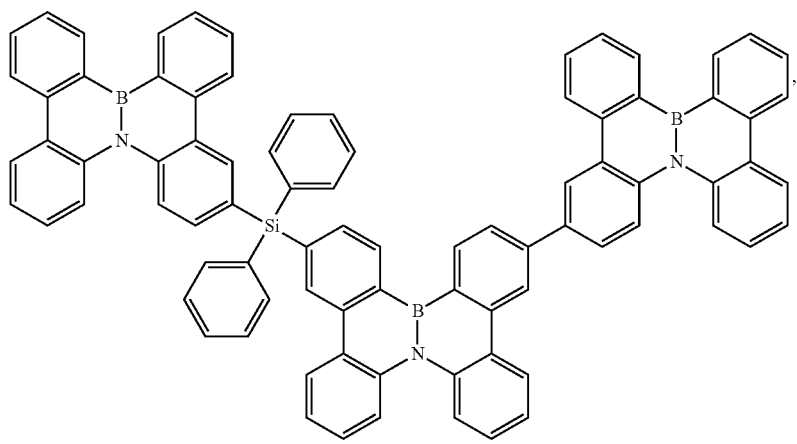
Structure B34
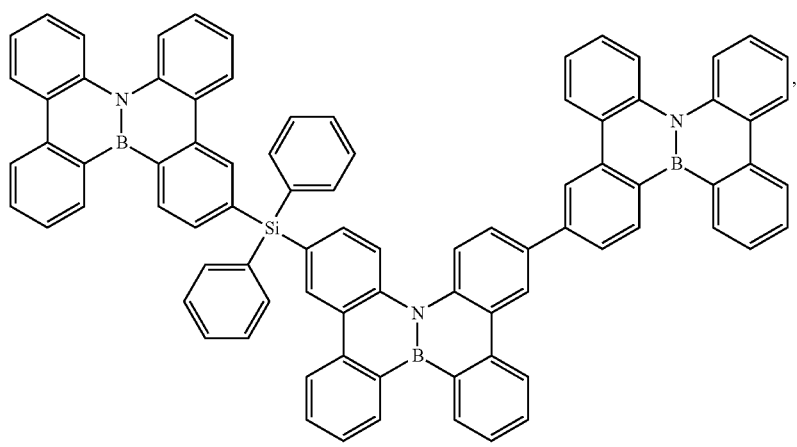
Structure B35
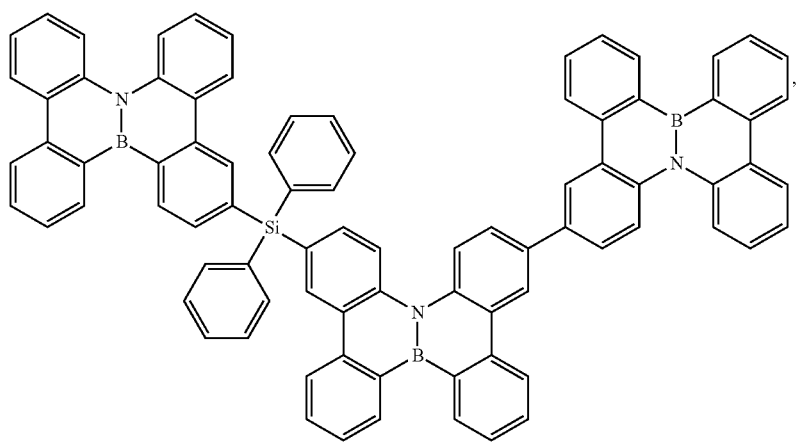
Structure B36

-continued
Structure B37
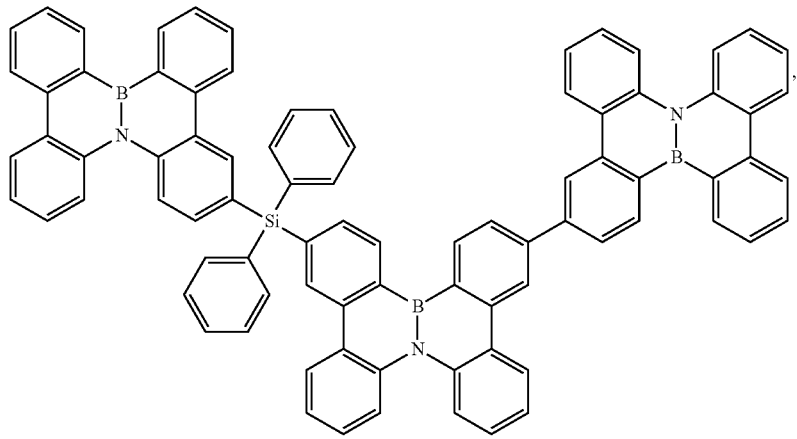
Structure B38                    Structure B39
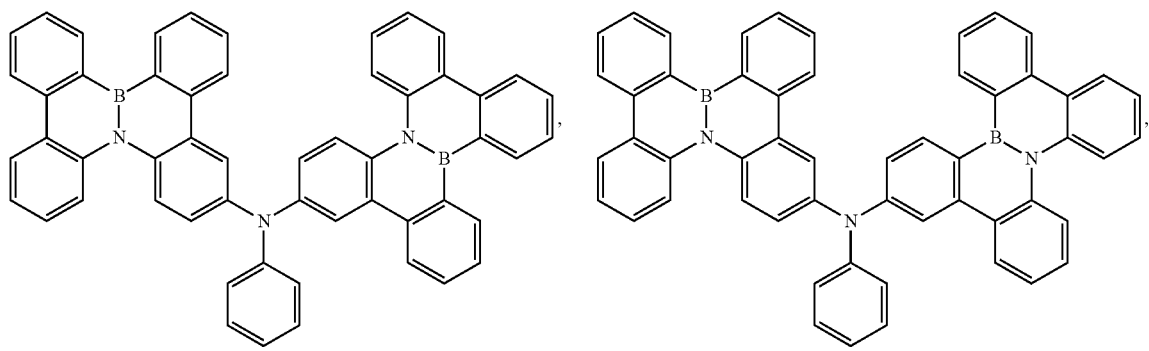
Structure B40                    Structure B41
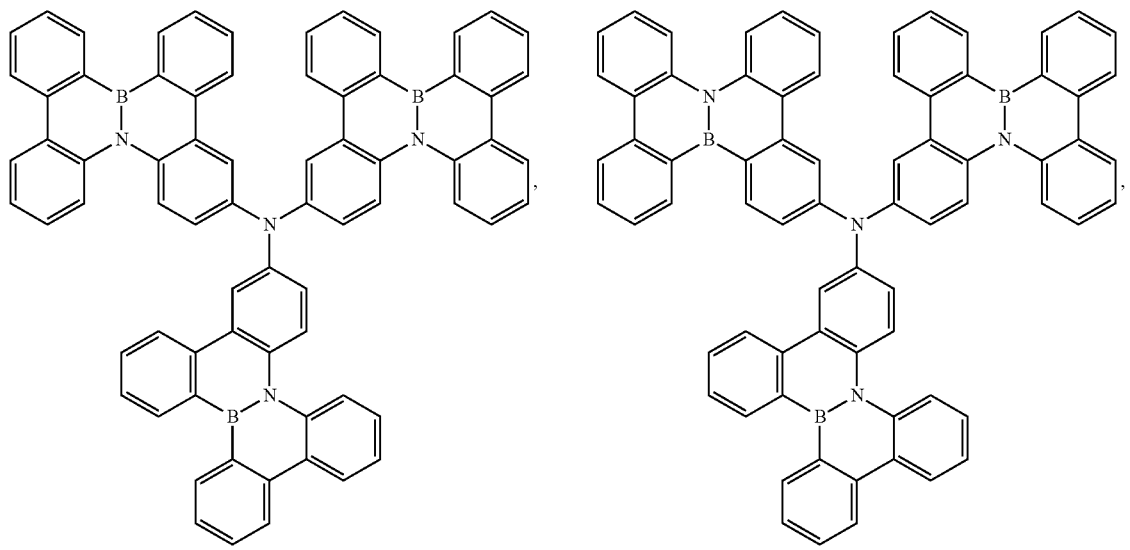

-continued
Structure B42
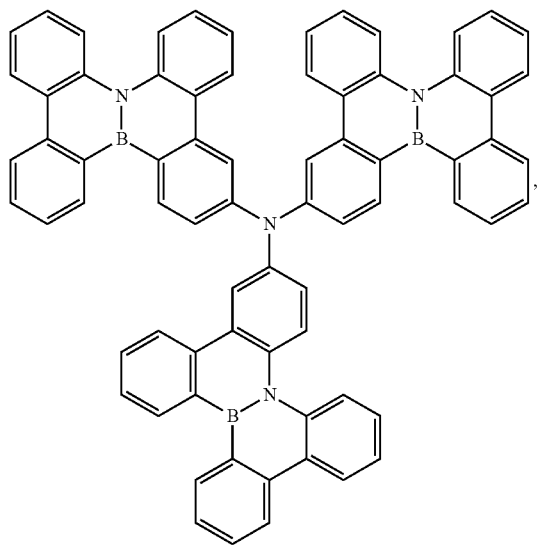
Structure B43
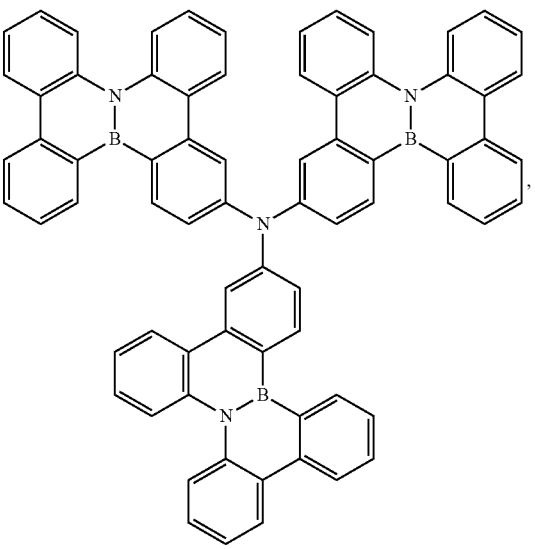
Structure B44
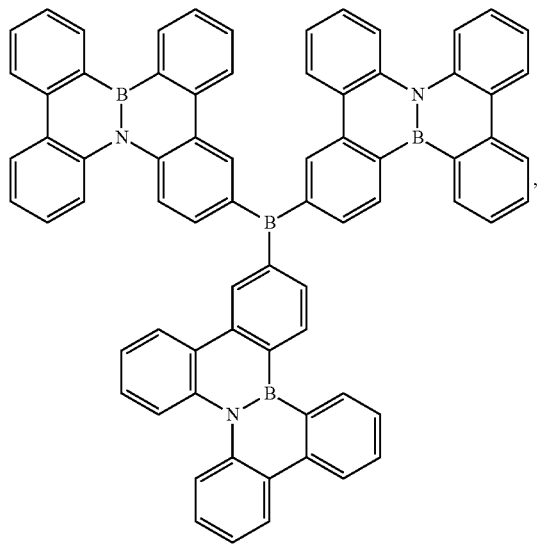
Structure B45
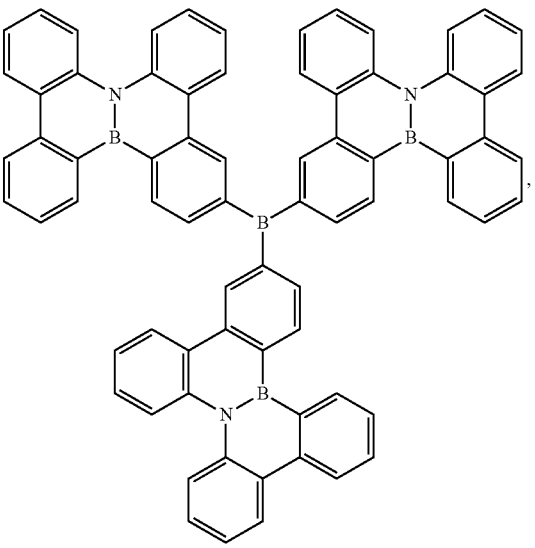

-continued
Structure B46
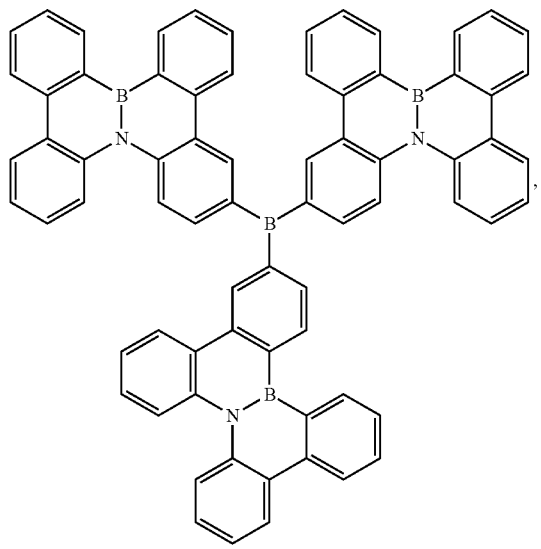
Structure B47
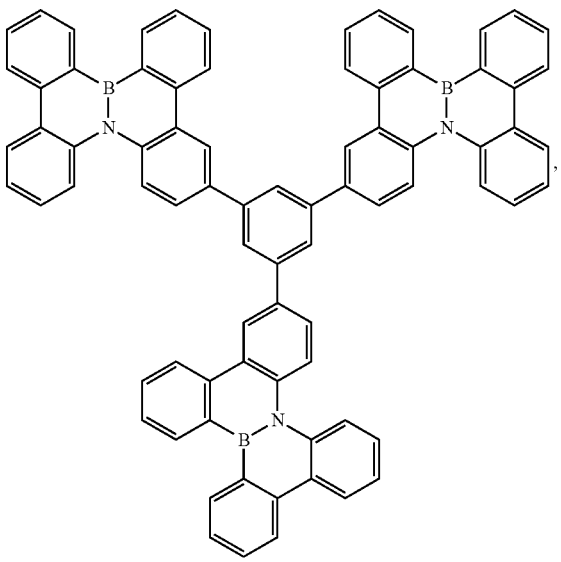
Structure B48
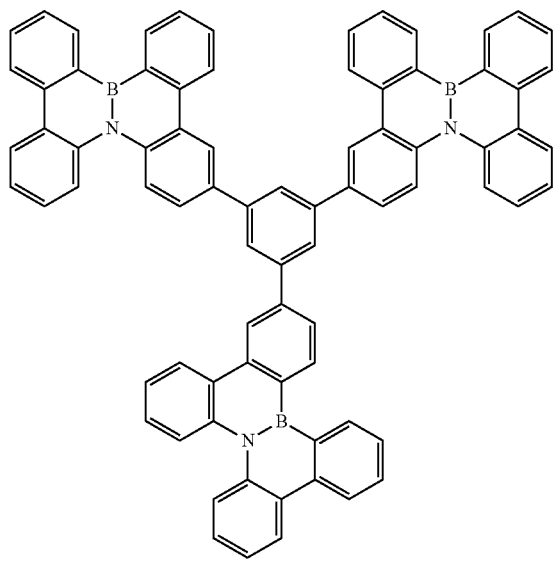
Structure B49
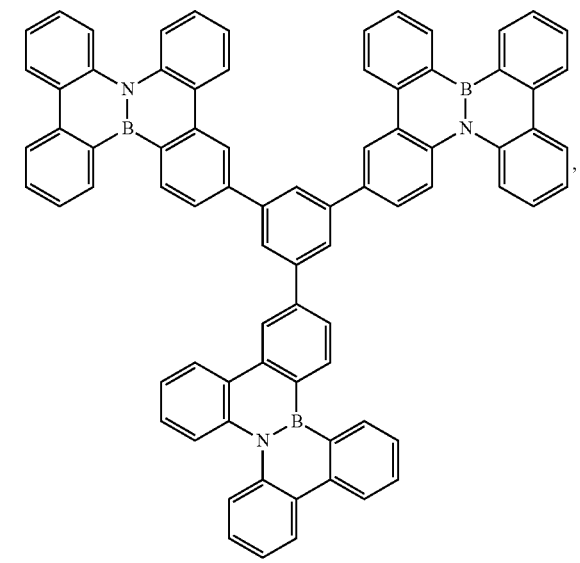

-continued
Structure B50
Structure B51
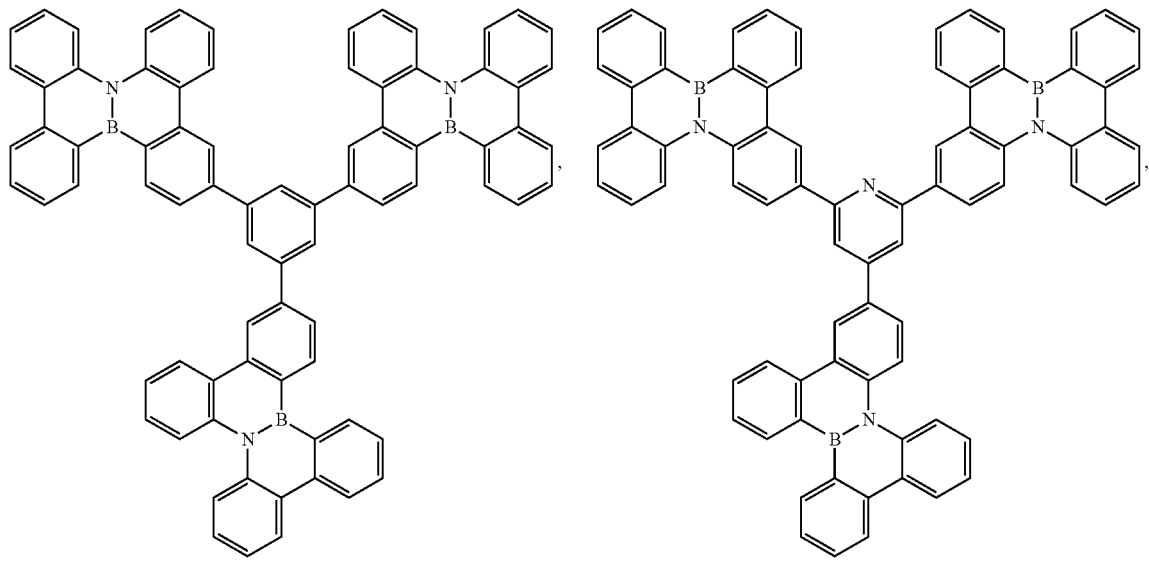
Structure B52
Structure B53
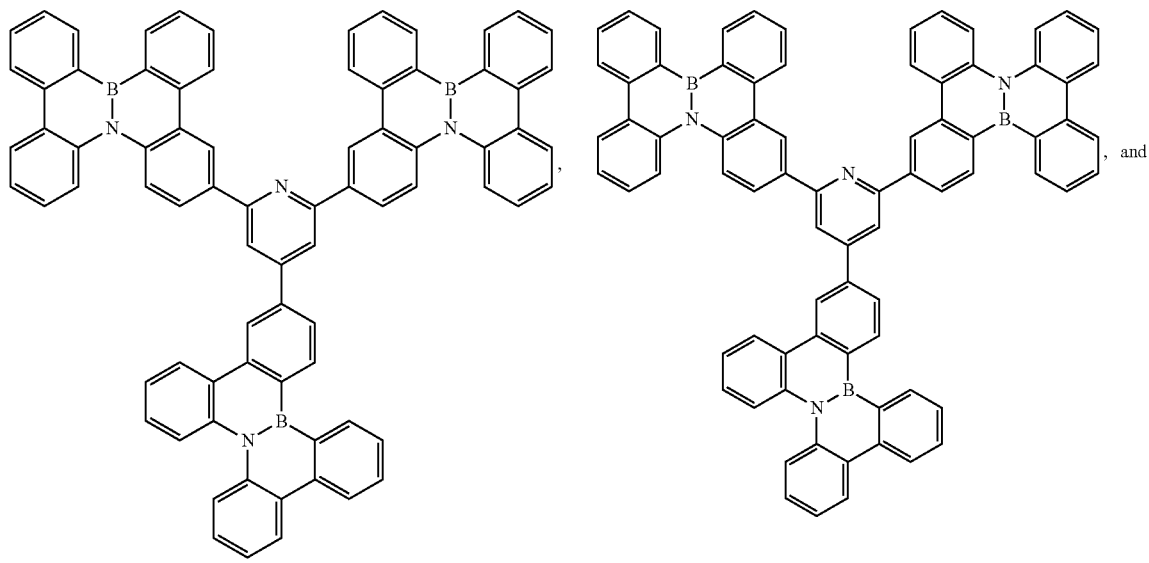
, and -continued Structure B54

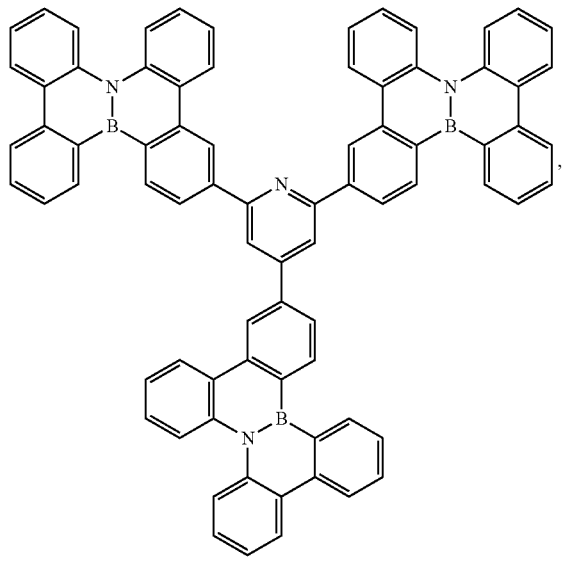

which may be further substituted by one or more substituents independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any adjacent substitutions are optionally joined or fused into a ring.

11. A compound having a formula:

Formula V

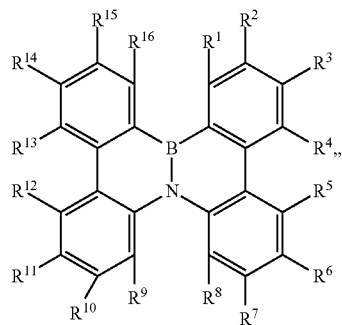

wherein at least two adjacent $R^1$ to $R^{16}$ on the same ring are:

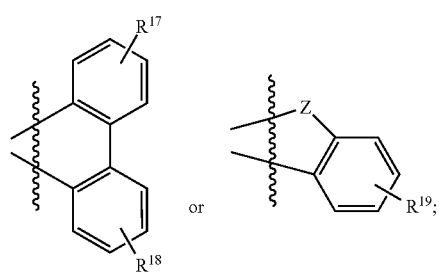

wherein $R^{17}$ to $R^{19}$ each independently represent mono, di, tri, or tetra substitution, or no substitution;

wherein Z is selected from the group consisting of NR", O, S and Se;

wherein R", $R^1$ to $R^{19}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any adjacent substitutions of $R^{17}$ to $R^{19}$ are optionally joined or fused into a ring.

12. The compound of claim 11, the compound is selected from the group consisting of:

Structure F1

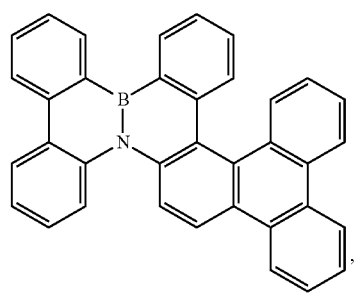

Structure F2

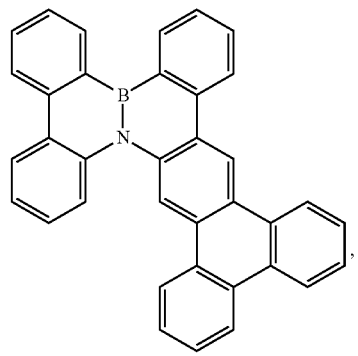

245
-continued
Structure F3
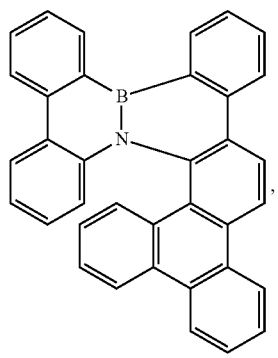
Structure F4
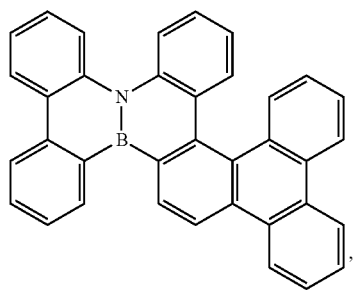
Structure F5
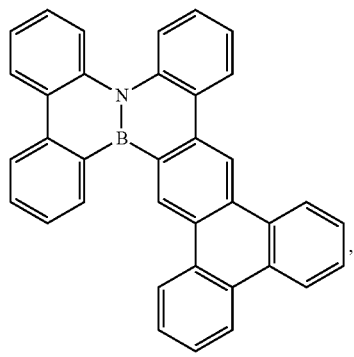
Structure F6
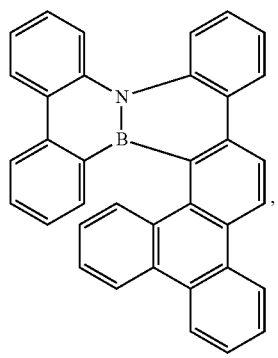
Structure F7
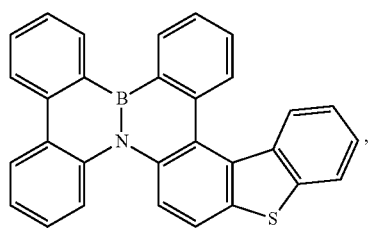
246
-continued
Structure F8
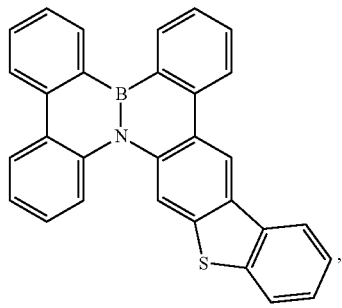
Structure F9
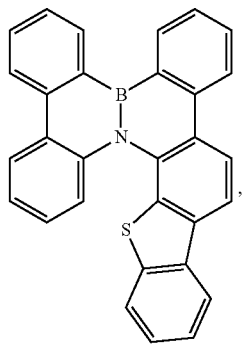
Structure F10
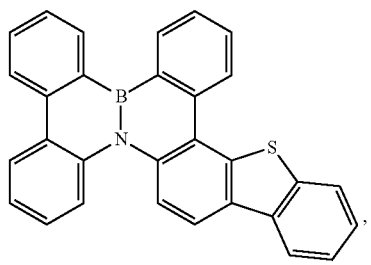
Structure F11
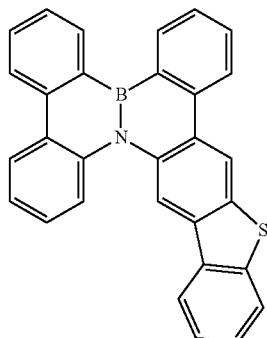
Structure F12
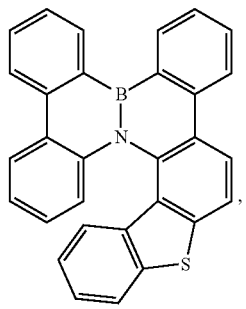

Structure F13
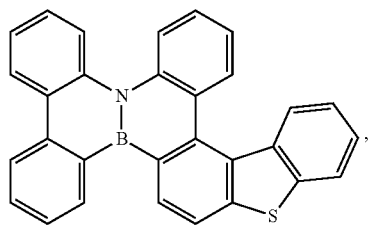
Structure F14
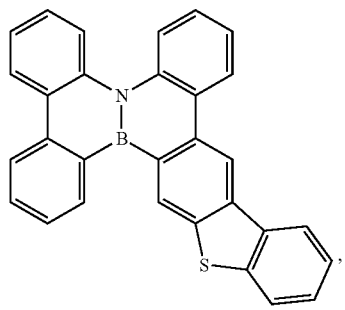
Structure F15
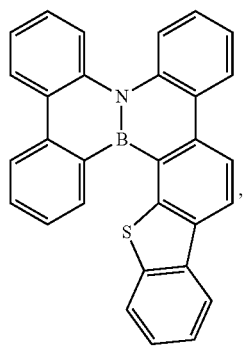
Structure F16
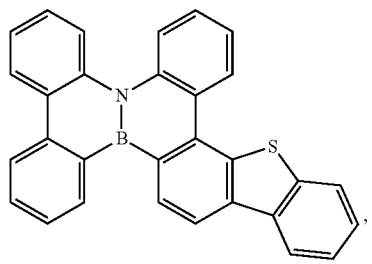
Structure F17
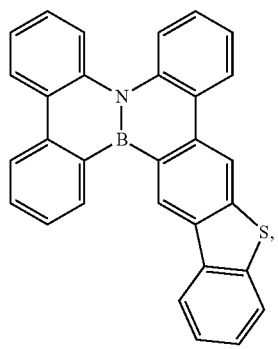
Structure F18
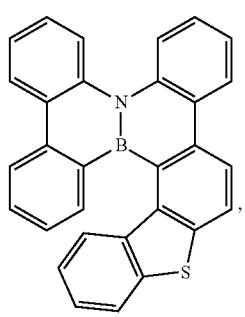
Structure F19
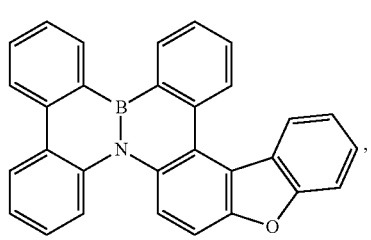
Structure F20
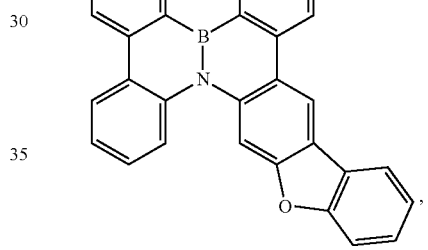
Structure F21
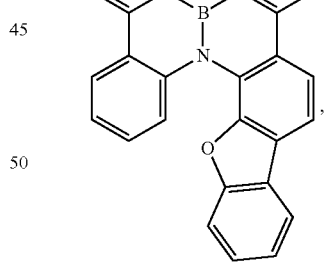
Structure F22
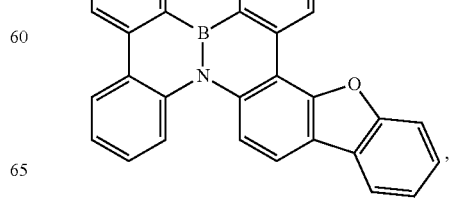

-continued
Structure F23
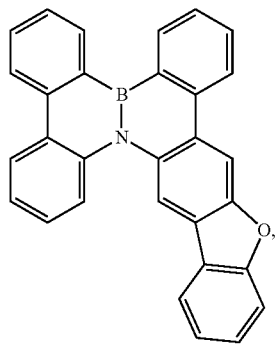
Structure F24
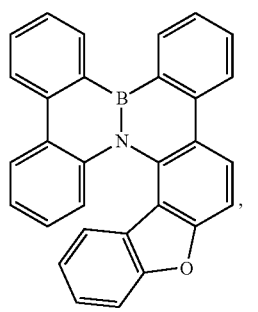
Structure F25
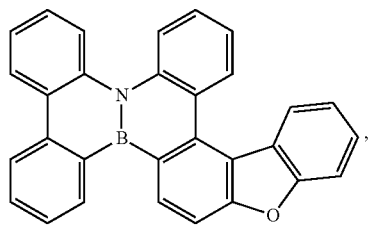
Structure F26
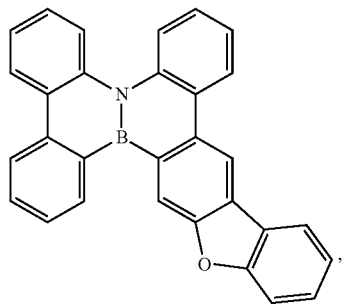
Structure F27
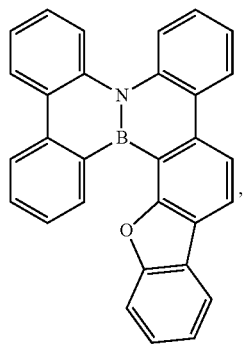
-continued
Structure F28
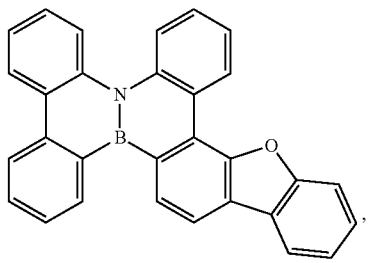
Structure F29
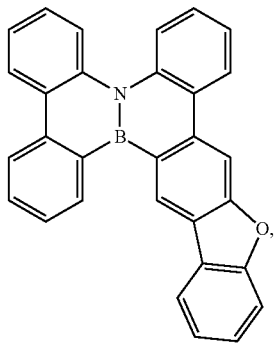
Structure F30
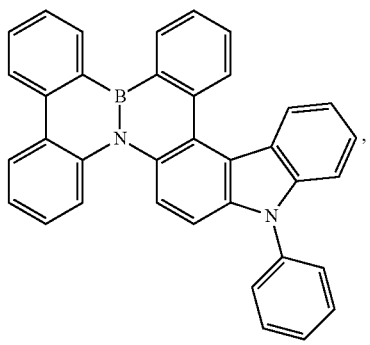
Structure F31
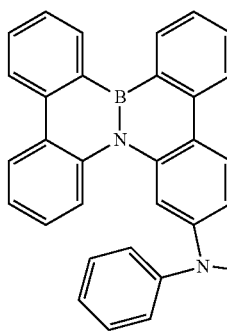
Structure F32
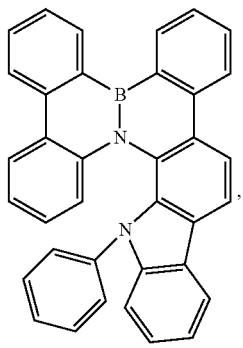

Structure F33
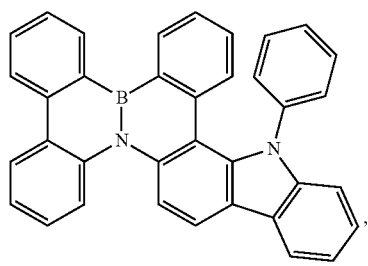
Structure F34
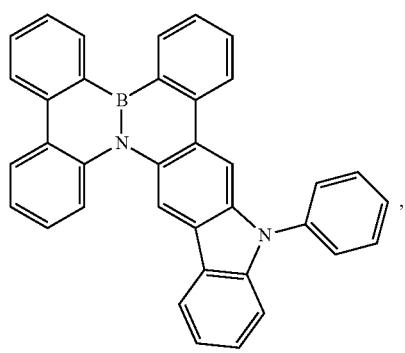
Structure F35
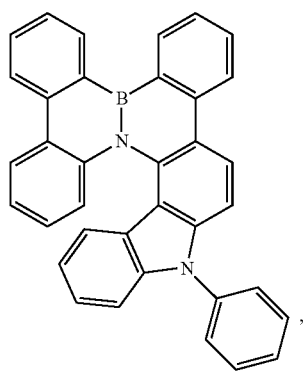
Structure F36
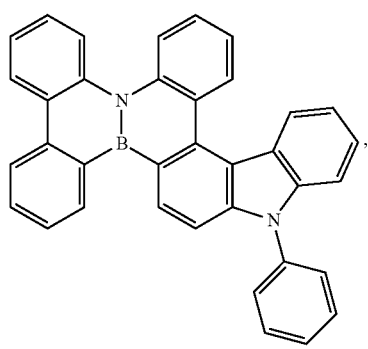
Structure F37
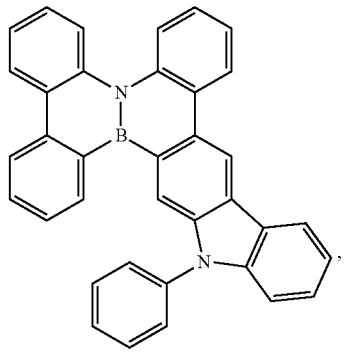
Structure F38
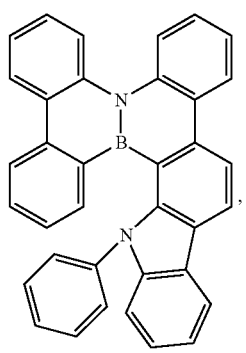
Structure F39
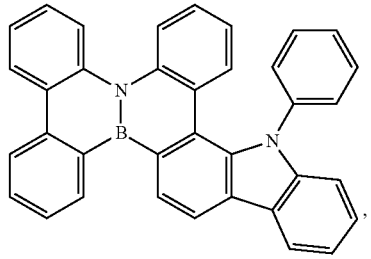
Structure F40
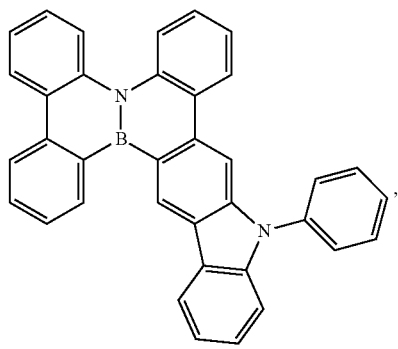

-continued
Structure F41
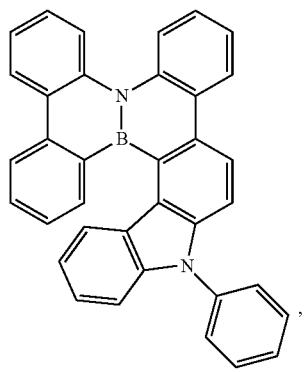
Structure F42
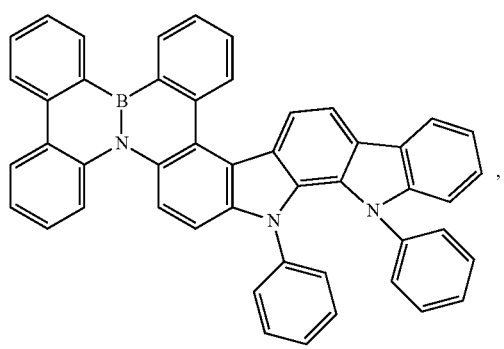
Structure F43
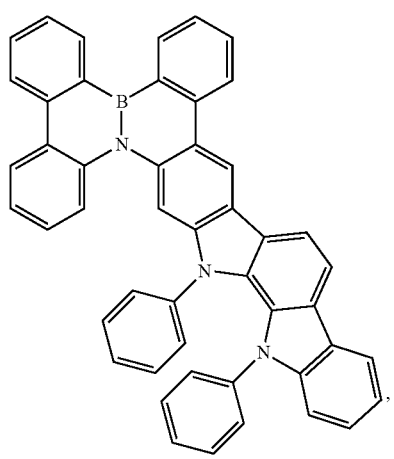
Structure F44
-continued
Structure F45
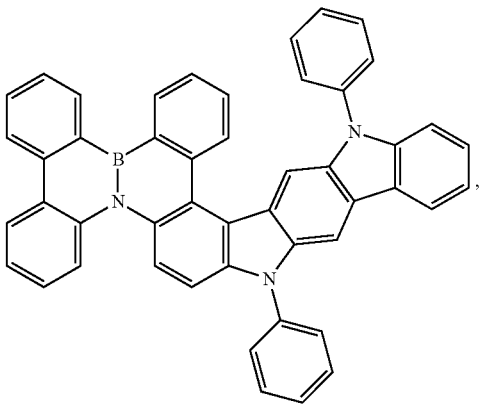
Structure F46
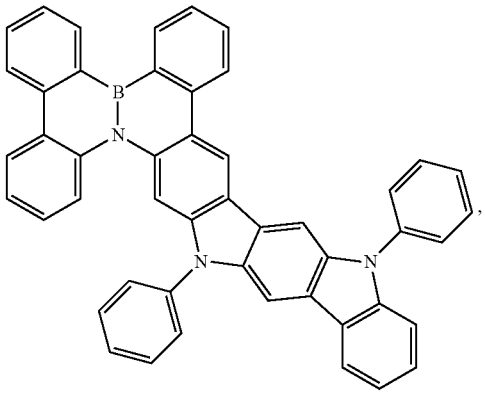
Structure F47
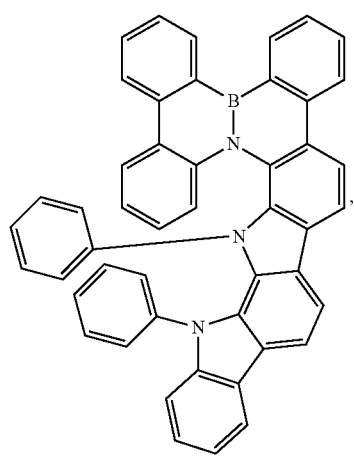
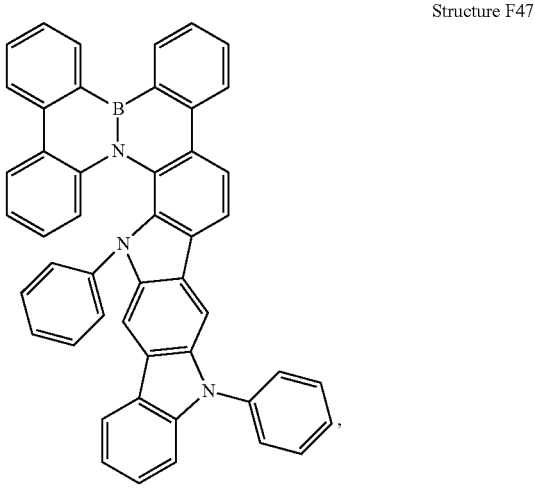

-continued
Structure F48
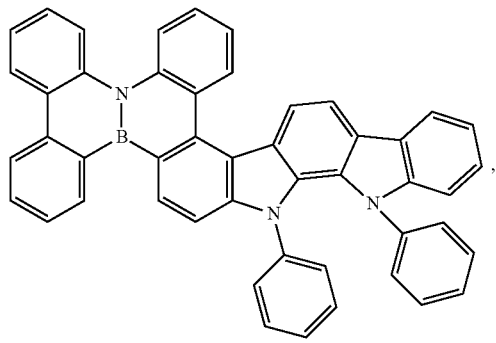
Structure F49
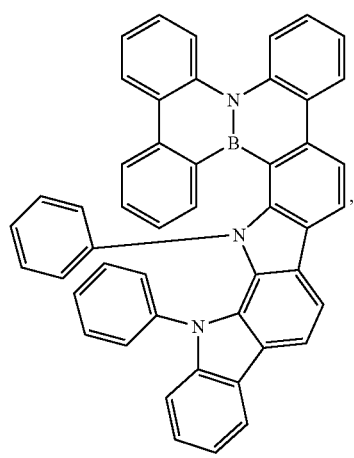
Structure F50
-continued
Structure F51
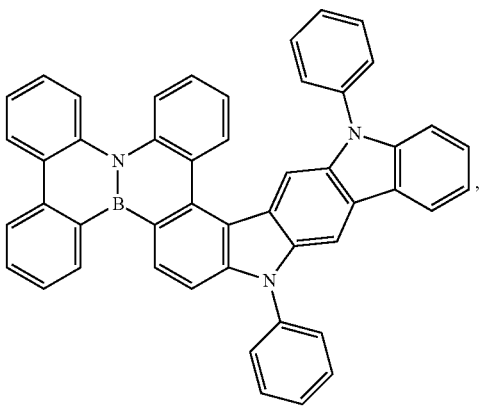
Structure F52
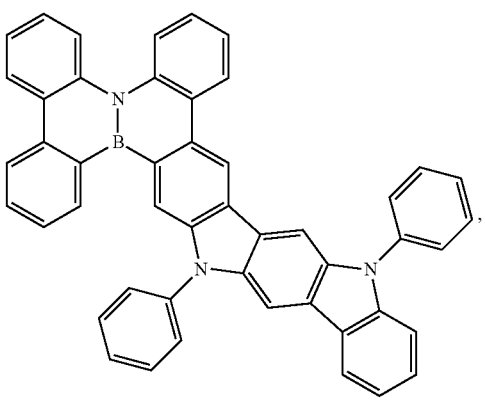
Structure F53
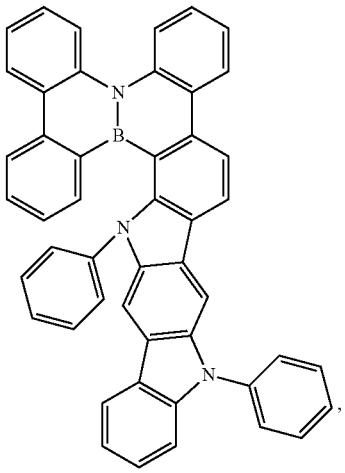

Structure F54
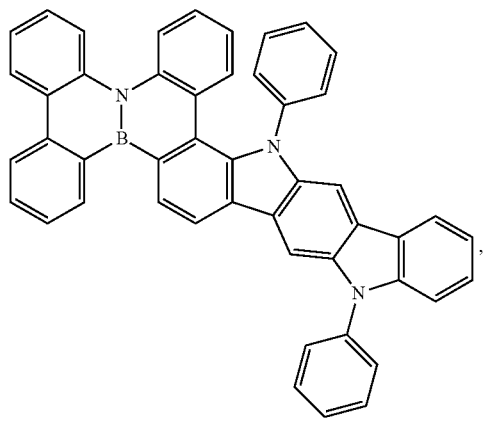
Structure F57
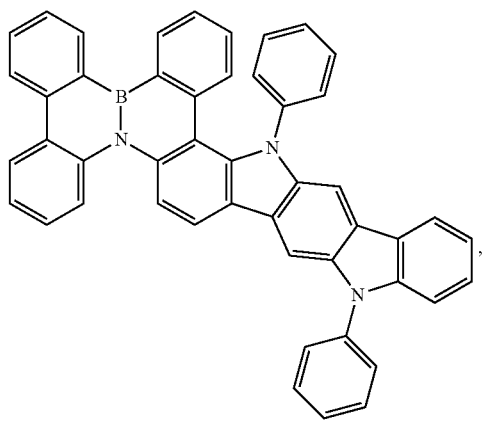
Structure F55
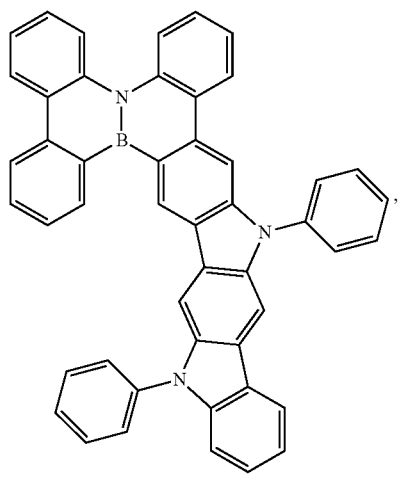
Structure F58
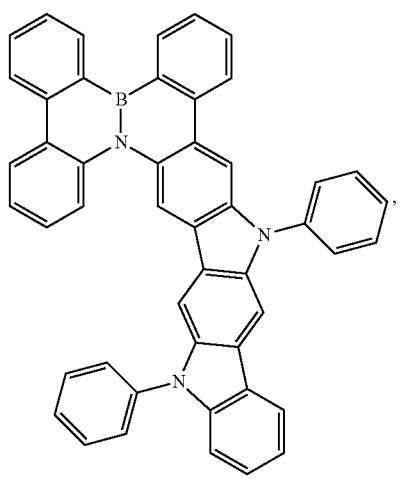
Structure F56
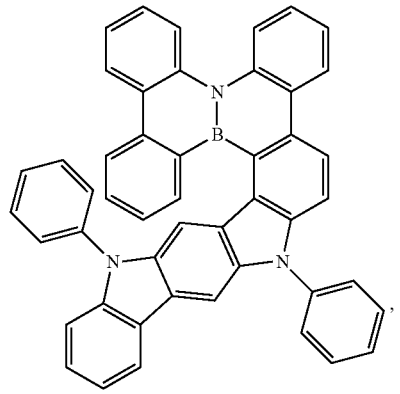
Structure F59
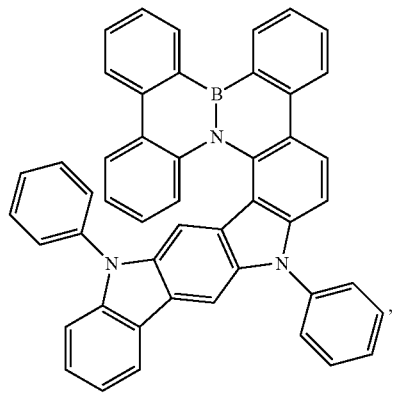

Structure F60
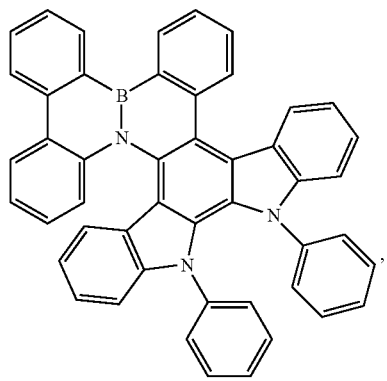
Structure F61
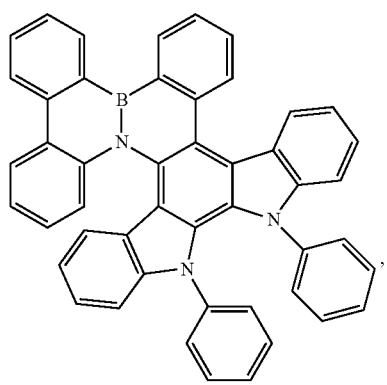
Structure F62
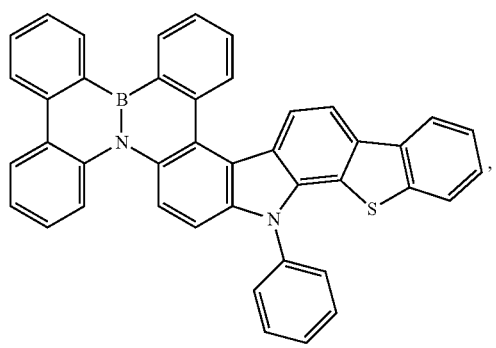
Structure F63
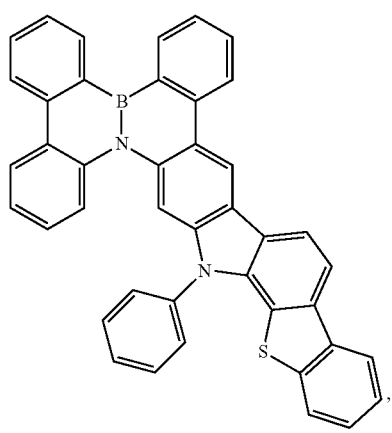
Structure F64
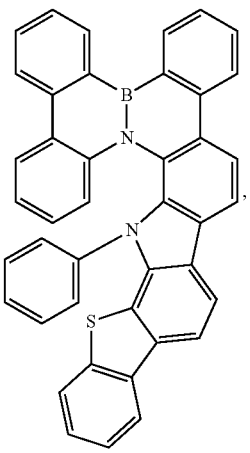
Structure F65
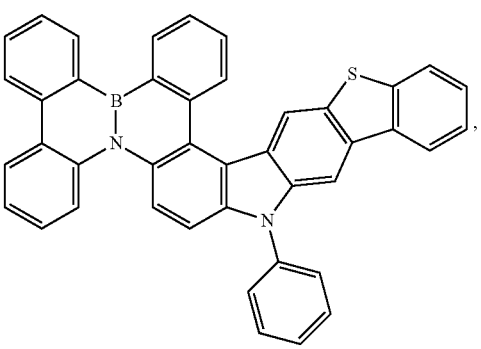
Structure F66
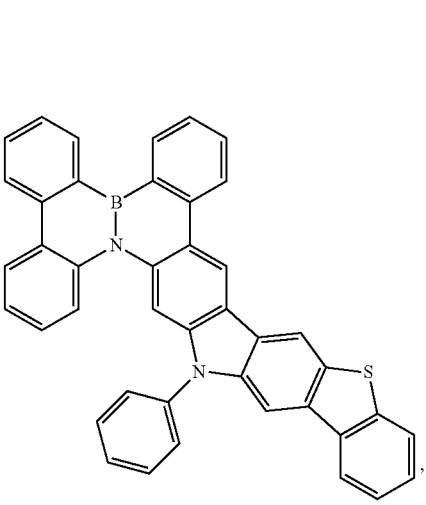

Structure F67
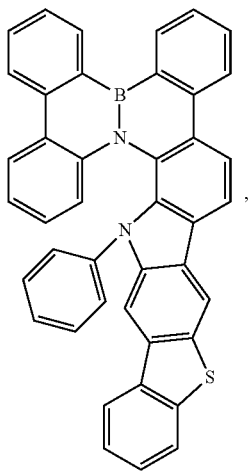
Structure F68
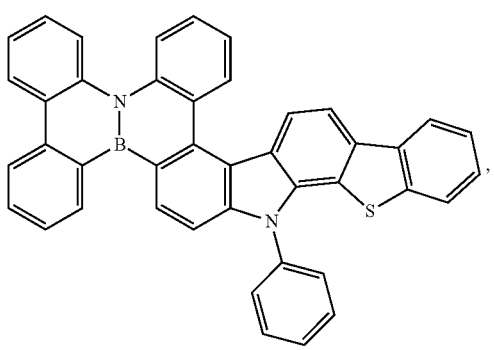
Structure F69
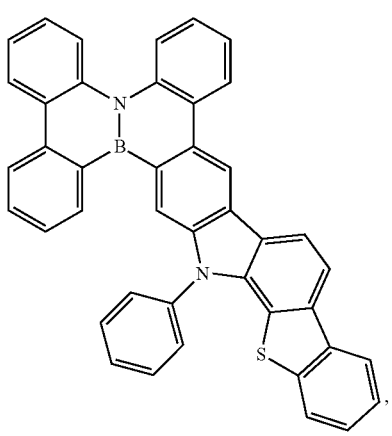
Structure F70
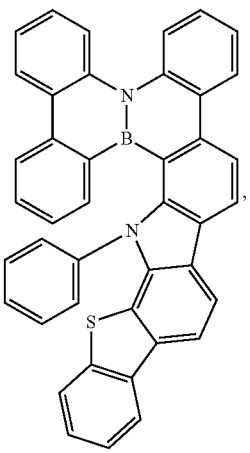
Structure F71
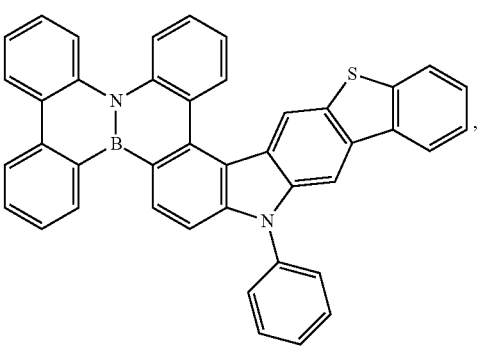
Structure F72
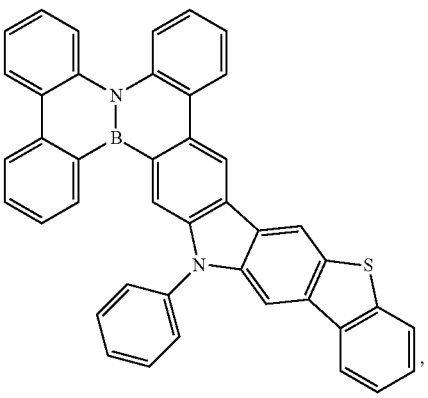

-continued
Structure F73
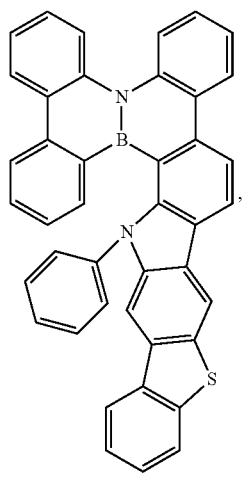
Structure F74
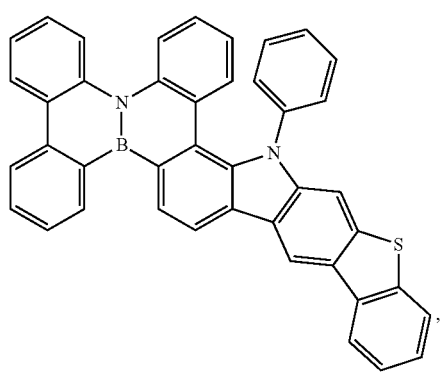
Structure F75
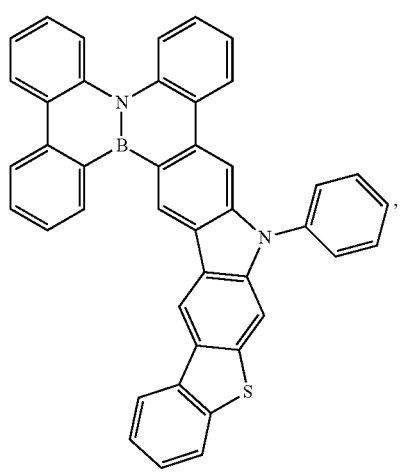
-continued
Structure F76
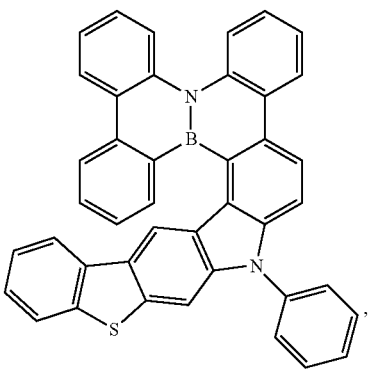
Structure F77
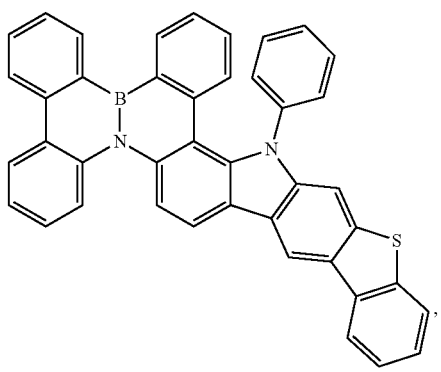
Structure F78
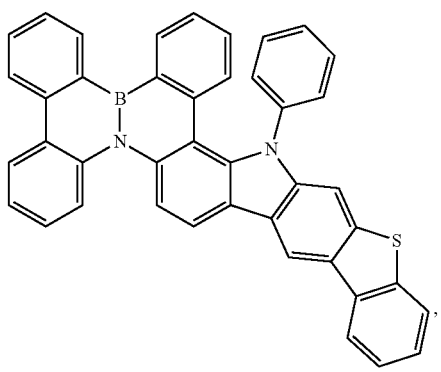
Structure F79
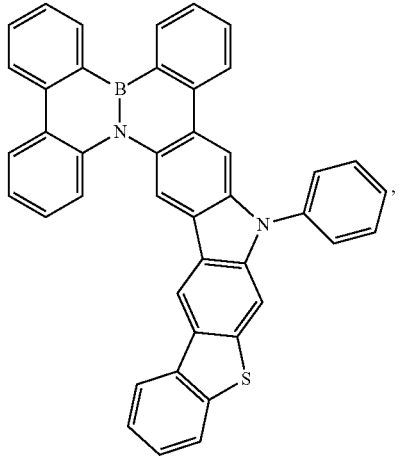

-continued
Structure F80
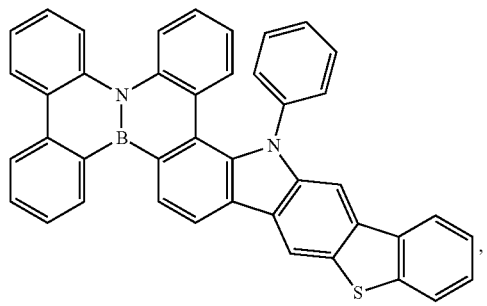
Structure F81
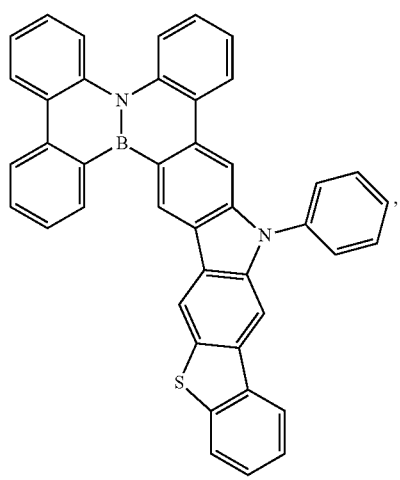
Structure F82
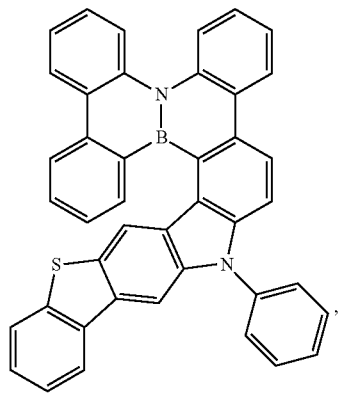
Structure F83
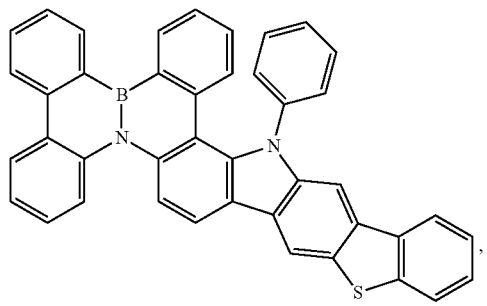
-continued
Structure F84
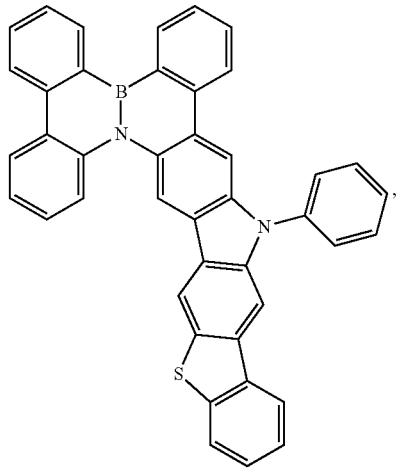
Structure F85
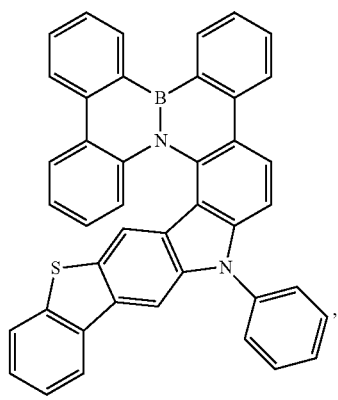
Structure F86
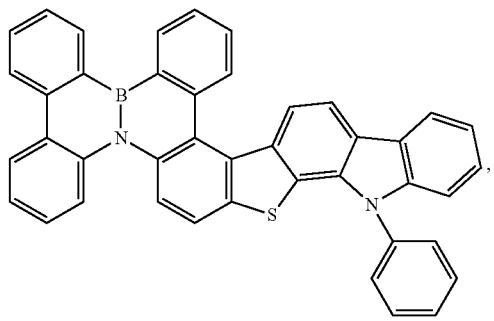
Structure F87
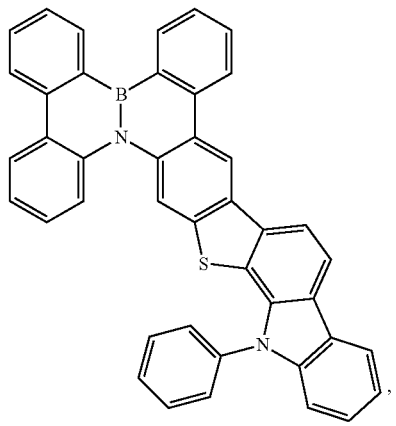

Structure F88
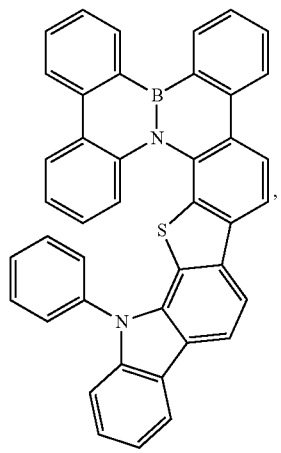
Structure F89
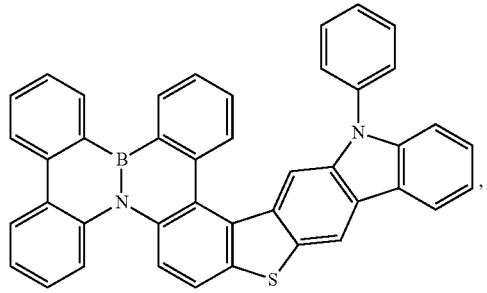
Structure F90
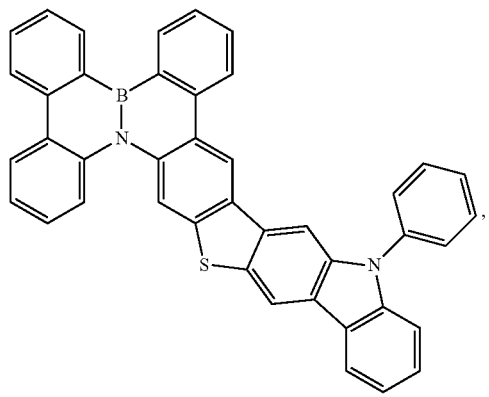
Structure F91
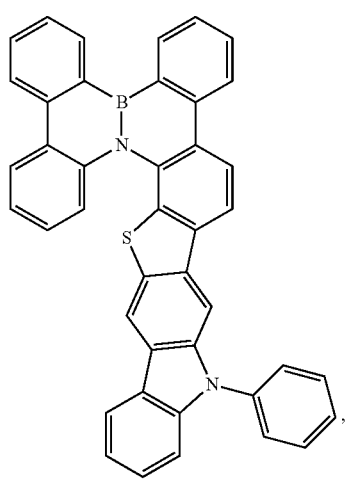
Structure F92
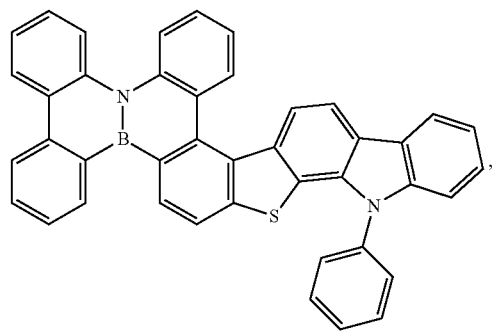
Structure F93
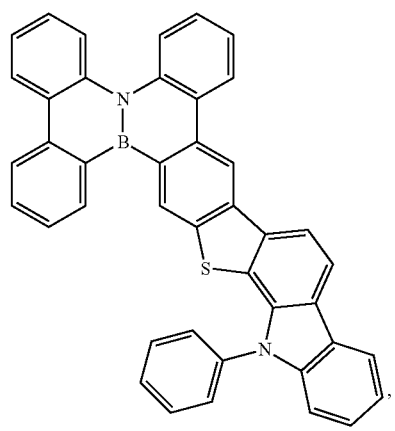
Structure F94
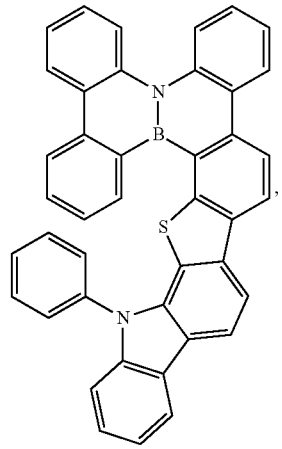
Structure F95
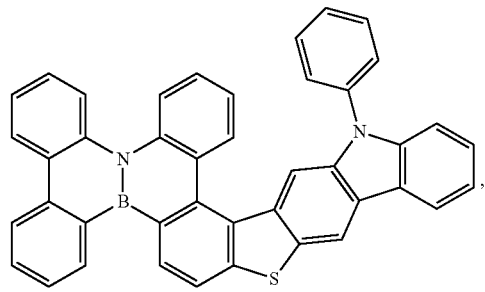

-continued
Structure F96
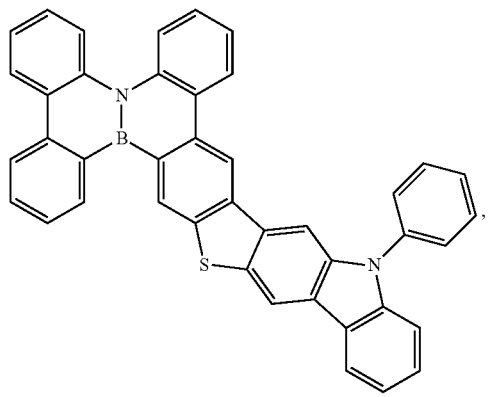
Structure F97
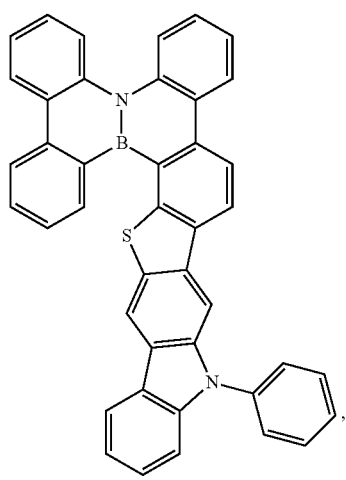
Structure F98
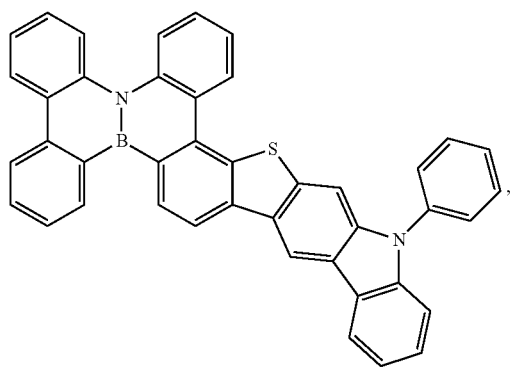
-continued
Structure F99
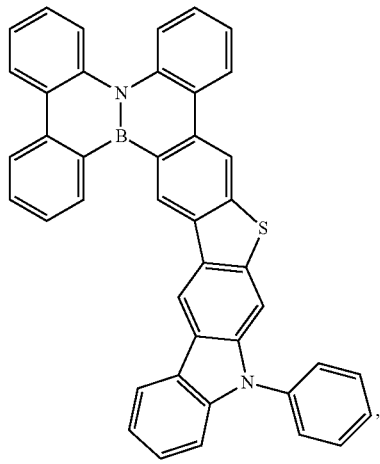
Structure F100
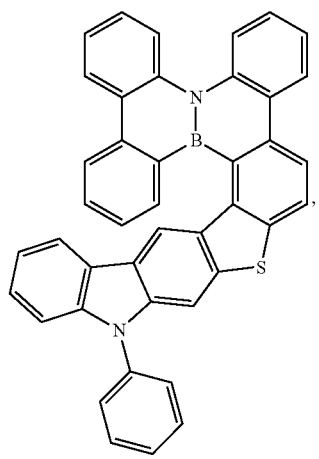
Structure F101
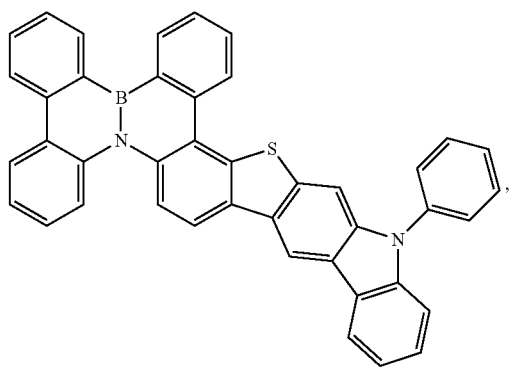

Structure F102
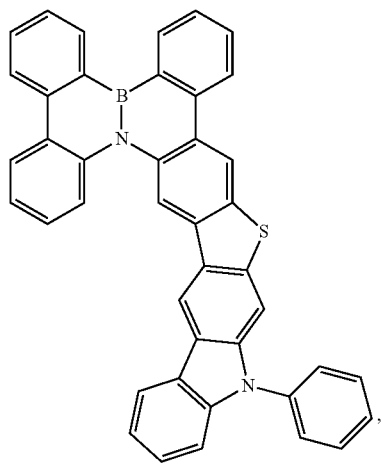
Structure F103
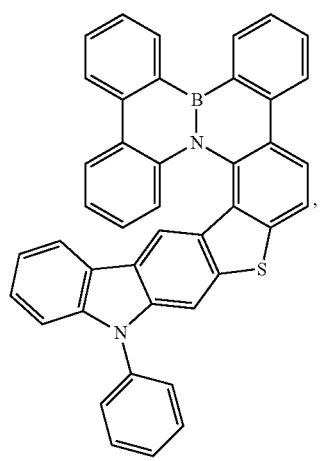
Structure F104
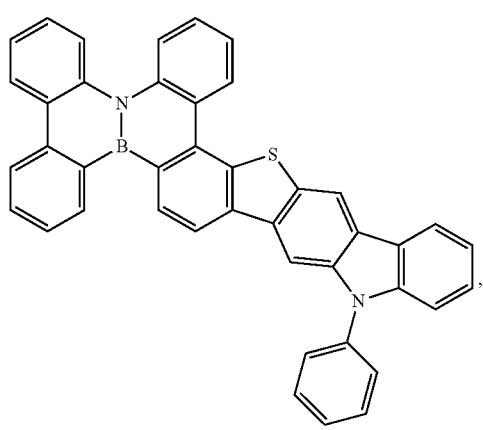
Structure F105
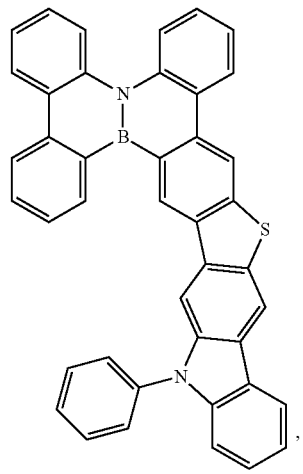
Structure F106
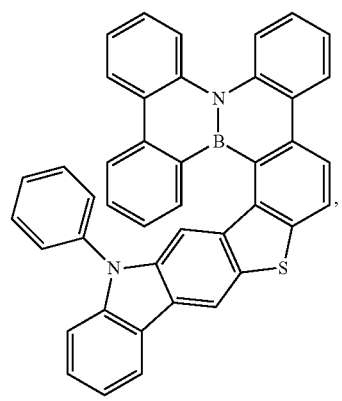
Structure F107
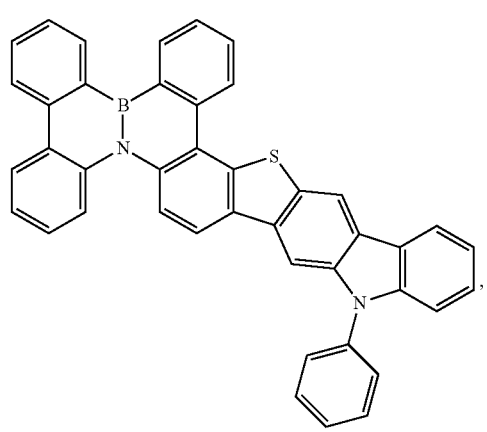

Structure F108
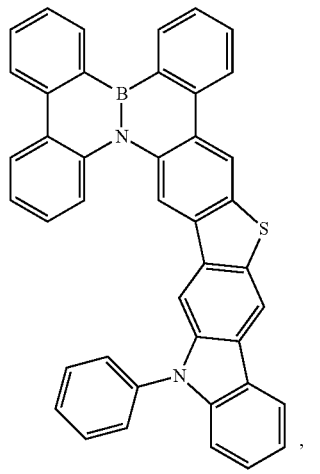
Structure F109
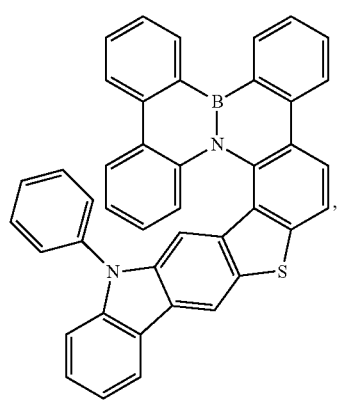
Structure F110
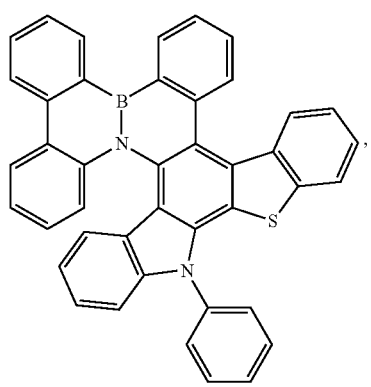
Structure F111
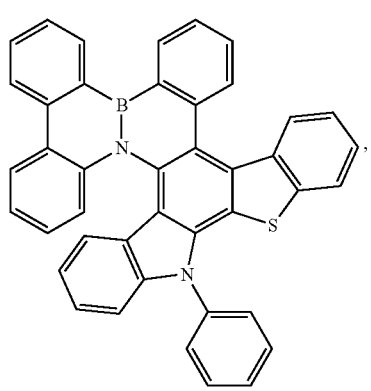
Structure F112
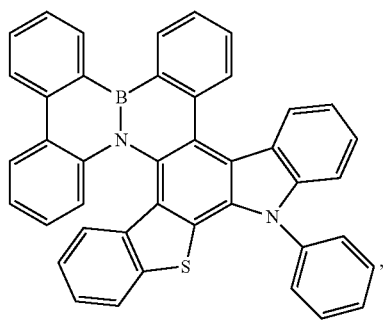
Structure F113
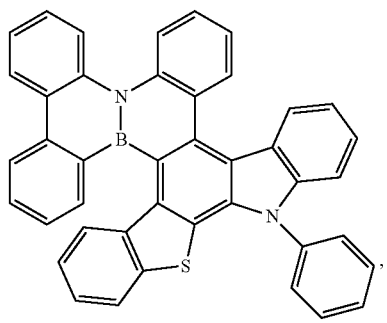
Structure F114
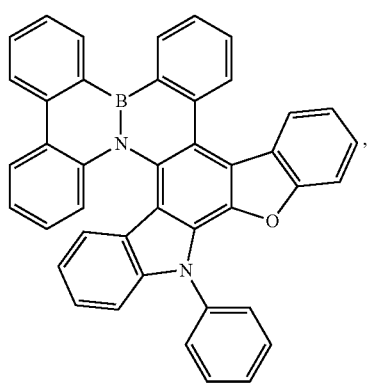
Structure F115
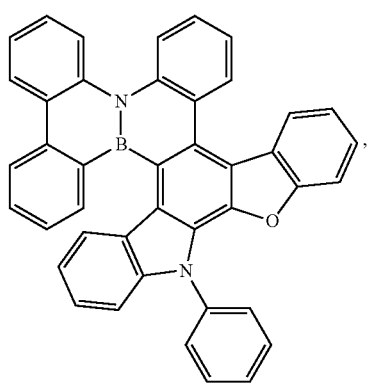

Structure F116
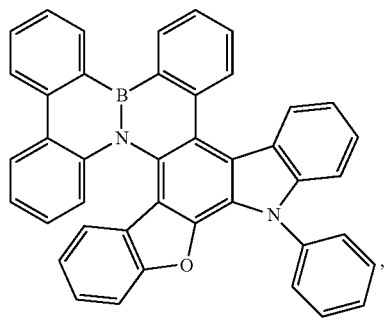
Structure F117
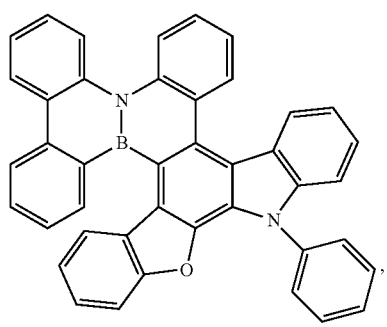
Structure F118
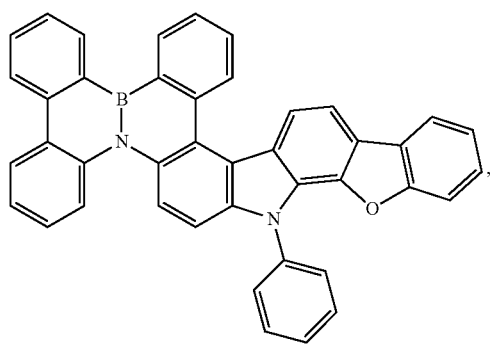
Structure F119
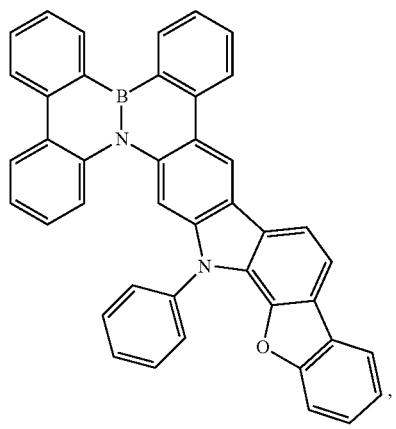
Structure F120
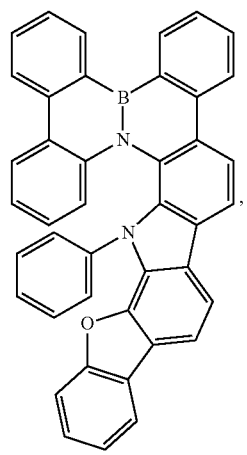
Structure F121
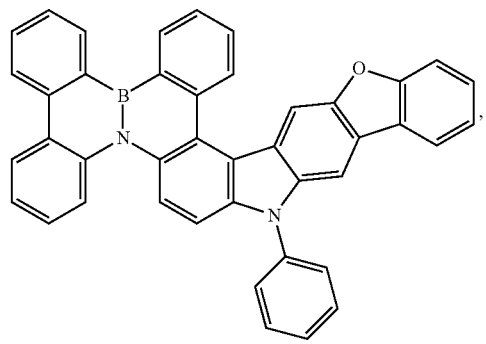
Structure F122
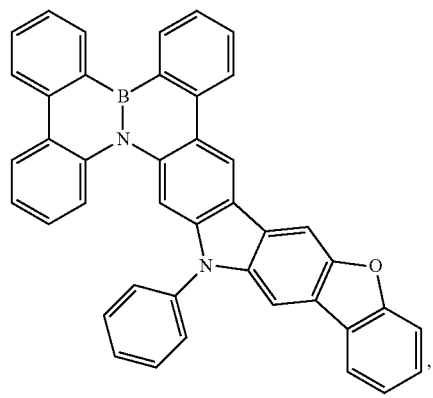

Structure F123
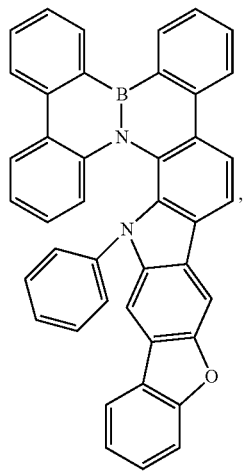
Structure F126
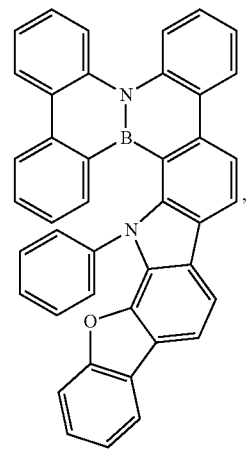
Structure F124
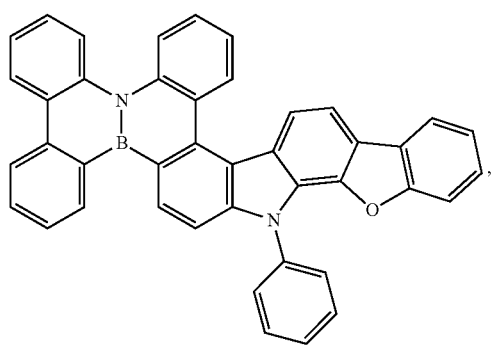
Structure F127
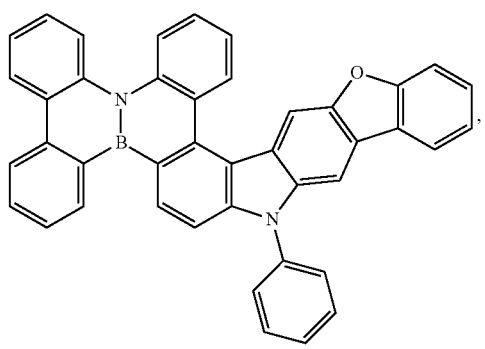
Structure F125
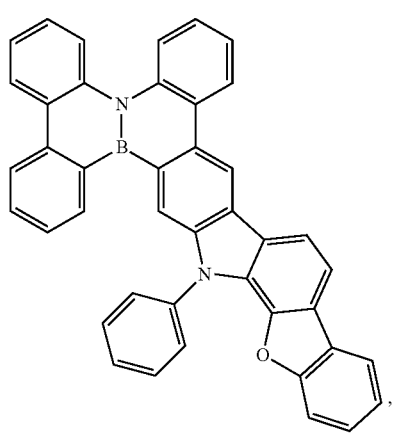
Structure F128
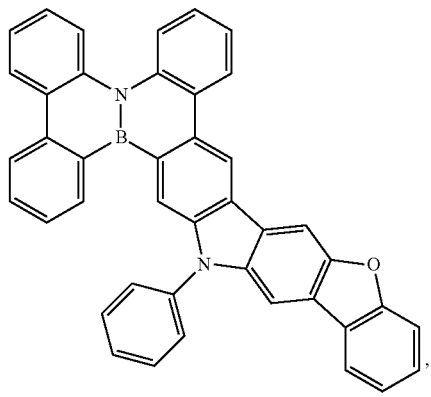

-continued
Structure F129
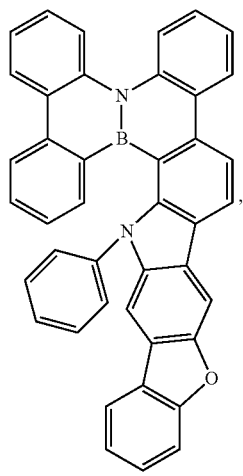
Structure F132
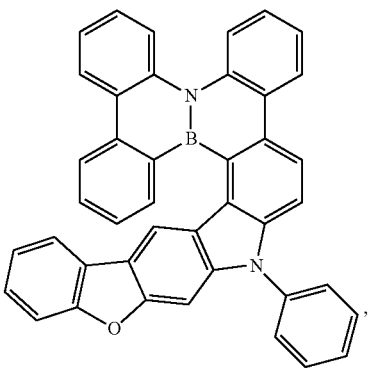
Structure F133
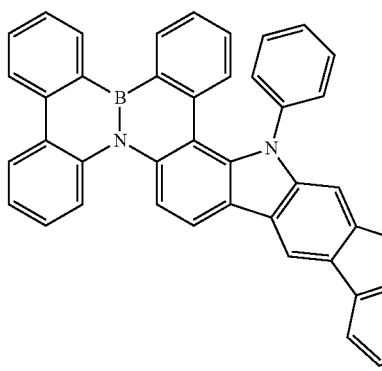
Structure F130
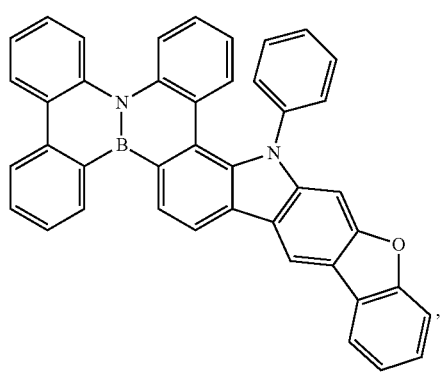
Structure F134
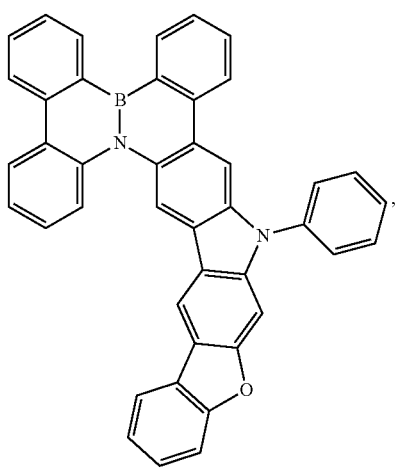
Structure F131
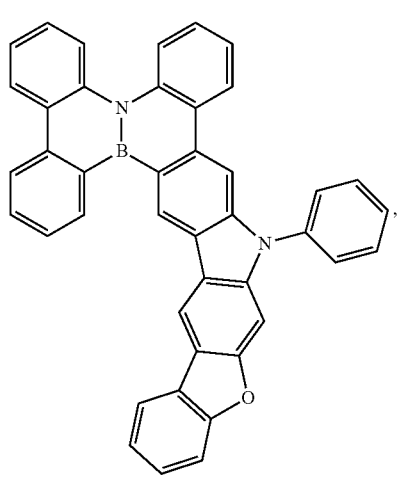
Structure F135
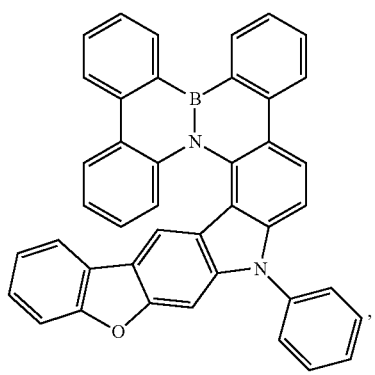

Structure F136
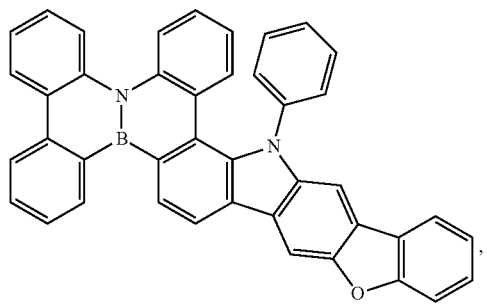
Structure F137
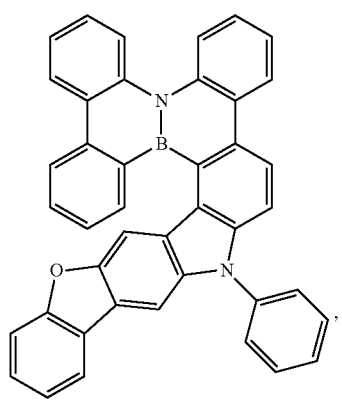
Structure F138
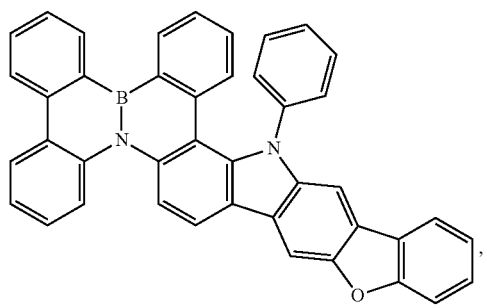
Structure F139
Structure F140
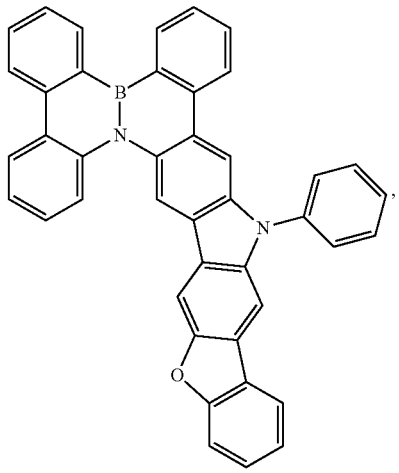
Structure F141
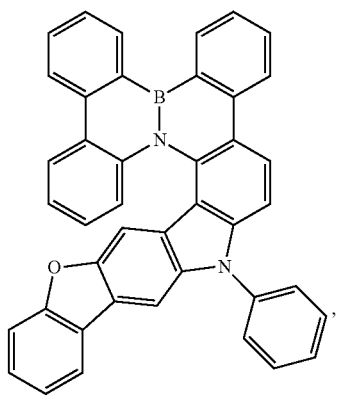
Structure F142
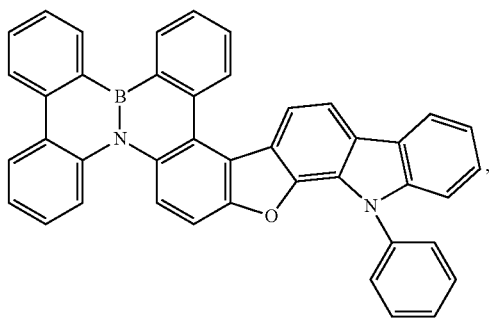
Structure F143
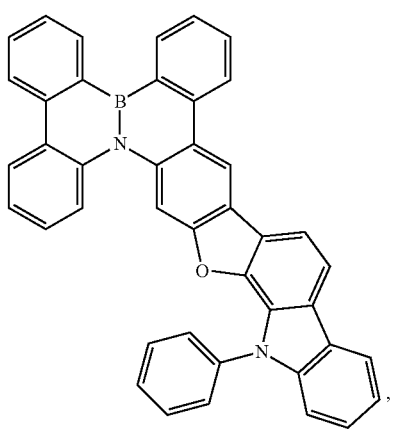

Structure F144
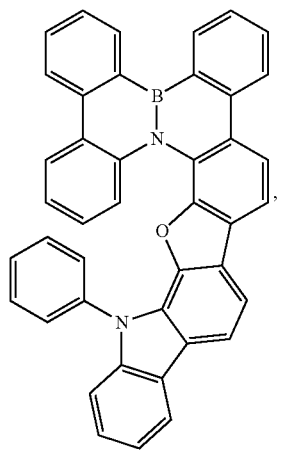
Structure F148
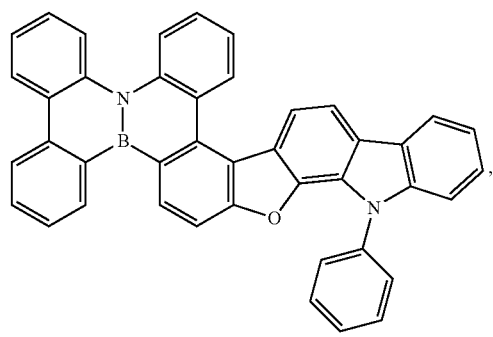
Structure F145
Structure F149
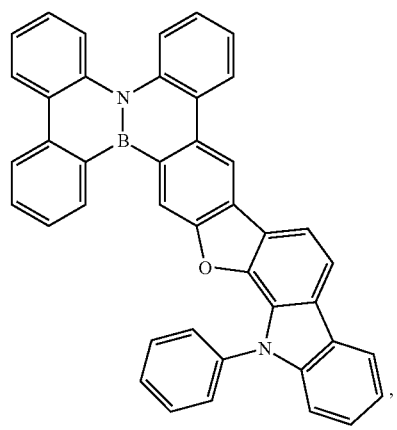
Structure F146
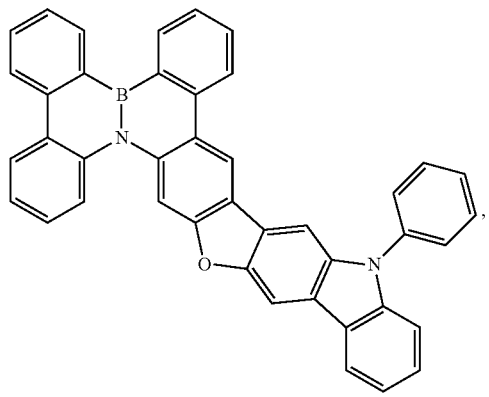
Structure F150
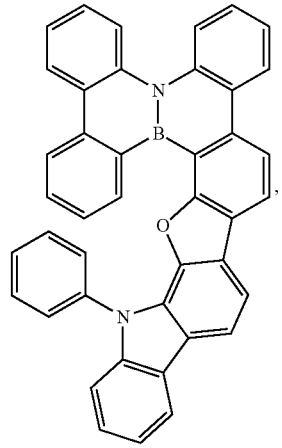
Structure F147
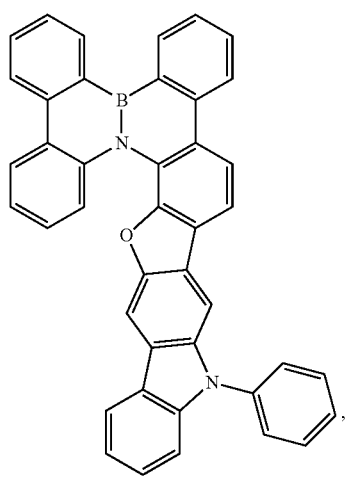
Structure F151
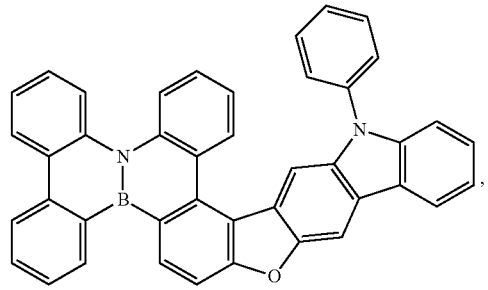

Structure F152
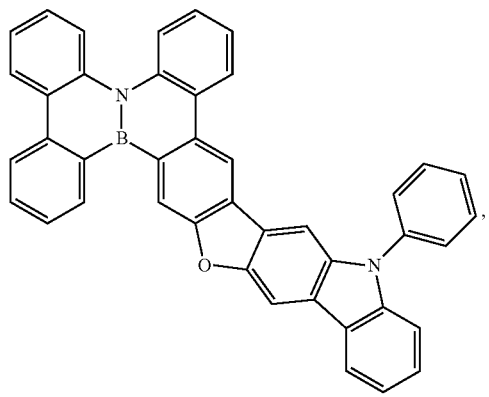
Structure F155
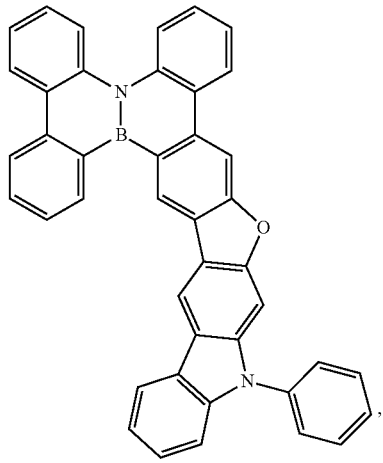
Structure F153
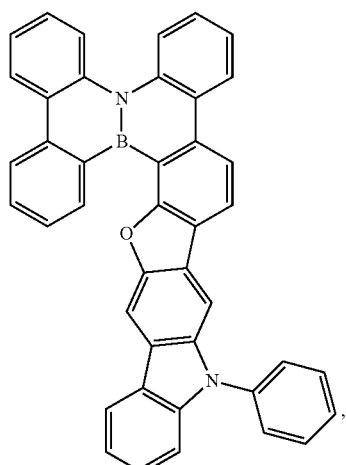
Structure F156
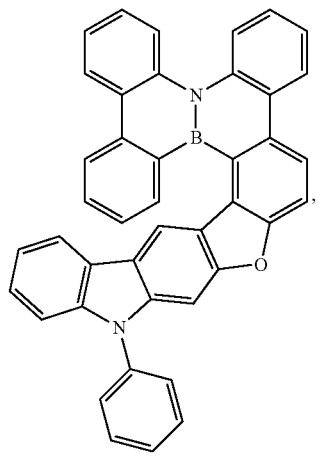
Structure F154
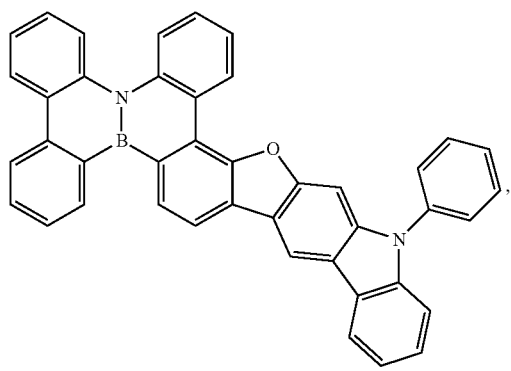
Structure F157
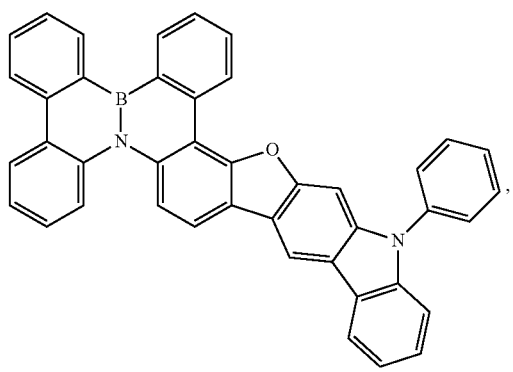

Structure F158
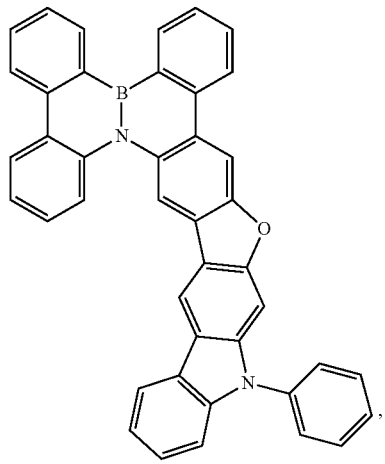
Structure F161
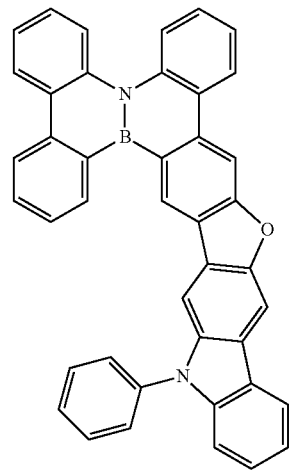
Structure F159
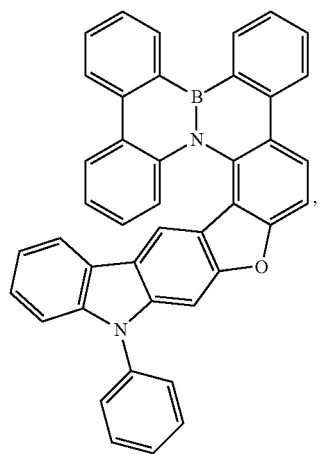
Structure F162
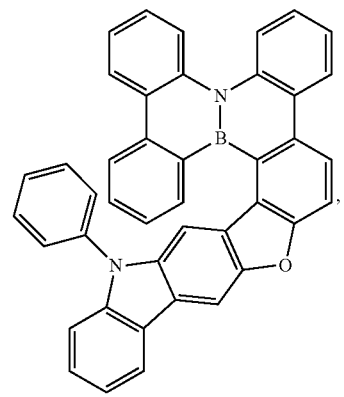
Structure F160
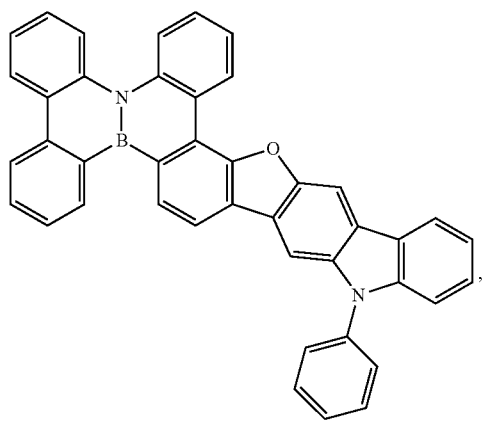
Structure F163
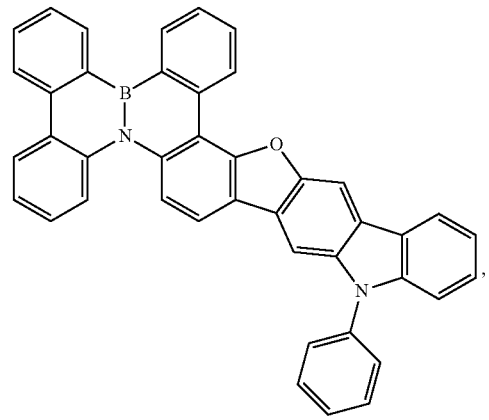

Structure F164
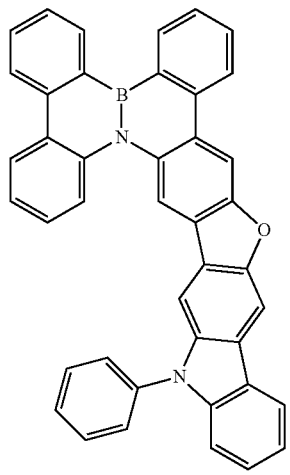
Structure F167
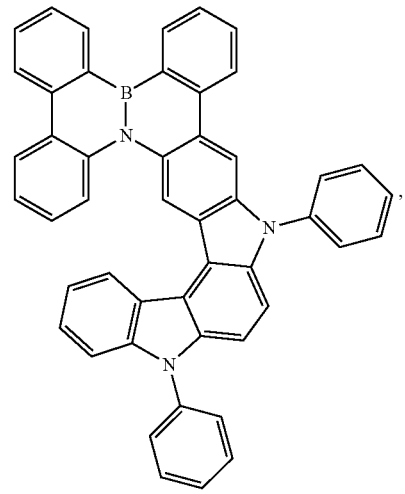
Structure F165
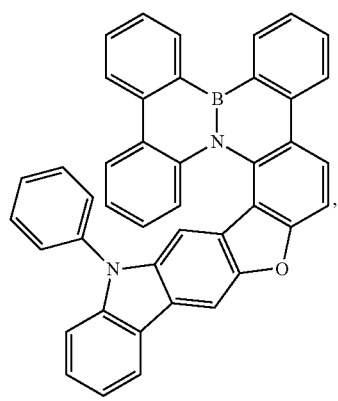
Structure F168
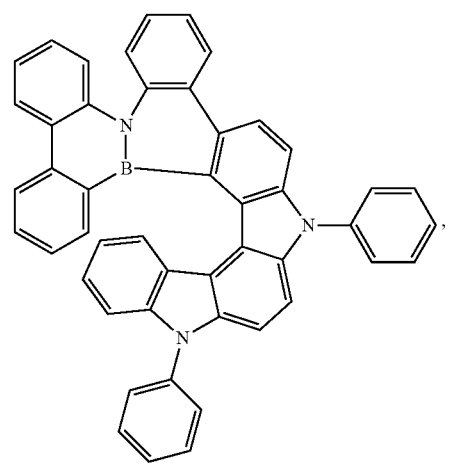
Structure F166
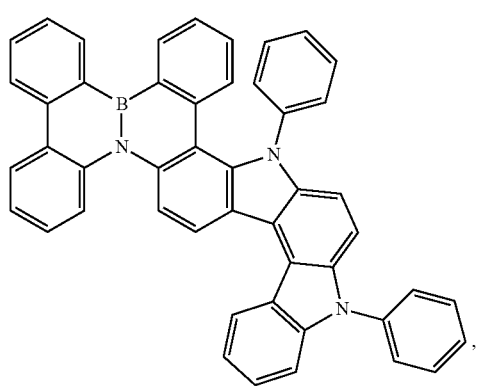
Structure F169
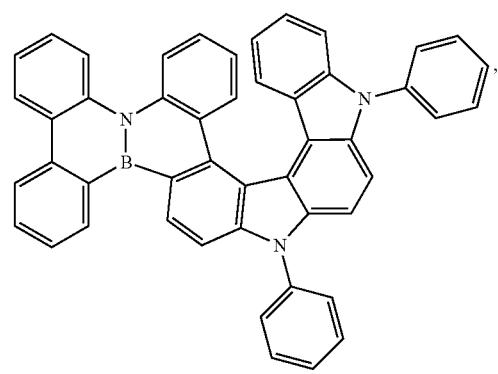

-continued
Structure F170
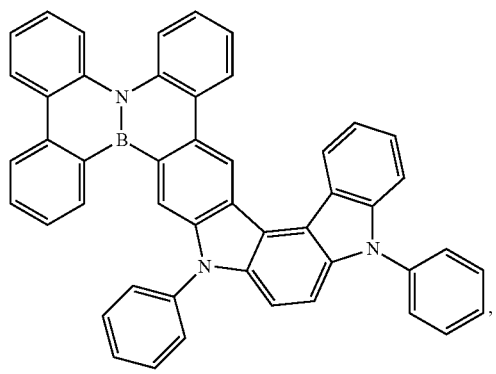
Structure F171
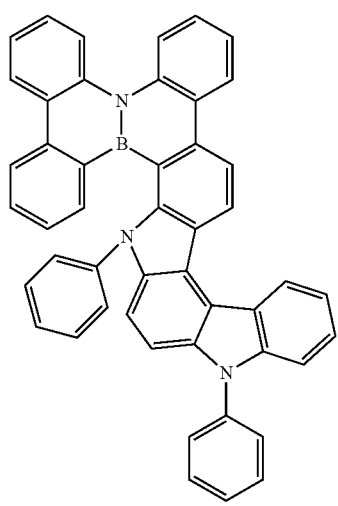
Structure F172
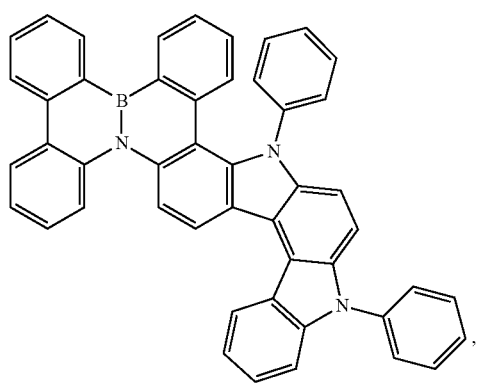
-continued
Structure F173
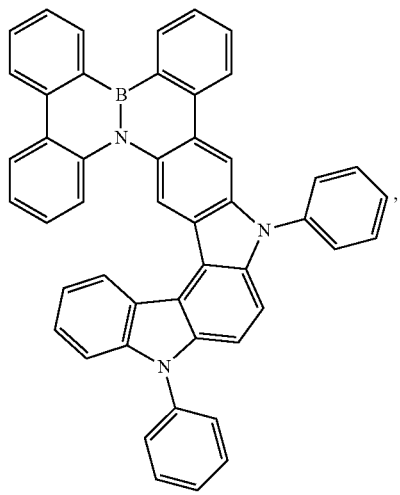
Structure F174
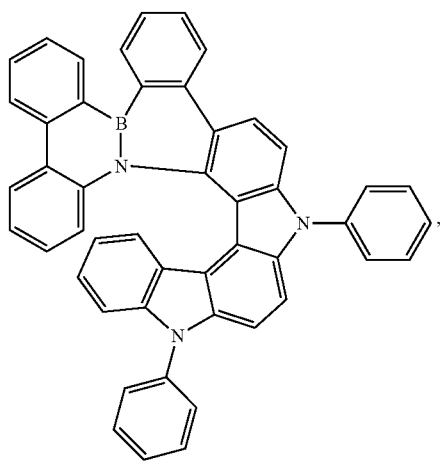
Structure F175
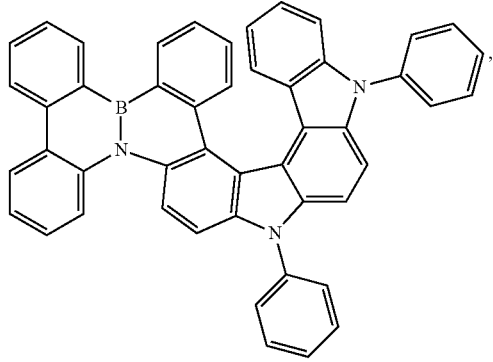

-continued

Structure F176

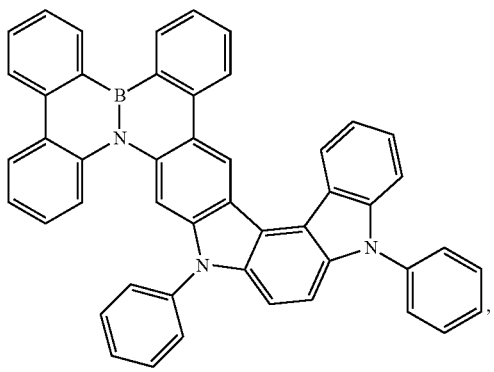

Structure F177

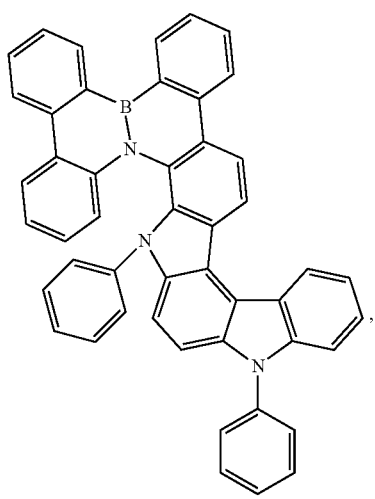

Structure F178

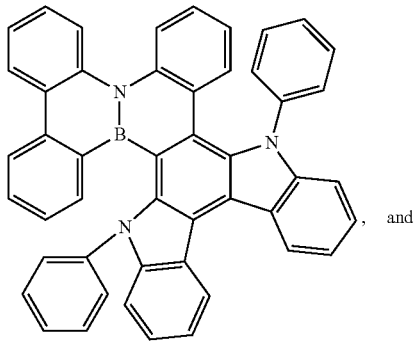

Structure F179

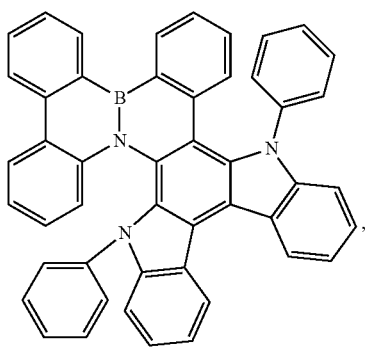

which may be further substituted by one or more substituents independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein any adjacent substitutions are optionally joined or fused into a ring.

13. A device comprising one or more organic light-emitting devices, at least one of the one or more organic light emitting devices comprising:
an anode;
a cathode; and
an organic layer, disposed between the anode and the cathode, comprising a compound having a structure of Formula I or Formula V:

$$G^1\text{-}L^1\text{-}G^2,\qquad \text{Formula I;}$$

Formula V

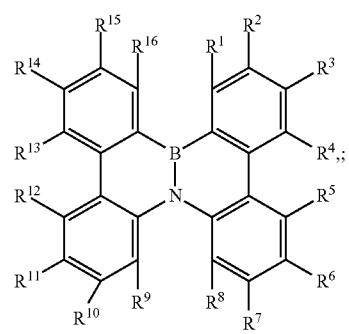

wherein $G^1$ and $G^2$ independently have a structure of Formula II:

Formula II

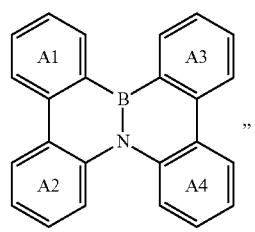

wherein $G^1$ and $G^2$ can be same or different;
wherein $L^1$ connects one of rings A1, A2, A3, and A4 of $G^1$ to one of rings A1, A2, A3, and A4 of $G^2$;
wherein $L^1$ is selected from the group consisting of a direct bond, BR, NR, PR, O, S, Se, C=O, S=O, $SO_2$, SiRR', GeRR', alkyl, cycloalkyl, aryl, heteroaryl, and combinations thereof;
wherein each ring A1, A2, A3, and A4 in Formula II can be further substituted by one or more substituents selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein at least two adjacent $R^1$ to $R^{16}$ on the same ring are:

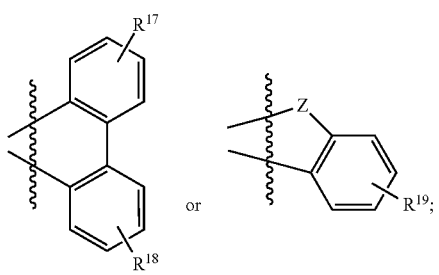

wherein $R^{17}$ to $R^{19}$ each independently represent mono, di, tri, or tetra substitution, or no substitution;

wherein Z is selected from the group consisting of NR", O, S and Se;

wherein R, R' R", and $R^1$ to $R^{19}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any adjacent substitutions of Formula I and any adjacent substitutions of $R^{17}$, $R^{18}$, $R^{19}$ of Formula V are optionally joined or fused into a ring.

14. The device of claim 13, wherein the organic layer is an emissive layer and the compound of Formula I or Formula V is a host.

15. The device of claim 13, wherein the organic layer further comprises an emissive dopant.

16. The device of claim 15, wherein the emissive dopant is a transition metal complex having at least one ligand or part of the ligand if the ligand is more than bidentate, selected from the group consisting of:

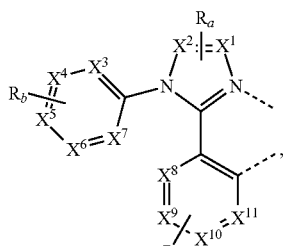

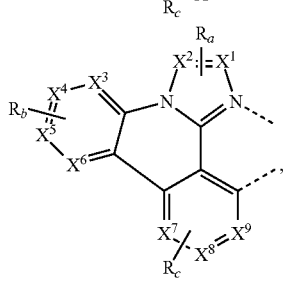

-continued

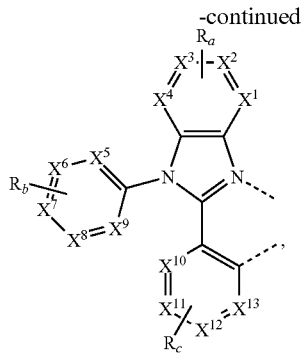

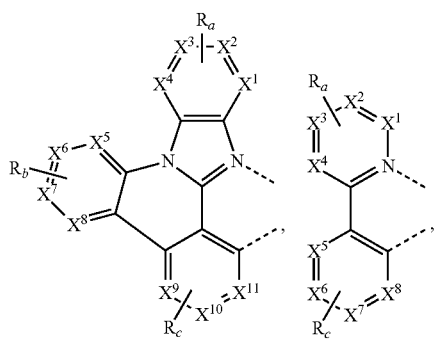

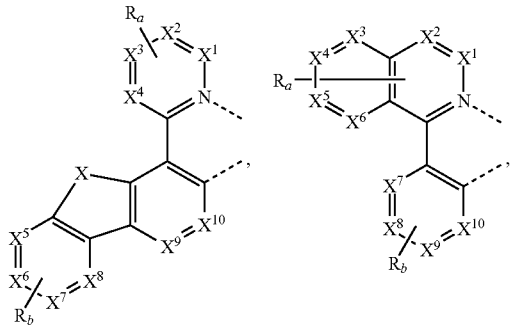

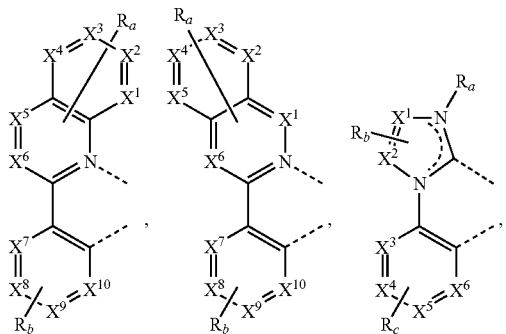

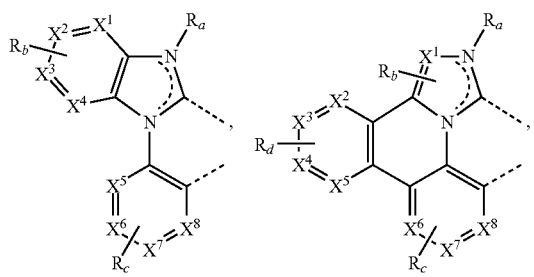

-continued

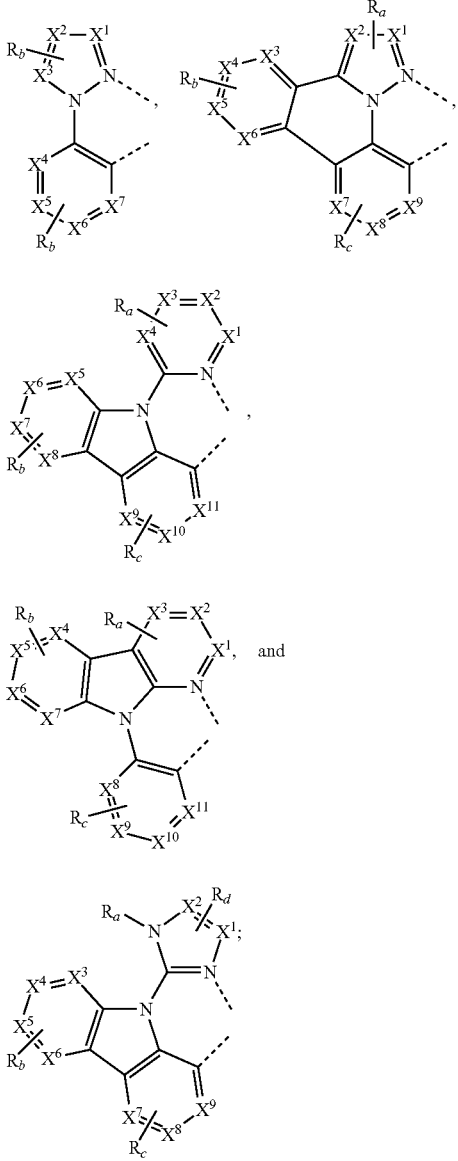

wherein each $X^1$ to $X^{13}$ are independently selected from the group consisting of carbon and nitrogen;
wherein X is selected from the group consisting of BR', NR', PR', O, S, Se, C=O, S=O, SO$_2$, CR'R", SiR'R", and GeR'R";
wherein R' and R" are optionally fused or joined to form a ring;
wherein each $R_a$, $R_b$, $R_c$, and $R_d$ may represent from mono substitution to the possible maximum number of substitution, or no substitution;
wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein any two adjacent substituents of $R_a$, $R_b$, $R_c$, and $R_d$ are optionally fused or joined to form a ring or form a multidentate ligand.

17. The device of claim 13, wherein the organic layer is a blocking layer and the compound of Formula I or Formula V is a blocking material in the organic layer.

18. The device of claim 13, wherein the organic layer is an electron transporting layer and the compound of Formula I or Formula V is an electron transporting material in the organic layer.

19. The device of claim 13, wherein the device is selected from the group consisting of a consumer product, an electronic component module, an organic light-emitting device, and a lighting panel.

20. A formulation comprising a compound having a structure of Formula I or Formula V:

Formula I
$$G^1—L^1—G^2;$$

Formula V
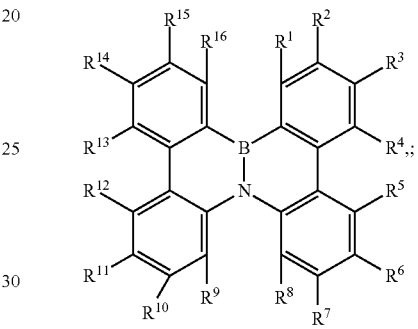

wherein $G^1$ and $G^2$ independently have a structure of Formula II:

Formula II
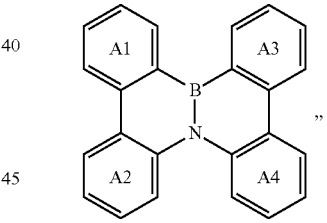

wherein $G^1$ and $G^2$ can be same or different;
wherein $L^1$ connects one of rings A1, A2, A3, and A4 of $G^1$ to one of rings A1, A2, A3, and A4 of $G^2$;
wherein $L^1$ is selected from the group consisting of a direct bond, BR, NR, PR, O, S, Se, C=O, S=O, SO$_2$, SiRR', GeRR', alkyl, cycloalkyl, aryl, heteroaryl, and combinations thereof;
wherein each ring A1, A2, A3, and A4 in Formula II can be further substituted by one or more substituents selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein at least two adjacent $R^1$ to $R^{16}$ on the same ring are:

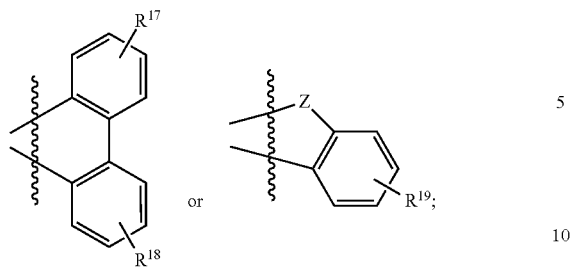

or wherein $R^{17}$ to $R^{19}$ each independently represent mono, di, tri, or tetra substitution, or no substitution;
wherein Z is selected from the group consisting of NR", O, S and Se;
wherein R, R' R", and $R^1$ to $R^{19}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein any adjacent substitutions of Formula I and any adjacent substitutions of $R^{17}$, $R^{18}$, $R^{19}$ of Formula V are optionally joined or fused into a ring.

* * * * *

UNITED STATES PATENT AND TRADEMARK OFFICE
CERTIFICATE OF CORRECTION

PATENT NO. : 9,871,212 B2
APPLICATION NO. : 14/933510
DATED : January 16, 2018
INVENTOR(S) : Raymond Kwong and Kit Yee Tsang It is certified that error appears in the above-identified patent and that said Letters Patent is hereby corrected as shown below:

In the Specification

Column 3, Line 58, please delete the word "sibyl" and insert --silyl--.

Column 9, Line 22, following the word nitrile, please insert --isonitrile,--.

Column 10, Line 66, please delete the word "nitrite" and insert --nitrile--.

Column 10, Line 66, following the word sulfanyl, please insert --sulfinyl,--.

Column 44, Line 34, following the word alkenyl, please insert --cycloalkenyl,--.

Column 124, Line 64, please delete the word "midazine" and insert --pyridazine--.

Column 125, Line 14, following the word halide, please insert --alkyl--.

Column 125, Line 15, following the word amino, please insert --silyl,--.

Column 125, Line 16, please delete the word "nitrite" and insert --nitrile--.

Column 126, Line 55, following the word oxadiazine, please insert --indole,--.

Column 126, Line 59, following the word benzofuropyridine, please insert --furodipyridine,--.

Column 127, Line 4, before the word aryloxy, please insert --alkoxy,--.

Column 127, Line 6, please delete the word "nitrite" and insert --nitrile--.

Column 129, Line 18, following the words and numbers from 1 to 20; please insert --$L^{101}$--.

Signed and Sealed this
Twenty-first Day of August, 2018

Andrei Iancu
*Director of the United States Patent and Trademark Office*